United States Patent
Cojocaru et al.

(10) Patent No.: US 9,617,336 B2
(45) Date of Patent: Apr. 11, 2017

(54) C1ORF32 ANTIBODIES, AND USES THEREOF FOR TREATMENT OF CANCER

(71) Applicant: COMPUGEN LTD., Tel Aviv (IL)

(72) Inventors: Gady S. Cojocaru, Ramat Hasharon (IL); Galit Rotman, Herzliyya (IL); Zurit Levine, Herzliyya (IL); Liat Dassa, Yehud (IL); Ofer Levi, Moshav Mesilat Zion (IL); Raffaella Briante, Burlingame, CA (US); Shweta Singh, Fremont, CA (US); Susan R. Watson, El Cerrito, CA (US); Tania Pergam, Rishon LeZion (IL)

(73) Assignee: COMPUGEN LTD, Holon (IL)

( * ) Notice: Subject to any disclaimer, the term of this patent is extended or adjusted under 35 U.S.C. 154(b) by 77 days.

(21) Appl. No.: 14/360,694

(22) PCT Filed: Jan. 31, 2013

(86) PCT No.: PCT/IL2013/050087
§ 371 (c)(1),
(2) Date: May 27, 2014

(87) PCT Pub. No.: WO2013/114367
PCT Pub. Date: Aug. 8, 2013

(65) Prior Publication Data
US 2015/0158947 A1     Jun. 11, 2015

Related U.S. Application Data

(60) Provisional application No. 61/593,344, filed on Feb. 1, 2012, provisional application No. 61/697,369, filed on Sep. 6, 2012.

(51) Int. Cl.
| | |
|---|---|
| *C07K 16/00* | (2006.01) |
| *A61K 39/00* | (2006.01) |
| *C07K 16/28* | (2006.01) |
| *C07K 16/30* | (2006.01) |
| *A61K 31/675* | (2006.01) |
| *A61K 39/395* | (2006.01) |
| *A61K 45/06* | (2006.01) |
| *A61K 49/00* | (2006.01) |
| *A61N 5/06* | (2006.01) |
| *A61N 5/10* | (2006.01) |
| *G01N 33/574* | (2006.01) |

(52) U.S. Cl.
CPC ........ *C07K 16/2803* (2013.01); *A61K 31/675* (2013.01); *A61K 39/0011* (2013.01); *A61K 39/3955* (2013.01); *A61K 45/06* (2013.01); *A61K 49/0004* (2013.01); *A61N 5/062* (2013.01); *A61N 5/10* (2013.01); *C07K 16/28* (2013.01); *C07K 16/30* (2013.01); *G01N 33/57407* (2013.01); *A61K 2039/505* (2013.01); *C07K 2317/34* (2013.01); *C07K 2317/734* (2013.01); *C07K 2317/76* (2013.01); *C07K 2319/00* (2013.01); *G01N 2333/70503* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,366,241 A | 12/1982 | Tom |
| 4,376,110 A | 3/1983 | David |
| 4,399,216 A | 8/1983 | Axel |
| 4,439,196 A | 3/1984 | Higuchi |
| 4,447,224 A | 5/1984 | DeCant, Jr. |
| 4,447,233 A | 5/1984 | Mayfield |
| 4,469,863 A | 9/1984 | Ts'o et al. |
| 4,475,196 A | 10/1984 | La Zor |
| 4,476,301 A | 10/1984 | Imbach |
| 4,486,194 A | 12/1984 | Ferrara |
| 4,487,603 A | 12/1984 | Harris |
| 4,517,288 A | 5/1985 | Giegel |
| 4,522,811 A | 6/1985 | Eppstein |
| 4,596,556 A | 6/1986 | Morrow |
| 4,634,665 A | 1/1987 | Axel |
| 4,790,824 A | 12/1988 | Morrow |
| 4,816,567 A | 3/1989 | Cabilly |
| 4,837,168 A | 6/1989 | De Jaeger |
| 4,837,306 A | 6/1989 | Ling et al. |
| 4,873,316 A | 10/1989 | Meade |
| 4,881,175 A | 11/1989 | Ladner |
| 4,941,880 A | 7/1990 | Burns |
| 4,946,778 A | 8/1990 | Ladner |
| 4,954,617 A | 9/1990 | Fanger |

(Continued)

FOREIGN PATENT DOCUMENTS

| | | |
|---|---|---|
| EP | 0154316 | 9/1985 |
| EP | 0264166 | 4/1988 |

(Continued)

OTHER PUBLICATIONS

Pirker et al. (Lancet, 2009, 373:1525-1531).*
Zhao et al. (Microenvironment and Immunology, 2010, 70:4850-4858).*
Office Action for related EP08829443.4 Mailed May 14, 2012.
Office Action for related AU2008296361 Mailed Nov. 26, 2012.
Search report and written opinion for related PCT application PCT/IB2011/052877, Mailed Aug. 9, 2012.
"CGEN-15001 An Example of Discovery on Demand", published Jul. 27, 2010, retrieved through the Internet, www.cgen.com.
"New membrane protein for the treatment of autoimmune diseases", published Feb. 3, 2010, retrieved through the Internet, themspodcast.com.
Gonzalez Rey et al, Arthritis and Rheumatism, vol. 54, Jan. 2006, pp. 864-876.

(Continued)

*Primary Examiner* — Julie Wu
(74) *Attorney, Agent, or Firm* — Graeser Associates International Inc; Dvorah Graeser

(57) ABSTRACT

This invention relates to C1ORF32-specific antibodies, antibody fragments, alternative scaffolds, conjugates and compositions comprising same, for treatment of cancer.

23 Claims, 32 Drawing Sheets

(56) References Cited

U.S. PATENT DOCUMENTS

| | | |
|---|---|---|
| 5,013,653 A | 5/1991 | Huston |
| 5,023,243 A | 6/1991 | Tullis |
| 5,034,506 A | 7/1991 | Summerton |
| 5,064,413 A | 11/1991 | McKinnon |
| 5,091,513 A | 2/1992 | Huston |
| 5,132,405 A | 7/1992 | Huston |
| 5,166,315 A | 11/1992 | Summerton |
| 5,177,196 A | 1/1993 | Meyer, Jr. |
| 5,179,017 A | 1/1993 | Axel |
| 5,185,444 A | 2/1993 | Summerton |
| 5,188,897 A | 2/1993 | Suhadolnik |
| 5,214,134 A | 5/1993 | Weis |
| 5,216,141 A | 6/1993 | Benner |
| 5,223,409 A | 6/1993 | Ladner |
| 5,225,538 A | 7/1993 | Capon et al. |
| 5,225,539 A | 7/1993 | Winter |
| 5,235,033 A | 8/1993 | Summerton |
| 5,258,498 A | 11/1993 | Huston |
| 5,260,203 A | 11/1993 | Ladner |
| 5,264,423 A | 11/1993 | Cohen |
| 5,264,562 A | 11/1993 | Matteucci |
| 5,264,564 A | 11/1993 | Matteucci |
| 5,276,019 A | 1/1994 | Cohen |
| 5,278,302 A | 1/1994 | Caruthers |
| 5,286,717 A | 2/1994 | Cohen |
| 5,312,335 A | 5/1994 | McKinnon |
| 5,321,131 A | 6/1994 | Agrawal |
| 5,374,548 A | 12/1994 | Caras |
| 5,383,851 A | 1/1995 | McKinnon, Jr. |
| 5,399,163 A | 3/1995 | Peterson |
| 5,399,331 A | 3/1995 | Loughrey |
| 5,399,676 A | 3/1995 | Froehler |
| 5,403,484 A | 4/1995 | Ladner |
| 5,405,938 A | 4/1995 | Summerton et al. |
| 5,405,939 A | 4/1995 | Suhadolnik et al. |
| 5,416,016 A | 5/1995 | Low |
| 5,427,908 A | 6/1995 | Dower |
| 5,434,257 A | 7/1995 | Matteucci |
| 5,453,496 A | 9/1995 | Caruthers |
| 5,455,030 A | 10/1995 | Ladner |
| 5,455,233 A | 10/1995 | Spielvogel |
| 5,466,677 A | 11/1995 | Baxter |
| 5,470,967 A | 11/1995 | Huie |
| 5,476,786 A | 12/1995 | Huston |
| 5,476,925 A | 12/1995 | Letsinger |
| 5,476,996 A | 12/1995 | Wilson |
| 5,482,858 A | 1/1996 | Huston |
| 5,489,677 A | 2/1996 | Sanghvi |
| 5,519,126 A | 5/1996 | Hecht |
| 5,530,101 A | 6/1996 | Queen |
| 5,536,821 A | 7/1996 | Agrawal |
| 5,539,082 A | 7/1996 | Nielsen |
| 5,541,306 A | 7/1996 | Agrawal |
| 5,541,307 A | 7/1996 | Cook |
| 5,545,806 A | 8/1996 | Lonberg |
| 5,545,807 A | 8/1996 | Surani |
| 5,550,111 A | 8/1996 | Suhadolnik |
| 5,561,225 A | 10/1996 | Maddry |
| 5,563,253 A | 10/1996 | Agrawal |
| 5,569,825 A | 10/1996 | Lonberg |
| 5,571,698 A | 11/1996 | Ladner |
| 5,571,799 A | 11/1996 | Tkachuk |
| 5,580,717 A | 12/1996 | Dower |
| 5,585,089 A | 12/1996 | Queen |
| 5,587,361 A | 12/1996 | Cook |
| 5,596,086 A | 1/1997 | Matteucci |
| 5,602,240 A | 2/1997 | De Mesmaeker |
| 5,608,046 A | 3/1997 | Cook |
| 5,610,289 A | 3/1997 | Cook |
| 5,618,704 A | 4/1997 | Sanghvi |
| 5,623,070 A | 4/1997 | Cook |
| 5,624,821 A | 4/1997 | Winter |
| 5,625,050 A | 4/1997 | Beaton |
| 5,625,126 A | 4/1997 | Lonberg |
| 5,625,825 A | 4/1997 | Rostoker |
| 5,633,360 A | 5/1997 | Bischofberger |
| 5,633,425 A | 5/1997 | Lonberg |
| 5,648,260 A | 7/1997 | Winter |
| 5,661,016 A | 8/1997 | Lonberg |
| 5,663,312 A | 9/1997 | Chaturvedula |
| 5,677,425 A | 10/1997 | Bodmer |
| 5,677,437 A | 10/1997 | Teng |
| 5,677,439 A | 10/1997 | Weis |
| 5,693,762 A | 12/1997 | Queen |
| 5,698,767 A | 12/1997 | Wilson |
| 5,714,331 A | 2/1998 | Buchardt |
| 5,714,350 A | 2/1998 | Co |
| 5,719,262 A | 2/1998 | Buchardt |
| 5,770,429 A | 6/1998 | Lonberg |
| 5,789,650 A | 8/1998 | Lonberg |
| 5,814,318 A | 9/1998 | Lonberg |
| 5,869,046 A | 2/1999 | Presta |
| 5,874,299 A | 2/1999 | Lonberg |
| 5,877,397 A | 3/1999 | Lonberg |
| 5,885,793 A | 3/1999 | Griffiths |
| 5,939,598 A | 8/1999 | Kucherlapati |
| 5,969,108 A | 10/1999 | McCafferty |
| 6,075,181 A | 6/2000 | Kucherlapati |
| 6,114,598 A | 9/2000 | Kucherlapati |
| 6,121,022 A | 9/2000 | Presta |
| 6,150,584 A | 11/2000 | Kucherlapati |
| 6,162,963 A | 12/2000 | Kucherlapati |
| 6,165,745 A | 12/2000 | Ward |
| 6,172,197 B1 | 1/2001 | McCafferty |
| 6,180,370 B1 | 1/2001 | Queen |
| 6,194,551 B1 | 2/2001 | Idusogie |
| 6,277,375 B1 | 8/2001 | Ward |
| 6,303,374 B1 | 10/2001 | Zhang |
| 6,350,861 B1 | 2/2002 | Co |
| 6,521,404 B1 | 2/2003 | Griffiths |
| 6,544,731 B1 | 4/2003 | Griffiths |
| 6,555,313 B1 | 4/2003 | Griffiths |
| 6,582,915 B1 | 6/2003 | Griffiths |
| 6,593,081 B1 | 7/2003 | Griffiths |
| 6,709,654 B1 | 3/2004 | Anderson et al. |
| 7,189,507 B2 | 3/2007 | Mack |
| 7,745,391 B2 | 6/2010 | Mintz et al. |
| 7,829,084 B2 | 11/2010 | Ledbetter et al. |
| 7,842,665 B2 | 11/2010 | Levin et al. |
| 7,982,017 B2 | 7/2011 | Lin et al. |
| 8,043,616 B2 | 10/2011 | Anderson et al. |
| 8,080,246 B2 | 12/2011 | Lin et al. |
| 8,183,207 B2 | 5/2012 | Lin et al. |
| 8,293,883 B2 | 10/2012 | Presta |
| 8,318,159 B2 | 11/2012 | Adam et al. |
| 8,318,168 B2 | 11/2012 | Sass et al. |
| 8,415,455 B2 | 4/2013 | Levine et al. |
| 2002/0037286 A1 | 3/2002 | Krause et al. |
| 2002/0193567 A1 | 12/2002 | Jacobs |
| 2004/0009481 A1 | 1/2004 | Schlegel |
| 2004/0110704 A1 | 6/2004 | Yamane |
| 2006/0034852 A1 | 2/2006 | Rixon |
| 2008/0299042 A1 | 12/2008 | Bechtel et al. |
| 2011/0151515 A1 | 6/2011 | Heifetz et al. |
| 2011/0281302 A1 | 11/2011 | Williams et al. |
| 2012/0128672 A1 | 5/2012 | Keer |
| 2012/0134997 A1 | 5/2012 | Levine et al. |
| 2012/0141573 A1 | 6/2012 | Ling et al. |
| 2012/0219559 A1 | 8/2012 | Chen |
| 2013/0160150 A1 | 6/2013 | Leibel et al. |

FOREIGN PATENT DOCUMENTS

| | | | |
|---|---|---|---|
| EP | 0338841 | 10/1989 | |
| EP | 0401384 | 12/1990 | |
| EP | 1176195 | 1/2002 | |
| EP | 2116259 A1 | 11/2009 | |
| EP | 2190469 A2 | 6/2010 | |
| IL | WO 2009032845 A2 * | 3/2009 | ........... C07K 14/705 |
| WO | WO 87/04462 | 7/1987 | |
| WO | WO 87/05330 | 9/1987 | |
| WO | WO 88/00052 | 1/1988 | |
| WO | WO 89/01036 | 2/1989 | |
| WO | WO 92/03918 | 3/1992 | |

(56) References Cited

FOREIGN PATENT DOCUMENTS

| WO | WO 93/12227 | 6/1993 |
|----|-------------|--------|
| WO | WO 94/10332 | 5/1994 |
| WO | WO 94/25585 | 11/1994 |
| WO | WO 94/29351 | 12/1994 |
| WO | WO 97/13852 | 4/1997 |
| WO | WO 98/24884 | 6/1998 |
| WO | WO 99/26972 | 6/1999 |
| WO | WO 99/45962 | 9/1999 |
| WO | WO 99/54342 | 10/1999 |
| WO | WO 99/60020 | 11/1999 |
| WO | WO 00/42072 | 7/2000 |
| WO | WO 01/09187 | 2/2001 |
| WO | WO 01/14424 | 3/2001 |
| WO | WO 02/26930 | 4/2002 |
| WO | WO 02/43478 | 6/2002 |
| WO | WO 02/092780 | 11/2002 |
| WO | WO 03/000012 | 2/2003 |
| WO | WO 03/027228 | 4/2003 |
| WO | WO 03/035835 | 5/2003 |
| WO | WO 03/074679 | 9/2003 |
| WO | WO 03/101283 | 12/2003 |
| WO | WO 2004/037999 | 5/2004 |
| WO | WO 2004/048550 | 6/2004 |
| WO | WO 2004/100774 | 11/2004 |
| WO | WO 2005/108415 | 11/2005 |
| WO | WO 2006/050247 | 5/2006 |
| WO | WO 2006/050262 | 5/2006 |
| WO | 2007008708 | 1/2007 |
| WO | 2007014123 A2 | 2/2007 |
| WO | 2007106056 A1 | 9/2007 |
| WO | 2008008766 | 1/2008 |
| WO | 2008049070 A2 | 4/2008 |
| WO | 2008131242 A1 | 10/2008 |
| WO | 2009032845 A2 | 3/2009 |
| WO | 2009055074 A2 | 4/2009 |
| WO | 2009076651 A2 | 6/2009 |
| WO | 2010017198 A2 | 2/2010 |
| WO | 2012001647 A2 | 1/2012 |
| WO | 2012006027 A1 | 1/2012 |
| WO | 2012144692 | 10/2012 |
| WO | 2013001517 | 1/2013 |
| WO | 2013114367 | 8/2013 |
| WO | 2013151663 | 10/2013 |

OTHER PUBLICATIONS

Gonzalez Rey et al, Ann Rheum Dis, vol. 69, Jan. 1, 2010, pp. 241-248.
IPRP for related PCT/IB2011/052877 mailed Jan. 8, 2013.
Office Action for related EP08829443.4 Mailed Oct. 16, 2013.
Office Action for related JP2011-505792 Mailed Feb. 18, 2014.
Office Action for related CN201180038162.9 Mailed Feb. 19, 2014.
Office Action for related AU2011272941 Mailed Feb. 19, 2014.
Crawford et al., Curr Opin Immunol. 2009;21:179-186.
Diepolder and Obst, Expert Rev Vaccines. Mar. 2010;9(3):243-7.
Follicular Helper CD4 T Cells (TFH), Crotty, Annu. Rev. Immunol. 29: 621-663, 2011.
Golden-Mason et al., J Virol. 2009;83:9122-30.
Ha et al, Immunol Rev. Jun. 2008;223:317-33.
Hofmeyer et al, J. Biomed. & Biotech. 2011, val 2011, The PD-1/PD-L1 (B7-H1) Pathway in Chronic Infection-InducedCytotoxic T Lymphocyte Exhaustion, Art. ID 451694, pp. 1-9.
Kaufmann et al., J Immunol2009;182:5891-5897.
Restoring function in exhausted CD8 T cells during chronic viral infection, Barber et al., Nature. 2006;439:682-7.
Rivas et al., J Immunol. 2009 ;183:4284-91.
Sharpe et al., Nat Immunol 2007;8:239-245.
Target-Dependent B7-H1 Regulation Contributes to Clearance of Central Nervous Sysyem Infection and DampensMorbidity, Phares et al., J Immunol. 2009: 182; 5430-5438.
Velu et al., Nature 2009;458:206-210, Enhancing SIV-specific immunity in vivo by PD-1 blockade.
Rentero, Inmaculada, and Christian Heinis. "Screening of large molecule diversities by phage display." CHIMIA International Journal for Chemistry 65.11 (2011): 843-845.
Extended European Search Report from related EP14162019 mailed on Jul. 28, 2014.
BLAST Search results from related U.S. Appl. No. 13/845,420—Dec. 2014.
Lederman, Seth, et al. "A single amino acid substitution in a common African allele of the CD4 molecule ablates binding of the monoclonal antibody, OKT4." Molecular immunology 28.11 (1991): 1171-1181.
Colman, Peter M. "Effects of amino acid sequence changes on antibody-antigen interactions." Research in Immunology 145.1 (1994): 33-36.
Sequence alignment and further information retrieved from Alignments Registry—Dec. 11, 2013.
Supplementary European SR dated May 7, 2015.
Smith et al, Cancer immunol immunother, 2011, vol. 60, pp. 1775-1787.
Kazarian et al, Molecular Cancer, 2011, vol. 10, pp. 1-19.
Antibody News, Dec. 1, 2011 Press Release by Compugen Ltd.
Nicolini et al, Medicinal Research Reviews, 2009, vol. 29, pp. 436-471.
Fillatreau et al.: "B cells regulate autoimmunity by provision of IL-10" Nature Immunology 3, 944-950 (2002).
Lowes at al.: "Psoriasis vulgaris lesions contain discrete populations of Th1 and Th17 T cells" Jour. of investigative dermatology (2008) vol. 128 p. 1207-1211.
Marija Dokmanovic-Chouinard et al.: "Positional Cloning of "Lisch-like", a Candidate Modifier of Susceptibility to Type 2 Diabetes in Mice", PLoS Genetics, Jul. 25, 2008, vol. 4, Issue 7, e1000137.
Search report from the Singaporean Patent Office, mailed Jun. 12, 2015.
Dong, Haidong, et al. "B7-H1, a third member of the B7 family, co-stimulates T-cell proliferation and interleukin-10 secretion." Nature medicine 5.12 (1999): 1365-1369.
Freeman, Gordon J., et al. "Engagement of the PD-1 immunoinhibitory receptor by a novel B7 family member leads to negative regulation of lymphocyte activation." The Journal of experimental medicine 192.7 (2000): 1027-1034.
Tamura, Hideto, et al. "B7-H1 costimulation preferentially enhances CD28-independent T-helper cell function." Blood 97.6 (2001): 1809-1816.
Latchman, Yvette, et al. "PD-L2 is a second ligand for PD-1 and inhibits T cell activation." Nature immunology 2.3 (2001): 261-268.
Greaves, Paul, and John G. Gribben. "The role of B7 family molecules in hematologic malignancy." Blood 121.5 (2013): 734-744.
Li, Yili, Qian Wang, and Roy A. Mariuzza. "Structure of the human activating natural cytotoxicity receptor NKp30 bound to its tumor cell ligand B7-H6." The Journal of experimental medicine 208.4 (2011): 703-714.
Teufel et al. 2009. Update on autoimmune hepatitis. World J Gastroenterol; 15(9): 1035-1041.
Foster GR. 2009. Recent advances in viral hepatitis. Clinical Medicine; 9(6): 613-616.
Rizzetto M. 2010. Hepatitis D: clinical features and therapy. Dig Dis.; 28:139-143.
Lucey et al. 2009. Alcoholic Hepatitis. N Engl J Med; 360:2758-2769.
Krasnokutski et al, Osteoarthritis and Cartilage (2008) 16, S1-S3.
Michels, Aaron W., and George S. Eisenbarth. "Immune intervention in type 1 diabetes." Seminars in immunology. vol. 23. No. 3. Academic Press, 2011.
Gillard, Pieter, and Chantal Mathieu. "Immune and cell therapy in type 1 diabetes: too little too late?." Expert opinion on biological therapy 11.5 (2011): 609-621.
Bluestone, Jeffrey A., and Hélène Bour-Jordan. "Current and future immunomodulation strategies to restore tolerance in autoimmune diseases." Cold Spring Harbor perspectives in biology 4.11 (2012): a007542.

(56) References Cited

OTHER PUBLICATIONS

Herrath, M., M. Peakman, and B. Roep. "Progress in immune-based therapies for type 1 diabetes." Clinical & Experimental Immunology 172.2 (2013): 186-202.
Coppieters, Ken T., Leonard C. Harrison, and Matthias G. von Herrath. "Trials in type 1 diabetes: Antigen-specific Therapies." Clinical Immunology149.3 (2013): 345-355.
Fulpius, Thierry, et al. "Glomerulopathy induced by IgG3 anti-trinitrophenyl monoclonal cryoglobulins derived from non-autoimmune mice." Kidney international 45.4 (1994): 962-971.
Office Action from related AU2013216320 mailed on Mar. 11, 2016.
Database Uniprot[Online](Jul. 5, 2004), Accession No. Q71H61.
Taylor et al, Human chromosome 11 DNA sequence and analysis including novel gene identification, Nature, 2006, 440(7083), 497-500.
Yan et al, Genome sequencing and comparison of two nonhuman primate animal models, the cynomolgus and Chinese rhesus macaques, Nature Biotechnology, 2011, 29(11), 1019-1023.
Zimin et al, A whole-genome assembly of the domestic cow, *Bos taurus*, Genome Biology, 2009, 10(4), R42.
Strausberg et al, Generation and initial analysis of more than 15,000 full-length human and mouse cDNA sequences, Proceedings of the National Academy of Sciences, 2002, 99(26), 16899-16903.
Li et al, The sequence and de novo assembly of the giant panda genome, Nature, 2010, 463(7279), 311-317.
Skarnes et al, A conditional knockout resource for the genome-wide study of mouse gene function, Nature, 2011, 474(7351), 337-342.
Kim et al, Genome sequencing reveals insights into physiology and longevity of the naked mole rat, Nature, 2011, 479(7372), 223-227.
OA for related JP2011-505792 mailed Jul. 2, 2013.
GenBank Accession EAW90779, Dec. 2006.
Search report and written opinion for related PCT/IB2012/053342, mailed Sep. 23, 2012.
International Search Report and Written Opinion for related PCT/US2008/075122 mailed Apr. 9, 2009.
Supplementary European Search Report for EP08829443.4 mailed Dec. 14, 2010.
Database UniProt [Online], Jul. 5, 2004, "RecName: Full=Immunoglobin-like-domain-containing receptor 2;" XP002614181 retrieved from EPI Database accession No. Q71H61.
Heidi Schultz, Towards a Comprehensive Description of the Human Retinal Transcriptome:Identification and Characterization of Differentially Expressed Genes, [Online], 2003, PhD Thesis—Würzburg University.
Valeria Roni et al., Mapping of transcription start sites of human retina expressed genes, BMC Genomics, 2007, vol. 8:42.
Office Action for related EP08829443.4 mailed Feb. 7, 2011.
Markomichelakis, et al., Regression of neovascular age-related macular degeneration following inflixirriab therapy, American Journal of Ophthalmology, 2005, vol. 139, Issue 3.
Nussenblatt et al., Perspectives: Age Related Macular Degeneration and the Immune Response—Implications for Therapy, American Journal of Ophthalmology, 2007, vol. 144, Issue 4.
Altschul, et al., Basic Local Allignment Search Tool, J Mol. Biol.; 1990; 215:403-10.
Arimochi et al., Interaction of Mat-8 (FXYD-3) with Na/K-ATPase in Colorectal Cancer Cells, Biol. Pharm. Bull., 2007; 30(4) 648-654.
Bibert et al.; Structural and Functional Properties of Two Human FXYD3 (Mat-8) Isoforms; The Journal of Biological Chemistry; 2006; vol. 281, 51:39142-39151.
Crambert et al.; FXYD3 (Mat-8), a New Regulator of Na,K-ATPase; Molecular Biology of the Cell; 2005; 16:2363-2371.
Fahrlander, P.D. and Klausner A., Amplifying DNA Probe Signals: A 'Christmas Tree' Approach; Bio/Technology; 1988; 6:1165.
Geering; FXYD proteins: new regulators of Na-K-ATPase; AJP—Renal Physiology; 2006; 290:F241-F250.
Gregory SG et al.; The DNA sequence and biological annotation of human chromosome 1; Nature; 2006, 441(7091):315-321.
Grzmil et al.; Up-regulated expression of the MAT-8 gene in prostate cancer and its siRNA-mediated inhibition of expression induces a decrease in proliferation of human prostate carcinoma cells; International Journal of Oncology; 2004; 24:97-105.
Huston et al.; Protein engineering of antibody binding sites: Recovery of specific activity in an anti-digoxin single-chain Fv analogue produced in *Escherichia coli*; Proc. Natl. Acad. Sci. USA; 1988; 85:5879-5883.
Kayed et al.; FXYD3 is overexpressed in pancreatic ductal adenocarcinoma and influences pancreatic cancer cell growth; Int. J. Cancer:; 2006; 118:43-54.
M. Clark; Chemical Immunol and Antibody Engineering; 1991 Cambridge; pp. 1-31.
Morrison et al.; Mat-8, a Novel Phospholemman-like Protein Expressed in Human Breast Tumors, Induces a Chloride Conductance in Xenopus Oocytes; The Journal of Biological Chemistry ; 1995; 270:2176-2182.
Needleman and Wunsch; A general method applicable to the search for similarities in the amino acid sequence of two proteins; J. Mol. Biol.; 1970; 48:444-453.
Scanlan et al.; Glycoprotein A34, a novel target for antibody-based cancer immunotherapy; Cancer Immunotherapy; 2006; 6:2.
Shields et al.; High Resolution Mapping of the Binding Site on Human IgG1 for FcgRI, FcgRII, FcgRIII, and FcRn and Design of IgG1 Variants with Improved Binding to the FcgR; The Journal of Biological Chemistry; 2001; 276:6591-6604.
Takebe Y. et al.; SR alpha promoter: an efficient and versatile mammalian cDNA expression system composed of the simian virus 40 early promoter and the R-U5 segment of human T-cell leukemia virus type 1 long terminal repeat; Mol. Cell. Biol.; 1988; 8:466-472.
Umana et al.; Engineered glycoforms of an antineuroblastoma IgG1 with optimized antibodydependent cellular cytotoxic activity; Nat. Biotech.; 1999; 17:176-180.
Urlaub and Chasin; Isolation of Chinese hamster cell mutants deficient in dihydrofolate reductase activity; Proc. Natl. Acad. Sci. USA; 1980; 77:4216-4220.
Altschul et al., Gapped BLAST and PSI-BLAST: a new generation of protein database search programs; Nucleic Acids Res.; 1997; 25(17):3389-3402.
Baldari, et al.; A novel leader peptide which allows efficient secretion of a fragment of human interleukin 1 beta in *Saccharomyces cerevisiae*; EMBO J.; 1987; 6:229-234.
Byrne et al.; Multiplex gene regulation: A two-tiered approach to transgene regulation in transgenic mice; Proc. Natl. Acad. Sci. USA; 1989; 86:5473-5477.
Chen, J. et al.; B cell development in mice that lack one or both immunoglobulin κ light chain genes; EMBO J.; 1993; 12:821-830.
Clark et al; The Secreted Protein Discovery Initiative (SPDI), a Large-Scale Effort to Identify Novel Human Secreted and Transmembrane Proteins: A Bioinformatics Assessment;Genome Res.; 2003; 13: 2265-2270.
Coruzzi et al.; Tissue-specific and light-regulated expression of a pea nuclear gene encoding the small subunit of ribulose-1,5-bisphosphate carboxylase; EMBO J.; 1984; 3:1671-1680.
Karpovsky et al.; Production of Target-Specific Effector Cells Using Hetero-Cross-Linked Aggregates Containing Anti-Target Cell and Anti-Fc3, Receptor Antibodies; J. Exp. Med.; 1984; 160:1686-1701.
Kaufman, et al., Translational efficiency of polycistronic mRNAs and their utilization to express heterologous genes in mammalian cells; EMBO J.; 1987; 6:187-195.
Kwoh et al., Transcription-based amplification system and detection of amplified human immunodeficiency virus type 1 with a bead-based sandwich hybridization format; Proc. Natl. Acad. Sci. USA; 1989; 86:1173-1177.
Liu, M A et al.; Heteroantibody duplexes target cells for lysis by cytotoxic T lymphocytes; Proc. Natl. Acad. Sci. USA; 1985; 82:8648-8652.
Owais et al.; Chloroquine Encapsulated in Malaria-Infected Erythrocyte-Specific Antibody-Bearing Liposomes Effectively Controls Chloroquine-Resistant Plasmodium berghei Infections in Mice†; Antimicrob. Agents Chemother.; 1995; 39:180-184.
Pinkert et al., An albumin enhancer located 10 kb upstream functions along with its promoter to direct efficient, liver-specific expression in transgenic mice; Genes and Development; 1987; 1:268-277.

(56) References Cited

OTHER PUBLICATIONS

Queen, C. et al.; A humanized antibody that binds to the interleukin 2 receptor; Proc. Natl. Acad. See. U.S.A.; 1989 86:10029-10033.
Shields, R. L. et al.; Lack of Fucose on Human IgG1 N-Linked Oligosaccharide Improves Binding to Human Fc.GAMA.RIII and Antibody-dependent Cellular Toxicity; J. Biol. Chem.; 2002; 277:26733-26740.
Singhal et al.; Glutathione, a first line of defense against cadmium toxicity; FASEB J.; 1987; 1:220-223.
Smith, et al., Production of Human Beta Interferon in Insect Cells Infected with a Baculovirus Expression Vector; Mol. Cell. Biol.; 1983; 3:2156-2165.
Takamatsu et al.; Expression of bacterial chloramphenicol acetyltransferase gene in tobacco plants mediated by TMV-RNA; EMBO J.; 1987; 6:307-311.
Taylor, L. et al.; A transgenic mouse that expresses a diversity of human sequence heavy and light chain immunoglobulins; Nucleic Acids Research; 1992; 20:6287-6295.
Tomizuka et al.; Double trans-chromosomic mice: Maintenance of two individual human chromosome fragments containing Ig heavy and k loci and expression of fully human antibodies; Proc. Natl. Acad Sci. USA; 2000; 97:722-727.
Tuaillon et al.; Human immunoglobulin heavy-chain minilocus recombination in transgenic mice: Gene-segment use in ,u and y transcripts; Proc. Natl. Acad. Sci. USA; 1993; 90:3720-3724.
Winoto and Baltimore; A novel, inducible and T cell-specific enhancer located at the 3' end of the T cell receptor alpha locus; EMBO J.; 1989; 8:729-733.
Office Action for related IL 204255 mailed Jan. 30, 2013.
"Compugen Announces Positive Therapeutic Effects of CGEN 15001 in Aminal Model of Rheumatoid Arthritis", published Dec. 14, 2010, retrieved through the Internet, www.cgen.com.
Riches et al. 2009. Recent insights into the pathogenesis of hyperuricaemia and gout. Hum Mol Genet.; 18:R177-84.
Masseoud et al. 2005. Overview of hyperuricaemia and gout. Curr Pharm Des.; 11(32):4117-24.
Bencardino and Hassankhani. 2003. Calcium pyrophosphate dihydrate crystal deposition disease. Semin Musculoskelet Radiol.; 7(3):175-85.
Zaka R. and Williams C.J. 2005. Genetics of chondrocalcinosis. OsteoArthritis and Cartilage; 13, 745-750.
Langford CA. 2010. Vasculitis. J Allergy Clin Immunol; 125:S216-225.
Khasnis and Langford. 2009. Update on vasculitis. J Allergy Clin Immunol; 123:1226-36.
Miller et al. 2010. An approach to the diagnosis and management of systemic vasculitis. Clinical and Experimental Immunology, 160: 143-160.
Gonzalez et al. 2009. Pediatric Henoch-Schönlein purpura. International Journal of Dermatology; 48: 1157-1165.
Pillebout et al. 2002. Henoch-Schönlein Purpura in Adults: Outcome and Prognostic Factors. J Am Soc Nephrol.; 13:1271-1278.
Genta et al. 2006. Systemic rheumatoid vasculitis: a review. Semin Arthritis Rheum; 36:88-98.
Dlivencia-Simmons I. 2007. Wegener's granulomatosis: Symptoms, diagnosis, and treatment. J. of the American Academy of Nurse Practitioners 19:315-320.
Hua et al. 2009. T-Lymphocytes and Disease Mechanisms in Wegener's Granulomatosis. Kidney Blood Press Res; 32:389-398.
Moosig et al. 2008. Wegener's Granulomatosis: The Current View. Clinic Rev Allerg Immunol; 35:19-21.
Khan MA. 2002. Update on spondyloarthropathies. Ann Intern Med.; 136(12):896-907.
Rostom et al. 2010. New tools for diagnosing spondyloarthropathy. Joint Bone Spine; 77:108-114.
FitzGerald and McInnes. 2006. Spondyloarthropathy: disease at the crossroads of immunity. Best Practice & Research Clinical Rheumatology; 20(5): 949-967.
Brown, 2008. Breakthroughs in genetic studies of ankylosing spondylitis. Rheumatology, vol. 47(2): 132-137.

Brionez and Reveille. 2008. The contribution of genes outside the major histocompatibility complex to susceptibility to ankylosing spondylitis. Curr Opin Rheumatol.; 20(4):384-91.
Kwiatkowska B. and Filipowicz?Sosnowska A. 2009. Reactive arthritis. Pol Arch Med Wewn; 119 (1?2): 60-65.
Rohekar S. and Pope J. 2009. Epidemiologic approaches to infection and immunity: the case of reactive arthritis. Curr Opin Rheumatol.; 21(4)386-90.
Kim et al. 2009. Reactive arthritis: a review. J Adolesc Health; 44(4):309-15.
Gladman et al. 2005. Psoriatic arthritis: epidemiology, clinical features, course, and outcome. Ann Rheum Dis.; 64(Suppl 2): ii14-ii17.
Leung et al. 2007. Psoriatic arthritis as a distinct disease entity. J Postgrad Med.; 53(1):63-71.
Ho et al. 2008. Investigating the role of the HLA-Cw*06 and HLA-DRB1 genes in susceptibility to psoriatic arthritis: comparison with psoriasis and undifferentiated inflammatory arthritis. Ann Rheum Dis 67(5):677-682.
Wollheim FA. 2001. Enteropathic arthritis: how do the joints talk with the gut? Curr Opin Rheumatol; 13:305-309.
Colombo et al. 2009. Enteropathic spondyloarthropathy: a common genetic background with inflammatory bowel disease? World J Gastroenterol.; 15(20):2456-62.
Nade S. 2003. Septic arthritis. Best Practice & Research Clinical Rheumatology; 17(2): 183-200.
Mathews CJ. and Coakley G. 2008. Septic arthritis: current diagnostic and therapeutic algorithm. Current Opinion in Rheumatology; 20:457-462.
Tarkowski A. 2006. Infectious arthritis. Best Practice & Research Clinical Rheumatology; 20(6): 1029-1044.
Marques AR. 2010. Lyme disease: A Review. Curr Allergy Asthma Rep; 10:13-20.
Murray TS. and Shapiro ED. 2010. Lyme disease. Clin Lab Med.; 30(1):311-28.
Bratton et al. 2008. Diagnosis and treatment of Lyme disease. Mayo Clinic Proceedings; 83(5):566-571.
Iannuzzi et al. 2007. Sarcoidosis. N Engl J Med; 357:2153-2165.
Chen and Moller. 2008. Etiology of sarcoidosis. Clin Chest Med. ;29(3):365-77.
Ben-Chetrit and Touitou I. 2009. Familial Mediterranean fever in the world. Arthritis Rheum.; 61(10):1447-53.
Chae et al. 2009. Advances in the understanding of familial Mediterranean fever and possibilities for targeted therapy. Br J Haematol.; 146(5):467-78.
van der Hilst et al. 2008. Long-term follow-up, clinical features, and quality of life in a series of 103 patients with hyperimmunoglobulinemia D syndrome. Medicine; 87(6):301-310.
Simon et al. 2001. Molecular analysis of the mevalonate kinase gene in a cohort of patients with the hyper-IgD and periodic fever syndrome: its application as a diagnostic tool. Ann Intern Med.; 135:338-343.
Rezaei N. 2006. TNF-receptor-associated periodic syndrome (TRAPS): an autosomal dominant multisystem disorder. Clin Rheumatol.; 25(6):773-7.
Kimberley et al. 2007. Falling into TRAPS-receptor misfolding in the TNF receptor 1-associated periodic fever syndrome. Arthritis Research & Therapy; 9(4):217.
Hull et al. 2002. The TNF receptor-associated periodic syndrome (TRAPS): emerging concepts of an autoinflammatory disorder. Medicine (Baltimore); 81(5):349-368.
Mason and Reed. 2005. Update in Juvenile Rheumatoid Arthritis. Arthritis & Rheumatism.; 53 (5): 796-799.
Stastny and Fink. 1979. Different HLA-D associations in adult and juvenile rheumatoid arthritis. J. Clin. Invest.; 63:124-1303.
Thomson et al. 2002. Juvenile idiopathic arthritis classi?ed by the ILAR criteria: HLA associations in UK patients. Rheumatology; 41:1183-1189.
Woo P. 2006. Systemic juvenile idiopathic arthritis: Diagnosis, management, and outcome. Nat Clin Pract Rheumatol.;2:28-34.
Buckwalter and Martin. 2006. Osteoarthritis. Adv Drug Deliv Rev.; 20;58(2):150-67.

(56) References Cited

OTHER PUBLICATIONS

Brandt et al. 2009. Etiopathogenesis of osteoarthritis. Med Clin North Am.; 93(1):1-24.

Ayonrinde et al. 2008. Clinical perspectives on hereditary hemochromatosis. Critical Reviews in Clinical Laboratory Sciences; 45(5):451-484.

Brissot et al. 2008. Current approach to hemochromatosis. Blood Reviews; 22: 195-210.

Adams PC and Barton JC 2007. Haemochromatosis. Lancet; 370: 1855-1860.

Esserman, Laura J., et al. "Vaccination with the extracellular domain of p185 neu prevents mammary tumor development in neu transgenic mice." Cancer Immunology, Immunotherapy 476(1999): 337-342.

Pirker, Robert, et al. "Cetuximab plus chemotherapy in patients with advanced non-small-cell lung cancer (FLEX): an open-label randomised phase III trial." The Lancet 373.9674 (2009): 1525-1531.

Zhao, Jie, et al. "Selective depletion of CD4+ CD25+ Foxp3+ regulatory T cells by low-dose cyclophosphamide is explained by reduced intracellular ATP levels." Cancer research 70.12 (2010): 4850-4858.

\* cited by examiner

SEQUENCE LISTING

<160> NUMBER OF SEQ ID NOS: 103

<210> SEQ ID NO 1
<211> LENGTH: 254
<212> TYPE: PRT
<213> ORGANISM: Homo Sapiens

<400> SEQUENCE: 1

```
Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Val Ala
            20                  25                  30

Met Leu Phe Gln Pro Thr Val Leu Arg Cys His Phe Ser Thr Ser Ser
            35                  40                  45

His Gln Pro Ala Val Val Gln Trp Lys Phe Lys Ser Tyr Cys Gln Asp
        50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
                100                 105                 110
```

```
Leu Gly Asp Phe Tyr Arg Gly Arg Glu Ile Thr Ile Val His Asp Ala
            115                 120                 125

Asp Leu Gln Ile Gly Lys Leu Met Trp Gly Asp Ser Gly Leu Tyr Tyr
        130                 135                 140

Cys Ile Ile Thr Thr Pro Asp Asp Leu Glu Gly Lys Asn Glu Asp Ser
145                 150                 155                 160

Val Glu Leu Leu Val Leu Gly Arg Thr Gly Leu Leu Ala Asp Leu Leu
                165                 170                 175

Pro Ser Phe Ala Val Glu Ile Met Pro Glu Trp Val Phe Val Gly Leu
            180                 185                 190

Val Leu Leu Gly Val Phe Leu Phe Phe Val Leu Val Gly Ile Cys Trp
        195                 200                 205

Cys Gln Cys Cys Pro His Ser Cys Cys Cys Tyr Val Arg Cys Pro Cys
    210                 215                 220

Cys Pro Asp Ser Cys Cys Cys Pro Gln Ala Cys Glu Tyr Ser Asp Arg
225                 230                 235                 240

Trp Gly Asp Arg Ala Ile Glu Arg Asn Val Tyr Leu Ser Thr
                245                 250

<210> SEQ ID NO 2
<211> LENGTH: 19
<212> TYPE: PRT
<213> ORGANISM: Artificial Sequence
<220> FEATURE:
<223> OTHER INFORMATION: synthetic peptide

<400> SEQUENCE: 2

Thr Arg Ala Gln Ser Leu Ser Lys Arg Asn Leu Glu Trp Asp Pro Tyr
1               5                   10                  15

Leu Asp Cys

<210> SEQ ID NO 3
<211> LENGTH: 16
<212> TYPE: PRT
<213> ORGANISM: Artificial Sequence
<220> FEATURE:
<223> OTHER INFORMATION: synthetic peptide

<400> SEQUENCE: 3

Thr Thr Pro Asp Asp Leu Glu Gly Lys Asn Glu Asp Ser Val Glu Leu
1               5                   10                  15

<210> SEQ ID NO 4
<211> LENGTH: 428
<212> TYPE: PRT
<213> ORGANISM: Artificial Sequence
<220> FEATURE:
<223> OTHER INFORMATION: Fusion protein: human C1ORF32-ECD fused to
      mouse IgG2a Fc

<400> SEQUENCE: 4

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Lys Val Ala
                20                  25                  30

Met Leu Phe Gln Pro Thr Val Leu Arg Cys His Phe Ser Thr Ser Ser
            35                  40                  45

His Gln Pro Ala Val Val Gln Trp Lys Phe Lys Ser Tyr Cys Gln Asp
        50                  55                  60

Arg Met Gly Glu Ser Leu Gly Met Ser Ser Thr Arg Ala Gln Ser Leu
```

```
                65                  70                  75                  80
        Ser Lys Arg Asn Leu Glu Trp Asp Pro Tyr Leu Asp Cys Leu Asp Ser
                        85                  90                  95

Arg Arg Thr Val Arg Val Val Ala Ser Lys Gln Gly Ser Thr Val Thr
                        100                 105                 110

Leu Gly Asp Phe Tyr Arg Gly Arg Glu Ile Thr Ile Val His Asp Ala
                        115                 120                 125

Asp Leu Gln Ile Gly Lys Leu Met Trp Gly Asp Ser Gly Leu Tyr Tyr
                130                 135                 140

Cys Ile Ile Thr Thr Pro Asp Asp Leu Glu Gly Lys Asn Glu Asp Ser
        145                 150                 155                 160

Val Glu Leu Leu Val Leu Gly Arg Thr Gly Leu Leu Ala Asp Leu Leu
                        165                 170                 175

Pro Ser Phe Ala Val Glu Ile Met Gly Ser Glu Asn Leu Tyr Phe Gln
                        180                 185                 190

Gly Ser Gly Glu Pro Arg Gly Pro Thr Ile Lys Pro Cys Pro Pro Cys
                        195                 200                 205

Lys Cys Pro Ala Pro Asn Leu Leu Gly Gly Pro Ser Val Phe Ile Phe
                210                 215                 220

Pro Pro Lys Ile Lys Asp Val Leu Met Ile Ser Leu Ser Pro Ile Val
        225                 230                 235                 240

Thr Cys Val Val Val Asp Val Ser Glu Asp Asp Pro Asp Val Gln Ile
                        245                 250                 255

Ser Trp Phe Val Asn Asn Val Glu Val His Thr Ala Gln Thr Gln Thr
                        260                 265                 270

His Arg Glu Asp Tyr Asn Ser Thr Leu Arg Val Val Ser Ala Leu Pro
                        275                 280                 285

Ile Gln His Gln Asp Trp Met Ser Gly Lys Glu Phe Lys Cys Lys Val
                290                 295                 300

Asn Asn Lys Asp Leu Pro Ala Pro Ile Glu Arg Thr Ile Ser Lys Pro
        305                 310                 315                 320

Lys Gly Ser Val Arg Ala Pro Gln Val Tyr Val Leu Pro Pro Pro Glu
                        325                 330                 335

Glu Glu Met Thr Lys Lys Gln Val Thr Leu Thr Cys Met Val Thr Asp
                        340                 345                 350

Phe Met Pro Glu Asp Ile Tyr Val Glu Trp Thr Asn Asn Gly Lys Thr
                        355                 360                 365

Glu Leu Asn Tyr Lys Asn Thr Glu Pro Val Leu Asp Ser Asp Gly Ser
                370                 375                 380

Tyr Phe Met Tyr Ser Lys Leu Arg Val Glu Lys Lys Asn Trp Val Glu
        385                 390                 395                 400

Arg Asn Ser Tyr Ser Cys Ser Val Val His Glu Gly Leu His Asn His
                        405                 410                 415

His Thr Thr Lys Ser Phe Ser Arg Thr Pro Gly Lys
                        420                 425

<210> SEQ ID NO 5
<211> LENGTH: 23
<212> TYPE: PRT
<213> ORGANISM: Homo Sapiens

<400> SEQUENCE: 5

Gln Asp Arg Met Gly Glu Ser Leu Gly Met Ser Ser Thr Arg Ala Gln
1               5                   10                  15
```

Ser Leu Ser Lys Arg Asn Leu
            20

<210> SEQ ID NO 6
<211> LENGTH: 17
<212> TYPE: PRT
<213> ORGANISM: Artificial Sequence
<220> FEATURE:
<223> OTHER INFORMATION: Synthetic polypeptide: C-terminal Cystein added
      to human peptide

<400> SEQUENCE: 6

Thr Thr Pro Asp Asp Leu Glu Gly Lys Asn Glu Asp Ser Val Glu Leu
1               5                   10                  15

Cys

<210> SEQ ID NO 7
<211> LENGTH: 254
<212> TYPE: PRT
<213> ORGANISM: Homo Sapiens

<400> SEQUENCE: 7

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Val Ala
            20                  25                  30

Met Leu Phe Gln Pro Thr Val Leu Arg Cys His Phe Ser Thr Ser Ser
        35                  40                  45

His Gln Pro Ala Val Val Gln Trp Lys Phe Lys Ser Tyr Cys Gln Asp
    50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Ala Ser Lys Gln Gly Ser Thr Val Thr
            100                 105                 110

Leu Gly Asp Phe Tyr Arg Gly Arg Glu Ile Thr Ile Val His Asp Ala
        115                 120                 125

Asp Leu Gln Ile Gly Lys Leu Met Trp Gly Asp Ser Gly Leu Tyr Tyr
    130                 135                 140

Cys Ile Ile Thr Thr Pro Asp Asp Leu Glu Gly Lys Asn Glu Gly Ser
145                 150                 155                 160

Leu Gly Leu Leu Val Leu Gly Arg Thr Gly Leu Leu Ala Asp Leu Leu
                165                 170                 175

Pro Ser Phe Ala Val Glu Ile Met Pro Glu Trp Val Phe Val Gly Leu
            180                 185                 190

Val Leu Leu Gly Val Phe Leu Phe Phe Val Leu Val Gly Ile Cys Trp
        195                 200                 205

Cys Gln Cys Cys Pro His Ser Cys Cys Cys Tyr Val Arg Cys Pro Cys
    210                 215                 220

Cys Pro Asp Ser Cys Trp Cys Pro Gln Ala Cys Glu Tyr Ser Asp Arg
225                 230                 235                 240

Trp Gly Asp Arg Ala Ile Glu Arg Asn Val Tyr Leu Ser Thr
                245                 250

<210> SEQ ID NO 8
<211> LENGTH: 254
<212> TYPE: PRT

<213> ORGANISM: Artificial Sequence
<220> FEATURE:
<223> OTHER INFORMATION: Synthetic polypeptide: chimeric mouse-human C1ORF3

<400> SEQUENCE: 8

```
Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Lys Val Ala
                20                  25                  30

Met Leu Phe Gln Pro Thr Val Leu Arg Cys His Phe Ser Thr Ser Ser
            35                  40                  45

His Gln Pro Ala Val Val Gln Trp Lys Phe Lys Ser Tyr Cys Gln Asp
        50                  55                  60

Arg Met Gly Glu Ser Leu Gly Met Ser Ser Pro Arg Ala Gln Ala Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Ala Ser Lys Gln Gly Ser Thr Val Thr
            100                 105                 110

Leu Gly Asp Phe Tyr Arg Gly Arg Glu Ile Thr Ile Val His Asp Ala
        115                 120                 125

Asp Leu Gln Ile Gly Lys Leu Met Trp Gly Asp Ser Gly Leu Tyr Tyr
    130                 135                 140

Cys Ile Ile Thr Thr Pro Asp Asp Leu Glu Gly Lys Asn Glu Asp Ser
145                 150                 155                 160

Val Glu Leu Leu Val Leu Gly Arg Thr Gly Leu Leu Ala Asp Leu Leu
                165                 170                 175

Pro Ser Phe Ala Val Glu Ile Met Pro Glu Trp Val Phe Val Gly Leu
            180                 185                 190

Val Leu Leu Gly Val Phe Leu Phe Phe Val Leu Val Gly Ile Cys Trp
        195                 200                 205

Cys Gln Cys Cys Pro His Ser Cys Cys Cys Tyr Val Arg Cys Pro Cys
    210                 215                 220

Cys Pro Asp Ser Cys Cys Cys Pro Gln Ala Cys Glu Tyr Ser Asp Arg
225                 230                 235                 240

Trp Gly Asp Arg Ala Ile Glu Arg Asn Val Tyr Leu Ser Thr
                245                 250
```

<210> SEQ ID NO 9
<211> LENGTH: 235
<212> TYPE: PRT
<213> ORGANISM: Homo Sapiens

<400> SEQUENCE: 9

```
Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Lys Val Ala
                20                  25                  30

Met Leu Phe Gln Pro Thr Val Leu Arg Cys His Phe Ser Thr Ser Ser
            35                  40                  45

His Gln Pro Ala Val Val Gln Trp Lys Phe Lys Ser Tyr Cys Gln Asp
        50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
```

```
                     85                  90                  95
Arg Arg Thr Val Arg Val Ala Ser Lys Gln Gly Ser Thr Val Thr
                100                 105                 110
Leu Gly Asp Phe Tyr Arg Gly Arg Glu Ile Thr Ile Val His Asp Ala
            115                 120                 125
Asp Leu Gln Ile Gly Lys Leu Met Trp Gly Asp Ser Gly Leu Tyr Tyr
    130                 135                 140
Cys Ile Ile Thr Thr Pro Asp Asp Leu Glu Gly Lys Asn Glu Gly Ser
145                 150                 155                 160
Leu Gly Leu Leu Val Leu Glu Trp Val Phe Gly Leu Val Leu Leu
                165                 170                 175
Gly Val Phe Leu Phe Val Leu Val Gly Ile Cys Trp Cys Gln Cys
                180                 185                 190
Cys Pro His Ser Cys Cys Cys Tyr Val Arg Cys Pro Cys Cys Pro Asp
            195                 200                 205
Ser Cys Trp Cys Pro Gln Ala Cys Glu Tyr Ser Asp Arg Trp Gly Asp
    210                 215                 220
Arg Ala Ile Glu Arg Asn Val Tyr Leu Ser Thr
225                 230                 235

<210> SEQ ID NO 10
<211> LENGTH: 166
<212> TYPE: PRT
<213> ORGANISM: Homo Sapiens

<400> SEQUENCE: 10

Leu Gln Val Thr Val Pro Asp Lys Lys Lys Val Ala Met Leu Phe Gln
1               5                   10                  15
Pro Thr Val Leu Arg Cys His Phe Ser Thr Ser Ser His Gln Pro Ala
                20                  25                  30
Val Val Gln Trp Lys Phe Lys Ser Tyr Cys Gln Asp Arg Met Gly Glu
            35                  40                  45
Ser Leu Gly Met Ser Ser Thr Arg Ala Gln Ser Leu Ser Lys Arg Asn
    50                  55                  60
Leu Glu Trp Asp Pro Tyr Leu Asp Cys Leu Asp Ser Arg Arg Thr Val
65                  70                  75                  80
Arg Val Val Ala Ser Lys Gln Gly Ser Thr Val Thr Leu Gly Asp Phe
                85                  90                  95
Tyr Arg Gly Arg Glu Ile Thr Ile Val His Asp Ala Asp Leu Gln Ile
                100                 105                 110
Gly Lys Leu Met Trp Gly Asp Ser Gly Leu Tyr Tyr Cys Ile Ile Thr
            115                 120                 125
Thr Pro Asp Asp Leu Glu Gly Lys Asn Glu Gly Ser Leu Gly Leu Leu
    130                 135                 140
Val Leu Gly Arg Thr Gly Leu Leu Ala Asp Leu Leu Pro Ser Phe Ala
145                 150                 155                 160
Val Glu Ile Met Pro Glu
                165

<210> SEQ ID NO 11
<211> LENGTH: 149
<212> TYPE: PRT
<213> ORGANISM: Homo Sapiens

<400> SEQUENCE: 11

Leu Gln Val Thr Val Pro Asp Lys Lys Lys Val Ala Met Leu Phe Gln
```

```
            1               5                  10                 15
          Pro Thr Val Leu Arg Cys His Phe Ser Thr Ser Ser His Gln Pro Ala
                          20                 25                 30

Val Val Gln Trp Lys Phe Lys Ser Tyr Cys Gln Asp Arg Met Gly Glu
                          35                 40                 45

Ser Leu Gly Met Ser Ser Thr Arg Ala Gln Ser Leu Ser Lys Arg Asn
                  50                 55                 60

Leu Glu Trp Asp Pro Tyr Leu Asp Cys Leu Asp Ser Arg Arg Thr Val
          65                  70                 75                 80

Arg Val Val Ala Ser Lys Gln Gly Ser Thr Val Thr Leu Gly Asp Phe
                          85                 90                 95

Tyr Arg Gly Arg Glu Ile Thr Ile Val His Asp Ala Asp Leu Gln Ile
                          100                105                110

Gly Lys Leu Met Trp Gly Asp Ser Gly Leu Tyr Tyr Cys Ile Ile Thr
                          115                120                125

Thr Pro Asp Asp Leu Glu Gly Lys Asn Glu Gly Ser Leu Gly Leu Leu
                          130                135                140

Val Leu Glu Trp Val
          145

<210> SEQ ID NO 12
<211> LENGTH: 233
<212> TYPE: PRT
<213> ORGANISM: Artificial Sequence
<220> FEATURE:
<223> OTHER INFORMATION: Synthetic polypeptide: CH2 and CH3 regions of
      murine IgG2a

<400> SEQUENCE: 12

Glu Pro Arg Gly Pro Thr Ile Lys Pro Cys Pro Pro Cys Lys Cys Pro
          1               5                  10                 15

Ala Pro Asn Leu Leu Gly Gly Pro Ser Val Phe Ile Phe Pro Pro Lys
                          20                 25                 30

Ile Lys Asp Val Leu Met Ile Ser Leu Ser Pro Ile Val Thr Cys Val
                          35                 40                 45

Val Val Asp Val Ser Glu Asp Asp Pro Asp Val Gln Ile Ser Trp Phe
                  50                 55                 60

Val Asn Asn Val Glu Val His Thr Ala Gln Thr Gln Thr His Arg Glu
          65                  70                 75                 80

Asp Tyr Asn Ser Thr Leu Arg Val Val Ser Ala Leu Pro Ile Gln His
                          85                 90                 95

Gln Asp Trp Met Ser Gly Lys Glu Phe Lys Cys Lys Val Asn Asn Lys
                          100                105                110

Asp Leu Pro Ala Pro Ile Glu Arg Thr Ile Ser Lys Pro Lys Gly Ser
                          115                120                125

Val Arg Ala Pro Gln Val Tyr Val Leu Pro Pro Pro Glu Glu Glu Met
                          130                135                140

Thr Lys Lys Gln Val Thr Leu Thr Cys Met Val Thr Asp Phe Met Pro
          145                 150                155                160

Glu Asp Ile Tyr Val Glu Trp Thr Asn Asn Gly Lys Thr Glu Leu Asn
                          165                170                175

Tyr Lys Asn Thr Glu Pro Val Leu Asp Ser Asp Gly Ser Tyr Phe Met
                          180                185                190

Tyr Ser Lys Leu Arg Val Glu Lys Lys Asn Trp Val Glu Arg Asn Ser
                          195                200                205
```

```
Tyr Ser Cys Ser Val Val His Glu Gly Leu His Asn His His Thr Thr
    210                 215                 220
Lys Ser Phe Ser Arg Thr Pro Gly Lys
225                 230
```

<210> SEQ ID NO 13
<211> LENGTH: 235
<212> TYPE: PRT
<213> ORGANISM: Homo Sapiens

<400> SEQUENCE: 13

```
Met Asp Arg Val Leu Leu Arg Trp Ile Ser Leu Phe Trp Leu Thr Ala
1               5                   10                  15
Met Val Glu Gly Leu Gln Val Thr Val Pro Asp Lys Lys Lys Val Ala
            20                  25                  30
Met Leu Phe Gln Pro Thr Val Leu Arg Cys His Phe Ser Thr Ser Ser
        35                  40                  45
His Gln Pro Ala Val Val Gln Trp Lys Phe Lys Ser Tyr Cys Gln Asp
    50                  55                  60
Arg Met Gly Glu Ser Leu Gly Met Ser Ser Thr Arg Ala Gln Ser Leu
65                  70                  75                  80
Ser Lys Arg Asn Leu Glu Trp Asp Pro Tyr Leu Asp Cys Leu Asp Ser
                85                  90                  95
Arg Arg Thr Val Arg Val Ala Ser Lys Gln Gly Ser Thr Val Thr
            100                 105                 110
Leu Gly Asp Phe Tyr Arg Gly Arg Glu Ile Thr Ile Val His Asp Ala
        115                 120                 125
Asp Leu Gln Ile Gly Lys Leu Met Trp Gly Asp Ser Gly Leu Tyr Tyr
    130                 135                 140
Cys Ile Ile Thr Thr Pro Asp Asp Leu Glu Gly Lys Asn Glu Asp Ser
145                 150                 155                 160
Val Glu Leu Leu Val Leu Glu Trp Val Phe Val Gly Leu Val Leu Leu
                165                 170                 175
Gly Val Phe Leu Phe Phe Val Leu Val Gly Ile Cys Trp Cys Gln Cys
            180                 185                 190
Cys Pro His Ser Cys Cys Cys Tyr Val Arg Cys Pro Cys Cys Pro Asp
        195                 200                 205
Ser Cys Cys Cys Pro Gln Ala Cys Glu Tyr Ser Asp Arg Trp Gly Asp
    210                 215                 220
Arg Ala Ile Glu Arg Asn Val Tyr Leu Ser Thr
225                 230                 235
```

<210> SEQ ID NO 14
<211> LENGTH: 166
<212> TYPE: PRT
<213> ORGANISM: Homo Sapiens

<400> SEQUENCE: 14

```
Leu Gln Val Thr Val Pro Asp Lys Lys Lys Val Ala Met Leu Phe Gln
1               5                   10                  15
Pro Thr Val Leu Arg Cys His Phe Ser Thr Ser Ser His Gln Pro Ala
            20                  25                  30
Val Val Gln Trp Lys Phe Lys Ser Tyr Cys Gln Asp Arg Met Gly Glu
        35                  40                  45
Ser Leu Gly Met Ser Ser Thr Arg Ala Gln Ser Leu Ser Lys Arg Asn
    50                  55                  60
```

```
Leu Glu Trp Asp Pro Tyr Leu Asp Cys Leu Asp Ser Arg Arg Thr Val
 65                  70                  75                  80

Arg Val Val Ala Ser Lys Gln Gly Ser Thr Val Thr Leu Gly Asp Phe
                 85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Gly Arg Thr Gly Leu Leu Ala Asp Leu Leu Pro Ser Phe Ala
145                 150                 155                 160

Val Glu Ile Met Pro Glu
                165

<210> SEQ ID NO 15
<211> LENGTH: 149
<212> TYPE: PRT
<213> ORGANISM: Homo Sapiens

<400> SEQUENCE: 15

Leu Gln Val Thr Val Pro Asp Lys Lys Lys Val Ala Met Leu Phe Gln
 1               5                  10                  15

Pro Thr Val Leu Arg Cys His Phe Ser Thr Ser Ser His Gln Pro Ala
             20                  25                  30

Val Val Gln Trp Lys Phe Lys Ser Tyr Cys Gln Asp Arg Met Gly Glu
         35                  40                  45

Ser Leu Gly Met Ser Ser Thr Arg Ala Gln Ser Leu Ser Lys Arg Asn
 50                  55                  60

Leu Glu Trp Asp Pro Tyr Leu Asp Cys Leu Asp Ser Arg Arg Thr Val
 65                  70                  75                  80

Arg Val Val Ala Ser Lys Gln Gly Ser Thr Val Thr Leu Gly Asp Phe
                 85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Glu Trp Val
145

<210> SEQ ID NO 16
<211> LENGTH: 5903
<212> TYPE: DNA
<213> ORGANISM: Homo Sapiens

<400> SEQUENCE: 16
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
```

```
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttggtacc    900
gagctcggat cgatatctgc ggcctagcta gccaccatgg ataggtctt gctgaggtgg    960
atttctctct tctggctaac agccatggtc gaaggccttc aggtcacagt gcccgacaag   1020
aagaaggtgg ccatgctctt ccagcccact gtgcttcgct gccacttctc aacatcctcc   1080
catcagcctg cagttgtgca gtggaagttc aagtcctact gccaggatcg catgggagaa   1140
tccttgggca tgtcctctac ccgggcccaa tctctcagca agagaaacct ggaatgggac   1200
ccctacttgg attgtttgga cagcaggagg actgttcgag tagtagcttc aaaacagggc   1260
tcgactgtca ccctgggaga tttctacagg ggcagagaga tcacgattgt tcatgatgca   1320
gatcttcaaa ttgaaagct tatgtgggga dacagcggac tctattactg tattatcacc   1380
accccagatg acctggaggg gaaaaatgag gactcagtgg aactgctggt gttgggcagg   1440
acagggctgc ttgctgatct cttgcccagt tttgctgtgg agattatgcc agagtgggtg   1500
tttgttggcc tggtgctcct gggcgtcttc ctcttcttcg tcctggtggg gatctgctgg   1560
tgccagtgct gccctcacag ctgctgctgc tatgtccgct gcccatgctg cccagattcc   1620
tgctgctgcc ctcaagcctg tgagtacagt gaccgctggg gagacagagc gatcgagaga   1680
aatgtctacc tctctacctg agaattcgga tccgcggccg catagataac tgatccagtg   1740
tgctggaatt aattcgctgt ctgcgagggc cagctgttgg ggtgagtact ccctctcaaa   1800
agcgggcatg acttctgcgc taagattgtc agttttccaaa aacgaggagg atttgatatt   1860
cacctggccc gcggtgatgc cttgagggt ggccgcgtcc atctggtcag aaaagacaat   1920
ctttttgttg tcaagcttga ggtgtggcag gcttgagatc tggccataca cttgagtgac   1980
aatgacatcc actttgcctt tctctccaca ggtgtccact cccaggtcca actgcaggtc   2040
gagcatgcat ctagggcggc caattccgcc cctctccccc cccccctct ccctccccc    2100
cccmtaacgt tactggccga agccgcttgg aataaggccg gtgtgcgttt gtctatatgt   2160
tattttccac catattgccg tcttttggca atgtgagggc ccggaaacct ggccctgtct   2220
tcttgacgag cattcctagg ggtctttccc ctctcgccaa aggaatgcaa ggtctgttga   2280
atgtcgtgaa ggaagcagtt cctctggaag cttcttgaag acaaacaacg tctgtagcga   2340
cccctttgcag gcagcggaac cccccacctg gcgacaggtg cctctgcggc caaaagccac   2400
gtgtataaga tacacctgca aaggcggcac aaccccagtg ccacgttgtg agttggatag   2460
ttgtggaaag agtcaaatgg ctctcctcaa gcgtattcaa caaggggctg aaggatgccc   2520
agaaggtacc ccattgtatg ggatctgatc tggggcctcg gtgcacatgc tttacatgtg   2580
tttagtcgag gttaaaaaaa cgtctaggcc ccccgaacca cggggacgtg gttttccttt   2640
gaaaaacacg atgataagct tgccacaacc cacaaggaga cgaccttcca tgaccgagta   2700
caagcccacg gtgcgcctcg ccacccgcga cgacgtcccc cgggccgtac gcaccctcgc   2760
```

```
cgccgcgttc gccgactacc ccgccacgcg ccacaccgtc gacccggacc gccacatcga   2820
gcgggtcacc gagctgcaag aactcttcct cacgcgcgtc gggctcgaca tcggcaaggt   2880
gtgggtcgcg gacgacggcg ccgcggtggc ggtctggacc acgccggaga gcgtcgaagc   2940
gggggcggtg ttcgccgaga tcggcccgcg catggccgag ttgagcggtt cccggctggc   3000
cgcgcagcaa cagatggaag gcctcctggc gccgcaccgg cccaaggagc cgcgtggtt    3060 cctggccacc gtcggcgtct cgcccgacca ccagggcaag ggtctgggca cgccgtcgt    3120 gctccccgga gtggaggcgg ccgagcgcgc cggggtgccc gccttcctgg agacctccgc   3180
gccccgcaac ctccccttct acgagcggct cggcttcacc gtcaccgccg acgtcgaggt   3240
gcccgaagga ccgcgcacct ggtgcatgac ccgcaagccc ggtgcctgac gcccgcccca   3300
cgacccgcag cgcccgaccg aaaggagcgc acgaccccat ggctccgacc gaagccaccc   3360
ggggcggccc cgccgacccc gcacccgccc ccgaggccca ccgactctag ataactgatc   3420
ataatcagcc ataccacatt tgtagaggtt ttacttgctt taaaaaacct cccacacctc   3480
cccctgaacc tgaaacataa aatgaatgca attgttgttg ttaacttgtt tattgcagct   3540
tataatggtt acaaataaag caatagcatc acaaatttca caaataaagc attttttca    3600 ctgcattcta gttgtggttt gtccaaactc atcaatgtat cttaacgctc gagtgcattc   3660
tagttgtggt ttgtccaaac tcatcaatgt atcttatcat gtctgtatac cgtcgacctc   3720
tagctagagc ttggcgtaat catggtcata gctgtttcct gtgtgaaatt gttatccgct   3780
cacaattcca cacaacatac gagccggaag cataaagtgt aaagcctggg gtgcctaatg   3840
agtgagctaa ctcacattaa ttgcgttgcg ctcactgccc gctttccagt cgggaaacct   3900
gtcgtgccag ctgcattaat gaatcggcc aacgcgcggg gagaggcggt ttgcgtattg    3960
ggcgctcttc cgcttcctcg ctcactgact cgctgcgctc ggtcgttcgg ctgcggcgag   4020
cggtatcagc tcactcaaag gcggtaatac ggttatccac agaatcaggg gataacgcag   4080
gaaagaacat gtgagcaaaa ggccagcaaa aggccaggaa ccgtaaaaag gccgcgttgc   4140
tggcgttttt ccataggctc cgcccccctg acgagcatca aaaaatcga cgctcaagtc   4200 agaggtggcg aaacccgaca ggactataaa gataccaggc gtttccccct ggaagctccc   4260
tcgtgcgctc tcctgttccg accctgccgc ttaccggata cctgtccgcc tttctccctt   4320
cgggaagcgt ggcgctttct caatgctcac gctgtaggta tctcagttcg gtgtaggtcg   4380
ttcgctccaa gctgggctgt gtgcacgaac cccccgttca gcccgaccgc tgcgccttat   4440
ccggtaacta tcgtcttgag tccaacccgg taagacacga cttatcgcca ctggcagcag   4500
ccactggtaa caggattagc agagcgaggt atgtaggcgg tgctacagag ttcttgaagt   4560
ggtggcctaa ctacggctac actagaagga cagtatttgg tatctgcgct ctgctgaagc   4620
cagttacctt cggaaaaaga gttggtagct cttgatccgg caaacaaacc accgctggta   4680
gcggtggttt ttttgtttgc aagcagcaga ttacgcgcag aaaaaaagga tctcaagaag   4740
atcctttgat cttttctacg gggtctgacg ctcagtggaa cgaaaactca cgttaaggga   4800
ttttggtcat gagattatca aaaaggatct tcacctagat ccttttaaat taaaaatgaa   4860
gttttaaatc aatctaaagt atatatgagt aaacttggtc tgacagttac caatgcttaa   4920
tcagtgaggc acctatctca gcgatctgtc tatttcgttc atccatagtt gcctgactcc   4980
ccgtcgtgta gataactacg atacgggagg gcttaccatc tggccccagt gctgcaatga   5040
taccgcgaga cccacgctca ccggctccag atttatcagc aataaaccag ccagccgaa    5100
```

```
gggccgagcg cagaagtggt cctgcaactt tatccgcctc catccagtct attaattgtt    5160
gccgggaagc tagagtaagt agttcgccag ttaatagttt gcgcaacgtt gttgccattg    5220
ctacaggcat cgtggtgtca cgctcgtcgt ttggtatggc ttcattcagc tccggttccc    5280
aacgatcaag gcgagttaca tgatccccca tgttgtgcaa aaagcggtt agctccttcg     5340
gtcctccgat cgttgtcaga agtaagttgg ccgcagtgtt atcactcatg gttatggcag    5400
cactgcataa ttctcttact gtcatgccat ccgtaagatg cttttctgtg actggtgagt    5460
actcaaccaa gtcattctga aatagtgta tgcggcgacc gagttgctct tgcccggcgt     5520
caatacggga taataccgcg ccacatagca aactttaaa agtgctcatc attggaaaac     5580
gttcttcggg gcgaaaactc tcaaggatct taccgctgtt gagatccagt tcgatgtaac    5640
ccactcgtgc acccaactga tcttcagcat ctttactt caccagcgtt tctgggtgag     5700
caaaaacagg aaggcaaaat gccgcaaaaa agggaataag ggcgacacgg aaatgttgaa    5760
tactcatact cttccttttt caatattatt gaagcattta tcagggttat tgtctcatga    5820
gcggatacat atttgaatgt atttagaaaa ataaacaaat aggggttccg cgcacatttc    5880
cccgaaaagt gccacctgac gtc                                            5903
```

<210> SEQ ID NO 17
<211> LENGTH: 639
<212> TYPE: PRT
<213> ORGANISM: Homo Sapiens

<400> SEQUENCE: 17

```
Met Asp Arg Val Leu Leu Arg Trp Ile Ser Leu Phe Trp Leu Thr Ala
1               5                  10                  15

Met Val Glu Gly Leu Gln Val Thr Val Pro Asp Lys Lys Val Ala
            20                  25                  30

Met Leu Phe Gln Pro Thr Val Leu Arg Cys His Phe Ser Thr Ser Ser
        35                  40                  45

His Gln Pro Ala Val Val Gln Trp Lys Phe Lys Ser Tyr Cys Gln Asp
    50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Ala Ser Lys Gln Gly Ser Thr Val Thr
            100                 105                 110

Leu Gly Asp Phe Tyr Arg Gly Arg Glu Ile Thr Ile Val His Asp Ala
        115                 120                 125

Asp Leu Gln Ile Gly Lys Leu Met Trp Gly Asp Ser Gly Leu Tyr Tyr
    130                 135                 140

Cys Ile Ile Thr Thr Pro Asp Asp Leu Glu Gly Lys Asn Glu Asp Ser
145                 150                 155                 160

Val Glu Leu Leu Val Leu Gly Arg Thr Gly Leu Leu Ala Asp Leu Leu
                165                 170                 175

Pro Ser Phe Ala Val Glu Ile Met Pro Glu Trp Val Phe Val Gly Leu
            180                 185                 190

Val Leu Gly Val Phe Leu Phe Phe Val Leu Val Gly Ile Cys Trp
        195                 200                 205

Cys Gln Cys Cys Pro His Ser Cys Cys Cys Tyr Val Arg Cys Pro Cys
    210                 215                 220

Cys Pro Asp Ser Cys Cys Cys Pro Gln Ala Leu Tyr Glu Ala Gly Lys
```

```
              225                 230                 235                 240
         Ala Ala Lys Ala Gly Tyr Pro Pro Ser Val Ser Gly Val Pro Gly Pro
                         245                 250                 255
         Tyr Ser Ile Pro Ser Val Pro Leu Gly Gly Ala Pro Ser Ser Gly Met
                         260                 265                 270
         Leu Met Asp Lys Pro His Pro Pro Leu Ala Pro Ser Asp Ser Thr
                         275                 280                 285
         Gly Gly Ser His Ser Val Arg Lys Gly Tyr Arg Ile Gln Ala Asp Lys
                         290                 295                 300
         Glu Arg Asp Ser Met Lys Val Leu Tyr Val Glu Lys Glu Leu Ala
         305                 310                 315                 320
         Gln Phe Asp Pro Ala Arg Arg Met Arg Gly Arg Tyr Asn Asn Thr Ile
                         325                 330                 335
         Ser Glu Leu Ser Ser Leu His Glu Glu Asp Ser Asn Phe Arg Gln Ser
                         340                 345                 350
         Phe His Gln Met Arg Ser Lys Gln Phe Pro Val Ser Gly Asp Leu Glu
                         355                 360                 365
         Ser Asn Pro Asp Tyr Trp Ser Val Met Gly Ser Ser Gly Ala
                         370                 375                 380
         Ser Arg Gly Pro Ser Ala Met Glu Tyr Asn Lys Glu Asp Arg Glu Ser
         385                 390                 395                 400
         Phe Arg His Ser Gln Pro Arg Ser Lys Ser Glu Met Leu Ser Arg Lys
                         405                 410                 415
         Asn Phe Ala Thr Gly Val Pro Ala Val Ser Met Asp Glu Leu Ala Ala
                         420                 425                 430
         Phe Ala Asp Ser Tyr Gly Gln Arg Pro Arg Arg Ala Asp Gly Asn Ser
                         435                 440                 445
         His Glu Ala Arg Gly Gly Ser Arg Phe Glu Arg Ser Gly Ser Arg Ala
                         450                 455                 460
         His Ser Gly Phe Tyr Gln Asp Asp Ser Leu Glu Glu Tyr Tyr Gly Gln
         465                 470                 475                 480
         Arg Ser Arg Ser Arg Glu Pro Leu Thr Asp Ala Asp Arg Gly Trp Ala
                         485                 490                 495
         Phe Ser Pro Ala Arg Arg Pro Ala Glu Asp Ala His Leu Pro Arg
                         500                 505                 510
         Leu Val Ser Arg Thr Pro Gly Thr Ala Pro Lys Tyr Asp His Ser Tyr
                         515                 520                 525
         Leu Gly Ser Ala Arg Glu Arg Gln Ala Arg Pro Glu Gly Ala Ser Arg
                         530                 535                 540
         Gly Gly Ser Leu Glu Thr Pro Ser Lys Arg Ser Ala Gln Leu Gly Pro
         545                 550                 555                 560
         Arg Ser Ala Ser Tyr Tyr Ala Trp Ser Pro Gly Thr Tyr Lys Ala
                         565                 570                 575
         Gly Ser Ser Gln Asp Asp Gln Glu Asp Ala Ser Asp Ala Leu Pro
                         580                 585                 590
         Pro Tyr Ser Glu Leu Glu Leu Thr Arg Gly Pro Ser Tyr Arg Gly Arg
                         595                 600                 605
         Asp Leu Pro Tyr His Ser Asn Ser Glu Lys Lys Arg Lys Lys Glu Pro
         610                 615                 620
         Ala Lys Lys Thr Asn Asp Phe Pro Thr Arg Met Ser Leu Val Val
                         625                 630                 635

<210> SEQ ID NO 18
```

<211> LENGTH: 408
<212> TYPE: PRT
<213> ORGANISM: Artificial Sequence
<220> FEATURE:
<223> OTHER INFORMATION: Fusion protein: human C1ORF32-ECD fused to
      mouse IgG2a Fc

<400> SEQUENCE: 18

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Gly Arg Thr Gly Leu Leu Ala Asp Leu Leu Pro Ser Phe Ala
145                 150                 155                 160

Val Glu Ile Met Gly Ser Glu Asn Leu Tyr Phe Gln Gly Ser Gly Glu
                165                 170                 175

Pro Arg Gly Pro Thr Ile Lys Pro Cys Pro Pro Cys Lys Cys Pro Ala
            180                 185                 190

Pro Asn Leu Leu Gly Gly Pro Ser Val Phe Ile Phe Pro Pro Lys Ile
        195                 200                 205

Lys Asp Val Leu Met Ile Ser Leu Ser Pro Ile Val Thr Cys Val Val
    210                 215                 220

Val Asp Val Ser Glu Asp Asp Pro Asp Val Gln Ile Ser Trp Phe Val
225                 230                 235                 240

Asn Asn Val Glu Val His Thr Ala Gln Thr Gln Thr His Arg Glu Asp
                245                 250                 255

Tyr Asn Ser Thr Leu Arg Val Val Ser Ala Leu Pro Ile Gln His Gln
            260                 265                 270

Asp Trp Met Ser Gly Lys Glu Phe Lys Cys Lys Val Asn Asn Lys Asp
        275                 280                 285

Leu Pro Ala Pro Ile Glu Arg Thr Ile Ser Lys Pro Lys Gly Ser Val
    290                 295                 300

Arg Ala Pro Gln Val Tyr Val Leu Pro Pro Glu Glu Glu Met Thr
305                 310                 315                 320

Lys Lys Gln Val Thr Leu Thr Cys Met Val Thr Asp Phe Met Pro Glu
                325                 330                 335

Asp Ile Tyr Val Glu Trp Thr Asn Asn Gly Lys Thr Glu Leu Asn Tyr
            340                 345                 350

Lys Asn Thr Glu Pro Val Leu Asp Ser Asp Gly Ser Tyr Phe Met Tyr
        355                 360                 365

Ser Lys Leu Arg Val Glu Lys Lys Asn Trp Val Glu Arg Asn Ser Tyr

```
                    370                375                380
Ser Cys Ser Val Val His Glu Gly Leu His Asn His His Thr Thr Lys
385                390                395                400

Ser Phe Ser Arg Thr Pro Gly Lys
                405
```

<210> SEQ ID NO 19
<211> LENGTH: 1920
<212> TYPE: DNA
<213> ORGANISM: Homo Sapiens

<400> SEQUENCE: 19

| | | | | | |
|---|---|---|---|---|---|
| atggataggg | tcttgctgag | gtggatttct | ctcttctggc | taacagccat | ggtcgaaggc | 60 |
| cttcaggtca | cagtgcccga | caagaagaag | gtggccatgc | tcttccagcc | cactgtgctt | 120 |
| cgctgccact | tctcaacatc | ctcccatcag | cctgcagttg | tgcagtggaa | gttcaagtcc | 180 |
| tactgccagg | atcgcatggg | agaatccttg | ggcatgtcct | ctacccgggc | ccaatctctc | 240 |
| agcaagagaa | acctggaatg | gaccccctac | ttggattgtt | tggacagcag | gaggactgtt | 300 |
| cgagtagtag | cttcaaaaca | gggctcgact | gtcaccctgg | agatttcta | caggggcaga | 360 |
| gagatcacga | ttgttcatga | tgcagatctt | caaattggaa | agcttatgtg | gggagacagc | 420 |
| ggactctatt | actgtattat | caccacccca | gatgacctgg | aggggaaaaa | tgaggactca | 480 |
| gtggaactgc | tggtgtttgg | gaggacaggg | ctgcttgctg | atctcttgcc | cagttttgct | 540 |
| gtggagatta | tgccagagtg | ggtgtttgtt | ggcctggtgc | tcctgggcgt | cttcctcttc | 600 |
| ttcgtcctgg | tggggatctg | ctggtgccag | tgctgccctc | acagctgctg | ctgctatgtc | 660 |
| cgctgcccat | gctgcccaga | ttcctgctgc | tgccctcaag | ccttgtatga | agcagggaaa | 720 |
| gcagcaaagg | ccgggtaccc | tcctctgtc | tccggtgtcc | ccggccctta | ctccatcccc | 780 |
| tctgtccctt | tgggaggagc | cccctcatct | ggcatgctga | tggacaagcc | gcatccacct | 840 |
| cccttggcac | caagtgactc | cactggagga | agccacagtg | ttcgcaaagg | ttaccggatc | 900 |
| caggctgaca | agagagaga | ctccatgaag | gtcctgtact | atgttgagaa | ggagctggct | 960 |
| cagtttgatc | cagccagaag | gatgagaggc | agatataaca | caccatctc | agaactcagc | 1020 |
| tccctacatg | aggaggacag | caatttccgc | cagtcttttc | catcagatgag | aagcaagcag | 1080 |
| ttccctgtgt | ctggggactt | ggagagcaat | cctgactatt | ggtcaggtgt | catgggaggc | 1140 |
| agcagtgggg | caagccgcgg | gccctcagcc | atggagtata | caaagagga | tcgagagagc | 1200 |
| ttcaggcaca | gccagccgcg | ctccaagtcg | gagatgctgt | cgcggaagaa | cttcgccacg | 1260 |
| ggggtgccgg | ccgtttccat | ggacgagctg | gcggccttcg | ctgactccta | cggccagcgg | 1320 |
| ccccgccggg | cagacggcaa | cagtcacgag | gcgcggggcg | ggagccgctt | cgagcgctcg | 1380 |
| gagtcgcggg | cgcacagcgg | cttctaccag | gacgactcct | ggaggagta | ctacggtcag | 1440 |
| cgcagccgca | gccgcgagcc | cctgaccgat | gctgaccgcg | gctgggcctt | cagccccgcg | 1500 |
| cgccgcagac | cgccgagga | cgcgcacctg | ccgcggctgg | tgagccgcac | gccaggcacc | 1560 |
| gcacccaaat | acgaccactc | gtacctgggc | agcgcgcggg | agcgccaggc | gcggcccgag | 1620 |
| ggcgccagcc | gcgtggcag | cctggagacg | ccatccaagc | ggagcgcgca | gctcggcccg | 1680 |
| cgcagcgcct | cctactacgc | ttggtcgccg | cccggcacct | acaaggccgg | ctcgtcgcag | 1740 |
| gacgaccagg | aggacgcgtc | cgacgacgcg | ctgccgccct | acagcgagct | ggagctgacc | 1800 |
| cgcggccgt | cctaccgcgg | ccgcgacctg | ccctaccaca | gcaactcgga | gaagaagagg | 1860 |
| aaaaggagc | ccgccaagaa | aaccaatgac | tttccaacca | ggatgtccct | tgtggtctga | 1920 |

<210> SEQ ID NO 20
<211> LENGTH: 765
<212> TYPE: DNA
<213> ORGANISM: Artificial Sequence
<220> FEATURE:
<223> OTHER INFORMATION: synthetic polynucleotide: mouse-C1ORF32-Flag

<400> SEQUENCE: 20

```
atggataggg tcttgctgag gtggatttct ctcttctggc taacagccat ggtcgaaggc    60
cttcaggtca cagtgcccga caagaagaag gtggccatgc tcttccagcc cactgtgctt   120
cgctgccact ctcaacatc ctcccatcag cctgcagttg tgcagtggaa gttcaagtcc   180
tactgccagg atcgcatggg agaatccttg gcatgtcct ctacccgggc ccaatctctc   240
agcaagagaa acctggaatg gaccccctac ttggattgtt tggacagcag gaggactgtt   300
cgagtagtag cttcaaaaca gggctcgact gtcaccctgg agatttcta caggggcaga   360
gagatcacga ttgttcatga tgcagatctt caaattggaa agcttatgtg gggagacagc   420
ggactctatt actgtattat caccacccca gatgacctgg aggggaaaaa tgaggactca   480
gtggaactgc tggtgttggg caggacaggg ctgcttgctg atctcttgcc cagttttgct   540
gtggagatta tgccagagtg ggtgtttgtt ggcctggtgc tcctgggcgt cttcctcttc   600
ttcgtcctgg tggggatctg ctggtgccag tgctgccctc acagctgctg ctgctatgtc   660
cgctgcccat gctgcccaga ttcctgctgc tgccctcaag cctgtgagta cagtgaccgc   720
tggggagaca gagcgatcga gagaaatgtc tacctctcta cctga                  765
```

<210> SEQ ID NO 21
<211> LENGTH: 669
<212> TYPE: PRT
<213> ORGANISM: Artificial Sequence
<220> FEATURE:
<223> OTHER INFORMATION: synthetic polypeptide: mouse-C1ORF32-Flag

<400> SEQUENCE: 21

```
Met Pro Ala Phe Pro Thr Leu Asp Leu Asp Gly Lys Leu Gly Lys Met
1               5                   10                  15
Asp Arg Val Val Leu Gly Trp Thr Ala Val Phe Trp Leu Thr Ala Met
                20                  25                  30
Val Glu Gly Leu Gln Val Thr Val Pro Asp Lys Lys Val Ala Met
            35                  40                  45
Leu Phe Gln Pro Thr Val Leu Arg Cys His Phe Ser Thr Ser Ser His
    50                  55                  60
Gln Pro Ala Val Val Gln Trp Lys Phe Lys Ser Tyr Cys Gln Asp Arg
65                  70                  75                  80
Met Gly Glu Ser Leu Gly Met Ser Ser Pro Arg Ala Gln Ala Leu Ser
                85                  90                  95
Lys Arg Asn Leu Glu Trp Asp Pro Tyr Leu Asp Cys Leu Asp Ser Arg
            100                 105                 110
Arg Thr Val Arg Val Ala Ser Lys Gln Gly Ser Thr Val Thr Leu
        115                 120                 125
Gly Asp Phe Tyr Arg Gly Arg Glu Ile Thr Ile Val His Asp Ala Asp
    130                 135                 140
Leu Gln Ile Gly Lys Leu Met Trp Gly Asp Ser Gly Leu Tyr Tyr Cys
145                 150                 155                 160
Ile Ile Thr Thr Pro Asp Asp Leu Glu Gly Lys Asn Glu Asp Ser Val
                165                 170                 175
```

```
Glu Leu Leu Val Leu Gly Arg Thr Gly Leu Leu Ala Asp Leu Leu Pro
            180                 185                 190

Ser Phe Ala Val Glu Ile Met Pro Glu Trp Val Phe Val Gly Leu Val
            195                 200                 205

Ile Leu Gly Ile Phe Leu Phe Phe Val Leu Val Gly Ile Cys Trp Cys
            210                 215                 220

Gln Cys Cys Pro His Ser Cys Cys Cys Tyr Val Arg Cys Pro Cys Cys
225                 230                 235                 240

Pro Asp Ser Cys Cys Cys Pro Gln Ala Leu Tyr Glu Ala Gly Lys Ala
                245                 250                 255

Ala Lys Ala Gly Tyr Pro Pro Ser Val Ser Gly Val Pro Gly Pro Tyr
            260                 265                 270

Ser Ile Pro Ser Val Pro Leu Gly Gly Ala Pro Ser Ser Gly Met Leu
            275                 280                 285

Met Asp Lys Pro His Pro Pro Leu Ala Pro Ser Asp Ser Thr Gly
290                 295                 300

Gly Ser His Ser Val Arg Lys Gly Tyr Arg Ile Gln Ala Asp Lys Glu
305                 310                 315                 320

Arg Asp Ser Met Lys Val Leu Tyr Tyr Val Glu Lys Glu Leu Ala Gln
                325                 330                 335

Phe Asp Pro Ala Arg Arg Met Arg Gly Arg Tyr Asn Asn Thr Ile Ser
                340                 345                 350

Glu Leu Ser Ser Leu His Asp Asp Ser Asn Phe Arg Gln Ser Tyr
                355                 360                 365

His Gln Met Arg Asn Lys Gln Phe Pro Met Ser Gly Asp Leu Glu Ser
    370                 375                 380

Asn Pro Asp Tyr Trp Ser Gly Val Met Gly Gly Asn Ser Gly Thr Asn
385                 390                 395                 400

Arg Gly Pro Ala Leu Glu Tyr Asn Lys Glu Asp Arg Glu Ser Phe Arg
                405                 410                 415

His Ser Gln Gln Arg Ser Lys Ser Glu Met Leu Ser Arg Lys Asn Phe
                420                 425                 430

Ala Thr Gly Val Pro Ala Val Ser Met Asp Glu Leu Ala Ala Phe Ala
            435                 440                 445

Asp Ser Tyr Gly Gln Arg Ser Arg Arg Ala Asn Gly Asn Ser His Glu
    450                 455                 460

Ala Arg Ala Gly Ser Arg Phe Glu Arg Ser Glu Ser Arg Ala His Gly
465                 470                 475                 480

Ala Phe Tyr Gln Asp Gly Ser Leu Asp Glu Tyr Tyr Gly Arg Gly Arg
                485                 490                 495

Ser Arg Glu Pro Pro Gly Asp Gly Glu Arg Gly Trp Thr Tyr Ser Pro
            500                 505                 510

Ala Pro Ala Arg Arg Pro Glu Asp Ala Pro Leu Pro Arg Leu
            515                 520                 525

Val Ser Arg Thr Pro Gly Thr Ala Pro Lys Tyr Asp His Ser Tyr Leu
            530                 535                 540

Ser Ser Val Leu Glu Arg Gln Ala Arg Pro Glu Ser Ser Ser Arg Gly
545                 550                 555                 560

Gly Ser Leu Glu Thr Pro Ser Lys Leu Gly Ala Gln Leu Gly Pro Arg
                565                 570                 575

Ser Ala Ser Tyr Tyr Ala Trp Ser Pro Pro Thr Thr Tyr Lys Ala Gly
            580                 585                 590
```

```
Ala Ser Glu Gly Glu Asp Glu Asp Ala Ala Asp Glu Asp Ala Leu
            595                 600                 605

Pro Pro Tyr Ser Glu Leu Glu Leu Ser Arg Gly Glu Leu Ser Arg Gly
            610                 615                 620

Pro Ser Tyr Arg Gly Arg Asp Leu Ser Phe His Ser Asn Ser Glu Lys
625                 630                 635                 640

Arg Arg Lys Lys Glu Pro Ala Lys Lys Pro Gly Asp Phe Pro Thr Arg
            645                 650                 655

Met Ser Leu Val Val Asp Tyr Lys Asp Asp Asp Lys
            660                 665

<210> SEQ ID NO 22
<211> LENGTH: 263
<212> TYPE: PRT
<213> ORGANISM: Artificial Sequence
<220> FEATURE:
<223> OTHER INFORMATION: synthetic polypeptide: human ILDR2-HA tag

<400> SEQUENCE: 22

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Lys Val Ala
            20                  25                  30

Met Leu Phe Gln Pro Thr Val Leu Arg Cys His Phe Ser Thr Ser Ser
        35                  40                  45

His Gln Tyr Pro Tyr Asp Val Pro Asp Tyr Ala Pro Ala Val Val Gln
    50                  55                  60

Trp Lys Phe Lys Ser Tyr Cys Gln Asp Arg Met Gly Glu Ser Leu Gly
65                  70                  75                  80

Met Ser Ser Thr Arg Ala Gln Ser Leu Ser Lys Arg Asn Leu Glu Trp
                85                  90                  95

Asp Pro Tyr Leu Asp Cys Leu Asp Ser Arg Arg Thr Val Arg Val Val
            100                 105                 110

Ala Ser Lys Gln Gly Ser Thr Val Thr Leu Gly Asp Phe Tyr Arg Gly
        115                 120                 125

Arg Glu Ile Thr Ile Val His Asp Ala Asp Leu Gln Ile Gly Lys Leu
    130                 135                 140

Met Trp Gly Asp Ser Gly Leu Tyr Tyr Cys Ile Ile Thr Thr Pro Asp
145                 150                 155                 160

Asp Leu Glu Gly Lys Asn Glu Asp Ser Val Glu Leu Val Leu Gly
                165                 170                 175

Arg Thr Gly Leu Leu Ala Asp Leu Leu Pro Ser Phe Ala Val Glu Ile
            180                 185                 190

Met Pro Glu Trp Val Phe Val Gly Leu Val Leu Leu Gly Val Phe Leu
        195                 200                 205

Phe Phe Val Leu Val Gly Ile Cys Trp Cys Gln Cys Cys Pro His Ser
    210                 215                 220

Cys Cys Cys Tyr Val Arg Cys Pro Cys Cys Pro Asp Ser Cys Cys Cys
225                 230                 235                 240

Pro Gln Ala Cys Glu Tyr Ser Asp Arg Trp Gly Asp Arg Ala Ile Glu
                245                 250                 255

Arg Asn Val Tyr Leu Ser Thr
            260

<210> SEQ ID NO 23
<211> LENGTH: 416
```

```
<212> TYPE: PRT
<213> ORGANISM: Artificial Sequence
<220> FEATURE:
<223> OTHER INFORMATION: Fusion protein: human C1ORF32-ECD fused to
      human IgG1 Fc

<400> SEQUENCE: 23

Met Asp Arg Val Leu Arg Trp Ile Ser Leu Phe Trp Leu Thr Ala
1               5                   10                  15

Met Val Glu Gly Leu Gln Val Thr Val Pro Asp Lys Lys Val Ala
                20                  25                  30

Met Leu Phe Gln Pro Thr Val Leu Arg Cys His Phe Ser Thr Ser Ser
                35                  40                  45

His Gln Pro Ala Val Val Gln Trp Lys Phe Lys Ser Tyr Cys Gln Asp
        50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Ala Ser Lys Gln Gly Ser Thr Val Thr
                100                 105                 110

Leu Gly Asp Phe Tyr Arg Gly Arg Glu Ile Thr Ile Val His Asp Ala
                115                 120                 125

Asp Leu Gln Ile Gly Lys Leu Met Trp Gly Asp Ser Gly Leu Tyr Tyr
        130                 135                 140

Cys Ile Ile Thr Thr Pro Asp Asp Leu Glu Gly Lys Asn Glu Asp Ser
145                 150                 155                 160

Val Glu Leu Leu Val Leu Gly Arg Thr Gly Leu Leu Ala Asp Leu Leu
                165                 170                 175

Pro Ser Phe Ala Val Glu Ile Met Glu Pro Lys Ser Ser Asp Lys Thr
                180                 185                 190

His Thr Cys Pro Pro Cys Pro Ala Pro Glu Leu Leu Gly Gly Pro Ser
                195                 200                 205

Val Phe Leu Phe Pro Pro Lys Pro Lys Asp Thr Leu Met Ile Ser Arg
        210                 215                 220

Thr Pro Glu Val Thr Cys Val Val Val Asp Val Ser His Glu Asp Pro
225                 230                 235                 240

Glu Val Lys Phe Asn Trp Tyr Val Asp Gly Val Glu Val His Asn Ala
                245                 250                 255

Lys Thr Lys Pro Arg Glu Glu Gln Tyr Asn Ser Thr Tyr Arg Val Val
                260                 265                 270

Ser Val Leu Thr Val Leu His Gln Asp Trp Leu Asn Gly Lys Glu Tyr
                275                 280                 285

Lys Cys Lys Val Ser Asn Lys Ala Leu Pro Ala Pro Ile Glu Lys Thr
        290                 295                 300

Ile Ser Lys Ala Lys Gly Gln Pro Arg Glu Pro Gln Val Tyr Thr Leu
305                 310                 315                 320

Pro Pro Ser Arg Asp Glu Leu Thr Lys Asn Gln Val Ser Leu Thr Cys
                325                 330                 335

Leu Val Lys Gly Phe Tyr Pro Ser Asp Ile Ala Val Glu Trp Glu Ser
                340                 345                 350

Asn Gly Gln Pro Glu Asn Asn Tyr Lys Thr Thr Pro Pro Val Leu Asp
        355                 360                 365

Ser Asp Gly Ser Phe Phe Leu Tyr Ser Lys Leu Thr Val Asp Lys Ser
370                 375                 380
```

-continued

```
Arg Trp Gln Gln Gly Asn Val Phe Ser Cys Ser Val Met His Glu Ala
385                 390                 395                 400

Leu His Asn His Tyr Thr Gln Lys Ser Leu Ser Leu Ser Pro Gly Lys
                405                 410                 415

<210> SEQ ID NO 24
<211> LENGTH: 417
<212> TYPE: PRT
<213> ORGANISM: Artificial Sequence
<220> FEATURE:
<223> OTHER INFORMATION: Fusion protein: human C1ORF32-ECD fused to
      mouse IgG2a Fc

<400> SEQUENCE: 24

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Lys Val Ala
                20                  25                  30

Met Leu Phe Gln Pro Thr Val Leu Arg Cys His Phe Ser Thr Ser Ser
            35                  40                  45

His Gln Pro Ala Val Val Gln Trp Lys Phe Lys Ser Tyr Cys Gln Asp
        50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
        115                 120                 125

Asp Leu Gln Ile Gly Lys Leu Met Trp Gly Asp Ser Gly Leu Tyr Tyr
130                 135                 140

Cys Ile Ile Thr Thr Pro Asp Asp Leu Glu Gly Lys Asn Glu Asp Ser
145                 150                 155                 160

Val Glu Leu Leu Val Leu Gly Arg Thr Gly Leu Leu Ala Asp Leu Leu
                165                 170                 175

Pro Ser Phe Ala Val Glu Ile Met Glu Pro Arg Gly Pro Thr Ile Lys
            180                 185                 190

Pro Cys Pro Pro Cys Lys Cys Pro Ala Pro Asn Leu Leu Gly Gly Pro
        195                 200                 205

Ser Val Phe Ile Phe Pro Pro Lys Ile Lys Asp Val Leu Met Ile Ser
210                 215                 220

Leu Ser Pro Ile Val Thr Cys Val Val Val Asp Val Ser Glu Asp Asp
225                 230                 235                 240

Pro Asp Val Gln Ile Ser Trp Phe Val Asn Asn Val Glu Val His Thr
                245                 250                 255

Ala Gln Thr Gln Thr His Arg Glu Asp Tyr Asn Ser Thr Leu Arg Val
            260                 265                 270

Val Ser Ala Leu Pro Ile Gln His Gln Asp Trp Met Ser Gly Lys Glu
        275                 280                 285

Phe Lys Cys Lys Val Asn Asn Lys Asp Leu Pro Ala Pro Ile Glu Arg
290                 295                 300

Thr Ile Ser Lys Pro Lys Gly Ser Val Arg Ala Pro Gln Val Tyr Val
305                 310                 315                 320

Leu Pro Pro Pro Glu Glu Glu Met Thr Lys Lys Gln Val Thr Leu Thr
```

```
                325                 330                 335
Cys Met Val Thr Asp Phe Met Pro Glu Asp Ile Tyr Val Glu Trp Thr
                340                 345                 350

Asn Asn Gly Lys Thr Glu Leu Asn Tyr Lys Asn Thr Glu Pro Val Leu
                355                 360                 365

Asp Ser Asp Gly Ser Tyr Phe Met Tyr Ser Lys Leu Arg Val Glu Lys
    370                 375                 380

Lys Asn Trp Val Glu Arg Asn Ser Tyr Ser Cys Ser Val Val His Glu
385                 390                 395                 400

Gly Leu His Asn His His Thr Thr Lys Ser Phe Ser Arg Thr Pro Gly
                    405                 410                 415

Lys

<210> SEQ ID NO 25
<211> LENGTH: 42
<212> TYPE: DNA
<213> ORGANISM: Artificial Sequence
<220> FEATURE:
<223> OTHER INFORMATION: Synthetic primer

<400> SEQUENCE: 25
ggcatgtcct ctccccgggc ccaagctctc agcaagagaa ac                        42

<210> SEQ ID NO 26
<211> LENGTH: 41
<212> TYPE: DNA
<213> ORGANISM: Artificial Sequence
<220> FEATURE:
<223> OTHER INFORMATION: Synthetic primer

<400> SEQUENCE: 26
tcttgctgag agcttgggcc cggggagagg acatgcccaa g                         41

<210> SEQ ID NO 27
<211> LENGTH: 33
<212> TYPE: DNA
<213> ORGANISM: Artificial Sequence
<220> FEATURE:
<223> OTHER INFORMATION: Synthetic primer

<400> SEQUENCE: 27
ctagctagcc accatggata gggtcttgct gag                                  33

<210> SEQ ID NO 28
<211> LENGTH: 53
<212> TYPE: DNA
<213> ORGANISM: Artificial Sequence
<220> FEATURE:
<223> OTHER INFORMATION: Synthetic primer

<400> SEQUENCE: 28
ctgcaggagc gtaatctgga acatcgtatg ggtactgatg gaggatgtt gag            53

<210> SEQ ID NO 29
<211> LENGTH: 30
<212> TYPE: DNA
<213> ORGANISM: Artificial Sequence
<220> FEATURE:
<223> OTHER INFORMATION: Synthetic primer

<400> SEQUENCE: 29
ggaattctca cctgggcttg tgggcaggtg                                      30
```

<210> SEQ ID NO 30
<211> LENGTH: 765
<212> TYPE: DNA
<213> ORGANISM: Artificial Sequence
<220> FEATURE:
<223> OTHER INFORMATION: chimeric mouse-human C1ORF32

<400> SEQUENCE: 30

```
atggataggg tcttgctgag gtggatttct ctcttctggc taacagccat ggtcgaaggc      60
cttcaggtca cagtgcccga caagaagaag gtggccatgc tcttccagcc cactgtgctt     120
cgctgccact tctcaacatc ctcccatcag cctgcagttg tgcagtggaa gttcaagtcc     180
tactgccagg atcgcatggg agaatccttg ggcatgtcct ctccccgggc ccaagctctc     240
agcaagagaa acctggaatg gaccccctac ttggattgtt tggacagcag gaggactgtt     300
cgagtagtag cttcaaaaca gggctcgact gtcaccctgg agatttctac aggggcaga     360
gagatcacga ttgttcatga tgcagatctt caaattggaa agcttatgtg gggagacagc     420
ggactctatt actgtattat caccaccca gatgacctga ggggaaaaa tgaggactca     480
gtggaactgc tggtgttggg caggacaggg ctgcttgctg atctcttgcc cagttttgct     540
gtggagatta tgccagagtg ggtgtttgtt ggcctggtgc tcctgggcgt cttcctcttc     600
ttcgtcctgg tggggatctg ctggtgccag tgctgccctc acagctgctg ctgctatgtc     660
cgctgcccat gctgcccaga ttcctgctgc tgccctcaag cctgtgagta cagtgaccgc     720
tggggagaca gagcgatcga gagaaatgtc tacctctcta cctga                    765
```

<210> SEQ ID NO 31
<211> LENGTH: 1958
<212> TYPE: DNA
<213> ORGANISM: Artificial Sequence
<220> FEATURE:
<223> OTHER INFORMATION: Codon-optimized cDNA of C1ORF32 for expression in murine cells

<400> SEQUENCE: 31

```
gcgcccggcc attacggcca tggatagggt gctgctgaga tggatttcac tgttctggct      60
gactgctatg gtggaaggac tgcaggtcac tgtgcccgat aaaagaagg tggcaatgct     120
gttccagcca accgtcctga ggtgccactt tagcacaagc tcccatcagc ccgccgtggt     180
ccagtggaag ttcaaatcat actgtcagga cagaatggga gaaagcctgg ggatgtctag     240
tacaagggcc cagtctctga gtaagagaaa cctggagtgg gatccatacc tggactgcct     300
ggattctagg agaactgtga gggtggtcgc ttcaaaacag gcagcactg tcaccctggg     360
ggacttttat cgaggcaggg agatcaccat tgtgcacgac gccgatctgc agatcggcaa     420
gctgatgtgg ggagatagcg ggctgtacta ttgtatcatt accacaccg acgatctgga     480
gggaaaaaat gaagacagcg tggagctgct ggtcctgggc cggactggac tgctggcaga     540
tctgctgccc tccttcgccg tggaaatcat gcctgagtgg gtgttcgtcg actggtgct     600
gctgggggtc tttctgttct ttgtgctggt cggcatttgc tggtgtcagt gctgtcccca     660
tagttgctgt tgctacgtgc gctgcccatg ttgccccgac agctgttgct gtcctcaggc     720
cctgtacgag gctggaaagg ccgctaaagc cgggtatcca ccttcagtga gcggagtccc     780
aggaccttac agcattcctt ccgtgccact gggaggagca ccatcaagcc gaatgctgat     840
ggacaagcct cacccacccc ctctggctcc atccgattct acaggggca gtcattcagt     900
gcggaaaggc taccgcatcc aggccgacaa ggaacgggat tctatgaaag tgctgtacta     960
```

```
tgtcgagaag gaactggcac agttcgaccc tgcacgacga atgagaggcc ggtataacaa    1020
tactattagc gagctgtcct ctctgcacga ggaagattca aacttccggc agagctttca    1080
tcagatgcgc agcaagcagt tcccgtgag  cggggacctg gaatctaatc cagattactg    1140
gtccggcgtg atgggaggaa gttcaggagc atcccgagga ccttctgcta tggagtataa    1200
caaagaggac cgagaaagtt tcaggcactc acagcctagg agcaagtccg aaatgctgtc    1260
cagaaaaaat ttcgctaccg gcgtgccagc agtctccatg gacgagctgg cagcctttgc    1320
cgattcttac ggccagaggc cacgaagggc tgacggaaac agtcacgagg cacggggcgg    1380
atcaaggttc gagagatctg aaagtcgcgc tcatagcggc ttctaccagg acgattccct    1440
ggaggaatac tatgggcaga ggagccgaag cagggaacca ctgacagacg ccgatagagg    1500
atgggcattt tctccagcca gacggcgccc cgctgaggac gcacacctgc caagactggt    1560
gagccgaaca ccaggaactg cccctaagta cgatcatagc tatctgggat ccgccagaga    1620
acgacaggct cgacctgagg gagcatctcg aggaggcagt ctggagactc cctctaagcg    1680
aagtgctcag ctgggacctc gctccgcttc ttactatgca tggagcccac ccggcaccta    1740
caaagcagga agctcccagg acgatcagga agacgcctct gacgatgctc tgcctccata    1800
tagtgagctg gaactgacca gaggaccatc ctaccgagga cgagatctgc catatcacag    1860
taattcagag aagaaaagaa aaaggagcc  tgccaaaaag actaatgact tccccacacg    1920
gatgtccctg gtcgtctgag gccgcctcgg ccgggcgc                            1958

<210> SEQ ID NO 32
<211> LENGTH: 803
<212> TYPE: DNA
<213> ORGANISM: Artificial Sequence
<220> FEATURE:
<223> OTHER INFORMATION: Codon-optimized cDNA of C1ORF32 for expression
      in murine cells

<400> SEQUENCE: 32
gcgcccggcc attacggcca tggatagggt gctgctgaga tggatttcac tgttctggct      60
gaccgcaatg gtggagggac tgcaggtgac cgtgcccgat aaaaagaagg tggcaatgct     120
gttccagcct acagtcctga gatgccactt ttccactagc tcccatcagc cagccgtggt     180
ccagtggaag ttcaaaagtt actgtcagga ccggatggga gaatcactgg ggatgtctag     240
tacccgagcc cagtcactga gcaagaggaa cctggagtgg atccatacc  tggactgcct     300 ggattctagg agaacagtgc gggtggtcgc ttccaaacag gctctactg  tgaccctggg     360 cgacttttat cggggacgcg aaatcactat tgtgcacgac gcagatctgc agatcggaaa     420
gctgatgtgg ggcgatagcg gactgtacta ttgtatcatt accacacccg acgatctgga     480
ggggaaaaat gaagactctg tggagctgct ggtcctgggg cgcacaggcc tgctggccga     540
tctgctgcca gtttcgctg  tggaaatcat gcccgagtgg gtgttcgtcg actggtgct      600 gctgggcgtc tttctgttct ttgtgctggt cggaatttgc tggtgtcagt gctgtcccca     660
tagctgctgt tgctatgtgc gatgcccctg ttgccctgac tcctgttgct gtcctcaggc     720
ttgtgagtat tctgaccgct gggggatcg  ggctattgaa agaaatgtct acctgagcac     780
ctgaggccgc ctcggccggg cgc                                             803

<210> SEQ ID NO 33
<211> LENGTH: 42
<212> TYPE: DNA
<213> ORGANISM: Artificial Sequence
<220> FEATURE:
```

-continued

<223> OTHER INFORMATION: Synthetic primer

<400> SEQUENCE: 33
ctctagacat gtcggatagg gtcttgctga ggtggatttc tc          42

<210> SEQ ID NO 34
<211> LENGTH: 41
<212> TYPE: DNA
<213> ORGANISM: Artificial Sequence
<220> FEATURE:
<223> OTHER INFORMATION: Synthetic primer

<400> SEQUENCE: 34
gcgatgcggc cgctcaggta gagaggtaga catttctctc g           41

<210> SEQ ID NO 35
<211> LENGTH: 20
<212> TYPE: DNA
<213> ORGANISM: Artificial Sequence
<220> FEATURE:
<223> OTHER INFORMATION: Synthetic primer

<400> SEQUENCE: 35
caggcagtcc aggtatggat                                    20

<210> SEQ ID NO 36
<211> LENGTH: 20
<212> TYPE: DNA
<213> ORGANISM: Artificial Sequence
<220> FEATURE:
<223> OTHER INFORMATION: Synthetic primer

<400> SEQUENCE: 36
tctggctgac tgctatggtg                                    20

<210> SEQ ID NO 37
<211> LENGTH: 20
<212> TYPE: DNA
<213> ORGANISM: Artificial Sequence
<220> FEATURE:
<223> OTHER INFORMATION: Synthetic primer

<400> SEQUENCE: 37
tgcccgataa aaagaaggtg                                    20

<210> SEQ ID NO 38
<211> LENGTH: 428
<212> TYPE: PRT
<213> ORGANISM: Artificial Sequence
<220> FEATURE:
<223> OTHER INFORMATION: human-mouse fused Fc containing N278A mutation

<400> SEQUENCE: 38

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Lys Val Ala
                20                  25                  30

Met Leu Phe Gln Pro Thr Val Leu Arg Cys His Phe Ser Thr Ser Ser
            35                  40                  45

His Gln Pro Ala Val Val Gln Trp Lys Phe Lys Ser Tyr Cys Gln Asp
        50                  55                  60

Arg Met Gly Glu Ser Leu Gly Met Ser Ser Thr Arg Ala Gln Ser Leu
65                  70                  75                  80

```
Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
        115                 120                 125

Asp Leu Gln Ile Gly Lys Leu Met Trp Gly Asp Ser Gly Leu Tyr Tyr
    130                 135                 140

Cys Ile Ile Thr Thr Pro Asp Asp Leu Glu Gly Lys Asn Glu Asp Ser
145                 150                 155                 160

Val Glu Leu Leu Val Leu Gly Arg Thr Gly Leu Leu Ala Asp Leu Leu
                165                 170                 175

Pro Ser Phe Ala Val Glu Ile Met Gly Ser Glu Asn Leu Tyr Phe Gln
            180                 185                 190

Gly Ser Gly Glu Pro Arg Gly Pro Thr Ile Lys Pro Cys Pro Pro Cys
        195                 200                 205

Lys Cys Pro Ala Pro Asn Leu Leu Gly Gly Pro Ser Val Phe Ile Phe
    210                 215                 220

Pro Pro Lys Ile Lys Asp Val Leu Met Ile Ser Leu Ser Pro Ile Val
225                 230                 235                 240

Thr Cys Val Val Val Asp Val Ser Glu Asp Asp Pro Asp Val Gln Ile
                245                 250                 255

Ser Trp Phe Val Asn Asn Val Glu Val His Thr Ala Gln Thr Gln Thr
            260                 265                 270

His Arg Glu Asp Tyr Ala Ser Thr Leu Arg Val Val Ser Ala Leu Pro
        275                 280                 285

Ile Gln His Gln Asp Trp Met Ser Gly Lys Glu Phe Lys Cys Lys Val
    290                 295                 300

Asn Asn Lys Asp Leu Pro Ala Pro Ile Glu Arg Thr Ile Ser Lys Pro
305                 310                 315                 320

Lys Gly Ser Val Arg Ala Pro Gln Val Tyr Val Leu Pro Pro Pro Glu
                325                 330                 335

Glu Glu Met Thr Lys Lys Gln Val Thr Leu Thr Cys Met Val Thr Asp
            340                 345                 350

Phe Met Pro Glu Asp Ile Tyr Val Glu Trp Thr Asn Asn Gly Lys Thr
        355                 360                 365

Glu Leu Asn Tyr Lys Asn Thr Glu Pro Val Leu Asp Ser Asp Gly Ser
    370                 375                 380

Tyr Phe Met Tyr Ser Lys Leu Arg Val Glu Lys Lys Asn Trp Val Glu
385                 390                 395                 400

Arg Asn Ser Tyr Ser Cys Ser Val Val His Glu Gly Leu His Asn His
                405                 410                 415

His Thr Thr Lys Ser Phe Ser Arg Thr Pro Gly Lys
            420                 425

<210> SEQ ID NO 39
<211> LENGTH: 411
<212> TYPE: DNA
<213> ORGANISM: Artificial Sequence
<220> FEATURE:
<223> OTHER INFORMATION: Synthetic polynucleotide encoding
      immunoglobulin heavy chain

<400> SEQUENCE: 39
atggcttggg tgtggaccct gctattcctg atggcagctg cccaaagtat ccaagcacag    60
```

```
atccagttgg tgcagtctgg acctgagctg aagaagcctg agagacagt caagatctcc    120 tgcaaggctt ctgcttatac cttcacagac tattcaatgc actgggtgaa gcaggctcca    180
ggaaagggtt taaagtggat gggctggata acactgaga ctggtgagcc aacatatgca    240
ggtgacttca agggacggtt tgccttctct ttggaaacct ctgccagcac tgcctatttg    300
cagatcaaca acctcaaaaa tgaggacacg gctacatatt tctgtgttag agctggttac    360
tacgactact ttgactactg gggccaaggc accactctca cagtctcctc a             411
```

<210> SEQ ID NO 40
<211> LENGTH: 137
<212> TYPE: PRT
<213> ORGANISM: Artificial Sequence
<220> FEATURE:
<223> OTHER INFORMATION: Synthetic polypeptide of immunoglobulin heavy chain

<400> SEQUENCE: 40

```
Met Ala Trp Val Trp Thr Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Ala Tyr Thr Phe
        35                  40                  45

Thr Asp Tyr Ser Met His Trp Val Lys Gln Ala Pro Gly Lys Gly Leu
    50                  55                  60

Lys Trp Met Gly Trp Ile Asn Thr Glu Thr Gly Glu Pro Thr Tyr Ala
65                  70                  75                  80

Gly Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Val Arg Ala Gly Tyr Tyr Asp Tyr Phe Asp Tyr Trp Gly
        115                 120                 125

Gln Gly Thr Thr Leu Thr Val Ser Ser
    130                 135
```

<210> SEQ ID NO 41
<211> LENGTH: 381
<212> TYPE: DNA
<213> ORGANISM: Artificial Sequence
<220> FEATURE:
<223> OTHER INFORMATION: Synthetic polynucleotide encoding immunoglobulin light chain

<400> SEQUENCE: 41

```
atggagacac attctcaggt ctttgtatac atgttgctgt ggttgtctgg tgttgaagga    60
gacattgtga tgacccagtc tcacaaattc atgtccacat cagtaggaga cagggtcagc   120
atcacctgca aggccagtca ggatgtggtt actgctgtag cctggtatca acagaaacca   180
ggtcaatctc ctaaactact gatttactgg gcatctaacc ggcacactgg agtccctgat   240
cgcttcacag gcagtggatc tgggacagat ttcactctca ccattaccaa tgtgcagtct   300
gaagacttgg cagattattt ctgtcagcaa tatagcagct atcctctcac gttcggaggg   360
gggaccaagc tggaaataaa a                                             381
```

<210> SEQ ID NO 42
<211> LENGTH: 127
<212> TYPE: PRT

<213> ORGANISM: Artificial Sequence
<220> FEATURE:
<223> OTHER INFORMATION: Synthetic polypeptide for immunoglobulin light
      chain

<400> SEQUENCE: 42

Met Glu Thr His Ser Gln Val Phe Val Tyr Met Leu Leu Trp Leu Ser
1               5                   10                  15

Gly Val Glu Gly Asp Ile Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Val Thr Ala Val Ala Trp Tyr Gln Gln Lys Pro Gly Gln Ser Pro
    50                  55                  60

Lys Leu Leu Ile Tyr Trp Ala Ser Asn Arg His Thr Gly Val Pro Asp
65                  70                  75                  80

Arg Phe Thr Gly Ser Gly Ser Gly Thr Asp Phe Thr Leu Thr Ile Thr
                85                  90                  95

Asn Val Gln Ser Glu Asp Leu Ala Asp Tyr Phe Cys Gln Gln Tyr Ser
            100                 105                 110

Ser Tyr Pro Leu Thr Phe Gly Gly Thr Lys Leu Glu Ile Lys
        115                 120                 125

<210> SEQ ID NO 43
<211> LENGTH: 30
<212> TYPE: DNA
<213> ORGANISM: Artificial Sequence
<220> FEATURE:
<223> OTHER INFORMATION: Synthetic polynucleotide encoding
      immunoglobulin CDR1

<400> SEQUENCE: 43
gcttatacct tcacagacta ttcaatgcac                                        30

<210> SEQ ID NO 44
<211> LENGTH: 51
<212> TYPE: DNA
<213> ORGANISM: Artificial Sequence
<220> FEATURE:
<223> OTHER INFORMATION: Synthetic polynucleotide encoding
      immunoglobulin CDR2

<400> SEQUENCE: 44
tggataaaca ctgagactgg tgagccaaca tatgcaggtg acttcaaggg a                51

<210> SEQ ID NO 45
<211> LENGTH: 27
<212> TYPE: DNA
<213> ORGANISM: Artificial Sequence
<220> FEATURE:
<223> OTHER INFORMATION: Synthetic polynucleotide encoding
      immunoglobulin CDR3

<400> SEQUENCE: 45
gctggttact acgactactt tgactac                                           27

<210> SEQ ID NO 46
<211> LENGTH: 10
<212> TYPE: PRT
<213> ORGANISM: Artificial Sequence
<220> FEATURE:
<223> OTHER INFORMATION: Synthetic polypeptide of immunoglobulin CDR1

<400> SEQUENCE: 46

```
Ala Tyr Thr Phe Thr Asp Tyr Ser Met His
1               5                   10

<210> SEQ ID NO 47
<211> LENGTH: 17
<212> TYPE: PRT
<213> ORGANISM: Artificial Sequence
<220> FEATURE:
<223> OTHER INFORMATION: Synthetic polypeptide of immunoglobulin CDR2

<400> SEQUENCE: 47

Trp Ile Asn Thr Glu Thr Gly Glu Pro Thr Tyr Ala Gly Asp Phe Lys
1               5                   10                  15

Gly

<210> SEQ ID NO 48
<211> LENGTH: 9
<212> TYPE: PRT
<213> ORGANISM: Artificial Sequence
<220> FEATURE:
<223> OTHER INFORMATION: Synthetic polypeptide of immunoglobulin CDR3

<400> SEQUENCE: 48

Ala Gly Tyr Tyr Asp Tyr Phe Asp Tyr
1               5

<210> SEQ ID NO 49
<211> LENGTH: 33
<212> TYPE: DNA
<213> ORGANISM: Artificial Sequence
<220> FEATURE:
<223> OTHER INFORMATION: Synthetic polynucleotide encoding
      immunoglobulin CDR1

<400> SEQUENCE: 49
aaggccagtc aggatgtggt tactgctgta gcc                                33

<210> SEQ ID NO 50
<211> LENGTH: 21
<212> TYPE: DNA
<213> ORGANISM: Artificial Sequence
<220> FEATURE:
<223> OTHER INFORMATION: Synthetic polynucleotide encoding
      immunoglobulin CDR2

<400> SEQUENCE: 50
tgggcatcta accggcacac t                                             21

<210> SEQ ID NO 51
<211> LENGTH: 27
<212> TYPE: DNA
<213> ORGANISM: Artificial Sequence
<220> FEATURE:
<223> OTHER INFORMATION: Synthetic polynucleotide encoding
      immunoglobulin CDR3

<400> SEQUENCE: 51
cagcaatata gcagctatcc tctcacg                                       27

<210> SEQ ID NO 52
<211> LENGTH: 11
<212> TYPE: PRT
<213> ORGANISM: Artificial Sequence
<220> FEATURE:
<223> OTHER INFORMATION: Synthetic polypeptide of immunoglobulin CDR1
```

<400> SEQUENCE: 52

Lys Ala Ser Gln Asp Val Val Thr Ala Val Ala
1               5                   10

<210> SEQ ID NO 53
<211> LENGTH: 7
<212> TYPE: PRT
<213> ORGANISM: Artificial Sequence
<220> FEATURE:
<223> OTHER INFORMATION: Synthetic polypeptide of immunoglobulin CDR2

<400> SEQUENCE: 53

Trp Ala Ser Asn Arg His Thr
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic polypeptide of immunoglobulin CDR3

<400> SEQUENCE: 54

Gln Gln Tyr Ser Ser Tyr Pro Leu Thr
1               5

<210> SEQ ID NO 55
<211> LENGTH: 420
<212> TYPE: DNA
<213> ORGANISM: Artificial Sequence
<220> FEATURE:
<223> OTHER INFORMATION: Synthetic polynucleotide encoding
      immunoglobulin heavy chain

<400> SEQUENCE: 55

```
atgaacttgg ggctcagctt gattttcctt gtccttgttt taaaaggtgt ccagtgtgaa    60
gtgaagatgg tggagtctgg gggaggctta gtgcagcctg agggtccct  gaaactctcc   120
tgtgcaacct ctggattcac tttcagtgac tattacatgt attgggttcg ccagactcca   180
gagaagaggc tggagtgggt cgcatacatt agtaatggtg gtggtagcac ctattatcca   240
gacactgtaa agggccgatt caccatctcc agagacaatg ccaagaacac cctgtacctg   300
caaatgagcc gtctgaagtc tgaggacaca gccatgtatt actgtgcaag acaagggtat   360
tactacggta gtagccccct tgcttactgg ggccaaggga ctctggtcac tgtatctgca   420
```

<210> SEQ ID NO 56
<211> LENGTH: 140
<212> TYPE: PRT
<213> ORGANISM: Artificial Sequence
<220> FEATURE:
<223> OTHER INFORMATION: Synthetic polypeptide of immunoglobulin heavy
      chain

<400> SEQUENCE: 56

Met Asn Leu Gly Leu Ser Leu Ile Phe Leu Val Leu Val Leu Lys Gly
1               5                   10                  15

Val Gln Cys Glu Val Lys Met Val Glu Ser Gly Gly Gly Leu Val Gln
            20                  25                  30

Pro Gly Gly Ser Leu Lys Leu Ser Cys Ala Thr Ser Gly Phe Thr Phe
        35                  40                  45

Ser Asp Tyr Tyr Met Tyr Trp Val Arg Gln Thr Pro Glu Lys Arg Leu
    50                  55                  60

```
Glu Trp Val Ala Tyr Ile Ser Asn Gly Gly Ser Thr Tyr Tyr Pro
 65                  70                  75                  80

Asp Thr Val Lys Gly Arg Phe Thr Ile Ser Arg Asp Asn Ala Lys Asn
                 85                  90                  95

Thr Leu Tyr Leu Gln Met Ser Arg Leu Lys Ser Glu Asp Thr Ala Met
            100                 105                 110

Tyr Tyr Cys Ala Arg Gln Gly Tyr Tyr Tyr Gly Ser Ser Pro Phe Ala
            115                 120                 125

Tyr Trp Gly Gln Gly Thr Leu Val Thr Val Ser Ala
        130                 135                 140

<210> SEQ ID NO 57
<211> LENGTH: 381
<212> TYPE: DNA
<213> ORGANISM: Artificial Sequence
<220> FEATURE:
<223> OTHER INFORMATION: Synthetic polynucleotide encoding
      immunoglobulin light chain

<400> SEQUENCE: 57
atggagtcac agattcaggt ctttgtattc gtgtttctct ggttgtctgg tgttgacgga      60
gacattgtga tgacccagtc tcacaaattc atgtccacat cagtaggaga cagggtcagc     120
atcacctgca aggccagtca ggatgtgagt actgctgtag cctggtatca acagaaacca     180
ggacaatctc ctaaactatt gatttactcg gcatcctacc ggtacactgg agtccctgat     240
cgcttcactg gcagtggatc tgggacggat ttcactttca ccatcagcag tgtgcaggct     300
gaagacctgg cagtttatta ctgtcagcaa cattatagta ctccgtacac gttcggaggg     360
gggaccaagc tggaaataaa a                                               381

<210> SEQ ID NO 58
<211> LENGTH: 127
<212> TYPE: PRT
<213> ORGANISM: Artificial Sequence
<220> FEATURE:
<223> OTHER INFORMATION: Synthetic polypeptide of immunoglobulin light
      chain

<400> SEQUENCE: 58

Met Glu Ser Gln Ile Gln Val Phe Val Phe Val Phe Leu Trp Leu Ser
 1               5                  10                  15

Gly Val Asp Gly Asp Ile Val Met Thr Gln Ser His Lys Phe Met Ser
                 20                  25                  30

Thr Ser Val Gly Asp Arg Val Ser Ile Thr Cys Lys Ala Ser Gln Asp
             35                  40                  45

Val Ser Thr Ala Val Ala Trp Tyr Gln Gln Lys Pro Gly Gln Ser Pro
 50                  55                  60

Lys Leu Leu Ile Tyr Ser Ala Ser Tyr Arg Tyr Thr Gly Val Pro Asp
 65                  70                  75                  80

Arg Phe Thr Gly Ser Gly Ser Gly Thr Asp Phe Thr Phe Thr Ile Ser
             85                  90                  95

Ser Val Gln Ala Glu Asp Leu Ala Val Tyr Tyr Cys Gln Gln His Tyr
            100                 105                 110

Ser Thr Pro Tyr Thr Phe Gly Gly Gly Thr Lys Leu Glu Ile Lys
            115                 120                 125

<210> SEQ ID NO 59
<211> LENGTH: 30
<212> TYPE: DNA
```

<213> ORGANISM: Artificial Sequence
<220> FEATURE:
<223> OTHER INFORMATION: Synthetic polynucleotide encoding
      immunoglobulin CDR1

<400> SEQUENCE: 59
ggattcactt tcagtgacta ttacatgtat                                      30

<210> SEQ ID NO 60
<211> LENGTH: 51
<212> TYPE: DNA
<213> ORGANISM: Artificial Sequence
<220> FEATURE:
<223> OTHER INFORMATION: Synthetic polynucleotide encoding
      immunoglobulin CDR2

<400> SEQUENCE: 60
tacattagta atggtggtgg tagcacctat atccagaca ctgtaaaggg c               51

<210> SEQ ID NO 61
<211> LENGTH: 36
<212> TYPE: DNA
<213> ORGANISM: Artificial Sequence
<220> FEATURE:
<223> OTHER INFORMATION: Synthetic polynucleotide encoding
      immunoglobulin CDR3

<400> SEQUENCE: 61
caagggtatt actacggtag tagccccttt gcttac                               36

<210> SEQ ID NO 62
<211> LENGTH: 10
<212> TYPE: PRT
<213> ORGANISM: Artificial Sequence
<220> FEATURE:
<223> OTHER INFORMATION: Synthetic polypeptide of immunoglobulin CDR1

<400> SEQUENCE: 62

Gly Phe Thr Phe Ser Asp Tyr Tyr Met Tyr
1               5                   10

<210> SEQ ID NO 63
<211> LENGTH: 17
<212> TYPE: PRT
<213> ORGANISM: Artificial Sequence
<220> FEATURE:
<223> OTHER INFORMATION: Synthetic polypeptide of immunoglobulin CDR2

<400> SEQUENCE: 63

Tyr Ile Ser Asn Gly Gly Gly Ser Thr Tyr Tyr Pro Asp Thr Val Lys
1               5                   10                  15
Gly

<210> SEQ ID NO 64
<211> LENGTH: 12
<212> TYPE: PRT
<213> ORGANISM: Artificial Sequence
<220> FEATURE:
<223> OTHER INFORMATION: Synthetic polypeptide of immunoglobulin CDR3

<400> SEQUENCE: 64

Gln Gly Tyr Tyr Tyr Gly Ser Ser Pro Phe Ala Tyr
1               5                   10

<210> SEQ ID NO 65
<211> LENGTH: 33

```
<212> TYPE: DNA
<213> ORGANISM: Artificial Sequence
<220> FEATURE:
<223> OTHER INFORMATION: Synthetic polynucleotide encoding
      immunoglobulin CDR1

<400> SEQUENCE: 65
aaggccagtc aggatgtgag tactgctgta gcc                              33

<210> SEQ ID NO 66
<211> LENGTH: 21
<212> TYPE: DNA
<213> ORGANISM: Artificial Sequence
<220> FEATURE:
<223> OTHER INFORMATION: Synthetic polynucleotide encoding
      immunoglobulin CDR2

<400> SEQUENCE: 66
tcggcatcct accggtacac t                                           21

<210> SEQ ID NO 67
<211> LENGTH: 27
<212> TYPE: DNA
<213> ORGANISM: Artificial Sequence
<220> FEATURE:
<223> OTHER INFORMATION: Synthetic polynucleotide encoding
      immunoglobulin CDR3

<400> SEQUENCE: 67
cagcaacatt atagtactcc gtacacg                                     27

<210> SEQ ID NO 68
<211> LENGTH: 11
<212> TYPE: PRT
<213> ORGANISM: Artificial Sequence
<220> FEATURE:
<223> OTHER INFORMATION: Synthetic polypeptide of immunoglobulin CDR1

<400> SEQUENCE: 68

Lys Ala Ser Gln Asp Val Ser Thr Ala Val Ala
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Synthetic polypeptide of immunoglobulin CDR2

<400> SEQUENCE: 69

Ser Ala Ser Tyr Arg Tyr Thr
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic polypeptide of immunoglobulin CDR3

<400> SEQUENCE: 70

Gln Gln His Tyr Ser Thr Pro Tyr Thr
1               5

<210> SEQ ID NO 71
<211> LENGTH: 411
<212> TYPE: DNA
```

<213> ORGANISM: Artificial Sequence
<220> FEATURE:
<223> OTHER INFORMATION: Synthetic polynucleotide encoding
      immunoglobulin heavy chain

<400> SEQUENCE: 71

```
atgggcaggc ttacttcttc attcttgcta ctgattgtcc ctgcctatgt cctggcccag      60
gttactctga aagagtctgg ccctgggata ttgcagccct cccagaccct caatctgact     120
tgttctttct ctgggttttc actgagttct tcttatatgg gtgtaggctg gattcgtcag     180
ccttcaggga agggtctgga gtggctggca cacatttggt gggatgatgt caagcgctat     240
aatccagccc tgaagagccg actgacaatc tccaaggata tctccaacaa ccaggttttc     300
ctaaagatcg ccagtgtgga cactgcagat tctgccacat attattgtgg tcgaatagac     360
agacactact ttgactactg gggccaaggc accattctca cggtctcctc c              411
```

<210> SEQ ID NO 72
<211> LENGTH: 137
<212> TYPE: PRT
<213> ORGANISM: Artificial Sequence
<220> FEATURE:
<223> OTHER INFORMATION: Synthetic polypeptide of immunoglobulin heavy
      chain

<400> SEQUENCE: 72

```
Met Gly Arg Leu Thr Ser Ser Phe Leu Leu Ile Val Pro Ala Tyr
1               5                   10                  15

Val Leu Ala Gln Val Thr Leu Lys Glu Ser Gly Pro Gly Ile Leu Gln
            20                  25                  30

Pro Ser Gln Thr Leu Asn Leu Thr Cys Ser Phe Ser Gly Phe Ser Leu
        35                  40                  45

Ser Ser Ser Tyr Met Gly Val Gly Trp Ile Arg Gln Pro Ser Gly Lys
    50                  55                  60

Gly Leu Glu Trp Leu Ala His Ile Trp Trp Asp Asp Val Lys Arg Tyr
65                  70                  75                  80

Asn Pro Ala Leu Lys Ser Arg Leu Thr Ile Ser Lys Asp Ile Ser Asn
                85                  90                  95

Asn Gln Val Phe Leu Lys Ile Ala Ser Val Asp Thr Ala Asp Ser Ala
            100                 105                 110

Thr Tyr Tyr Cys Gly Arg Ile Asp Arg His Tyr Phe Asp Tyr Trp Gly
        115                 120                 125

Gln Gly Thr Ile Leu Thr Val Ser Ser
    130                 135
```

<210> SEQ ID NO 73
<211> LENGTH: 381
<212> TYPE: DNA
<213> ORGANISM: Artificial Sequence
<220> FEATURE:
<223> OTHER INFORMATION: Synthetic polynucleotide encoding
      immunoglobulin light chain

<400> SEQUENCE: 73

```
atgaggaccc ctgctcagtt tcttggaatc ttgttgctct ggtttccagg tatcaaatgt      60
gacatcaaga tgacccagtc tccatcttcc atatatgcat ctctaggaga gagagtcact     120
atcacttgca aggcgagtca ggacattaat ggatatttaa cctggttcca gcagaaacca     180
ggaaaatctc ctaagaccct gatctatcgc gcaaacagat tgttagatgg tgtcccatca     240
aggttcagtg gcagtggatc tgggcaagat tattctctca ccatcagcag cctggattat     300
```
gaagatatgg gaatttacta ttgtctgcag tatgatgagt ttccgtggac gttcggtgga    360
ggcaccaaac tggaaatcaa a                                              381

<210> SEQ ID NO 74
<211> LENGTH: 127
<212> TYPE: PRT
<213> ORGANISM: Artificial Sequence
<220> FEATURE:
<223> OTHER INFORMATION: Synthetic polypeptide of immunoglobulin light
      chain

<400> SEQUENCE: 74

Met Arg Thr Pro Ala Gln Phe Leu Gly Ile Leu Leu Leu Trp Phe Pro
1               5                   10                  15

Gly Ile Lys Cys Asp Ile Lys Met Thr Gln Ser Pro Ser Ser Ile Tyr
            20                  25                  30

Ala Ser Leu Gly Glu Arg Val Thr Ile Thr Cys Lys Ala Ser Gln Asp
        35                  40                  45

Ile Asn Gly Tyr Leu Thr Trp Phe Gln Gln Lys Pro Gly Lys Ser Pro
    50                  55                  60

Lys Thr Leu Ile Tyr Arg Ala Asn Arg Leu Leu Asp Gly Val Pro Ser
65                  70                  75                  80

Arg Phe Ser Gly Ser Gly Ser Gly Gln Asp Tyr Ser Leu Thr Ile Ser
                85                  90                  95

Ser Leu Asp Tyr Glu Asp Met Gly Ile Tyr Tyr Cys Leu Gln Tyr Asp
            100                 105                 110

Glu Phe Pro Trp Thr Phe Gly Gly Gly Thr Lys Leu Glu Ile Lys
        115                 120                 125

<210> SEQ ID NO 75
<211> LENGTH: 36
<212> TYPE: DNA
<213> ORGANISM: Artificial Sequence
<220> FEATURE:
<223> OTHER INFORMATION: Synthetic polynucleotide encoding
      immunoglobulin CDR1

<400> SEQUENCE: 75
gggttttcac tgagttcttc ttatatgggt gtaggc                              36

<210> SEQ ID NO 76
<211> LENGTH: 48
<212> TYPE: DNA
<213> ORGANISM: Artificial Sequence
<220> FEATURE:
<223> OTHER INFORMATION: Synthetic polynucleotide encoding
      immunoglobulin CDR2

<400> SEQUENCE: 76
cacatttggt gggatgatgt caagcgctat aatccagccc tgaagagc                 48

<210> SEQ ID NO 77
<211> LENGTH: 24
<212> TYPE: DNA
<213> ORGANISM: Artificial Sequence
<220> FEATURE:
<223> OTHER INFORMATION: Synthetic polynucleotide encoding
      immunoglobulin CDR3

<400> SEQUENCE: 77
atagacagac actactttga ctac                                           24

<210> SEQ ID NO 78
<211> LENGTH: 12
<212> TYPE: PRT
<213> ORGANISM: Artificial Sequence
<220> FEATURE:
<223> OTHER INFORMATION: Synthetic polypeptide for immunoglobulin CDR1

<400> SEQUENCE: 78

Gly Phe Ser Leu Ser Ser Ser Tyr Met Gly Val Gly
1               5                   10

<210> SEQ ID NO 79
<211> LENGTH: 16
<212> TYPE: PRT
<213> ORGANISM: Artificial Sequence
<220> FEATURE:
<223> OTHER INFORMATION: Synthetic polypeptide for immunoglobulin CDR2

<400> SEQUENCE: 79

His Ile Trp Trp Asp Asp Val Lys Arg Tyr Asn Pro Ala Leu Lys Ser
1               5                   10                  15

<210> SEQ ID NO 80
<211> LENGTH: 8
<212> TYPE: PRT
<213> ORGANISM: Artificial Sequence
<220> FEATURE:
<223> OTHER INFORMATION: Synthetic polypeptide for immunoglobulin CDR3

<400> SEQUENCE: 80

Ile Asp Arg His Tyr Phe Asp Tyr
1               5

<210> SEQ ID NO 81
<211> LENGTH: 33
<212> TYPE: DNA
<213> ORGANISM: Artificial Sequence
<220> FEATURE:
<223> OTHER INFORMATION: Synthetic polynucleotide encoding
      immunoglobulin CDR1

<400> SEQUENCE: 81
aaggcgagtc aggacattaa tggatattta acc                                    33

<210> SEQ ID NO 82
<211> LENGTH: 21
<212> TYPE: DNA
<213> ORGANISM: Artificial Sequence
<220> FEATURE:
<223> OTHER INFORMATION: Synthetic polynucleotide encoding
      immunoglobulin CDR2

<400> SEQUENCE: 82
cgcgcaaaca gattgttaga t                                                 21

<210> SEQ ID NO 83
<211> LENGTH: 27
<212> TYPE: DNA
<213> ORGANISM: Artificial Sequence
<220> FEATURE:
<223> OTHER INFORMATION: Synthetic polynucleotide encoding
      immunoglobulin CDR3

<400> SEQUENCE: 83
ctgcagtatg atgagtttcc gtggacg                                           27

<210> SEQ ID NO 84
<211> LENGTH: 11
<212> TYPE: PRT
<213> ORGANISM: Artificial Sequence
<220> FEATURE:
<223> OTHER INFORMATION: Synthetic polypeptide for immunoglobulin CDR1

<400> SEQUENCE: 84

Lys Ala Ser Gln Asp Ile Asn Gly Tyr Leu Thr
1               5                   10

<210> SEQ ID NO 85
<211> LENGTH: 7
<212> TYPE: PRT
<213> ORGANISM: Artificial Sequence
<220> FEATURE:
<223> OTHER INFORMATION: Synthetic polypeptide for immunoglobulin CDR2

<400> SEQUENCE: 85

Arg Ala Asn Arg Leu Leu Asp
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic polypeptide for immunoglobulin CDR3

<400> SEQUENCE: 86

Leu Gln Tyr Asp Glu Phe Pro Trp Thr
1               5

<210> SEQ ID NO 87
<211> LENGTH: 411
<212> TYPE: DNA
<213> ORGANISM: Artificial Sequence
<220> FEATURE:
<223> OTHER INFORMATION: Synthetic polynucleotide encoding
      immunoglobulin heavy chain

<400> SEQUENCE: 87

```
atgggcaggc ttacttcttc attcctgcta ctgattgtcc ctgcatatgt cctgtcccag      60
gttactctga aagagtctga ccctgggata ttgcagccct cccagaccct cagtctgact     120
tgttctttct ctgggttttc actgagcact tctggtatgg gtgtaggctg gattcgtcag     180
ccatcaggga agggtctgga atggctggca cacatttggt gggatgatgt caagcgctat     240
aactcagccc tgaagaaccg actgactatc tccaaggata cctccagcag ccaggtattc     300
ctcaagatcg ccaatgtgga cactgcagat actgccacat actactgtgc tcgaatagcc     360
cggcacttct ttgactactg gggccaaggc accactctca cagtctcctc a              411
```

<210> SEQ ID NO 88
<211> LENGTH: 137
<212> TYPE: PRT
<213> ORGANISM: Artificial Sequence
<220> FEATURE:
<223> OTHER INFORMATION: Synthetic polypeptide for immunoglobulin heavy
      chain

<400> SEQUENCE: 88

Met Gly Arg Leu Thr Ser Ser Phe Leu Leu Leu Ile Val Pro Ala Tyr
1               5                   10                  15

Val Leu Ser Gln Val Thr Leu Lys Glu Ser Asp Pro Gly Ile Leu Gln
                20                  25                  30

```
Pro Ser Gln Thr Leu Ser Leu Thr Cys Ser Phe Ser Gly Phe Ser Leu
        35                  40                  45

Ser Thr Ser Gly Met Gly Val Gly Trp Ile Arg Gln Pro Ser Gly Lys
    50                  55                  60

Gly Leu Glu Trp Leu Ala His Ile Trp Trp Asp Asp Val Lys Arg Tyr
 65                  70                  75                  80

Asn Ser Ala Leu Lys Asn Arg Leu Thr Ile Ser Lys Asp Thr Ser Ser
                85                  90                  95

Ser Gln Val Phe Leu Lys Ile Ala Asn Val Asp Thr Ala Asp Thr Ala
            100                 105                 110

Thr Tyr Tyr Cys Ala Arg Ile Ala Arg His Phe Phe Asp Tyr Trp Gly
            115                 120                 125

Gln Gly Thr Thr Leu Thr Val Ser Ser
        130                 135
```

<210> SEQ ID NO 89
<211> LENGTH: 381
<212> TYPE: DNA
<213> ORGANISM: Artificial Sequence
<220> FEATURE:
<223> OTHER INFORMATION: Synthetic polynucleotide encoding
      immunoglobulin light chain

<400> SEQUENCE: 89

```
atgaggaccc ctgctcagtt tcttggaatc ttgttgctct ggtttccagg tatcaaatgt    60
gacatcaaga tgacccagtc tccatcttcc atgtatgcat ctctgggaga gagagtcact   120
atcacttgca aggcgagtca ggacattcat ggctatttaa gctggttcca ccagaaaccc   180
gtgaaatctc ctaagaccct gatctatcgt gcaaacagat tgatagatgg ggtcccatca   240
aggttcagtg gcagtggatc tgggcaagat tattttctca ccatcagcag cctggagtat   300
gaagatatgg gaatttatta ttgtctacag tatgatgagt ttccgtggac gttcggtgga   360
ggcaccaagc tggaaatcaa a                                             381
```

<210> SEQ ID NO 90
<211> LENGTH: 127
<212> TYPE: PRT
<213> ORGANISM: Artificial Sequence
<220> FEATURE:
<223> OTHER INFORMATION: Synthetic polypeptide for immunoglobulin light
      chain

<400> SEQUENCE: 90

```
Met Arg Thr Pro Ala Gln Phe Leu Gly Ile Leu Leu Leu Trp Phe Pro
 1               5                  10                  15

Gly Ile Lys Cys Asp Ile Lys Met Thr Gln Ser Pro Ser Ser Met Tyr
            20                  25                  30

Ala Ser Leu Gly Glu Arg Val Thr Ile Thr Cys Lys Ala Ser Gln Asp
        35                  40                  45

Ile His Gly Tyr Leu Ser Trp Phe His Gln Lys Pro Val Lys Ser Pro
    50                  55                  60

Lys Thr Leu Ile Tyr Arg Ala Asn Arg Leu Ile Asp Gly Val Pro Ser
 65                  70                  75                  80

Arg Phe Ser Gly Ser Gly Ser Gly Gln Asp Tyr Phe Leu Thr Ile Ser
                85                  90                  95

Ser Leu Glu Tyr Glu Asp Met Gly Ile Tyr Tyr Cys Leu Gln Tyr Asp
            100                 105                 110
```

Glu Phe Pro Trp Thr Phe Gly Gly Gly Thr Lys Leu Glu Ile Lys
        115                 120                 125

<210> SEQ ID NO 91
<211> LENGTH: 36
<212> TYPE: DNA
<213> ORGANISM: Artificial Sequence
<220> FEATURE:
<223> OTHER INFORMATION: Synthetic polynucleotide encoding
      immunoglobulin CDR1

<400> SEQUENCE: 91
gggttttcac tgagcacttc tggtatgggt gtaggc                            36

<210> SEQ ID NO 92
<211> LENGTH: 48
<212> TYPE: DNA
<213> ORGANISM: Artificial Sequence
<220> FEATURE:
<223> OTHER INFORMATION: Synthetic polynucleotide encoding
      immunoglobulin CDR2

<400> SEQUENCE: 92
cacatttggt gggatgatgt caagcgctat aactcagccc tgaagaac               48

<210> SEQ ID NO 93
<211> LENGTH: 24
<212> TYPE: DNA
<213> ORGANISM: Artificial Sequence
<220> FEATURE:
<223> OTHER INFORMATION: Synthetic polynucleotide encoding
      immunoglobulin CDR3

<400> SEQUENCE: 93
atagcccggc acttctttga ctac                                        24

<210> SEQ ID NO 94
<211> LENGTH: 12
<212> TYPE: PRT
<213> ORGANISM: Artificial Sequence
<220> FEATURE:
<223> OTHER INFORMATION: Synthetic polypeptide of immunoglobulin CDR1

<400> SEQUENCE: 94

Gly Phe Ser Leu Ser Thr Ser Gly Met Gly Val Gly
1               5                   10

<210> SEQ ID NO 95
<211> LENGTH: 16
<212> TYPE: PRT
<213> ORGANISM: Artificial Sequence
<220> FEATURE:
<223> OTHER INFORMATION: Synthetic polypeptide of immunoglobulin CDR2

<400> SEQUENCE: 95

His Ile Trp Trp Asp Asp Val Lys Arg Tyr Asn Ser Ala Leu Lys Asn
1               5                   10                  15

<210> SEQ ID NO 96
<211> LENGTH: 8
<212> TYPE: PRT
<213> ORGANISM: Artificial Sequence
<220> FEATURE:
<223> OTHER INFORMATION: Synthetic polypeptide of immunoglobulin CDR3

<400> SEQUENCE: 96

Ile Ala Arg His Phe Phe Asp Tyr

<210> SEQ ID NO 97
<211> LENGTH: 33
<212> TYPE: DNA
<213> ORGANISM: Artificial Sequence
<220> FEATURE:
<223> OTHER INFORMATION: Synthetic polynucleotide encoding
      immunoglobulin CDR1

<400> SEQUENCE: 97
aaggcgagtc aggacattca tggctattta agc                                33

<210> SEQ ID NO 98
<211> LENGTH: 21
<212> TYPE: DNA
<213> ORGANISM: Artificial Sequence
<220> FEATURE:
<223> OTHER INFORMATION: Synthetic polynucleotide encoding
      immunoglobulin CDR2

<400> SEQUENCE: 98
cgtgcaaaca gattgataga t                                             21

<210> SEQ ID NO 99
<211> LENGTH: 27
<212> TYPE: DNA
<213> ORGANISM: Artificial Sequence
<220> FEATURE:
<223> OTHER INFORMATION: Synthetic polynucleotide encoding
      immunoglobulin CDR3

<400> SEQUENCE: 99
ctacagtatg atgagtttcc gtggacg                                       27

<210> SEQ ID NO 100
<211> LENGTH: 11
<212> TYPE: PRT
<213> ORGANISM: Artificial Sequence
<220> FEATURE:
<223> OTHER INFORMATION: Synthetic polypeptide of immunoglobulin CDR1

<400> SEQUENCE: 100

Lys Ala Ser Gln Asp Ile His Gly Tyr Leu Ser
1               5                   10

<210> SEQ ID NO 101
<211> LENGTH: 7
<212> TYPE: PRT
<213> ORGANISM: Artificial Sequence
<220> FEATURE:
<223> OTHER INFORMATION: Synthetic polypeptide of immunoglobulin CDR2

<400> SEQUENCE: 101

Arg Ala Asn Arg Leu Ile Asp
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic polypeptide of immunoglobulin CDR3

<400> SEQUENCE: 102

Leu Gln Tyr Asp Glu Phe Pro Trp Thr
1               5

```
<210> SEQ ID NO 103
<211> LENGTH: 166
<212> TYPE: PRT
<213> ORGANISM: Homo Sapiens

<400> SEQUENCE: 103

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Pro Arg Ala Gln Ala Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
        130                 135                 140

Val Leu Gly Arg Thr Gly Leu Leu Ala Asp Leu Leu Pro Ser Phe Ala
145                 150                 155                 160

Val Glu Ile Met Pro Glu
                165
```

C1ORF32 ANTIBODIES, AND USES THEREOF FOR TREATMENT OF CANCER

FIELD OF THE PRESENT INVENTION

This invention relates in at least some aspects to C1ORF32-specific antibodies, antibody fragments, conjugates, alternative scaffolds, compositions comprising same, and uses thereof, for treatment of cancer.

BACKGROUND OF THE PRESENT INVENTION

T-cell activation plays a central role in driving both protective and pathogenic immune responses, and it requires the completion of a carefully orchestrated series of specific steps that can be preempted or disrupted by any number of critical events. Naïve T cells must receive two independent signals from antigen-presenting cells (APC) in order to become productively activated. The first, Signal 1, is antigen-specific and occurs when T cell antigen receptors encounter the appropriate antigen-MHC complex on the APC. This signal is necessary but not sufficient for the determination of the faith of the immune response. This is determined by a second, antigen-independent signal (Signal 2) which is delivered through a T cell costimulatory molecule that engages its APC-expressed ligand. This second signal could be either stimulatory (positive costimulation) or inhibitory (negative costimulation or coinhibition). In the absence of a costimulatory signal, or in the presence of a coinhibitory signal, T-cell activation is impaired or aborted, which may lead to a state of antigen-specific unresponsiveness (known as T-cell anergy), or may result in T-cell apoptotic death.

Costimulatory molecule pairs usually consist of ligands expressed on APCs and their cognate receptors expressed on T cells. The prototype ligand/receptor pairs of costimulatory molecules are B7/CD28 and CD40/CD40L.

Tumor cells often express negative costimulatory molecules and thus take advantage of the immunomodulatory activity of these molecules to evade immune surveillance. Such tumor expressed B7s serve as tumor-associated antigens (TAAs) and have become attractive cancer biomarkers as well as drug targets for active (vaccination) and passive (antibody-mediated) cancer immunotherapy providing strategies to break immune tolerance and stimulate the immune system.

Cancer vaccination involves the administration of tumor antigens and is used to break immune tolerance and induce an active T-cell response to the tumor. Vaccine therapy includes the use of naked DNA, peptides, recombinant protein, and whole cell therapy, where the patient's own tumor cells are used as the source of the vaccine.

The applications of anti-TAA antibodies for treatment of cancer include therapy with naked antibody, therapy with a drug/toxin-conjugated antibody, adoptive immunotherapy and fusion therapy with cellular immunity (development of cytotoxic T-lymphocyte (CTL) or natural killer (NK)-cell populations with anti-TAA antibody activity). The antigenic epitopes that are targeted by these therapeutic approaches are present at the cell surface, overexpressed in tumor cells compared to non-tumor cells, and are targeted by antibodies that block functional activity, inhibit cell proliferation, or induce cell death.

Negative regulators of the immune system, called immune checkpoints, play critical roles in maintenance of tolerance to self-antigens. Immune checkpoints are used by the tumor and become barriers to generating effective tumor immunity, playing important roles in restraining otherwise effective anti-tumor immunologic responses. Several immune checkpoints are negative costimulatory proteins, members of the B7/CD28 family of immune regulators. Immunomodulatory antibody therapies that target these negative regulator checkpoints, such as those directed against CTLA4 and PD-1, have demonstrated promising clinical results.

Passive immunotherapy strategies are well established in oncology and involve passive transfer of anti-cancer monoclonal antibodies as targeted therapy. In contrast, active immunotherapy strategies are aimed to elicit the body's anti-tumor immunity, and have only recently began to show success in treatment of cancer. Activating the immune system for therapeutic benefit in cancer has long been a goal in oncology. Among several active immunotherapy approaches, immunomodulatory antibody therapy refers to the use of monoclonal antibodies that directly enhance the function of components of the anti-tumor immune response, such as T cells, or block immunologic checkpoints that would otherwise restrain effective anti-tumor immunity. Recently this strategy, also named immune regulatory antibodies, has finally gained proof of concept in clinical trials. The blockade of immune checkpoints seems to unleash the potential of the anti-tumor immune response in a fashion that is transforming human cancer therapeutics. Most notably is the ability of the anti-CTLA4 antibody, Ipilimumab, to achieve a significant increase in survival for patients with metastatic melanoma, for which conventional therapies have failed. Substantial clinical responses have also been obtained in patients treated with an anti-PD-1 antibody, MDX1106.

Highly immunogenic tumors, such as malignant melanoma, are most responsive to immune system manipulation, and thus many of these treatment modalities have been first applied to patients with melanoma. However, numerous ongoing clinical studies are geared at targeting a variety of tumors by combining agents that target immune checkpoints with other more conventional approaches such as targeted therapy, chemotherapy and radiotherapy, or with other novel immunotherapeutic approaches, including therapeutic cancer vaccines. Extensive preclinical data has indeed shown that therapeutic agents that result in tumor cell death liberate tumor antigens and provide the right fuel for checkpoint-blocking antibodies even in poorly immunogenic tumors, leading to impressive therapeutic synergy among such agents. Similar observations were obtained in multiple preclinical studies, demonstrating the synergistic efficacy of therapeutic cancer vaccines and checkpoint blockade.

Such agents could be administered in conjunction with tumor-specific antigens, as an adjuvant that serves to enhance the immune response to the antigen in the patient. In addition, such agents could be of use in other types of cancer immunotherapy, such as adoptive immunotherapy, in which tumor-specific T cell populations are expanded and directed to attack and kill tumor cells. Agents capable of augmenting such anti-tumor response have great therapeutic potential and may be of value in the attempt to overcome the obstacles to tumor immunotherapy.

Regulating costimulation using agonists and antagonists to various costimulatory proteins has been extensively studied as a strategy for treating autoimmune diseases, graft rejection, allergy and cancer. This field has been clinically pioneered by CTLA4-Ig (Abatacept, Orencia®) that is approved for treatment of RA, and by the anti-CTLA4 antibody (Ipilimumab, Yervoy®), recently approved for the treatment of melanoma. Other costimulation regulators are currently in advanced stages of clinical development including anti PD-1 antibody (MDX-1106) which is in development for treatment of advanced/metastatic clear-cell renal cell carcinoma (RCC) and anti-CD40L Antibody (BG9588, Antova®) for treatment of renal allograft transplantation. Furthermore, the accumulating evidence linking regulation of costimulation and various types of infections support a promising potential for such agents as therapy for infectious diseases. In accordance with this, such agents are in clinical development for viral infections, for example the anti PD-1 Ab, MDX-1106, is being tested for treatment of hepatitis C. Another example is CP-675,206 (tremelimumab) and anti-CTLA4 Ab is in a clinical trial in hepatitis C virus-infected patients with hepatocellular carcinoma.

Accumulations of inducible regulatory T cells (iTregs) are commonly seen in many tumors, and form the major subset of immune suppressor cells in the tumor tissue. Tregs create an immunosuppressive environment and regulate anti-tumor immunity, and thus represent a major tumor resistance mechanism from immune surveillance. iTregs are therefore viewed as important cellular targets for cancer therapy.

In addition to their function in dampening effector T cell responses, multiple immune-checkpoint receptors, such as CTLA4 and PD-1, and others like TIM3 and LAG3, are expressed at high levels on the surface of iTregs and directly promote Treg cell-mediated suppression of effector immune responses. Many of the immune-checkpoint antibodies in clinical testing most likely block the immunosuppressive activity of iTregs as a mechanism of enhancing anti-tumor immunity. Indeed, two important factors in the mode of action of CTLA4 blockade by ipilimumab are the enhancement of effector T cell activity, and inhibition of Treg immunosuppressive activity.

Several strategies, used alone or in combination with conventional treatments or immunotherapies, are in development in order to disarm iTregs and restore antitumor functions of effector T cells.

B cells play a critical role in recognition of foreign antigens and they produce the antibodies necessary to provide protection against various type of infectious agents. T cell help to B cells is a pivotal process of adaptive immune responses. Follicular helper T (Tfh) cells are a subset of CD4+ T cells specialized in B cell help (reviewed by Crotty, Annu. Rev. Immunol. 29: 621-663, 2011). Tfh cells express the B cell homing chemokine receptor, CXCR5, which drives Tfh cell migration into B cell follicles within lymph nodes in a CXCL13-dependent manner. The requirement of Tfh cells for B cell help and T cell-dependent antibody responses, indicates that this cell type is of great importance for protective immunity against various types of infectious agents, as well as for rational vaccine design.

BRIEF SUMMARY OF THE PRESENT INVENTION

Despite recent progress in the understanding of cancer biology and cancer treatment, the success rate for cancer therapy remains low. Therefore, there is an unmet need for new therapies which can successfully treat cancer, such as for example, specific blocking antibodies, which have a therapeutic application in stimulating the immune system against tumors.

By "blocking antibody" it is meant any antibody that binds to a particular protein or epitope on a protein, and then optionally blocks interactions of that protein with one or more other binding partners.

According to at least some embodiments, the present invention provides monoclonal and/or polyclonal antibodies and antigen binding fragments and/or alternative scaffolds and/or conjugates and/or immunoconjugates containing same that specifically bind any one of C1ORF32 (ILDR2) proteins, selected from the group consisting of any one of SEQ ID NOs: 1, 7, 9, 13, 17, 103, and/or their corresponding extracellular domains, selected from the group consisting of any one of SEQ ID NOs: 14, 10, 11, 15, and/or fragments, and/or epitopes thereof, wherein these antibodies are adapted to be used as therapeutic and/or diagnostic agents (both in vitro and in vivo diagnostic methods), particularly for treatment and/or diagnosis of cancer and malignancies, wherein the cancer is non-metastatic, invasive or metastatic. As used herein, the term "antibody" may optionally refer to any of the following (and also optionally combinations of the following): monoclonal and/or polyclonal antibodies and antigen binding fragments and/or alternative scaffolds and/or conjugates and/or immunoconjugates.

Surprisingly, C1ORF32-Ig protein was shown to enhance the differentiation of CD4 T cells to iTregs, suggesting that the C1ORF32 pathway is involved in iTregs induction and differentiation. According to at least some embodiments of the present invention, targeting C1ORF32 with blocking monoclonal antibodies inhibits iTregs accumulation and immunosuppressive function. According to at least some embodiments of the present invention, such blocking C1ORF32 antibodies enhance effector T cell activity. According to at least some embodiments, the present invention provides blocking antibody that specifically binds any one of C1ORF32 (ILDR2) proteins, selected from the group consisting of any one of SEQ ID NOs: 1, 7, 9, 13, 17, 103, and/or their corresponding extracellular domains, selected from the group consisting of any one of SEQ ID NOs: 14, 10, 11, 15, and/or fragments, and/or epitopes thereof, may optionally and preferably be specifically applied to cancer immunotherapy, alone or in combination with a potentiating agent(s), which increase an endogenous anti-tumor responses.

Furthermore, surprisingly, it has been found that an antibody that specifically binds any one of C1ORF32 (ILDR2) proteins, selected from the group consisting of any one of SEQ ID NOs: 1, 7, 9, 13, 17, 103, and/or their corresponding extracellular domains, selected from the group consisting of any one of SEQ ID NOs: 14, 10, 11, 15, and/or fragments, and/or epitopes thereof, may optionally and preferably be specifically applied to treatment of certain cancers, against which such an antibody demonstrates particular efficacy. Pharmaceutical compositions comprising such an antibody, in conjunction with a pharmaceutically acceptable carrier, are also provided herein.

Furthermore, surprisingly, it has been found that said antibody demonstrates particular efficacy in specific cancers, including cancers in which C1ORF32 is expressed on malignant cells, immune cells infiltrating into the tumor (such as T-cells, B-cell, macrophages, myeloid derive suppressor cells, mast cells) and/or stromal tumor cells. C1ORF32 expression on any of the cells listed above could be either present prior to treatment by standard of care agents or induced post treatment.

Such specific cancers include any one or more of Thyroid Carcinoma, squamous cell carcinoma of the esophagus; breast carcinoma, breast comedocarcinoma, breast invasive ductal carcinoma, breast Medullary Carcinoma, ovarian carcinoma, ovarian Papillary Serous and Mucinous cancer, ovarian Granular cell tumour, Surface epithelial-stromal tumor (Adenocarcinoma) of the ovary, ovarian cystadenocarcinoma, ovarian Endometrioid tumor; kidney cancer, kidney Clear cell carcinoma, kidney Chromophobe adenoma, kidney sarcomatoides carcinoma, Prostate adenocarcinoma, Benign prostatic hyperplasia, Hepatocellular carcinoma, malignant hepatoma, fibrolamellar of the liver, pseudoglandular (adenoid) of the liver, pleomorphic (giant cell) of the liver, clear cell carcinoma of the liver, Cholangiocarcinoma, Pancreas cancer, Ductal and Mucinous Adenocarcinoma of the pancreas, Islet cell carcinoma, familial atypical multiple mole melanoma-pancreatic cancer syndrome (FAMMM-PC), Exocrine pancreas cancer, ductal adenocarcinoma of the pancreas, pancreas denosquamous carcinoma, pancreas signet ring cell carcinoma, pancreas hepatoid carcinoma, pancreas colloid carcinoma, pancreas undifferentiated carcinoma, undifferentiated carcinoma with osteoclast-like giant cells of the pancreas, Low- to intermediate-grade neuroendocrine carcinoma of the pancreas, pancreatic carcinoid tumor; Malignant melanoma; bone sarcoma, cartilage sarcoma, soft tissue sarcoma, Lymphoma, Uterine cancer, Bladder cancer, Lung cancer, testicular seminoma, Colo-rectal cancer, and spinal cord tumor, wherein:

1. Thyroid Carcinoma preferably comprises one or more of Thyroid Papillary Carcinoma, Thyroid Follicular Carcinoma (preferably stage II and III), incidental papillary carcinoma (IPC), Medullary thyroid cancer, Anaplastic thyroid cancer.

2. Breast carcinoma preferably comprises Invasive Ductal Carcinoma, preferably stage II to IV and/or poorly differentiated Invasive Ductal Carcinoma, comedocarcinoma and Medullary Carcinoma, preferably Grade 2.

3. Ovarian carcinoma preferably comprises one or more of Papillary Serous and Mucinous (preferably stages Ic to IIIb), Granular cell tumour, Surface epithelial-stromal tumor (Adenocarcinoma), cystadenocarcinoma and Endometrioid tumor.

4. Kidney (renal) cancer preferably comprises one or more of Clear cell carcinoma (preferably stage I to II), Chromophobe adenoma, sarcomatoides carcinoma.

5. Prostate adenocarcinoma preferably comprises any suitable stage of prostate adenocarcinoma, preferably stage I to III, Benign prostatic hyperplasia, or prostate adenocarcinoma having a Gleason score of 5 or higher. In one particular embodiment, the prostate adenocarcinoma is selected from Gleason scores 5 or higher.

6. Hepatocellular carcinoma (HCC) preferably comprises one or more of stage II and III hepatocellular carcinoma, malignant hepatoma, fibrolamellar, pseudoglandular (adenoid), pleomorphic (giant cell) and clear cell HCC and Cholangiocarcinoma.

7. Pancreatic cancer preferably comprises one or more of Ductal and Mucinous Adenocarcinoma, Islet cell carcinoma, familial atypical multiple mole melanoma-pancreatic cancer syndrome (FAMMM-PC), Exocrine pancreas cancers, ductal adenocarcinoma, denosquamous carcinomas, signet ring cell carcinomas, hepatoid carcinomas, colloid carcinomas, undifferentiated carcinomas, and undifferentiated carcinomas with osteoclast-like giant cells, Low- to intermediate-grade neuroendocrine carcinomas and pancreatic carcinoid tumors.

8. Malignant melanoma preferably comprises stage IV malignant melanoma and/or one or more of Lentigo maligna Lentigo maligna melanoma, Superficial spreading melanoma, Acral lentiginous melanoma, Mucosal melanoma, Nodular melanoma, Polypoid melanoma, Desmoplastic melanoma, Amelanotic melanoma and Soft-tissue melanoma.

9. Sarcoma preferably comprises one or more of sarcomas of bone, cartilage and of soft tissue including but not limited to Osteogenic sarcoma, Chondrosarcoma, Leiomyosarcoma, Angiosarcoma, Askin's Tumor, Ewing's sarcoma, Kaposi's sarcoma, Liposarcoma, Malignant fibrous histiocytoma, Rhabdomyosarcoma and Neurofibrosarcoma.

10. Lymphoma preferably comprises one or more of Hodgkin's lymphoma (Nodular sclerosing, Mixed-cellularity subtype, Lymphocyte-rich or Lymphocytic predominance, Lymphocyte depleted and Unspecified), B-cell Lymphoma (Diffuse large B cell lymphoma, Follicular lymphoma, Mucosa-Associated Lymphatic Tissue lymphoma (MALT), Small cell lymphocytic lymphoma, Burkitt lymphoma, Mediastinal large B cell lymphoma, Waldenström macroglobulinemia, Nodal marginal zone B cell lymphoma (NMZL), Splenic marginal zone lymphoma (SMZL), Intravascular large B-cell lymphoma, Primary effusion lymphoma, Lymphomatoid granulomatosis), Mantle cell lymphoma (MCL), T-cell Lymphoma (Extranodal T cell lymphoma, Cutaneous T cell lymphomas: Sézary syndrome and Mycosis fungoides, Anaplastic large cell lymphoma, Angioimmunoblastic T cell lymphoma).

11. Uterine cancer preferably comprises uterine cancer is selected from Endometroid Adenocarcinoma (preferably stages I to IIIc).

12. Bladder cancer preferably comprises Transitional Cell carcinoma (preferably stage II to IV).

13. Lung cancer preferably comprises Small Cell Lung Cancer (preferably stage I, to IIIb), Non Small Cell Lung Cancer (preferably poorly to moderately differentiated squamous and adeno carcinoma) and Large-cell carcinoma.

14. Colo-rectal cancer preferably comprises colon and rectal adenocarcinoma (preferably Moderate to Poorly Differentiated).

According to at least some embodiments, for any of the above described cancers, optionally each of the above described cancer type or subtype may optionally form a separate embodiment and/or may optionally be combined as embodiments or subembodiments.

According to at least some embodiments, for any of the above described cancers, methods of treatment and also uses of the antibodies and pharmaceutical compositions described herein are provided wherein the cancer expresses C1ORF32 polypeptides comprised in SEQ ID NOs: 1, 7, 9, 13, 17, 103, and/or their corresponding extracellular domains, selected from the group consisting of any one of SEQ ID NOs: 10, 14, 11, 15, and/or fragments, and/or epitopes thereof, on the cancer cells or in the immune cells infiltrating the tumor.

As used herein, when the term "epitopes thereof" appears, it may optionally and without limitation refer to epitopes as embodied in SEQ ID NOs 2, 3, 5, or 6.

According to at least some embodiments, the present invention provides a pharmaceutical composition comprising monoclonal and/or polyclonal antibodies and/or antigen binding fragments that specifically bind any one of C1ORF32 proteins, selected from the group consisting of any one of SEQ ID NOs: 1, 7, 9, 13, 17, 103, and/or their corresponding extracellular domains, selected from the group consisting of any one of SEQ ID NOs: 14, 10, 11, 15, and/or fragments, and/or epitopes thereof, for treatment of cancer and malignancies, optionally wherein the cancer is non-metastatic, invasive or metastatic. Optionally for any application or use described herein, any of the described monoclonal antibodies may be used.

According to at least some embodiments, there is provided a monoclonal or polyclonal antibody or an antigen binding fragment thereof comprising an antigen binding site that binds specifically to any of SEQ ID NOS: 2, 3, 5, 6.

According to at least some embodiments, there is provided a monoclonal or polyclonal antibody or an antigen binding fragment thereof comprising an antigen binding site that binds specifically to any one of the C1ORF32 polypeptides having the sequence of any one of SEQ ID NOs: 1, 7-10, 11, 13-15, 17, 103, and/or fragments, and/or epitopes thereof, adapted for treatment of cancer, wherein the cancer is selected from the group consisting of Thyroid Carcinoma, carcinoma of the esophagus, Invasive Ductal breast Carcinoma, breast comedocarcinoma, breast Medullary Carcinoma Grade 2, ovarian cancer selected from the group consisting of Serous and Mucinous, Granular cell tumor, Surface epithelial-stromal tumor (Adenocarcinoma), cystadenocarcinoma and Endometrioid tumor; kidney cancer selected from the group consisting of Clear cell carcinoma, Chromophobe adenoma, and sarcomatoides carcinoma; prostate adenocarcinoma having a Gleason score of 5 or higher, stage I to III prostate adenocarcinoma, Benign prostatic hyperplasia, stage II and III hepatocellular carcinoma, malignant hepatoma, fibrolamellar hepatocellular carcinoma, pseudoglandular (adenoid) hepatocellular carcinoma, pleomorphic (giant cell) hepatocellular carcinoma, clear cell HCC, Cholangiocarcinoma, pancreas cancer selected from Ductal and Mucinous Adenocarcinoma, Islet cell carcinoma, familial atypical multiple mole melanoma-pancreatic cancer syndrome (FAMMM-PC), Exocrine pancreas cancers, ductal adenocarcinoma, denosquamous carcinomas, signet ring cell carcinomas, hepatoid carcinomas, colloid carcinomas, undifferentiated carcinomas, and undifferentiated carcinomas with osteoclast-like giant cells, Low- to intermediate-grade neuroendocrine carcinomas and pancreatic carcinoid tumors, stage IV malignant melanoma, Lentigo maligna melanoma, Superficial spreading melanoma, Acral lentiginous melanoma, Mucosal melanoma, Nodular melanoma, Polypoid melanoma, Desmoplastic melanoma, Amelanotic melanoma, Soft-tissue melanoma, Osteogenic sarcoma, Chondrosarcoma, Leiomyosarcoma, Angiosarcoma, Askin's Tumor, Ewing's sarcoma, Kaposi's sarcoma, Liposarcoma, Malignant fibrous histiocytoma, Rhabdomyosarcoma, Neurofibrosarcoma, Hodgkin's lymphoma, B-cell Lymphoma, Mantle cell lymphoma (MCL), T-cell Lymphoma, Endometroid Adenocarcinoma, Bladder Transitional Cell carcinoma, Small Cell Lung Cancer, Non Small Cell Lung Cancer, Large-cell lung carcinoma, testicular seminoma, moderate to poorly differentiated Colo-rectal adenocarcinoma, and spinal cord tumor.

According to at least some embodiments, there is provided a monoclonal or polyclonal antibody or an antigen binding fragment thereof comprising an antigen binding site that binds specifically to any of SEQ ID NOS: 2, 3, 5, 6.

According to at least some embodiments, there is provided a monoclonal antibody having the amino acid sequence that comprises:

at least one of a light chain variable region comprising a CDR1 region comprising the sequence selected from SEQ ID NO: 52, SEQ ID NO: 68, SEQ ID NO: 84, and SEQ ID NO: 100; a CDR2 region comprising the sequence selected from SEQ ID NO: 53, SEQ ID NO: 69, SEQ ID NO: 85 and SEQ ID NO: 101; or a CDR3 region comprising the sequence selected from SEQ ID NO: 54, SEQ ID NO: 70, SEQ ID NO: 86, and SEQ ID NO: 102, or a sequence having at least 90% homology thereto, or a sequence having at least 95% homology thereto; or at least one of a heavy chain variable region comprising a CDR1 region comprising the sequence selected from SEQ ID NO: 62, SEQ ID NO: 46, SEQ ID NO: 78, and SEQ ID NO: 94; a CDR2 region comprising the sequence selected from SEQ ID NO: 63, SEQ ID NO: 47, SEQ ID NO: 79 and SEQ ID NO: 95; or a CDR3 region comprising the sequence selected from SEQ ID NO: 64, SEQ ID NO: 48, SEQ ID NO: 80, and SEQ ID NO: 96, or a sequence having at least 90% homology thereto, or a sequence having at least 95% homology thereto.

Optionally, for example in some optional embodiments, the antibody comprises:

at least one light chain variable region comprising a CDR1 region comprising the sequence selected from SEQ ID NO: 52, SEQ ID NO: 68, SEQ ID NO: 84, and SEQ ID NO: 100; a CDR2 region comprising the sequence selected from SEQ ID NO: 53, SEQ ID NO: 69, SEQ ID NO: 85 and SEQ ID NO: 101; and a CDR3 region comprising the sequence selected from SEQ ID NO: 54, SEQ ID NO: 70 SEQ ID NO: 86, and SEQ ID NO: 102, or a sequence having at least 90% homology thereto, or a sequence having at least 95% homology thereto; and/or at least one heavy chain variable region comprising a CDR1 region comprising the sequence selected from SEQ ID NO: 62, SEQ ID NO: 46, SEQ ID NO: 78, and SEQ ID NO: 94; a CDR2 region comprising the sequence selected from SEQ ID NO: 63, SEQ ID NO: 47, SEQ ID NO: 79 and SEQ ID NO: 95; and a CDR3 region comprising the sequence selected from SEQ ID NO: 64, SEQ ID NO: 48, SEQ ID NO: 80, and SEQ ID NO: 96, or a sequence having at least 90% homology thereto, or a sequence having at least 95% homology thereto.

Optionally, for example in some optional embodiments, the antibody comprises:

1) at least one light chain variable region comprising a CDR1 region comprising the sequence set forth in SEQ ID NO: 52; a CDR2 region comprising the sequence set forth in SEQ ID NO: 53; and a CDR3 region comprising the sequence set forth in SEQ ID NO: 54, or a sequence having at least 90% homology thereto, or a sequence having at least 95% homology thereto; and/or 2) at least one heavy chain variable region comprising a CDR1 region comprising the sequence set forth in SEQ ID NO: 62; a CDR2 region comprising the sequence set forth in SEQ ID NO: 63; and a CDR3 region comprising the sequence set forth in SEQ ID NO: 64, or a sequence having at least 90% homology thereto, or a sequence having at least 95% homology thereto.

Optionally, for example in alternative embodiments, the antibody comprises:

1) at least one light chain variable region comprising a CDR1 region comprising the sequence set forth in SEQ ID NO: 68; a CDR2 region comprising the sequence set forth in SEQ ID NO: 69; and a CDR3 region comprising the sequence set forth in SEQ ID NO: 70, or a sequence having at least 90% homology thereto, or a sequence having at least 95% homology thereto; and/or 2) at least one heavy chain variable region comprising a CDR1 region comprising the sequence set forth in SEQ ID NO: 46; a CDR2 region comprising the sequence set forth in SEQ ID NO: 47; and a CDR3 region comprising the sequence set forth in SEQ ID NO: 48, or a sequence having at least 90% homology thereto, or a sequence having at least 95% homology thereto.

Optionally, for example in alternative embodiments, the antibody comprises:

1) at least one light chain variable region comprising a CDR1 region comprising the sequence set forth in SEQ ID NO: 84; a CDR2 region comprising the sequence set forth in SEQ ID NO: 85; and a CDR3 region comprising the sequence set forth in SEQ ID NO: 86, or a sequence having at least 95% homology thereto, or a sequence having at least 90% homology thereto; and/or 2) at least one heavy chain variable region comprising a CDR1 region comprising the sequence set forth in SEQ ID NO: 78; a CDR2 region comprising the sequence set forth in SEQ ID NO: 79; and a CDR3 region comprising the sequence set forth in SEQ ID NO: 80, or a sequence having at least 95% homology thereto, or a sequence having at least 90% homology thereto.

Optionally, for example in alternative embodiments, the antibody comprises:

1) at least one light chain variable region comprising a CDR1 region comprising the sequence set forth in SEQ ID NO: 100; a CDR2 region comprising the sequence set forth in SEQ ID NO: 101; and a CDR3 region comprising the sequence set forth in SEQ ID NO: 102, or a sequence having at least 95% homology thereto, or a sequence having at least 90% homology thereto; and/or 2) at least one heavy chain variable region comprising a CDR1 region comprising the sequence set forth in SEQ ID NO: 94; a CDR2 region comprising the sequence set forth in SEQ ID NO: 95; and a CDR3 region comprising the sequence set forth in SEQ ID NO: 96, or a sequence having at least 95% homology thereto, or a sequence having at least 90% homology thereto.

Optionally, the antibody has the amino acid sequence of the heavy chain selected from any one of SEQ ID NOs: 40, 56, 72, 88, and/or the amino acid sequence of the light chain selected from any one of SEQ ID NOs: 42, 58, 74, 90, or a sequence having at least 85% homology thereto, or a sequence having at least 90% homology thereto, or a sequence having at least 95% homology thereto.

Optionally, the antibody has the amino acid sequence of the heavy chain set forth in SEQ ID NO: 40, and/or the amino acid sequence of the light chain set forth in SEQ ID NO: 42.

Optionally, the antibody has the amino acid sequence of the heavy chain set forth in SEQ ID NO: 56, and/or the amino acid sequence of the light chain set forth in SEQ ID NO: 58.

Optionally, the antibody has the amino acid sequence of the heavy chain set forth in SEQ ID NO: 72, and/or the amino acid sequence of the light chain set forth in SEQ ID NO: 74.

Optionally, the antibody has the amino acid sequence of the heavy chain set forth in SEQ ID NO: 88, and/or the amino acid sequence of the light chain set forth in SEQ ID NO: 90.

According to at least some embodiments, there is provided a monoclonal antibody having the amino acid sequence encoded by the nucleic acid sequence that comprises:

1) at least one light chain variable region comprising a CDR1 region encoded by a nucleic acid sequence selected from SEQ ID NO: 49, SEQ ID NO: 65, SEQ ID NO: 81, and SEQ ID NO: 97; a CDR2 region encoded by a nucleic acid sequence selected from SEQ ID NO: 50, SEQ ID NO: 66, SEQ ID NO: 82 and SEQ ID NO: 98; and a CDR3 region encoded by a nucleic acid sequence selected from SEQ ID NO: 51, SEQ ID NO: 67, SEQ ID NO: 83 and SEQ ID NO: 99, or a degenerative variant thereof; and/or 2) at least one heavy chain variable region comprising a CDR1 region encoded by a nucleic acid sequence selected from SEQ ID NO: 43, SEQ ID NO: 59, SEQ ID NO: 75, and SEQ ID NO: 91; a CDR2 region encoded by a nucleic acid sequence selected from SEQ ID NO: 44, SEQ ID NO: 60, SEQ ID NO: 76, and SEQ ID NO: 92; and a CDR3 region encoded by a nucleic acid sequence selected from SEQ ID NO: 45, SEQ ID NO: 61, SEQ ID NO: 77, and SEQ ID NO: 93, or a degenerative variant thereof.

According to at least some embodiments, there is provided a monoclonal antibody having the amino acid sequence encoded by the nucleic acid sequence that comprises:

1) at least one light chain variable region comprising a CDR1 region encoded by a nucleic acid sequence set forth in SEQ ID NO: 49; a CDR2 region encoded by a nucleic acid sequence set forth in SEQ ID NO: 50; and a CDR3 region encoded by a nucleic acid sequence set forth in SEQ ID NO: 51; and/or 2) at least one heavy chain variable region comprising a CDR1 region encoded by a nucleic acid sequence set forth in SEQ ID NO: 43; a CDR2 region encoded by a nucleic acid sequence set forth in SEQ ID NO: 44; and a CDR3 region encoded by a nucleic acid sequence set forth in SEQ ID NO: 45.

In some embodiments, the antibody is encoded by a nucleic acid sequence that comprises:

1) at least one light chain variable region comprising a CDR1 region encoded by a nucleic acid sequence set forth in SEQ ID NO: 65; a CDR2 region encoded by a nucleic acid sequence set forth in SEQ ID NO: 66; and a CDR3 region encoded by a nucleic acid sequence set forth in SEQ ID NO: 67; and/or 2) at least one heavy chain variable region comprising a CDR1 region encoded by a nucleic acid sequence set forth in SEQ ID NO: 59; a CDR2 region encoded by a nucleic acid sequence set forth in SEQ ID NO: 60; and a CDR3 region encoded by a nucleic acid sequence set forth in SEQ ID NO: 61.

In some embodiments, the antibody is encoded by a nucleic acid sequence that comprises:

1) at least one light chain variable region comprising a CDR1 region encoded by a nucleic acid sequence set forth in SEQ ID NO: 81; a CDR2 region encoded by a nucleic acid sequence set forth in SEQ ID NO: 82; and a CDR3 region encoded by a nucleic acid sequence set forth in SEQ ID NO: 83; and/or 2) at least one heavy chain variable region comprising a CDR1 region encoded by a nucleic acid sequence set forth in SEQ ID NO: 75; a CDR2 region encoded by a nucleic acid sequence set forth in SEQ ID NO: 76; and a CDR3 region encoded by a nucleic acid sequence set forth in SEQ ID NO: 77.

In some embodiments, the antibody is encoded by a nucleic acid sequence that comprises:

1) at least one light chain variable region comprising a CDR1 region encoded by a nucleic acid sequence set forth in SEQ ID NO: 97; a CDR2 region encoded by a nucleic acid sequence set forth in SEQ ID NO: 98; and a CDR3 region encoded by a nucleic acid sequence set forth in SEQ ID NO: 99; and/or 2) at least one heavy chain variable region comprising a CDR1 region encoded by a nucleic acid sequence set forth in SEQ ID NO: 91; a CDR2 region encoded by a nucleic acid sequence set forth in SEQ ID NO: 92; and a CDR3 region encoded by a nucleic acid sequence set forth in SEQ ID NO: 93.

Optionally, the antibody has the amino acid sequence of the heavy chain encoded by a nucleic acid sequence selected from any one of SEQ ID NOs: 39, 55, 71, 87, and the amino acid sequence of the light chain encoded by a nucleic acid sequence selected from any one of SEQ ID NOs: 41, 57, 73, 89, or a degenerative variant thereof.

Optionally, the antibody has the amino acid sequence of the heavy chain encoded by a nucleic acid sequence set forth in SEQ ID NO: 39, and the amino acid sequence of the light chain encoded by a nucleic acid sequence set forth in SEQ ID NO: 41.

Optionally, the antibody has the amino acid sequence of the heavy chain encoded by a nucleic acid sequence set forth in SEQ ID NO: 55, and the amino acid sequence of the light chain encoded by a nucleic acid sequence set forth in SEQ ID NO: 57.

Optionally, the antibody has the amino acid sequence of the heavy chain encoded by a nucleic acid sequence set forth in SEQ ID NO: 71, and the amino acid sequence of the light chain encoded by a nucleic acid sequence set forth in SEQ ID NO: 73.

Optionally, the antibody has the amino acid sequence of the heavy chain encoded by a nucleic acid sequence set forth in SEQ ID NO: 87, and the amino acid sequence of the light chain encoded by a nucleic acid sequence set forth in SEQ ID NO: 89.

Optionally, the antibody comprises CDR amino acid sequences selected from the group consisting of (a) sequences as listed herein; (b) sequences that differ from those CDR amino acid sequences specified in (a) by 1, 2, 3, 4, 5, 6, 7, 8, 9, 10 or more conservative amino acid substitutions except for the Serine residue in heavy chain CDR3 at position 100A (Kabat numbering system); (c) amino acid sequences having 90% or greater, 95% or greater, 98% or greater, or 99% or greater sequence identity to the sequences specified in (a) or (b); (d) a polypeptide having an amino acid sequence encoded by a polynucleotide having a nucleic acid sequence encoding the amino acids as listed herein.

Optionally, any of the above antibodies may be secreted by a hybridoma, transformed with a vector comprising any suitable nucleic acid sequence encoding for the amino acid sequence, for example as described herein.

Optionally, the antibody is secreted by 5166-2 and/or 5166-9 hybridoma deposited according to the provisions of the Budapest Treaty with the American Type Culture Collection (ATCC) Patent Depository 10801 University Boulevard, Manassas, Va. 20110-2209 U.S.A., received by the ATCC Receiving Department on Jan. 18, 2013, having a Provisional Accession Number: XXXXX and/or XXXXX, respectively.

According to at least some embodiments, there is provided a hybridoma, deposited according to the provisions of the Budapest Treaty with the American Type Culture Collection (ATCC) Patent Depository 10801 University Boulevard, Manassas, Va. 20110-2209 U.S.A., received by the ATCC Receiving Department on Jan. 18, 2013, having a Provisional Accession Number: XXXXX and/or XXXXX, respectively.

According to at least some embodiments, there is provided an antibody produced by the above hybridoma.

Optionally for any antibody or fragment described herein, the cancer expresses one or more C1ORF32 polypeptides on the cancer cells or in the immune cells infiltrating cancer cells congregated as a tumor. Optionally said one or more C1ORF32 polypeptides comprises one or more of SEQ ID NOs: 1, 7, 9, 13, 17, 103, and/or their corresponding extracellular domains, selected from the group consisting of any one of SEQ ID NOs: 10, 14, 11, 15, and/or fragments, and/or epitopes thereof.

Optionally for any antibody or fragment described herein, the antibody is a fully human antibody, chimeric antibody, humanized or primatized antibody.

Optionally for any antibody or fragment described herein, the antibody is selected from the group consisting of Fab, Fab', F(ab')2, F(ab'), F(ab), Fv or scFv fragment and minimal recognition unit.

Optionally, for any antibody or fragment described herein, the antibody may be bispecific, meaning that one arm of the Ig molecule is specific for binding to the target protein or epitope as described herein, and the other arm of the Ig molecule has a different specificity that can enhance or redirect the biological activity of the antibody or fragment. In this regard, a multi-specific antibody is also considered to be at least bispecific. The antibody or fragment also can be multi-specific in the sense of being multi-valent.

Optionally for any antibody or fragment described herein, the antibody is coupled to a moiety selected from a drug, a radionuclide, a fluorophore, an enzyme, a toxin, a therapeutic agent, or a chemotherapeutic agent; and wherein the detectable marker is a radioisotope, a metal chelator, an enzyme, a fluorescent compound, a bioluminescent compound or a chemiluminescent compound.

Optionally for any antibody or fragment described herein, a pharmaceutical composition comprises such an antibody or an antigen binding fragment.

Optionally for any antibody or fragment described herein, or the pharmaceutical composition described herein, there is a use provided for treatment of cancer, wherein the cancer exhibit the expression of C1ORF32 polypeptides comprised in SEQ ID NOs: 1, 7, 9, 13, 17, 103, and/or their corresponding extracellular domains, selected from the group consisting of any one of SEQ ID NOs: 10, 14, 11, 15, and/or fragments, and/or epitopes thereof, on the cancer cells or in the immune cells infiltrating the tumor, and wherein the cancer is selected from the group consisting of Thyroid Carcinoma, carcinoma of the esophagus, Invasive Ductal breast Carcinoma, breast comedocarcinoma, breast Medullary Carcinoma Grade 2, ovarian cancer selected from the group consisting of Serous and Mucinous, Granular cell tumor, Surface epithelial-stromal tumor (Adenocarcinoma), cystadenocarcinoma and Endometrioid tumor; kidney cancer selected from the group consisting of Clear cell carcinoma, Chromophobe adenoma, and sarcomatoides carcinoma; prostate adenocarcinoma having a Gleason score of 5 or higher, stage I to III prostate adenocarcinoma, Benign prostatic hyperplasia, stage II and III hepatocellular carcinoma, malignant hepatoma, fibrolamellar hepatocellular carcinoma, pseudoglandular (adenoid) hepatocellular carcinoma, pleomorphic (giant cell) hepatocellular carcinoma, clear cell HCC, Cholangiocarcinoma, pancreas cancer selected from Ductal and Mucinous Adenocarcinoma, Islet cell carcinoma, familial atypical multiple mole melanoma-pancreatic cancer syndrome (FAMMM-PC), Exocrine pancreas cancers, ductal adenocarcinoma, denosquamous carcinomas, signet ring cell carcinomas, hepatoid carcinomas, colloid carcinomas, undifferentiated carcinomas, and undifferentiated carcinomas with osteoclast-like giant cells, Low- to intermediate-grade neuroendocrine carcinomas and pancreatic carcinoid tumors, stage IV malignant melanoma, Lentigo maligna melanoma, Superficial spreading melanoma, Acral lentiginous melanoma, Mucosal melanoma, Nodular melanoma, Polypoid melanoma, Desmoplastic melanoma, Amelanotic melanoma, Soft-tissue melanoma, Osteogenic sarcoma, Chondrosarcoma, Leiomyosarcoma, Angiosarcoma, Askin's Tumor, Ewing's sarcoma, Kaposi's sarcoma, Liposarcoma, Malignant fibrous histiocytoma, Rhabdomyosarcoma, Neurofibrosarcoma, Hodgkin's lymphoma, B-cell Lymphoma, Mantle cell lymphoma (MCL), T-cell Lymphoma, Endometroid Adenocarcinoma, Bladder Transitional Cell carcinoma, Small Cell Lung Cancer, Non Small Cell Lung Cancer, Large-cell lung carcinoma, testicular seminoma, moderate to poorly differentiated Colo-rectal adenocarcinoma, and spinal cord tumor.

According to at least some embodiments, there is provided a method for treating cancer, wherein the cancer exhibit the expression of C1ORF32 polypeptides comprising SEQ ID NOs: 1, 7, 9, 13, 17, 103, and/or their corresponding extracellular domains, selected from the group consisting of any one of SEQ ID NOs: 10, 14, 11, 15, and/or fragments, and/or epitopes thereof, on the cancer cells or in the immune cells infiltrating the tumor, and wherein the cancer is selected from the group consisting of Thyroid Carcinoma, carcinoma of the esophagus, Invasive Ductal breast Carcinoma, breast comedocarcinoma, breast Medullary Carcinoma Grade 2, ovarian cancer selected from the group consisting of Serous and Mucinous, Granular cell tumor, Surface epithelial-stromal tumor (Adenocarcinoma), cystadenocarcinoma and Endometrioid tumor; kidney cancer selected from the group consisting of Clear cell carcinoma, Chromophobe adenoma, and sarcomatoides carcinoma; prostate adenocarcinoma having a Gleason score of 5 or higher, stage I to III prostate adenocarcinoma, Benign prostatic hyperplasia, stage II and III hepatocellular carcinoma, malignant hepatoma, fibrolamellar hepatocellular carcinoma, pseudoglandular (adenoid) hepatocellular carcinoma, pleomorphic (giant cell) hepatocellular carcinoma, clear cell HCC, Cholangiocarcinoma, pancreas cancer selected from Ductal and Mucinous Adenocarcinoma, Islet cell carcinoma, familial atypical multiple mole melanoma-pancreatic cancer syndrome (FAMMM-PC), Exocrine pancreas cancers, ductal adenocarcinoma, denosquamous carcinomas, signet ring cell carcinomas, hepatoid carcinomas, colloid carcinomas, undifferentiated carcinomas, and undifferentiated carcinomas with osteoclast-like giant cells, Low- to intermediate-grade neuroendocrine carcinomas and pancreatic carcinoid tumors, stage IV malignant melanoma, Lentigo maligna melanoma, Superficial spreading melanoma, Acral lentiginous melanoma, Mucosal melanoma, Nodular melanoma, Polypoid melanoma, Desmoplastic melanoma, Amelanotic melanoma, Soft-tissue melanoma, Osteogenic sarcoma, Chondrosarcoma, Leiomyosarcoma, Angiosarcoma, Askin's Tumor, Ewing's sarcoma, Kaposi's sarcoma, Liposarcoma, Malignant fibrous histiocytoma, Rhabdomyosarcoma, Neurofibrosarcoma, Hodgkin's lymphoma, B-cell Lymphoma, Mantle cell lymphoma (MCL), T-cell Lymphoma, Endometroid Adenocarcinoma, Bladder Transitional Cell carcinoma, Small Cell Lung Cancer, Non Small Cell Lung Cancer, Large-cell lung carcinoma, testicular seminoma, moderate to poorly differentiated Colo-rectal adenocarcinoma, and spinal cord tumor, comprising administering to a subject in need thereof an effective amount of any one of the antibody, or antibody binding fragment, as described herein, or the pharmaceutical composition as described herein.

Optionally the treatment is combined with another moiety or therapy useful for treating cancer.

Optionally the therapy is radiation therapy, antibody therapy, chemotherapy, photodynamic therapy, adoptive T cell therapy, Treg depletion, surgery or in combination therapy with conventional drugs.

Optionally the moiety is selected from the group consisting of immunosuppressants, cytotoxic drugs, tumor vaccines, antibodies (e.g. bevacizumab, erbitux), peptides, pepti-bodies, small molecules, chemotherapeutic agents such as cytotoxic and cytostatic agents (e.g. paclitaxel, cisplatin, vinorelbine, docetaxel, gemcitabine, temozolomide, irinotecan, 5FU, carboplatin), immunological modifiers such as interferons and interleukins, immunostimulatory antibodies, growth hormones or other cytokines, folic acid, vitamins, minerals, aromatase inhibitors, RNAi, Histone Deacetylase Inhibitors, and proteasome inhibitors.

Optionally for any antibody or fragment described herein, there is a use provided for diagnosis of cancer, wherein the cancer exhibit the expression of C1ORF32 polypeptides comprising SEQ ID NOs: 1, 7, 9, 13, 17, 103, and/or their corresponding extracellular domains, selected from the group consisting of any one of SEQ ID NOs: 10, 14, 11, 15, and/or fragments, and/or epitopes thereof, on the cancer cells or in the immune cells infiltrating the tumor, and wherein the cancer is selected from the group consisting of Thyroid Carcinoma, carcinoma of the esophagus, Invasive Ductal breast Carcinoma, breast comedocarcinoma, breast Medullary Carcinoma Grade 2, ovarian cancer selected from the group consisting of Serous and Mucinous, Granular cell tumor, Surface epithelial-stromal tumor (Adenocarcinoma), cystadenocarcinoma and Endometrioid tumor; kidney cancer selected from the group consisting of Clear cell carcinoma, Chromophobe adenoma, and sarcomatoides carcinoma; prostate adenocarcinoma having a Gleason score of 5 or higher, stage I to III prostate adenocarcinoma, Benign prostatic hyperplasia, stage II and III hepatocellular carcinoma, malignant hepatoma, fibrolamellar hepatocellular carcinoma, pseudoglandular (adenoid) hepatocellular carcinoma, pleomorphic (giant cell) hepatocellular carcinoma, clear cell HCC, Cholangiocarcinoma, pancreas cancer selected from Ductal and Mucinous Adenocarcinoma, Islet cell carcinoma, familial atypical multiple mole melanoma-pancreatic cancer syndrome (FAMMM-PC), Exocrine pancreas cancers, ductal adenocarcinoma, denosquamous carcinomas, signet ring cell carcinomas, hepatoid carcinomas, colloid carcinomas, undifferentiated carcinomas, and undifferentiated carcinomas with osteoclast-like giant cells, Low- to intermediate-grade neuroendocrine carcinomas and pancreatic carcinoid tumors, stage IV malignant melanoma, Lentigo maligna melanoma, Superficial spreading melanoma, Acral lentiginous melanoma, Mucosal melanoma, Nodular melanoma, Polypoid melanoma, Desmoplastic melanoma, Amelanotic melanoma, Soft-tissue melanoma, Osteogenic sarcoma, Chondrosarcoma, Leiomyosarcoma, Angiosarcoma, Askin's Tumor, Ewing's sarcoma, Kaposi's sarcoma, Liposarcoma, Malignant fibrous histiocytoma, Rhabdomyosarcoma, Neurofibrosarcoma, Hodgkin's lymphoma, B-cell Lymphoma, Mantle cell lymphoma (MCL), T-cell Lymphoma, Endometroid Adenocarcinoma, Bladder Transitional Cell carcinoma, Small Cell Lung Cancer, Non Small Cell Lung Cancer, Large-cell lung carcinoma, testicular seminoma, moderate to poorly differentiated Colo-rectal adenocarcinoma, and spinal cord tumor.

According to at least some embodiments, there is provided a method for diagnosing cancer in a subject, wherein the cancer is selected from the group consisting of Thyroid Carcinoma, carcinoma of the esophagus, Invasive Ductal breast Carcinoma, breast comedocarcinoma, breast Medullary Carcinoma Grade 2, ovarian cancer selected from the group consisting of Serous and Mucinous, Granular cell tumor, Surface epithelial-stromal tumor (Adenocarcinoma), cystadenocarcinoma and Endometrioid tumor; kidney cancer selected from the group consisting of Clear cell carcinoma, Chromophobe adenoma, and sarcomatoides carcinoma; prostate adenocarcinoma having a Gleason score of 5 or higher, stage I to III prostate adenocarcinoma, Benign prostatic hyperplasia, stage II and III hepatocellular carcinoma, malignant hepatoma, fibrolamellar hepatocellular carcinoma, pseudoglandular (adenoid) hepatocellular carcinoma, pleomorphic (giant cell) hepatocellular carcinoma, clear cell HCC, Cholangiocarcinoma, pancreas cancer selected from Ductal and Mucinous Adenocarcinoma, Islet cell carcinoma, familial atypical multiple mole melanoma-pancreatic cancer syndrome (FAMMM-PC), Exocrine pancreas cancers, ductal adenocarcinoma, denosquamous carcinomas, signet ring cell carcinomas, hepatoid carcinomas, colloid carcinomas, undifferentiated carcinomas, and undifferentiated carcinomas with osteoclast-like giant cells, Low- to intermediate-grade neuroendocrine carcinomas and pancreatic carcinoid tumors, stage IV malignant melanoma, Lentigo maligna melanoma, Superficial spreading melanoma, Acral lentiginous melanoma, Mucosal melanoma, Nodular melanoma, Polypoid melanoma, Desmoplastic melanoma, Amelanotic melanoma, Soft-tissue melanoma, Osteogenic sarcoma, Chondrosarcoma, Leiomyosarcoma, Angiosarcoma, Askin's Tumor, Ewing's sarcoma, Kaposi's sarcoma, Liposarcoma, Malignant fibrous histiocytoma, Rhabdomyosarcoma, Neurofibrosarcoma, Hodgkin's lymphoma, B-cell Lymphoma, Mantle cell lymphoma (MCL), T-cell Lymphoma, Endometroid Adenocarcinoma, Bladder Transitional Cell carcinoma, Small Cell Lung Cancer, Non Small Cell Lung Cancer, Large-cell lung carcinoma, testicular seminoma, moderate to poorly differentiated Colo-rectal adenocarcinoma, and spinal cord tumor, comprising detecting in the subject or in a sample obtained from said subject any one of the C1ORF32 polypeptides comprised in SEQ ID NOs: 1, 7, 9, 13, 17, 103, and/or their corresponding extracellular domains, selected from the group consisting of any one of SEQ ID NOs: 10, 14, 11, 15, and/or fragments, and/or epitopes thereof.

Optionally, detecting the polypeptide is performed in vivo or in vitro. Also optionally, the detection is conducted by immunoassay. Also optionally, the detection is conducted using antibodies or fragments as described herein.

The below embodiments and sub-embodiments are optionally implemented with any of the antibodies, methods, compositions or uses as described herein, optionally wherein said Thyroid Carcinoma is selected from one or more of Thyroid Papillary Carcinoma, Thyroid Follicular Carcinoma (preferably stage II and III), incidental papillary carcinoma (IPC), Medullary thyroid cancer, Anaplastic thyroid cancer.

Optionally said carcinoma of the esophagus is a squamous cell carcinoma of the esophagus.

Optionally said Invasive Ductal Carcinoma is selected from stage II to IV and/or poorly differentiated Invasive Ductal Carcinoma, and/or wherein said Medullary Carcinoma is Grade 2 Medullary Carcinoma.

Optionally said Serous and Mucinous ovarian carcinoma is selected from stages Ic to IIIb Serous and Mucinous ovarian carcinoma.

Optionally said kidney Clear cell carcinoma is selected from stage I to II renal Clear cell carcinoma.

Optionally said hepatocellular carcinoma is selected from stage II and III hepatocellular carcinoma.

Optionally said Hodgkin's lymphoma is selected from Nodular sclerosing, Mixed-cellularity subtype, Lymphocyte-rich or Lymphocytic predominance, Lymphocyte depleted and Unspecified.

Optionally said B-cell Lymphoma is selected from the group consisting of Diffuse large B cell lymphoma, Follicular lymphoma, Mucosa-Associated Lymphatic Tissue lymphoma (MALT), Small cell lymphocytic lymphoma, Burkitt lymphoma, Mediastinal large B cell lymphoma, Waldenström macroglobulinemia, Nodal marginal zone B cell lymphoma (NMZL), Splenic marginal zone lymphoma (SMZL), Intravascular large B-cell lymphoma, Primary effusion lymphoma, Lymphomatoid granulomatosis.

Optionally said T-cell Lymphoma is selected from the group consisting of Extranodal T cell lymphoma, Cutaneous T cell lymphomas: Sézary syndrome and Mycosis fungoides, Anaplastic large cell lymphoma, and Angioimmunoblastic T cell lymphoma.

Optionally said Endometroid Adenocarcinoma is selected from stage I to IIIc Endometroid Adenocarcinoma.

Optionally said bladder Transitional Cell carcinoma is selected from stage II to IV Transitional Cell carcinoma.

Optionally said Small Cell Lung Cancer is selected from stage I to IIIb Small Cell Lung Cancer, and/or wherein said Non Small Cell Lung Cancer is selected from poorly to moderately differentiated squamous and adeno carcinoma.

Optionally said antibody or fragment inhibits activities elicited by C1ORF32.

Optionally said antibody or fragment modulates B7 related costimulation, increases T cell activation, alleviates T-cell suppression, increases cytokine secretion, increases IL-2 secretion; increases interferon-gamma production by T-cells, increases Th1 response, decreases Th2 response, promotes cancer epitope spreading, reduces inhibition of T cell activation, increases T cell response in a mammal, stimulates antigen-specific memory responses, elicits apoptosis or lysis of cancer cells, stimulates cytotoxic or cytostatic effect on cancer cells, induces direct killing of cancer cells, induces complement dependent cytotoxicity and/or antibody dependent cell-mediated cytotoxicity.

Optionally said antibody or fragment increases immune response against the cancer.

Optionally said antibody or fragment reduces activity of regulatory T lymphocytes (T-regs).

Optionally said antibody or fragment inhibits iTreg differentiation,

Optionally the antibody, method, composition or use as described herein features administration of the antibody and/or composition to a subject in combination with a potentiating agent to obtain a therapeutic effect, wherein said potentiating agent is selected from the group consisting of radiotherapy, conventional/classical chemotherapy potentiating anti-tumor immune responses, Targeted therapy potentiating anti-tumor immune responses, Therapeutic agents targeting Tregs and/or MDSCs, Immunostimulatory antibodies, Therapeutic cancer vaccines, Adoptive cell transfer.

Optionally the conventional/classical chemotherapy agent is selected from Gemcitabine, Oxaliplatin, cisplatin, carboplatin (and other platinum based compounds), Cyclophosphamide, Anthracyclines, such as doxorubicin, daunorubicin, Taxanes, such as paclitaxel, docetaxel, microtubule inhibitors, such as vincristine, Folate antagonists, such as methotrexate, mTOR pathway inhibitors, such as temsirolimus and rapamycin, oxaliplatin, cyclophosphamide, doxorubicin, and mitoxantrone.

Optionally the Targeted therapy agent is selected from histone deacetylase (HDAC) inhibitors, such as vorinostat, sodium butyrate and MS-275), Bortezomib, Vemurafenib, JAK2 inhibitors, tyrosine kinase inhibitors (TKIs) such as erlotinib, imatinib, sunitinib, sorafenib, therapeutic monoclonal antibodies, such as anti-EGFR mAbs cetuximab, anatimumab, trastuzumab.

Optionally the Therapeutic agent targeting immunosuppressive cells Tregs and/or MDSCs is selected from antimitotic drugs such as cyclophosphamide, gemcitabine, mitoxantrone, fludarabine, thalidomide and thalidomide derivatives, COX-2 inhibitors, depleting or killing antibodies that directly target Tregs through recognition of Treg cell surface receptors such as anti-CD25 daclizumab and basiliximab, ligand-directed toxins such as denileukin diftitox (Ontak)—a fusion protein of human IL-2 and diphtheria toxin, or LMB-2—a fusion between an scFv against CD25 and the *pseudomonas* exotoxin, antibodies targeting Treg cell surface receptors, TLR modulators, agents that interfere with the adenosinergic pathway, such as ectonucleotidase inhibitors, or inhibitors of the A2A adenosine receptor, TGF-β inhibitors, chemokine receptor inhibitors, retinoic acid, all-trans retinoic acid (ATRA), Vitamin D3, phosphodiesterase 5 inhibitors like sildenafil, ROS inhibitors such as nitroaspirin.

Optionally the Immunostimulatory antibody is selected from antagonistic antibodies targeting immune checkpoints such as CTLA4 (example: ipilimumab), PD-1 (example: BMS-936558/MDX-1106), PDL-1 (example: BMS-936559/MDX-1105), LAG-3 (example: IMP-321), TIM-3, BTLA and/or Agonistic antibodies targeting immunostimulatory proteins, such as CD40 (example: CP-870,893), CD137 (example: BMS-663513), OX40 (example: Anti-OX40), GITR (example: TRX518).

Optionally the Therapeutic cancer vaccine is selected from exogenous cancer vaccines including proteins or peptides used to mount an immunogenic response to a tumor antigen, recombinant virus and bacteria vectors encoding tumor antigens, DNA-based vaccines encoding tumor antigens, proteins targeted to dendritic cells, dendritic cells, gene modified tumor cells expressing GM-CSF and/or Flt3-ligand.

Optionally the Therapeutic cancer vaccine comprises Dendritic-cell-based vaccines.

Optionally for any of the above-described antibodies the cancer expresses one or more C1ORF32 polypeptides on the cancer cells or in the immune cells infiltrating cancer cells congregated as a tumor.

According to at least some embodiments, the present invention provides the foregoing antibodies and fragments thereof, wherein the antibody is a chimeric, humanized, fully human antibody and/or is an antibody or antibody fragment having CDC or ADCC activities on target cells.

Included in particular are antibodies and fragments that are immune activating or immune suppressing such as antibodies or fragments that target cells via ADCC (antibody dependent cellular cytotoxicity) or CDC (complement dependent cytotoxicity) activities.

According to at least some embodiments, the present invention provides the foregoing antibody fragments and conjugates containing useful in the foregoing therapies and related diagnostic methods including but not limited to Fab, F(ab')2, Fv or scFv fragment.

According to at least some embodiments of the present invention the subject antibodies and fragments are directly or indirectly attached to markers and other effector moieties such as a detectable marker, or to an effector moiety such as an enzyme, a toxin, a therapeutic agent, or a chemotherapeutic agent.

According to at least some embodiments, the present invention provides the foregoing antibodies or fragments attached directly or indirectly to a radioisotope, a metal chelator, an enzyme, a fluorescent compound, a bioluminescent compound or a chemiluminescent compound.

According to at least some embodiments, the present invention provides pharmaceutical and/or diagnostic compositions that comprise a therapeutically and/or diagnostically effective form of a foregoing antibody or antibody fragment.

According to at least some embodiments the present invention provides methods for treating or preventing cancer, comprising administering to a patient an effective amount of the foregoing antibody and/or pharmaceutical composition.

Optionally as described herein, the treatment is combined with another moiety or therapy useful for treating cancer. Optionally, the therapy is radiation therapy, antibody therapy, chemotherapy, photodynamic therapy, adoptive T cell therapy, Treg depletion, surgery or in combination therapy with conventional drugs.

According to at least some embodiments, the present invention provides assays for detecting the presence and/or levels of C1ORF32 proteins in vitro or in vivo in a biological sample or an individual, comprising contacting the sample with the foregoing antibody, and detecting the binding of C1ORF32 protein in the sample and/or in the individual.

According to at least some embodiments, the present invention provides methods for detecting cancer, diagnosing cancer, monitoring cancer progression or treatment efficacy or relapse of cancer, or selecting a therapy for cancer, detect cells affected by cancer, comprising detecting expression of a C1ORF32.

Such diagnostic methods optionally comprise detecting in the subject or in a sample obtained from said subject any one of the C1ORF32 polypeptides comprised in SEQ ID NOs: 1, 7, 9, 13, 17, 103, and/or their corresponding extracellular domains, selected from the group consisting of any one of SEQ ID NOs: 10, 14, 11, 15, and/or fragments, and/or epitopes thereof. Optionally, detecting the polypeptide is performed in vivo or in vitro, optionally by immunoassay and also optionally by using antibodies or fragments According to one embodiment, detecting the presence and/or levels of the C1ORF32 polypeptide in a sample is indicative of the presence of cancer and/or its severity and/or its progress. According to another embodiment, a change in the expression and/or the level of the C1ORF32 polypeptide compared to its expression and/or level in a healthy subject or a sample obtained therefrom is indicative of the presence of cancer and/or its severity and/or its progress. According to a further embodiment, a change in the expression and/or level of the polypeptide compared to its level and/or expression in said subject or in a sample obtained therefrom at earlier stage is indicative of the progress of cancer. According to still further embodiment, detecting the presence and/or relative change in the expression and/or level of the polypeptide is useful for selecting a treatment and/or monitoring a treatment of the cancer.

According to at least some embodiments, the present invention provides antibodies and fragments as described herein, optionally and preferably wherein the antibody binds to human C1ORF32 with a KD of 1×10-8 M or less, and wherein the antibody exhibits at least one of the following properties: modulates B7 related costimulation, increases T cell activation, alleviates T-cell suppression, increases cytokine secretion, increases IL-2 secretion; increases interferon-gamma production by T-cells, increases Th1 response, decreases Th2 response, promotes cancer epitope spreading, reduces inhibition of T cell activation, increases T cell response in a mammal, stimulates antigen-specific memory responses, elicits apoptosis or lysis of cancer cells, stimulates cytotoxic or cytostatic effect on cancer cells, induces direct killing of cancer cells, induces complement dependent cytotoxicity and/or antibody dependent cell-mediated cytotoxicity.

Optionally the antibody or fragment increases immune response against the cancer.

Optionally the antibody or fragment reduces activity of regulatory T lymphocytes (T-regs).

Optionally the antibody or fragment inhibits iTreg differentiation.

According to at least some embodiments, the present invention provides a bispecific molecule comprising the foregoing antibody, or antigen-binding portion thereof, linked to a second functional moiety having the same or a different antigen binding target or specificity than said foregoing antibody, or antigen-binding portion thereof.

Nucleic acid molecules encoding the antibodies, or antigen-binding portions thereof, of the present invention are also encompassed by the present invention, as well as expression vectors comprising such nucleic acids and host cells comprising such expression vectors. Moreover, the present invention provides a transgenic mouse comprising human immunoglobulin heavy and light chain transgenes, wherein the mouse expresses an antibody of the present invention, as well as hybridomas prepared from such a mouse, wherein the hybridoma produces the antibody of the present invention.

According to at least some embodiments, the present invention provides a use of the foregoing monoclonal and/or polyclonal antibodies and antigen binding fragments and/or pharmaceutical composition comprising same, for treatment of cancer, wherein the cancer exhibit the expression of C1ORF32 proteins on the tumor cells or in the immune cells infiltrating the tumor. Optionally, although examples are provided herein for monoclonal and polyclonal antibodies, fragments of such, and/or alternative scaffolds and/or conjugates and/or immunoconjugates containing same may also optionally be included as part of such embodiments.

Anti C1ORF32 antibody, a fragment, a conjugate thereof and/or a pharmaceutical composition comprising same, according to at least some embodiments of the present invention also can be administered in combination therapy, i.e., combined with other potentiating agents and/or therapies, for example with any of the known in the art standart of care cancer treatment (as can be found, for example, in http://www.cancer.gov/cancertopics).

According to at least some non-limiting embodiments, the antibody or fragment may optionally be administered to a subject in combination with a potentiating agent to obtain a therapeutic effect, wherein said potentiating agent is selected from the group consisting of radiotherapy, conventional/classical chemotherapy potentiating anti-tumor immune responses, Targeted therapy potentiating anti-tumor immune responses, Therapeutic agents targeting Tregs and/or MDSCs, Immunostimulatory antibodies, Therapeutic cancer vaccines, Adoptive cell transfer.

Optionally the conventional/classical chemotherapy agent is selected from Gemcitabine, Oxaliplatin, cisplatin, carboplatin (and other platinum based compounds), Cyclophosphamide, Anthracyclines, such as doxorubicin, daunorubicin, Taxanes, such as paclitaxel, docetaxel, microtubule inhibitors, such as vincristine, Folate antagonists, such as methotrexate, mTOR pathway inhibitors, such as temsirolimus and rapamycin, oxaliplatin, cyclophosphamide, doxorubicin, and mitoxantrone.

Optionally the Targeted therapy agent is selected from histone deacetylase (HDAC) inhibitors, such as vorinostat, sodium butyrate and MS-275), Bortezomib, Vemurafenib, JAK2 inhibitors, tyrosine kinase inhibitors (TKIs) such as erlotinib, imatinib, sunitinib, sorafenib, therapeutic monoclonal antibodies, such as anti-EGFR mAbs cetuximab, anatimumab, trastuzumab.

Optionally the Therapeutic agent targeting immunosuppressive cells Tregs and/or MDSCs is selected from antimitotic drugs such as cyclophosphamide, gemcitabine, mitoxantrone, fludarabine, thalidomide and thalidomide derivatives, COX-2 inhibitors, depleting or killing antibodies that directly target Tregs through recognition of Treg cell surface receptors such as anti-CD25 daclizumab and basiliximab, ligand-directed toxins such as denileukin diftitox (Ontak)—a fusion protein of human IL-2 and diphtheria toxin, or LMB-2—a fusion between an scFv against CD25 and the *pseudomonas* exotoxin, antibodies targeting Treg cell surface receptors, TLR modulators, agents that interfere with the adenosinergic pathway, such as ectonucleotidase inhibitors, or inhibitors of the A2A adenosine receptor, TGF-β inhibitors, chemokine receptor inhibitors, retinoic acid, all-trans retinoic acid (ATRA), Vitamin D3, phosphodiesterase 5 inhibitors like sildenafil, ROS inhibitors such as nitroaspirin.

Optionally the Immunostimulatory antibody is selected from antagonistic antibodies targeting immune checkpoints such as CTLA4 (example: ipilimumab), PD-1 (example: BMS-936558/MDX-1106), PDL-1 (example: BMS-936559/MDX-1105), LAG-3 (example: IMP-321), TIM-3, BTLA and/or Agonistic antibodies targeting immunostimulatory proteins, such as CD40 (example: CP-870,893), CD137 (example: BMS-663513), OX40 (example: Anti-OX40), GITR (example: TRX518).

Optionally the Therapeutic cancer vaccine is selected from exogenous cancer vaccines including proteins or peptides used to mount an immunogenic response to a tumor antigen, recombinant virus and bacteria vectors encoding tumor antigens, DNA-based vaccines encoding tumor antigens, proteins targeted to dendritic cells, dendritic cells, proteins targeted to dendritic cells, dendritic cells.

Optionally the Therapeutic cancer vaccine comprises Dendritic-cell-based vaccines.

BRIEF DESCRIPTION OF THE FIGURES

FIG. 5 demonstrates membrane expression of the various C1ORF32 proteins using mouse monoclonal anti C1ORF32 antibodies (20 ug/ml) as compared to non-relevant IgG1 control anti Cephalosporin, followed by Donkey Anti mouse IgG DyLight 549 conjugated secondary Ab diluted 1:250.

FIG. 12 C presents HEK 293T cells expressing C1ORF32 (SEQ ID NO: 1) or the pRp vector, seeded at concentrations of 25, 50 or 100K per well, in wells coated with 0.1 or 0.25 of anti-CD3 (OKT clone), incubated O.N with 50K Jurkat cells. Jurkat cells were analyzed for the expression of CD69 by flow cytometry. ΔMFI values are shown. FIG. 12 D presents HEK 293T cells expressing C1ORF32 (SEQ ID NO: 1) or the pRp vector, seeded at concentrations of 50K per well, in wells coated with 0.1 or 0.25 of anti-CD3 (OKT clone), incubated O.N with 50K Jurkat cells with or without 2 µg/ml of soluble anti CD28. Jurkat cells were analyzed for the expression of CD69 by flow cytometry. ΔMFI values are shown.

FIG. 15 shows that ectopic expression of C1ORF32 (SEQ ID NO: 1) suppresses mouse CD4 T cell divisions upon TCR stimulation.

DETAILED DESCRIPTION OF THE PRESENT INVENTION

Figure 1:
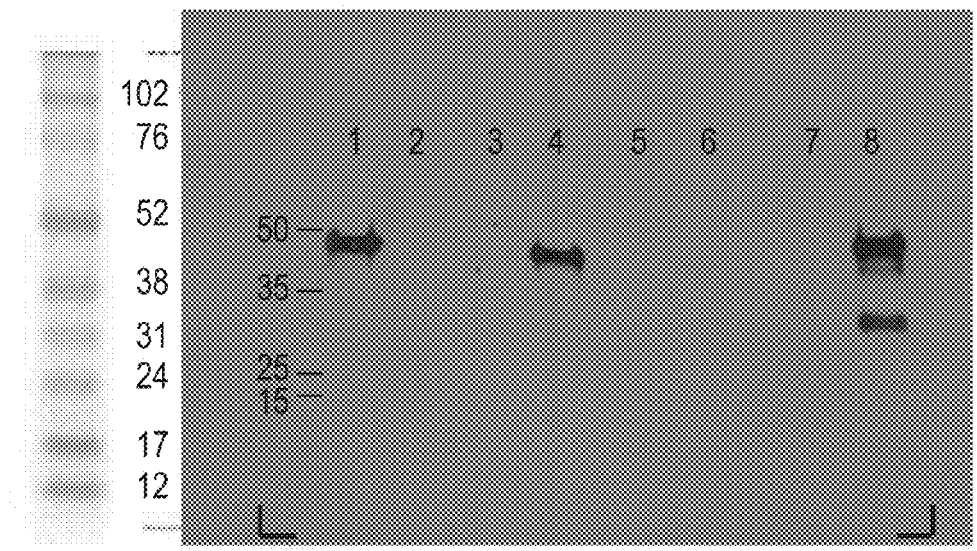
FIG. 1 presents western blot analysis results, on the extracellular domain of C1ORF32 fused to mouse IgG2a protein (C1ORF32-ECD-mouse IgG2a-fused protein) (SEQ ID NO:4), using test bleeds from immunized and pre-immunized rabbits serum (1:250). The results demonstrate that the specific anti C1ORF32 antibodies (serum from immunized rabbits #R1 (R7531), R2 (R7532), R4 (R7534)) recognize the recombinant C1ORF32-ECD-mouse IgG2a-fused protein (SEQ ID NO:4) at the expected band size (~50 kDa), while serum from the immunized rabbit R3 did not detect any specific signal. Legend: lane 1 represents R1(R7531) immunized serum; lane 2 represents R1(R7531) pre-immunized serum; lane 3 represents R2 (R7532) pre-immunized serum; lane 4 represents R2 (R7532) immunized serum; lane 5 represents R3 (R7533) pre-immunized serum; lane 6 represents R3 (R7533) immunized serum; lane 7 represents R4 (R7534) pre-immunized serum; and lane 8 represents R4 (R7534) immunized serum.

The present invention, in at least some embodiments, relates to polyclonal and monoclonal antibodies and fragments and/or conjugates thereof, and/or pharmaceutical composition comprising same, and/or diagnostic composition comprising same, wherein these antibodies specifically bind C1ORF32 proteins, and wherein said antibodies are adapted to be used as therapeutic and/or diagnostic agents, particularly for treatment and/or diagnosis of cancer, particularly human, humanized or chimeric monoclonal antibodies, including those that promote or inhibit activities elicited by C1ORF32.

Without wishing to be limited by a closed list or by a single hypothesis, an antibody according to various embodiments of the present invention may optionally have one or more of the following properties. Such neutralizing antibody may optionally promote Th2 to Th1 shift, thereby potentially reverting the shift towards a Th2/M2 environment induced in the tumor micro-environment that reduces the immune response towards the tumor. The antibody may therefore optionally promote the immune system component which acts against the tumor (Th1), while inhibiting the component which promotes the cancer (Th2).

According to at least some embodiments of the present invention, such an antibody may optionally inhibit iTregs accumulation and immunosuppressive function, and/or enhance effector T cell activity.

The term "cancer" as used herein should be understood to encompass any neoplastic disease (whether invasive or metastatic) which is characterized by abnormal and uncontrolled cell division causing malignant growth or tumor, non-limiting examples of which are described herein.

According to at least some embodiments of the present invention, the antibodies are derived from particular heavy and light chain germline sequences and/or comprise particular structural features such as at least one CDR regions comprising particular amino acid sequences. According to at least some embodiments, the present invention provides isolated antibodies, methods of making such antibodies, immunoconjugates and bispecific molecules comprising such antibodies and pharmaceutical and diagnostic compositions containing the antibodies, immunoconjugates, alternative scaffolds or bispecific molecules according to at least some embodiments of the present invention.

According to at least some embodiments the present invention relates to in vitro and in vivo methods of using the antibodies and fragments thereof, to detect any one of C1ORF32 proteins.

According to at least some embodiments the present invention further relates to methods of using the foregoing antibodies and fragments and/or conjugates thereof and/or pharmaceutical composition comprising same, to treat cancer, as described herein. C1ORF32 protein is disclosed in PCT Application Nos. WO/2009/032845 and WO/2012/001647, owned in common with the present application, which are hereby incorporated by reference, as if fully set forth herein. These applications demonstrate that the ECD sequence of C1ORF32 molecule fused to mouse IgG2a inhibits both human and mouse T-cell activation, induced by anti CD3 and anti-CD28, cytokine secretion. The C1ORF32 fusion protein also inhibits Th1 activation while inducing Th2, implying that the C1ORF32 has a specific role in T-cell biology, rather then a global suppression of T-cells. The fusion protein ameliorates disease symptoms in mice model of multiple sclerosis (EAE model) and rheumatoid arthritis (CIA) models, demonstrating that C1ORF32 has an important role in immune modulation. The WO/2012/001647 application demonstrates C1ORF32 immunomodulatory function, and particularly its inhibitory activity on T cell activation, in various experimental systems, including in vitro, ex vivo and in vivo studies. Taken together, these results indicate that C1ORF32, which is a member of the B7/CD28 family of negative costimulators, is a novel immune checkpoint.

WO2009/032845 discloses C1ORF32 specific antibodies are potentially useful as therapeutics and/or diagnostic agents (both in vitro and in vivo diagnostic methods). Included in particular are antibodies and fragments that are immune activating or immune suppressing such as antibodies or fragments that target cells via ADCC (antibody dependent cellular cytotoxicity) or CDC (complement dependent cytotoxicity) activities, particularly for treating conditions wherein the C1ORF32 antigen is differentially expressed including various cancers and malignancies.

In at least some embodiments of this invention, C1ORF32 was found to be involved in iTregs induction and differentiation. Without wishing to be limited by a single hypothesis, blocking monoclonal antibodies specific to C1ORF32 was found to inhibit iTregs accumulation and immunosuppressive function and enhance effector T cell activity. Thus, C1ORF32 blocking antibodies are optionally and preferably applied to cancer immunotherapy, alone or in combination with a potentiating agent(s), which increase endogenous anti-tumor responses.

Furthermore, it has surprisingly been found that an antibody according to various embodiments of the present invention is particularly useful for treatment of specific cancers as described herein.

In order that the present invention may be more readily understood, certain terms are first defined. Additional definitions are set forth throughout the detailed description.

An "immune cell" refers to any cell from the hemopoietic origin including but not limited to T cells, B cells, monocytes, dendritic cells, and macrophages.

As used herein, the term "polypeptide" refers to a chain of amino acids of any length, regardless of modification (e.g., phosphorylation or glycosylation). As used herein, a "costimulatory polypeptide" or "costimulatory molecule" is a polypeptide that, upon interaction with a cell-surface molecule on T cells, modulates T cell responses.

As used herein, "costimulatory signaling" is the signaling activity resulting from the interaction between costimulatory polypeptides on antigen presenting cells and their receptors on T cells during antigen-specific T cell responses. Without wishing to be limited by a single hypothesis, the antigen-specific T cell response is believed to be mediated by two signals: 1) engagement of the T cell Receptor (TCR) with antigenic peptide presented in the context of MHC (signal 1), and 2) a second antigen-independent signal delivered by contact between different costimulatory receptor/ligand pairs (signal 2). Without wishing to be limited by a single hypothesis, this "second signal" is critical in determining the type of T cell response (activation vs inhibition) as well as the strength and duration of that response, and is regulated by both positive and negative signals from costimulatory molecules, such as the B7 family of proteins.

As used herein, the term "B7" polypeptide means a member of the B7 family of proteins that costimulate T cells including, but not limited to B7-1, B7-2, B7-DC, B7-H5, B7-H1, B7-H2, B7-H3, B7-H4, B7-H6, B7-S3 and biologically active fragments and/or variants thereof. Representative biologically active fragments include the extracellular domain or fragments of the extracellular domain that costimulate T cells.

As used herein, the term C1ORF32 refers to any one of the proteins set forth in anyone of SEQ ID NOs: 1, 7, 9, 13, 17, 103, and/or their corresponding extracellular domains, selected from the group consisting of any one of SEQ ID NOs: 14, 10, 11, 15, and/or variants thereof, and/or orthologs and/or fragments thereof, and/or nucleic acid sequences encoding for same, that are differentially expressed in cancer, on the cancer cells or in the immune cells infiltrating the tumor.

As used herein, the terms "immunologic", "immunological" or "immune" response is the development of a beneficial humoral (antibody mediated) and/or a cellular (mediated by antigen-specific T cells or their secretion products) response directed against a peptide in a recipient patient. Such a response can be an active response induced by administration of immunogen or a passive response induced by administration of antibody or primed T-cells. Without wishing to be limited by a single hypothesis, a cellular immune response is elicited by the presentation of polypeptide epitopes in association with Class II or Class I MHC molecules to activate antigen-specific CD4+ T helper cells and/or CD8+ cytotoxic T cells, respectively. The response may also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays (CD4+ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

An "immunogenic agent" or "immunogen" is capable of inducing an immunological response against itself on administration to a mammal, optionally in conjunction with an adjuvant.

The term "antibody" as referred to herein includes whole polyclonal and monoclonal antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of at least one heavy chain variable region (abbreviated herein as VH) and a heavy chain constant region. The heavy chain constant region is comprised of three domains, CH1, CH2 and CH3. Each light chain is comprised of at least one light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., C1ORF32 molecules, and/or a fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the V Light, V Heavy, Constant light (CL) and CH1 domains; (ii) a F(ab').2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds C1ORF32 proteins and/or fragments thereof, and is substantially free of antibodies that specifically bind antigens other than C1ORF32, respectively. An isolated antibody that specifically binds C1ORF32 proteins may, however, have cross-reactivity to other antigens, such as C1ORF32 molecules from other species, respectively. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies according to at least some embodiments of the present invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

As used herein, an antibody that "specifically binds to human C1ORF32 proteins" is intended to refer to an antibody that binds to C1ORF32 proteins, preferably one with a KD of $5\times10^{-8}$ M or less, more preferably $3\times10^{-8}$ M or less, even more preferably $1\times10^{-9}$ M or less, even more preferably $1\times10^{-10}$ M, even more preferably $1\times10^{-11}$ M and even more preferably $1\times10^{-12}$ M or less.

The term "K-assoc" or "Ka", as used herein, is intended to refer to the association rate of a particular antibody-antigen interaction, whereas the term "Kdiss" or "Kd," as used herein, is intended to refer to the dissociation rate of a particular antibody-antigen interaction. The term "KD", as used herein, is intended to refer to the dissociation constant, which is obtained from the ratio of Kd to Ka (i.e., Kd/Ka) and is expressed as a molar concentration (M). KD values for antibodies can be determined using methods well established in the art. A preferred method for determining the KD of an antibody is by using surface Plasmon resonance, preferably using a biosensor system such as a Biacore® system.

As used herein, the term "high affinity" for an IgG antibody refers to an antibody having a KD of $10^{-8}$ M or less, more preferably $10^{-9}$ M or less and even more preferably $10^{-10}$ M or less for a target antigen. However, "high affinity" binding can vary for other antibody isotypes. For example, "high affinity" binding for an IgM isotype refers to an antibody having a KD of $10^{-7}$ M or less, more preferably $10^{-8}$ M or less.

As used herein, the term "subject" or "patient" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

As used herein, the term "vaccine" refers to a biological preparation that improves immunity to a particular disease, wherein the vaccine includes an antigen, such as weakened or killed forms of pathogen, its toxins or one of its surface proteins, against which immune responses are elicited. A vaccine typically includes an adjuvant as immune potentiator to stimulate the immune system. As used herein, the terms "therapeutic vaccine" and/or "therapeutic vaccination" refer to a vaccine used to treat ongoing disease, such as infectious disease or cancer.

As used herein, the term "adjuvant" refers to an agent used to stimulate the immune system and increase the response to a vaccine, without having any specific antigenic effect in itself.

Various aspects of the present invention are described in further detail in the following subsections.

Anti C1ORF32 Antibodies

The antibodies according to at least some embodiments of the present invention including those having the particular germline sequences, homologous antibodies, antibodies with conservative modifications, engineered and modified antibodies are characterized by particular functional features or properties of the antibodies. For example, the antibodies bind specifically to human C1ORF32. Preferably, an antibody according to at least some embodiments of the present invention binds to corresponding C1ORF32 with high affinity, for example with a KD of $10^{-8}$ M or less or $10^{-9}$ M or less or even $10^{-10}$ M or less. The C1ORF32-specific antibodies according to at least some embodiments of the present invention preferably exhibit one or more of the following characteristics:

(i) bind to corresponding human C1ORF32 with a KD of $5\times10^{-8}$ M or less, for example optionally as described herein;

(ii) modulate (enhances or inhibits) immune costimulation and related activities and functions such a T cell responses involved in antitumor immunity and autoimmunity;

(iii) bind to C1ORF32 antigen expressed by cancer cells, but does not substantially bind to normal cells;

(iv) increase T-cell proliferation;

(v) increase interferon-gamma production by T-cells;

(vi) increase IL-2 secretion;

(vii) increase Th1 response;

(e) decrease Th2 responses (f) stimulate antigen-specific memory responses;

(g) stimulate antibody responses; and/or (h) inhibit cancer cell growth in vivo, wherein the cancer is selected from the group consisting of Thyroid Carcinoma, preferably Thyroid Papillary Carcinoma, Thyroid Follicular Carcinoma (preferably stage II and III), incidental papillary carcinoma (IPC), Medullary thyroid cancer, Anaplastic thyroid cancer; Squamous cell carcinoma, squamous cell carcinoma of the esophagus; breast carcinoma, preferably stage II to IV and/or poorly differentiated Invasive Ductal Carcinoma, comedocarcinoma and Medullary Carcinoma, preferably Grade 2, ovarian carcinoma, Papillary Serous and Mucinous (preferably stages Ic to IIIb), Granular cell tumour, Surface epithelial-stromal tumor (Adenocarcinoma), cystadenocarcinoma and Endometrioid tumor; kidney cancer, Clear cell carcinoma (preferably stage I to II), Chromophobe adenoma, sarcomatoides carcinoma; Prostate adenocarcinoma, preferably stage I to III, Benign prostatic hyperplasia, Hepatocellular carcinoma, preferably stage II and III, malignant hepatoma, fibrolamellar, pseudoglandular (adenoid), pleomorphic (giant cell) and clear cell HCC and Cholangiocarcinoma, Pancreas cancer, Ductal and Mucinous Adenocarcinoma, Islet cell carcinoma, familial atypical multiple mole melanoma-pancreatic cancer syndrome (FAMMM-PC), Exocrine pancreas cancers, ductal adenocarcinoma, denosquamous carcinomas, signet ring cell carcinomas, hepatoid carcinomas, colloid carcinomas, undifferentiated carcinomas, and undifferentiated carcinomas with osteoclast-like giant cells, Low- to intermediate-grade neuroendocrine carcinomas and pancreatic carcinoid tumors; Malignant melanoma, preferably stage IV malignant melanoma and/or one or more of Lentigo maligna Lentigo maligna melanoma, Superficial spreading melanoma, Acral lentiginous melanoma, Mucosal melanoma, Nodular melanoma, Polypoid melanoma, Desmoplastic melanoma, Amelanotic melanoma and Soft-tissue melanoma; sarcomas of bone, cartilage and of soft tissue including but not limited to Osteogenic sarcoma, Chondrosarcoma, Leiomyosarcoma, Angiosarcoma, Askin's Tumor, Ewing's sarcoma, Kaposi's sarcoma, Liposarcoma, Malignant fibrous histiocytoma, Rhabdomyosarcoma and Neurofibrosarcoma; Lymphoma, preferably comprising Hodgkin's lymphoma (Nodular sclerosing, Mixed-cellularity subtype, Lymphocyte-rich or Lymphocytic predominance, Lymphocyte depleted and Unspecified), B-cell Lymphoma (Diffuse large B cell lymphoma, Follicular lymphoma, Mucosa-Associated Lymphatic Tissue lymphoma (MALT), Small cell lymphocytic lymphoma, Burkitt lymphoma, Mediastinal large B cell lymphoma, Waldenström macroglobulinemia, Nodal marginal zone B cell lymphoma (NMZL), Splenic marginal zone lymphoma (SMZL), Intravascular large B-cell lymphoma, Primary effusion lymphoma, Lymphomatoid granulomatosis), Mantle cell lymphoma (MCL), T-cell Lymphoma (Extranodal T cell lymphoma, Cutaneous T cell lymphomas: Sézary syndrome and Mycosis fungoides, Anaplastic large cell lymphoma, Angioimmunoblastic T cell lymphoma); Uterine cancer, preferably comprising Endometroid Adenocarcinoma (preferably stages I to IIIc); Bladder cancer, preferably comprising Transitional Cell carcinoma (preferably stage II to IV); Lung cancer preferably comprising Small Cell Lung Cancer (preferably stage I, to IIIb), Non Small Cell Lung Cancer (preferably poorly to moderately differentiated squamous and adeno carcinoma) and Large-cell carcinoma, testicular seminoma, Colo-rectal cancer preferably comprises colon and rectal adenocarcinoma (preferably Moderate to Poorly Differentiated); and spinal cord tumors.

In addition, preferably these antibodies and/or conjugates thereof are effective in eliciting selective killing of such cancer cells and for modulating immune responses involved in autoimmunity and cancer.

Standard assays to evaluate the binding ability of the antibodies toward C1ORF32 are known in the art, including for example, ELISAs, Western blots and RIAs. Suitable assays are described in detail in the Examples. The binding kinetics (e.g., binding affinity) of the antibodies also can be assessed by standard assays known in the art, such as by Biacore analysis.

Upon production of C1ORF32-specific antibody sequences from antibodies can bind to C1ORF32 the VH and VL sequences can be "mixed and matched" to create other antiC1ORF32, binding molecules according to at least some embodiments of the present invention. C1ORF32 binding of such "mixed and matched" antibodies can be tested using the binding assays described above. e.g., ELISAs). Preferably, when VH and VL chains are mixed and matched, a VH sequence from a particular VH/VL pairing is replaced with a structurally similar VH sequence. Likewise, preferably a VL sequence from a particular VH/VL pairing is replaced with a structurally similar VL sequence. For example, the VH and VL sequences of homologous antibodies are particularly amenable for mixing and matching.

Antibodies Having Particular Germline Sequences

In certain embodiments, an antibody of the present invention comprises a heavy chain variable region from a particular germline heavy chain immunoglobulin gene and/or a light chain variable region from a particular germline light chain immunoglobulin gene.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody.

A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95, %, 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody of the present invention comprises heavy and light chain variable regions comprising amino acid sequences that are homologous to isolated anti-C1ORF32 amino acid sequences of preferred anti-C1ORF32 antibodies, respectively, wherein the antibodies retain the desired functional properties of the parent anti-C1ORF32 antibodies.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available commercially), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) J Mol. Biol. 215:403-10. BLAST protein searches can be performed with the XBLAST program, score=50, wordlength=3 to obtain amino acid sequences homologous to the antibody molecules according to at least some embodiments of the present invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

Antibodies with Conservative Modifications

In certain embodiments, an antibody of the present invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on preferred anti-C1ORF32 antibodies isolated and produced using methods herein, or conservative modifications thereof, and wherein the antibodies retain the desired functional properties of the anti-C1ORF32 antibodies according to at least some embodiments of the present invention, respectively.

In various embodiments, the anti-C1ORF32 antibody can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody according to at least some embodiments of the present invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, 1, 2, 3, 4, 5, 6, 7, 8, 9, or 10 amino acid residues within the CDR regions of an antibody according to at least some embodiments of the present invention can be replaced with other amino acid residues from the same side chain family and the altered antibody can be tested for retained function (i.e., the functions set forth in (c) through (j) above) using the functional assays described herein. Also computer programs are available to perform these and other simultaneous optimizations as are well known in the art.

In some embodiments, only one substitution is made. In some embodiments, 2-3 substitutions are made. In still other embodiments, 4-6 substitutions are made. In still other embodiments, 7-10 substitutions are made.

Antibodies that Bind to the Same Epitope as anti-C1ORF32 according to at least some embodiments of the present invention.

In another embodiment, the present invention provides antibodies that bind to preferred epitopes on human C1ORF32 which possess desired functional properties such as modulation of B7 co-stimulation and related functions. Other antibodies with desired epitope specificity may be selected and will have the ability to cross-compete for binding to C1ORF32 antigen with the desired antibodies.

Engineered and Modified Antibodies

An antibody according to at least some embodiments of the present invention further can be prepared using an antibody having one or more of the VH and/or VL sequences derived from an anti-C1ORF32 antibody starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant regions, for example to alter the effector functions of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332:323-327; Jones, P. et al. (1986) Nature 321:522-525; Queen, C. et al. (1989) Proc. Natl. Acad. See. U.S.A. 86:10029-10033; U.S. Pat. No. 5,225,539 to Winter, and U.S. Pat. Nos. 5,530,101; 5,585,089; 5,693,762 and 6,180,370 to Queen et al.)

Suitable framework sequences can be obtained from public DNA databases or published references that include germline antibody gene sequences. For example, germline DNA sequences for human heavy and light chain variable region genes can be found in the "VBase" human germline sequence database (available on the Internet), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline VH Sequences Reveals about Fifty Groups of VH Segments with Different Hypervariable Loops" J. Mol. Biol. 227:776-798; and Cox, J. P. L. et al. (1994) "A Directory of Human Germ-line VH Segments Reveals a Strong Bias in their Usage" Eur. J Immunol. 24:827-836; the contents of each of which are expressly incorporated herein by reference.

Another type of variable region modification is to mutate amino acid residues within the VH and/or VL CDR 1, CDR2 and/or CDR3 regions to thereby improve one or more binding properties (e.g., affinity) of the antibody of interest. Site-directed mutagenesis or PCR-mediated mutagenesis can be performed to introduce the mutations and the effect on antibody binding, or other functional property of interest, can be evaluated in appropriate in vitro or in vivo assays. Preferably conservative modifications (as discussed above) are introduced. The mutations may be amino acid substitutions, additions or deletions, but are preferably substitutions. Moreover, typically no more than one, two, three, four or five residues within a CDR region are altered.

Engineered antibodies according to at least some embodiments of the present invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

In addition or alternative to modifications made within the framework or CDR regions, antibodies according to at least some embodiments of the present invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody according to at least some embodiments of the present invention may be chemically modified (e.g., one or more chemical moieties can be attached to the antibody) or be modified to alter its glycosylation, again to alter one or more functional properties of the antibody. Such embodiments are described further below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for Fc grammar, Fc gamma RII, Fc gammaRIII and FcRn have been mapped and variants with improved binding have been described (see Shields, R. L. et al. (2001) J. Biol. Chem. 276:6591-6604). Specific mutations at positions 256, 290, 298, 333, 334 and 339 are shown to improve binding to FcγRIII. Additionally, the following combination mutants are shown to improve Fcgamma.RIII binding: T256A/S298A, S298A/E333A, S298A/K224A and S298A/E333A/K334A. Furthermore, mutations such as M252Y/S254T/T256E or M428L/N434S improve binding to FcRn and increase antibody circulation half-life (see Chan C A and Carter P J (2010) Nature Rev Immunol 10:301-316).

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies according to at least some embodiments of the present invention to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8.−/− cell lines are created by the targeted disruption of the FUT8 gene in CHO/DG44 cells using two replacement vectors (see U.S. Patent Publication No. 20040110704 by Yamane et al. and Yamane-Ohnuki et al. (2004) Biotechnol Bioeng 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn (297)-linked carbohydrates, also resulting in hypofucosylation of antibodies expressed in that host cell (see also Shields, R. L. et al. (2002) J. Biol. Chem. 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) Biochem. 14:5516-23).

Another modification of the antibodies herein that is contemplated by the present invention is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies according to at least some embodiments of the present invention. See for example, EP 0 154 316 by Nishimura et al. and EP 0 401 384 by Ishikawa et al.

Methods of Engineering Antibodies

As discussed above, anti-C1ORF32 antibodies having VH and VK sequences disclosed herein can be used to create new anti-C1ORF32 antibodies, respectively, by modifying the VH and/or VL sequences, or the constant regions attached thereto. Thus, in another aspect according to at least some embodiments of the present invention, the structural features of an anti-C1ORF32 antibody according to at least some embodiments of the present invention, are used to create structurally related anti-C1ORF32 antibodies that retain at least one functional property of the antibodies according to at least some embodiments of the present invention, such as binding to human C1ORF32, respectively. For example, one or more CDR regions of one C1ORF32 antibody or mutations thereof, can be combined recombinantly with known framework regions and/or other CDRs to create additional, recombinantly-engineered, anti-C1ORF32 antibodies according to at least some embodiments of the present invention, as discussed above. Other types of modifications include those described in the previous section. The starting material for the engineering method is one or more of the VH and/or VK sequences provided herein, or one or more CDR regions thereof. To create the engineered antibody, it is not necessary to actually prepare (i.e., express as a protein) an antibody having one or more of the VH and/or VK sequences provided herein, or one or more CDR regions thereof. Rather, the information contained in the sequences is used as the starting material to create a "second generation" sequences derived from the original sequences and then the "second generation" sequences is prepared and expressed as a protein.

Standard molecular biology techniques can be used to prepare and express altered antibody sequence.

Preferably, the antibody encoded by the altered antibody sequences is one that retains one, some or all of the functional properties of the anti-C1ORF32 antibodies, respectively, produced by methods and with sequences provided herein, which functional properties include binding to C1ORF32 antigen with a specific KD level or less and/or modulating B7 costimulation and/or selectively binding to desired target cells such as for example cancer cells, that express C1ORF32 antigen.

The functional properties of the altered antibodies can be assessed using standard assays available in the art and/or described herein.

In certain embodiments of the methods of engineering antibodies according to at least some embodiments of the present invention, mutations can be introduced randomly or selectively along all or part of an anti-C1ORF32 antibody coding sequence and the resulting modified anti-C1ORF32 antibodies can be screened for binding activity and/or other desired functional properties.

Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies

Another aspect of the present invention pertains to nucleic acid molecules that encode the antibodies according to at least some embodiments of the present invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid according to at least some embodiments of the present invention can be, for example, DNA or RNA and may or may not contain intronic sequences. In a preferred embodiment, the nucleic acid is a cDNA molecule.

Nucleic acids according to at least some embodiments of the present invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker.

The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence (Gly4-Ser)3, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

Production of Anti-C1ORF32 Monoclonal Antibodies

Monoclonal antibodies (mAbs) of the present invention can be produced by a variety of techniques, including conventional monoclonal antibody methodology e.g., the standard somatic cell hybridization technique of Kohler and Milstein (1975) Nature 256:495. Although somatic cell hybridization procedures are preferred, in principle, other techniques for producing monoclonal antibody can be employed e.g., viral or oncogenic transformation of B lymphocytes.

A preferred animal system for preparing hybridomas is the murine system. Hybridoma production in the mouse is a very well-established procedure Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693, 762 and 6,180,370 to Queen et al.).

According to at least some embodiments of the present invention, the antibodies are human monoclonal antibodies. Such human monoclonal antibodies directed against C1ORF32 can be generated using transgenic or transchromosomic mice carrying parts of the human immune system rather than the mouse system. These transgenic and transchromosomic mice include mice referred to herein as the HuMAb Mouse® and KM Mouse®, respectively, and are collectively referred to herein as "human Ig mice." The HuMAb Mouse™. (Medarex. Inc.) contains human immunoglobulin gene miniloci that encode unrearranged human heavy (mu and gamma) and kappa light chain immunoglobulin sequences, together with targeted mutations that inactivate the endogenous mu and kappa chain loci (see e.g., Lonberg, et al. (1994) Nature 368(6474): 856-859). Accordingly, the mice exhibit reduced expression of mouse IgM or kappa, and in response to immunization, the introduced human heavy and light chain transgenes undergo class switching and somatic mutation to generate high affinity human IgGkappa. monoclonal (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). The preparation and use of the HuMab Mouse®, and the genomic modifications carried by such mice, is further described in Taylor, L. et al. (1992) Nucleic Acids Research 20:6287-6295; Chen, J. et al. (1993) International Immunology 5:647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Taylor, L. et al. (1994) International Immunology 6:579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies according to at least some embodiments of the present invention can be raised using a mouse that carries human immunoglobulin sequences on transgenes and transchomosomes, such as a mouse that carries a human heavy chain transgene and a human light chain transchromosome. Such mice, referred to herein as "KM Mice™.", are described in detail in PCT Publication WO 02/43478 to Ishida et al.

Still further, alternative transgenic animal systems expressing human immunoglobulin genes are available in the art and can be used to raise anti-C1ORF32 antibodies according to at least some embodiments of the present invention. For example, an alternative transgenic system referred to as the Xenomouse (Abgenix, Inc.) can be used; such mice are described in, for example, U.S. Pat. Nos. 5,939,598; 6,075,181; 6,114,598; 6, 150,584 and 6,162,963 to Kucherlapati et al.

Moreover, alternative transchromosomic animal systems expressing human immunoglobulin genes are available in the art and can be used to raise anti-C1ORF32 antibodies according to at least some embodiments of the present invention. For example, mice carrying both a human heavy chain transchromosome and a human light chain transchromosome, referred to as "TC mice" can be used; such mice are described in Tomizuka et al. (2000) Proc. Natl. Acad Sci. USA 97:722-727. Furthermore, cows carrying human heavy and light chain transchromosomes have been described in the art (Kuroiwa et al. (2002) Nature Biotechnology 20:889-894) and can be used to raise anti-C1ORF32 antibodies according to at least some embodiments of the present invention.

Human monoclonal antibodies according to at least some embodiments of the present invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885, 793; 6,521,404; 6,544,731; 6,555,313; 6,582,915 and 6,593, 081 to Griffiths et al.

Human monoclonal antibodies according to at least some embodiments of the present invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies according to at least some embodiments of the present invention, such mice can be immunized with a purified or enriched preparation of C1ORF32 antigen and/or recombinant C1ORF32 fusion protein, as described by Lonberg, N. et al. (1994) Nature 368(6474): 856-859; Fishwild, D. et al. (1996) Nature Biotechnology 14: 845-851; and PCT Publication WO 98/24884 and WO 01/14424. Preferably, the mice will be 6-16 weeks of age upon the first infusion. For example, a purified or recombinant preparation (5-50 microgram) of C1ORF32 antigen can be used to immunize the human Ig mice intraperitoneally.

Prior experience with various antigens by others has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-C1ORF32 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene can be bred together into a single mouse having two different human heavy chain transgenes (HCo7/HCo12). Alternatively or additionally, the KM Mouse® strain can be used.

Generation of Hybridomas Producing Human Monoclonal Antibodies

To generate hybridomas producing human monoclonal antibodies according to at least some embodiments of the present invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 non-secreting mouse myeloma cells (ATCC, CRL 1580) with 50% PEG. Cells are plated at approximately $2 \times 10-5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-Sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80 degrees C.

Generation of Transfectomas Producing Monoclonal Antibodies

Antibodies according to at least some embodiments according to at least some embodiments of the present invention also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segments within the vector and the VK segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors according to at least some embodiments of the present invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or .beta.-globin promoter. Still further, regulatory elements composed of sequences from different sources, such as the SR alpha. promoter system, which contains sequences from the SV40 early promoter and the long terminal repeat of human T cell leukemia virus type 1 (Takebe, Y. et al. (1988) Mol. Cell. Biol. 8:466-472).

In addition to the antibody chain genes and regulatory sequences, the recombinant expression vectors according to at least some embodiments of the present invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr– host cells with methotrexate selection/amplification) and the neo gene (for G418 selection).

For expression of the light and heavy chains, the expression vectors encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies according to at least some embodiments of the present invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) Immunology Today 6:12-13).

Preferred mammalian host cells for expressing the recombinant antibodies according to at least some embodiments of the present invention include Chinese Hamster Ovary (CHO cells) (including dhfr– CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Characterization of Antibody Binding to Antigen

Antibodies according to at least some embodiments of the present invention can be tested for binding to C1ORF32 by, for example, standard ELISA. Briefly, microtiter plates are coated with purified C1ORF32 at 0.25 microgram/ml in PBS, and then blocked with 5% bovine serum albumin in PBS. Dilutions of antibody (e.g., dilutions of plasma from—immunized mice) are added to each well and incubated for 1-2 hours at 37 degrees C. The plates are washed with PBS/Tween and then incubated with secondary reagent (e.g., for human antibodies, a goat-anti-human IgG Fc-specific polyclonal reagent) conjugated to alkaline phosphatase for 1 hour at 37 degrees C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with C1ORF32 immunogen. Hybridomas that bind with high avidity to C1ORF32 are subcloned and further characterized. One clone from each hybridoma, which retains the reactivity of the parent cells (by ELISA), can be chosen for making a 5-10 vial cell bank stored at −140 degrees C., and for antibody purification.

To purify anti-C1ORF32 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80 degrees C.

To determine if the selected anti-C1ORF32 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using C1ORF32 coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 microgram/ml of anti-human immunoglobulin overnight at 4 degrees C. After blocking with 1% BSA, the plates are reacted with 1 mug/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-C1ORF32 human IgGs can be further tested for reactivity with C1ORF32 antigen, respectively, by Western blotting. Briefly, C1ORF32 antigen can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Alternative Scaffolds

According to at least some embodiments the present invention relates to protein scaffolds with specificities and affinities in a range similar to specific antibodies. According to at least some embodiments the present invention relates to an antigen-binding construct comprising a protein scaffold which is linked to one or more epitope-binding domains. Such engineered protein scaffolds are usually obtained by designing a random library with mutagenesis focused at a loop region or at an otherwise permissible surface area and by selection of variants against a given target via phage display or related techniques. According to at least some embodiments the present invention relates to alternative scaffolds including, but not limited to, anticalins, DARPins, Armadillo repeat proteins, protein A, lipocalins, fibronectin domain, ankyrin consensus repeat domain, thioredoxin, chemically constrained peptides and the like. According to at least some embodiments the present invention relates to alternative scaffolds that are used as therapeutic agents for treatment of cancer, autoimmune and infectious diseases as well as for in vivo diagnostics.

According to at least some embodiments the present invention further provides a pharmaceutical composition comprising an antigen binding construct as described herein a pharmaceutically acceptable carrier.

The term 'Protein Scaffold' as used herein includes but is not limited to an immunoglobulin (Ig) scaffold, for example an IgG scaffold, which may be a four chain or two chain antibody, or which may comprise only the Fc region of an antibody, or which may comprise one or more constant regions from an antibody, which constant regions may be of human or primate origin, or which may be an artificial chimera of human and primate constant regions. Such protein scaffolds may comprise antigen-binding sites in addition to the one or more constant regions, for example where the protein scaffold comprises a full IgG. Such protein scaffolds will be capable of being linked to other protein domains, for example protein domains which have antigen-binding sites, for example epitope-binding domains or ScFv domains.

A "domain" is a folded protein structure which has tertiary structure independent of the rest of the protein. Generally, domains are responsible for discrete functional properties of proteins and in many cases may be added, removed or transferred to other proteins without loss of function of the remainder of the protein and/or of the domain. A "single antibody variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

The phrase "immunoglobulin single variable domain" refers to an antibody variable domain (VH, V HH, V L) that specifically binds an antigen or epitope independently of a different V region or domain. An immunoglobulin single variable domain can be present in a format (e.g., homo- or hetero-multimer) with other, different variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" which is capable of binding to an antigen as the term is used herein. An immunoglobulin single variable domain may be a human antibody variable domain, but also includes single antibody variable domains from other species such as rodent (for example, as disclosed in WO 00/29004), nurse shark and Camelid V HH dAbs. Camelid V HH are immunoglobulin single variable domain polypeptides that are derived from species including camel, llama, alpaca, dromedary, and guanaco, which produce heavy chain antibodies naturally devoid of light chains. Such V HH domains may be humanised according to standard techniques available in the art, and such domains are still considered to be "domain antibodies" according to the present invention. As used herein "VH includes camelid V HH domains. NARV are another type of immunoglobulin single variable domain which were identified in cartilaginous fish including the nurse shark. These domains are also known as Novel Antigen Receptor variable region (commonly abbreviated to V(NAR) or NARV). For further details see MoI. Immunol. 44, 656-665 (2006) and US20050043519A.

The term "epitope-binding domain" refers to a domain that specifically binds an antigen or epitope independently of a different V region or domain, this may be a domain antibody (dAb), for example a human, camelid or shark immunoglobulin single variable domain or it may be a domain which is a derivative of a scaffold selected from the group consisting of CTLA-4 (Evibody); lipocalin; Protein A derived molecules such as Z-domain of Protein A (Affibody, SpA), A-domain (Avimer/Maxibody); Heat shock proteins such as GroEI and GroES; transferrin (trans-body); ankyrin repeat protein (DARPin); peptide aptamer; C-type lectin domain (Tetranectin); human γ—crystallin and human ubiquitin (affilins); PDZ domains; scorpion toxinkunitz type domains of human protease inhibitors; Armadillo repeat proteins, thioredoxin, and fibronectin (adnectin); which has been subjected to protein engineering in order to obtain binding to a ligand other than the natural ligand.

Loops corresponding to CDRs of antibodies can be substituted with heterologous sequence to confer different binding properties i.e. Evibodies. For further details see Journal of Immunological Methods 248 (1-2), 31-45 (2001) Lipocalins are a family of extracellular proteins which transport small hydrophobic molecules such as steroids, bilins, retinoids and lipids. They have a rigid secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), US7250297B1 and US20070224633. An affibody is a scaffold derived from Protein A of Staphylococcus aureus which can be engineered to bind to antigen. The domain consists of a three-helical bundle of approximately 58 amino acids. Libraries have been generated by randomisation of surface residues. For further details see Protein Eng. Des. SeI. 17, 455-462 (2004) and EP1641818A1 Avimers are multidomain proteins derived from the A-domain scaffold family. The native domains of approximately 35 amino acids adopt a defined disulphide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007) A transferrin is a monomeric serum transport glycoprotein. Transferrins can be engineered to bind different target antigens by insertion of peptide sequences in a permissive surface loop. Examples of engineered transferrin scaffolds include the Trans-body. For further details see J. Biol. Chem 274, 24066-24073 (1999).

Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two alpha helices;—beta turn. They can be engineered to bind different target antigens by randomising residues in the first alpha-helix and a beta-turn of each repeat. Their binding interface can be increased by increasing the number of modules (a method of affinity maturation). For further details see J. MoI. Biol. 332, 489-503 (2003), PNAS 100(4), 1700-1705 (2003) and J. MoI. Biol. 369, 1015-1028 (2007) and US20040132028A1.

Fibronectin is a scaffold which can be engineered to bind to antigen. Adnectins consists of a backbone of the natural amino acid sequence of the 10th domain of the 15 repeating units of human fibronectin type III (FN3). Three loops at one end of the beta;—sandwich can be engineered to enable an Adnectin to specifically recognize a therapeutic target of interest. For further details see Protein Eng. Des. SeI. 18, 435-444 (2005), US200801 39791, WO2005056764 and US6818418B1.

Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5. 783-797 (2005).

Microbodies are derived from naturally occurring microproteins of 25-50 amino acids in length which contain 3-4 cysteine bridges—examples of microproteins include KalataBI and conotoxin and knottins. The microproteins have a loop which can be engineered to include upto 25 amino acids without affecting the overall fold of the microprotein. For further details of engineered knottin domains, see WO2008098796.

Other epitope binding domains include proteins which have been used as a scaffold to engineer different target antigen binding properties include human γbeta-crystallin and human ubiquitin (affilins), kunitz type domains of human protease inhibitors, PDZ-domains of the Ras-binding protein AF-6, scorpion toxins (charybdotoxin), C-type lectin domain (tetranectins) are reviewed in Chapter 7—Non-Antibody Scaffolds from Handbook of Therapeutic Antibodies (2007, edited by Stefan Dubel) and Protein Science 15:14-27 (2006). Epitope binding domains of the present invention could be derived from any of these alternative protein domains.

Conjugates or Immunoconjugates

The present invention encompasses conjugates for use in immune therapy comprising the C1ORF32 antigen and soluble portions thereof including the ectodomain or portions or variants thereof. For example the present invention encompasses conjugates wherein the ECD of the C1ORF32 antigen is attached to an immunoglobulin or fragment thereof. The present invention contemplates the use thereof for promoting or inhibiting C1ORF32 antigen activities such as immune costimulation and the use thereof in treating transplant, autoimmune, and cancer indications described herein.

In another aspect, the present invention features immunoconjugates comprising an anti-C1ORF32 antibody, or a fragment thereof, conjugated to a therapeutic moiety, such as a cytotoxin, a drug (e.g., an immunosuppressant) or a radiotoxin. Such conjugates are referred to herein as "immunoconjugates" Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, anti-metabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody according to at least some embodiments of the present invention include duocarmycins, calicheamicins, maytansines and auristatins, and derivatives thereof. An example of a calicheamicin antibody conjugate is commercially available (Mylotarg™; Wyeth).

Cytotoxins can be conjugated to antibodies according to at least some embodiments of the present invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine 131, indium 111, yttrium 90 and lutetium 177. Method for preparing radioimmunconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies according to at least some embodiments of the present invention.

The antibody conjugates according to at least some embodiments of the present invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-gamma; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

In another aspect, the present invention features bispecific molecules comprising an anti-C1ORF32 antibody, or a fragment thereof, according to at least some embodiments of the present invention. An antibody according to at least some embodiments of the present invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody according to at least some embodiments of the present invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule according to at least some embodiments of the present invention, an antibody can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for C1ORF32 and a second binding specificity for a second target epitope. According to at least some embodiments of the present invention, the second target epitope is an Fc receptor, e.g., human Fc gamma RI (CD64) or a human Fc alpha receptor (CD89). Therefore, the present invention includes bispecific molecules capable of binding both to Fc gamma. R, Fc alpha R or Fc epsilon R expressing effector cells (e.g., monocytes, macrophages or polymorphonuclear cells (PMNs)), and to target cells expressing C1ORF32. These bispecific molecules target C1ORF32 expressing cells to effector cell and trigger Fc receptor-mediated effector cell activities, such as phagocytosis of an C1ORF32 expressing cells, antibody dependent cell-mediated cytotoxicity (ADCC), cytokine release, or generation of superoxide anion.

According to at least some embodiments of the present invention in which the bispecific molecule is multispecific, the molecule can further include a third binding specificity, in addition to an anti-Fc binding specificity and an anti-6f binding specificity. In one embodiment, the third binding specificity is an anti-enhancement factor (EF) portion, e.g., a molecule which binds to a surface protein involved in cytotoxic activity and thereby increases the immune response against the target cell.

The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g., via CD2, CD3, CD8, CD28, CD4, CD40, ICAM-1 or other immune cell, or to a surface protein involved in cytotoxic activity, that results in an increased immune response against the target cell).

According to at least some embodiments of the present invention, the bispecific molecules comprise as a binding specificity at least one antibody, or an antibody fragment thereof, including, e.g., an Fab, Fab', F(ab').sub.2, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

According to at least some embodiments of the present invention, the bispecific molecules are produced based on any technology known in the art, including, but not limited to: "Dual variable domain" (DVD) antibodies, Abbott, as described in U.S. Pat. No. 7,612,181, the content of which is expressly incorporated by reference; "Dual-affinityretargeting" (DART) (Macrogenics, Blood. 2011; 117(17): 4542-4551); "Modular antibody technology by F-star" (Protein Eng Des Sel. 2010; 23(4):289); "Bispecific T-cell engager technology" („BITE) (Micromet, J Immunother. 2009 June; 32(5):452-64); "Bicycle technology" (Bicycle Therapeutics, Nature Chemical Biology 2009; 5, 502-507); "Dual targeting domain antibodies" (dAbs, Domantis, US Patent Application 20100247515).

In one embodiment, the binding specificity for an Fcγ receptor is provided by a monoclonal antibody, the binding of which is not blocked by human immunoglobulin G (IgG). As used herein, the term "IgG receptor" refers to any of the eight gamma-chain genes located on chromosome 1. These genes encode a total of twelve transmembrane or soluble receptor isoforms which are grouped into three Fc gamma receptor classes: Fc gamma R1 (CD64), Fc gamma RII (CD32), and Fc gamma.RIII (CD 16). In one preferred embodiment, the Fc gamma. receptor a human high affinity Fc.gamma RI. The human Fc gammaRI is a 72 kDa molecule, which shows high affinity for monomeric IgG ($10^{-8}$-$10^{-9}$ M.-1).

The production and characterization of certain preferred anti-Fc gamma. monoclonal antibodies are described by Fanger et al. in PCT Publication WO 88/00052 and in U.S. Pat. No. 4,954,617, the teachings of which are fully incorporated by reference herein. These antibodies bind to an epitope of Fc gammaR1, FcγRII or FcγRIII at a site which is distinct from the Fc gamma binding site of the receptor and, thus, their binding is not blocked substantially by physiological levels of IgG. Specific anti-Fc gammaRI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) J. Immunol. 155 (10): 4996-5002 and PCT Publication WO 94/10332. The H22 antibody producing cell line is deposited at the American Type Culture Collection under the designation HAO22CL1 and has the accession no. CRL 11177.

In still other preferred embodiments, the binding specificity for an Fc receptor is provided by an antibody that binds to a human IgA receptor, e.g., an Fc-alpha receptor (Fc alpha.RI (CD89)), the binding of which is preferably not blocked by human immunoglobulin A (IgA). The term "IgA receptor" is intended to include the gene product of one alpha.-gene (Fc alpha.RI) located on chromosome 19. This gene is known to encode several alternatively spliced transmembrane isoforms of 55 to 10 kDa.

Fc.alpha.RI (CD89) is constitutively expressed on monocytes/macrophages, eosinophilic and neutrophilic granulocytes, but not on non-effector cell populations. Fc alpha RI has medium affinity (Approximately $5\times10^{-7}$ M-1) for both IgA1 and IgA2, which is increased upon exposure to cytokines such as G-CSF or GM-CSF (Morton, H. C. et al. (1996) Critical Reviews in Immunology 16:423-440). Four FcαRI-specific monoclonal antibodies, identified as A3, A59, A62 and A77, which bind Fc.alpha.RI outside the IgA ligand binding domain, have been described (Monteiro, R. C. et al. (1992) J. Immunol. 148:1764).

Fc. alpha. RI and Fc gamma. RI are preferred trigger receptors for use in the bispecific molecules according to at least some embodiments of the present invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

While human monoclonal antibodies are preferred, other antibodies which can be employed in the bispecific molecules according to at least some embodiments of the present invention are murine, chimeric and humanized monoclonal antibodies.

The bispecific molecules of the present invention can be prepared by conjugating the constituent binding specificities, e.g., the anti-FcR and anti-C1ORF32 binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) J. Exp. Med. 160:1686; Liu, M A et al. (1985) Proc. Natl. Acad. Sci. USA 82:8648). Other methods include those described in Paulus (1985) Behring Ins. Mitt. No. 78, 118-132; Brennan et al. (1985) Science 229:81-83), and Glennie et al. (1987) J. Immunol. 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAbXmAb, mAbXFab, FabXF(ab')2 or ligandXFab fusion protein. A bispecific molecule according to at least some embodiments of the present invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma. counter or a scintillation counter or by autoradiography.

Pharmaceutical Compositions and Uses Thereof

In another aspect, the present invention provides a composition, e.g., a pharmaceutical composition, containing one or a combination of C1ORF32 specific monoclonal antibodies, or antigen-binding portions thereof, formulated together with a pharmaceutically acceptable carrier. Such compositions may include one or a combination of (e.g., two or more different) antibodies, and/or immunoconjugates and/or alternative scaffolds and/or bispecific molecules according to at least some embodiments of the present invention. For example, a pharmaceutical composition according to at least some embodiments of the present invention can comprise a combination of antibodies (or immunoconjugates or bispecifics) that bind to different epitopes on the target antigen or that have complementary activities.

C1ORF32 specific antibodies, particularly human antibodies and antibody compositions, have numerous therapeutic utilities and in vitro and in vivo diagnostic utilities, involving the treatment and diagnosis of cancer, selected from the group consisting of Thyroid Carcinoma, preferably Thyroid Papillary Carcinoma, Thyroid Follicular Carcinoma (preferably stage II and III), incidental papillary carcinoma (IPC), Medullary thyroid cancer, Anaplastic thyroid cancer; Squamous cell carcinoma, squamous cell carcinoma of the esophagus; breast carcinoma, preferably stage II to IV and/or poorly differentiated Invasive Ductal Carcinoma, comedocarcinoma and Medullary Carcinoma, preferably Grade 2, ovarian carcinoma, Papillary Serous and Mucinous (preferably stages Ic to IIIb), Granular cell tumour, Surface epithelial-stromal tumor (Adenocarcinoma), cystadenocarcinoma and Endometrioid tumor; kidney cancer, Clear cell carcinoma (preferably stage I to II), Chromophobe adenoma, sarcomatoides carcinoma; Prostate adenocarcinoma, preferably stage I to III, Benign prostatic hyperplasia, Hepatocellular carcinoma, preferably stage II and III, malignant hepatoma, fibrolamellar, pseudoglandular (adenoid), pleomorphic (giant cell) and clear cell HCC and Cholangiocarcinoma, Pancreas cancer, Ductal and Mucinous Adenocarcinoma, Islet cell carcinoma, familial atypical multiple mole melanoma-pancreatic cancer syndrome (FAMMM-PC), Exocrine pancreas cancers, ductal adenocarcinoma, denosquamous carcinomas, signet ring cell carcinomas, hepatoid carcinomas, colloid carcinomas, undifferentiated carcinomas, and undifferentiated carcinomas with osteoclast-like giant cells, Low- to intermediate-grade neuroendocrine carcinomas and pancreatic carcinoid tumors; Malignant melanoma, preferably stage IV malignant melanoma and/or one or more of Lentigo maligna Lentigo maligna melanoma, Superficial spreading melanoma, Acral lentiginous melanoma, Mucosal melanoma, Nodular melanoma, Polypoid melanoma, Desmoplastic melanoma, Amelanotic melanoma and Soft-tissue melanoma; sarcomas of bone, cartilage and of soft tissue including but not limited to Osteogenic sarcoma, Chondrosarcoma, Leiomyosarcoma, Angiosarcoma, Askin's Tumor, Ewing's sarcoma, Kaposi's sarcoma, Liposarcoma, Malignant fibrous histiocytoma, Rhabdomyosarcoma and Neurofibrosarcoma; Lymphoma, preferably comprising Hodgkin's lymphoma (Nodular sclerosing, Mixed-cellularity subtype, Lymphocyte-rich or Lymphocytic predominance, Lymphocyte depleted and Unspecified), B-cell Lymphoma (Diffuse large B cell lymphoma, Follicular lymphoma, Mucosa-Associated Lymphatic Tissue lymphoma (MALT), Small cell lymphocytic lymphoma, Burkitt lymphoma, Mediastinal large B cell lymphoma, Waldenström macroglobulinemia, Nodal marginal zone B cell lymphoma (NMZL), Splenic marginal zone lymphoma (SMZL), Intravascular large B-cell lymphoma, Primary effusion lymphoma, Lymphomatoid granulomatosis), Mantle cell lymphoma (MCL), T-cell Lymphoma (Extranodal T cell lymphoma, Cutaneous T cell lymphomas: Sézary syndrome and Mycosis fungoides, Anaplastic large cell lymphoma, Angioimmunoblastic T cell lymphoma); Uterine cancer, preferably comprising Endometroid Adenocarcinoma (preferably stages I to IIIc); Bladder cancer, preferably comprising Transitional Cell carcinoma (preferably stage II to IV); Lung cancer preferably comprising Small Cell Lung Cancer (preferably stage I, to IIIb), Non Small Cell Lung Cancer (preferably poorly to moderately differentiated squamous and adeno carcinoma) and Large-cell carcinoma, testicular seminoma, Colo-rectal cancer preferably comprises colon and rectal adenocarcinoma (preferably Moderate to Poorly Differentiated); and spinal cord tumors.

Without wishing to be limited by a single hypothesis, anti-C1ORF32 antibodies may prevent negative regulation of of T cell stimulation aimed against cancer cells. For example, these molecules can be administered to cells in culture, in vitro or ex vivo, or to human subjects, e.g., in vivo, to treat, prevent and to diagnose a variety of disorders.

The antibodies (e.g., human antibodies, multispecific and bispecific molecules, immunoconjugates, alternative scaffolds and compositions) according to at least some embodiments of the present invention can be used to elicit in vivo or in vitro one or more of the following biological activities: to inhibit the growth of and/or kill a cell expressing C1ORF32; to mediate phagocytosis or ADCC of a cell expressing C1ORF32 in the presence of human effector cells, or to block C1ORF32 ligand binding to C1ORF32.

"Treatment" refers to both therapeutic treatment and prophylactic or preventative measures. Those in need of treatment include those already with cancer as well as those in which the cancer is to be prevented. Hence, the mammal to be treated herein may have been diagnosed as having the cancer or may be predisposed or susceptible to the cancer. As used herein the term "treating" refers to preventing, delaying the onset of, curing, reversing, attenuating, alleviating, minimizing, suppressing, halting the deleterious effects or stabilizing of discernible symptoms of the above-described cancerous diseases, disorders or conditions. It also includes managing the cancer as described above. By "manage" it is meant reducing the severity of the disease, reducing the frequency of episodes of the disease, reducing the duration of such episodes, reducing the severity of such episodes, slowing/reducing cancer cell growth or proliferation, slowing progression of at least one symptom, ameliorization of at least one measurable physical parameter and the like.

"Mammal" for purposes of treatment refers to any animal classified as a mammal, including humans, domestic and farm animals, and zoo, sports, or pet animals, such as dogs, horses, cats, cows, etc. Preferably, the mammal is human.

The term "therapeutically effective amount" refers to an amount of agent according to the present invention that is effective to treat a disease or disorder in a mammal.

The therapeutic agents of the present invention can be provided to the subject alone, or as part of a pharmaceutical composition where they are mixed with a pharmaceutically acceptable carrier.

Anti C1ORF32 antibody, a fragment, a conjugate thereof and/or a pharmaceutical composition comprising same, according to at least some embodiments of the present invention also can be administered in combination therapy, i.e., combined with other potentiating agents and/or other therapies. According to at least some embodiments, the anti C1ORF 32 antibody could be used in combination with any of the known in the art standart of care cancer treatment (as can be found, for example, in http://www.cancer.gov/cancertopics).

For example, the combination therapy can include an anti C1ORF32 antibody, a fragment, a conjugate thereof and/or a pharmaceutical composition comprising same, combined with at least one other therapeutic or immune modulatory agent, other compounds or immunotherapies, or immunostimulatory strategy, including, but not limited to, tumor vaccines, adoptive T cell therapy, Treg depletion, antibodies (e.g. bevacizumab, erbitux, Ipilimumab), peptides, peptibodies, small molecules, chemotherapeutic agents such as cytotoxic and cytostatic agents (e.g. paclitaxel, cisplatin, vinorelbine, docetaxel, gemcitabine, temozolomide, irinotecan, 5FU, carboplatin), immunological modifiers such as interferons and interleukins, immunostimulatory antibodies, growth hormones or other cytokines, folic acid, vitamins, minerals, aromatase inhibitors, RNAi, Histone Deacetylase Inhibitors, proteasome inhibitors, and so forth. In another example, the combination therapy can include an anti-C1ORF32 antibody or C1ORF32 modulating agent according to at least some embodiments of the present invention, such as a soluble polypeptide conjugate containing the ectodomain of the C1ORF32 antigen or a small molecule such as a peptide, ribozyme, aptamer, siRNA, or other drug that binds C1ORF32, combined with at least one other therapeutic or immune modulatory agent.

According to at least some embodiments of the present invention, therapeutic agents that can be used in combination with anti-C1ORF32 antibodies, are potentiating agents that enhance anti-tumor responses.

Various strategies are available for combining an anti-ILDR2 blocking antibody with potentiating agents for cancer immunotherapy. According to at least some embodiments of the present invention, anti-C1ORF32 antibody for cancer immunotherapy is used in combination with potentiating agents that are primarily geared to increase endogenous anti-tumor responses, such as:

a. Combination with other cancer immunotherapies, such as adoptive T cell therapy, therapeutic cancer vaccines, or immunostimulatory antibodies;
b. Certain lethal stimuli and apoptosis inducers, such as radiotherapy and some classical chemotherapies, lead to immunogenic cell death, whereby the succumbing cancer cells serve as an endogenous therapeutic vaccine and stimulate anti-tumor immune responses;
c. Several anticancer agents, including classical chemotherapies and targeted therapies, stimulate tumor-specific immune response by inducing the immunogenic death of tumor cells or by engaging immune effector mechanisms (Galluzzi et al 2012). In this regard, metronomic chemotherapy appears to have immunostimulatory rather than immunosuppressive effects.

Conventional/classical chemotherapies as agents potentiating anti-tumor immune responses are selected from the group consistin of but not limited to:

Gemcitabine, that increases expression of MCH class I on malignant cells, enhances cross presentation of tumor antigens to T cells, and selectively kills myeloid-derived suppressor cells (MDSCs);

Oxaliplatin, cisplatin, carboplatin (and other platinum based compounds), which also increase expression of MCH class I on malignant cells, leading to enhanced cross presentation of tumor antigens to T cells;

Cyclophosphamide, which also increases expression of MCH class I on malignant cells. In addition, low dose of cyclophosphamide selectively suppresses inhibitory cell subsets, including MDSCs and Tregs, and favors the differentiation of CD4 helper cells to a IL-17 secreting anti-tumor subtype, restores NK and T cell effector functions, and inhibits the generation of immunosuppressive cytokines (i.e. IL-10, IL-4, IL-13);

Anthracyclines, such as doxorubicin—which enhances proliferation of tumor antigen-specific CD8 T cells, and promotes tumor infiltration by IL-17 producing γδ T cells and activated CD8 T cells, and daunorubicin—which exacerbates antigen expression by cancer cells;

Taxanes, such as paclitaxel—which impairs cytokine production and viability of Tregs, and docetaxel—which decreases levels of MDSCs;

Other microtubule inhibitors, such as vincristine—which increases the abundance of specific DC subsets, and stimulates DC-mediated antigen presentation;

Folate antagonists, such as methotrexate—which at low concentration appears to boost the maturation of DCs and their ability to stimulate T cells. mTOR pathway inhibitors, such as temsirolimus and rapamycin, can have an immunostimulatory effect and enhance CD8 T cell activation while decreasing IDO expression and Tregs.

Certain chemotherapeutic agents, such as oxaliplatin, cyclophosphamide, doxorubicin, and mitoxantrone, trigger immunogenic cell death.

Some chemotherapies, that can be used in combination with anti-C1ORF32 antibody, such as paclitaxel, cisplatin, and doxorubicin, have the capacity to increase the permeability of tumor cells to granzyme B, thereby rendering them susceptible to CTL-mediated lysis even if they do not express the antigen recognized by the CTLs (i.e. bystander effect).

According to at least some embodiments of the present invention, anti-C1ORF32 antibody for cancer immunotherapy is used in combination with Bisphosphonates, especially amino-bisphosphonates (ABP), which have shown to have anti-cancer activity. Some of the activities associated with ABPs are on human γδ T cells that straddle the interface of innate and adaptive immunity and have potent anti-tumour activity.

According to at least some embodiments of the present invention, anti-C1ORF32 antibody for cancer immunotherapy is used in combination with Targeted therapies as agents potentiating anti-tumor immune responses (Galluzzi et al 2012; Vanneman and Dranoff 2012):

Several targeted agents appear to exert their therapeutic efficacy, at least in part, on off-target mechanisms, some of which are mediated by the immune system.

For example, several histone deacetylase (HDAC) inhibitors, such as vorinostat, sodium butyrate and MS-275) increase the expression of NK-activating receptor ligands on the surface of cancer cells, thereby facilitating tumor cell recognition by NK cells. Bortezomib, a proteasome inhibitor, sensitizes tumor cells to CTL-mediated or NK-mediated cell lysis.

Vemurafenib, a BRAF inhibitor, increases expression of tumor antigens, and decreases tumor secretion of immunosuppressive cytokines. JAK2 inhibitors, enhance DC maturation and DC-mediated antigen presentation and T cell priming.

Certain tyrosine kinase inhibitors (TKIs) such as erlotinib, imatinib, sunitinib, sorafenib. promote cancer-directed immune responses by increasing MHC class II expression, induction of immunogenic cell death, decreased levels of tumor infiltrating immunosuppressive cells—Tregs and MDSCs, reducing the expression of the immunosuppressive enzyme IDO by tumor cells, and/or inhibition of DC functions.

Certain therapeutic monoclonal antibodies, such as anti-EGFR mAbs cetuximab and panatimumab, or anti-HER2 trastuzumab, favor the generation of tumor-specific cytotoxic CD8 T cells, and NK cells infiltration to the tumor and NK cell mediated mAb-dependent cell cytotoxicity. Bevacizumab reduces Tregs and favors the differentiation of DCs.

Not all targeted therapies potentiate anti-tumor immune responses, as some of them actually engage unwanted immunosuppressive mechanisms which would be detrimental for mounting immune responses against the tumor.

According to at least some embodiments of the present invention, anti-C1ORF32 antibody for cancer immunotherapy is used in combination with Therapeutic agents targeting Tregs (Facciabene et al 2012; Byrne et al 2011; Gabrilovich and Nagaraj 2009):

A number of commonly used chemotherapeutics reduce the number or the immunosuppressive capacity of regulatory T cells (Tregs). These drugs, which exert non-specific targeting of Tregs, include antimitotic drugs such as cyclophosphamide, gemcitabine, mitoxantrone, and fludarabine, as well as thalidomide and thalidomide derivatives and COX-2 inhibitors.

Novel Treg-specific targeting agents include: 1) depleting or killing antibodies that directly target Tregs through recognition of Treg cell surface receptors such as anti-CD25 daclizumab and basiliximab or 2) ligand-directed toxins such as denileukin diftitox (Ontak)—a fusion protein of human IL-2 and diphtheria toxin, or LMB-2—a fusion between an scFv against CD25 and the *pseudomonas* exotoxin. 3) antibodies targeting Treg cell surface receptors such as CTLA4, PD-1, OX40 and GITR.

Other options for disrupting Treg function include TLR modulation, or agents that interfere with the adenosinergic pathway, such as ectonucleotidase inhibitors, or inhibitors of the A2A adenosine receptor.

Options for blockade of Tregs induction include TGF-β inhibitors, and blockade of Tregs recruitment to tumor tissues include chemokine receptor inhibitors, such as the CCL2/CCR4 pathway.

Options for targeting MDSCs include promoting their differentiation in to mature myeloid cells that do not have suppressive functions. VitaminA metabolites, such as retinoic acid, all-trans retinoic acid (ATRA), have been found to stimulate the differentiation of MDSCs into DCs and macrophages. Vitamin D3 has recently been shown to have a similar effect on MDSCs.

Another option is inhibition of MDSCs suppressive activity by COX2 inhibitors, phosphodiesterase 5 inhibitors like sildenafil, ROS inhibitors such as nitroaspirin.

According to at least some embodiments of the present invention, anti-C1ORF32 antibody for cancer immunotherapy is used in combination with Immunostimulatory antibodies as agents potentiating anti-tumor immune responses (Pardoll 2012):

Immunostimulatory antibodies promote anti-tumor immunity by directly modulating immune functions, i.e. blocking other inhibitory targets or enhancing costimulatory proteins. Among these are antagonistic antibodies targeting immune checkpoints such as CTLA4 (example: ipilimumab), PD-1 (example: BMS-936558/MDX-1106), PDL-1 (example: BMS-936559/MDX-1105), LAG-3 (example: IMP-321), TIM-3, BTLA and/or Agonistic antibodies targeting immunostimulatory proteins, such as CD40 (example: CP-870,893), CD137 (example: BMS-663513), OX40 (example: Anti-OX40), GITR (example: TRX518).

According to at least some embodiments of the present invention, anti-C1ORF32 antibody for cancer immunotherapy is used in combination with Therapeutic cancer vaccines, that allow for improved priming of T cells and improved antigen presentation, as agents potentiating anti-tumor immune responses (Mellman et al 2011; Palucka and Banchereau 2012).

Non limiting examples of such therapeutic cancer vaccines are include Exogenous cancer vaccines and Dendritic-cell-based vaccines.

Exogenous cancer vaccines include proteins or peptides used to mount an immunogenic response to a tumor antigen (possibly with attractants of dendritic cells such as GM-CSF), recombinant virus and bacteria vectors encoding tumor antigens (possibly with proinflammatory or other attractants such as GM-CSF), DNA-based vaccines encoding tumor antigens, proteins targeted to dendritic cells, dendritic cells, proteins targeted to dendritic cells, dendritic cells.

Dendritic cells (DC) can be isolated from the cancer patient and primed for presenting tumor-specific T cells by several ways: DCs can be loaded with fusion proteins or peptides of tumor antigens with stimulating factor (such as GM-CSF), or coupled to DC-targeted mAbs, or loaded with tumor cells or lysates, activated and matured ex vivo, then re-infused back into the patient. Similar approaches can be carried out with monocytes. Dendritic cells can also be primed in vivo by injection of irradiated, cytokine secreting whole tumor cells (such as GM-CSF) back to the tumor patients—dendritic cells phagocytose the tumor cells and present tumor antigens in vivo to T cells.

According to at least some embodiments of the present invention, anti-C1ORF32 antibody for cancer immunotherapy is used in combination with Adoptive cell transfer to potentiate anti-tumor immune responses (Restifo et al 2012):

One approach to immunotherapy is based on the adoptive transfer of naturally occurring or gene-engineered tumor-specific cells. Treatment of patients with cell populations that have been expanded ex vivo is termed adoptive cell transfer (ACT). Cells that are infused back into a patient after ex vivo expansion can traffic to the tumor and mediate its destruction. Ex vivo, T cells extracted from tumor masses that have the desired T cell receptor (TCR) specificity, can be selected and expanded and then adoptively transferred into patients with cancer. Prior to this adoptive transfer, hosts can be immunodepleted by irradiation and/or chemotherapy. The combination of lymphodepletion, adoptive cell transfer, and a T cell growth factor (such as IL-2), can lead to prolonged tumor eradication in tumor patients. Additionally, T cells can be genetically engineered ex vivo to confer specificity for tumor-associated antigens. For example, clones of TCRs of T cells with particularly good anti-tumor responses can be inserted into viral expression vectors and used to infect autologous T cells from the patient to be treated. Another option is the use of chimeric antigen receptors (CARs) which have antibody-like specificities and recognize MHC-nonrestricted structures on the surface of target cells, grafted onto the TCR intracellular domains capable of activating T cells.

The C1ORF32 specific antibodies, and/or alternative scaffolds and/or multispecific and bispecific molecules and immunoconjugates, compositions comprising same according to at least some embodiments of the present invention can be co-administered together with one or more other therapeutic agents, which acts in conjunction with or synergistically with the composition according to at least some embodiments of the present invention to treat or prevent the cancer. The C1ORF32 related therapeutic agents and the one or more other therapeutic agents can be administered in either order or simultaneously. The other therapeutic agents are for example, a cytotoxic agent, a radiotoxic agent or an immunosuppressive agent. The composition can be linked to the agent (as an immunocomplex) or can be administered separately from the agent. In the latter case (separate administration), the composition can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/ml dose once every 21 days. Co-administration of the human anti-C1ORF32 antibodies, or antigen binding fragments and/or alternative scaffolds thereof, according to at least some embodiments of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody. In other embodiments, the subject can be additionally treated with an agent that modulates, e.g., enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-gamma (IFN-gamma), and tumor necrosis factor (TNF).

Target-specific effector cells, e.g., effector cells linked to compositions (e.g., human antibodies, multispecific and bispecific molecules) according to at least some embodiments of the present invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of 10-8 to 10-9 but will vary depending on the therapeutic purpose. In general, the amount will be sufficient to obtain localization at the target cell, e.g., a tumor cell expressing C1ORF32 proteins, and to effect cell killing by, e.g., phagocytosis. Routes of administration can also vary.

Therapy with target-specific effector cells can be performed in conjunction with other techniques for removal of targeted cells. For example, anti-tumor therapy using the compositions (e.g., human antibodies, multispecific and bispecific molecules) according to at least some embodiments of the present invention and/or effector cells armed with these compositions can be used in conjunction with chemotherapy. Additionally, combination immunotherapy may be used to direct two distinct cytotoxic effector populations toward tumor cell rejection. For example, anti-C1ORF32 antibodies linked to anti-Fc-gamma RI or anti-CD3 may be used in conjunction with IgG- or IgA-receptor specific binding agents.

Bispecific and multispecific molecules according to at least some embodiments of the present invention can also be used to modulate FcgammaR or FcgammaR levels on effector cells, such as by capping and elimination of receptors on the cell surface. Mixtures of anti-Fc receptors can also be used for this purpose.

The therapeutic compositions (e.g., human antibodies, alternative scaffolds multispecific and bispecific molecules and immunoconjugates) according to at least some embodiments of the present invention which have complement binding sites, such as portions from IgG1, -2, or -3 or IgM which bind complement, can also be used in the presence of complement. In one embodiment, ex vivo treatment of a population of cells comprising target cells with a binding agent according to at least some embodiments of the present invention and appropriate effector cells can be supplemented by the addition of complement or serum containing complement. Phagocytosis of target cells coated with a binding agent according to at least some embodiments of the present invention can be improved by binding of complement proteins. In another embodiment target cells coated with the compositions (e.g., human antibodies, multispecific and bispecific molecules) according to at least some embodiments of the present invention can also be lysed by complement. In yet another embodiment, the compositions according to at least some embodiments of the present invention do not activate complement.

The therapeutic compositions (e.g., human antibodies, alternative scaffolds multispecific and bispecific molecules and immunoconjugates) according to at least some embodiments of the present invention can also be administered together with complement. Thus, according to at least some embodiments of the present invention there are compositions, comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules according to at least some embodiments of the present invention and the complement or serum can be administered separately.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., soluble polypeptide conjugate containing the ectodomain of the C1ORF32 antigen, antibody, immunoconjugate, alternative scaffolds, and/or bispecific molecule, may be coated in a material to protect the compound from the action of acids and other natural conditions that may inactivate the compound. The pharmaceutical compounds according to at least some embodiments of the present invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition according to at least some embodiments of the present invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. Examples of suitable aqueous and nonaqueous carriers that may be employed in the pharmaceutical compositions according to at least some embodiments of the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions according to at least some embodiments of the present invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about I percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms according to at least some embodiments of the present invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an antibody according to at least some embodiments of the present invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 mug/ml and in some methods about 25-300 microgram/ml.

Alternatively, therapeutic agent can be administered as a sustained release formulation, in which case less frequent administration is required. Dosage and frequency vary depending on the half-life of the therapeutic agent in the patient. In general, human antibodies show the longest half life, followed by humanized antibodies, chimeric antibodies, and nonhuman antibodies. The half-life for fusion proteins may vary widely. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-C1ORF32 antibody according to at least some embodiments of the present invention preferably results in a decrease in severity of disease symptoms, an increase in frequency and duration of disease symptom-free periods, an increase in lifepan, disease remission, or a prevention or reduction of impairment or disability due to the disease affliction. For example, for the treatment of C1ORF32 positive tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject.

One of ordinary skill in the art would be able to determine a therapeutically effective amount based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for therapeutic agents according to at least some embodiments of the present invention include intravascular delivery (e.g. injection or infusion), intravenous, intramuscular, intradermal, intraperitoneal, subcutaneous, spinal, oral, enteral, rectal, pulmonary (e.g. inhalation), nasal, topical (including transdermal, buccal and sublingual), intravesical, intravitreal, intraperitoneal, vaginal, brain delivery (e.g. intra-cerebroventricular, intracerebral, and convection enhanced diffusion), CNS delivery (e.g. intrathecal, perispinal, and intra-spinal) or parenteral (including subcutaneous, intramuscular, intravenous and intradermal), transmucosal (e.g., sublingual administration), administration or administration via an implant, or other parenteral routes of administration, for example by injection or infusion, or other delivery routes and/or forms of administration known in the art. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. In a specific embodiment, a protein, a therapeutic agent or a pharmaceutical composition according to at least some embodiments of the present invention can be administered intraperitoneally or intravenously.

Alternatively, a C1ORF32 specific antibody and/or their conjugates and/or alternative scaffolds and/or combinations thereof that modulates a C1ORF32 protein activity can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in a preferred embodiment, a therapeutic composition according to at least some embodiments of the present invention can be administered with a needles hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the antibodies can be formulated to ensure proper distribution in vivo. For example, the blood-brain barrier (BBB) excludes many highly hydrophilic compounds. To ensure that the therapeutic compounds according to at least some embodiments of the present invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J Physiol. 1233:134); p120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The anti-C1ORF32 antibodies, according to at least some embodiments of the present invention, can be used as neutralizing antibodies. A Neutralizing antibody (Nabs), is an antibody that is capable of binding and neutralizing or inhibiting a specific antigen thereby inhibiting its biological effect, for example by blocking the receptors on the cell or the virus, inhibiting the binding of the virus to the host cell. NAbs will partially or completely abrogate the biological action of an agent by either blocking an important surface molecule needed for its activity or by interfering with the binding of the agent to its receptor on a target cell.

Formulations for Parenteral Administration

In a further embodiment, compositions disclosed herein, including those containing peptides and polypeptides, are administered in an aqueous solution, by parenteral injection. The formulation may also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., water soluble antioxidants such as ascorbic acid, sodium metabisulfite, cysteine hydrochloride, sodium bisulfate, sodium metabisulfite, sodium sulfite; oil-soluble antioxidants, such as ascorbyl palmitate, butylated hydroxyanisole (BHA), butylated hydroxytoluene (BHT), lecithin, propyl gallate, alpha-tocopherol; and metal chelating agents, such as citric acid, ethylenediamine tetraacetic acid (EDTA), sorbitol, tartaric acid, phosphoric acid), and preservatives (e.g., Thimersol, benzyl alcohol) and bulking substances (e.g., lactose, mannitol). Examples of non-aqueous solvents or vehicles are ethanol, propylene glycol, polyethylene glycol, vegetable oils, such as olive oil and corn oil, gelatin, and injectable organic esters such as ethyl oleate. The formulations may be freeze dried (lyophilized) or vacuum dried and redissolved/resuspended immediately before use. The formulation may be sterilized by, for example, filtration through a bacteria retaining filter, by incorporating sterilizing agents into the compositions, by irradiating the compositions, or by heating the compositions.

Formulations for Topical Administration

C1ORF32 polypeptides, fragments, fusion polypeptides, nucleic acids, and vectors disclosed herein can be applied topically. Topical administration does not work well for most peptide formulations, although it can be effective especially if applied to the lungs, nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns. A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets or lozenges. Transdermal formulations may also be prepared. These will typically be ointments, lotions, sprays, or patches, all of which can be prepared using standard technology. Transdermal formulations will require the inclusion of penetration enhancers.

Controlled Delivery Polymeric Matrices

C1ORF32 polypeptides, fragments, fusion polypeptides, nucleic acids, and vectors disclosed herein may also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where peptides are dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel. Either non-biodegradable or biodegradable matrices can be used for delivery of polypeptides or nucleic acids encoding the polypeptides, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, J. Controlled Release, 5:13-22 (1987); Mathiowitz, et al., Reactive Polymers, 6:275-283 (1987); and Mathiowitz, et al., J. Appl Polymer ScL, 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

Diagnostic Uses of Anti-C1ORF32 Antibodies

According to at least some embodiments of the present invention, the antibodies (e.g., human monoclonal antibodies, multispecific and bispecific molecules and compositions) can be used to detect levels of C1ORF32 or levels of cells which contain C1ORF32 on their membrane surface, which levels can then be linked to certain disease symptoms. Alternatively, the antibodies can be used to inhibit or block C1ORF32 function which, in turn, can be linked to the prevention or amelioration of cancer. This can be achieved by contacting a sample and a control sample with the anti-C1ORF32 antibody under conditions that allow for the formation of a complex between the corresponding antibody and C1ORF32. Any complexes formed between the antibody and C1ORF32 are detected and compared in the sample and the control.

According to at least some embodiments of the present invention, the antibodies (e.g., human antibodies, multispecific and bispecific molecules and compositions) can be initially tested for binding activity associated with therapeutic or diagnostic use in vitro. For example, compositions according to at least some embodiments of the present invention can be tested using low cytometric assays.

Also within the scope of the present invention are kits comprising the C1ORF32 specific antibody according to at least some embodiments of the present invention (e.g., human antibodies, alternative scaffolds, bispecific or multi-specific molecules, or immunoconjugates) and instructions for use. The kit can further contain one or more additional reagents, such as an immunosuppressive reagent, a cytotoxic agent or a radiotoxic agent, or one or more additional human antibodies according to at least some embodiments of the present invention (e.g., a human antibody having a complementary activity which binds to an epitope in the antigen distinct from the first human antibody).

The antibodies according to at least some embodiments of the present invention can also be used to target cells expressing Fc gamma R or C1ORF32 for example for labeling such cells. For such use, the binding agent can be linked to a molecule that can be detected. Thus, the present invention provides methods for localizing ex vivo or in vitro cells expressing Fc receptors, such as Fc gamma R, or C1ORF32 antigen. The detectable label can be, e.g., a radioisotope, a fluorescent compound, an enzyme, or an enzyme co-factor.

In a particular embodiment, the present invention provides methods for detecting the presence and/or level of C1ORF32 antigen in a sample, or measuring the amount of C1ORF32 antigen, respectively, comprising contacting the sample, and a control sample, with an antibody, or an antigen binding portion thereof, which specifically binds to C1ORF32, under conditions that allow for formation of a complex between the antibody or portion thereof and C1ORF32. The formation of a complex is then detected, wherein a difference complex formation between the sample compared to the control sample is indicative the presence of C1ORF32 antigen in the sample. As noted the present invention in particular embraces assays for detecting C1ORF32 antigen in vitro and in vivo such as immunoassays, radioimmunassays, radio assays, radioimaging assays, ELISAs, Western blot, FACS, slot blot, immunohistochemical assays, and other assays well known to those skilled in the art.

In yet another embodiment, immunoconjugates of the present invention can be used to target compounds (e.g., therapeutic agents, labels, cytotoxins, radiotoxins immunosuppressants, etc.) to cells which have C1ORF32 cell surface receptors by linking such compounds to the antibody. Thus, the present invention also provides methods for localizing ex vivo or in vivo cells expressing C1ORF32 (e.g., with a detectable label, such as a radioisotope, a fluorescent compound, an enzyme, or an enzyme co-factor). Alternatively, the immunoconjugates can be used to kill cells which have C1ORF32 cell surface receptors by targeting cytotoxins or radiotoxins to C1ORF32 antigen.

According to at least some embodiments, the present invention provides a method for imaging an organ or tissue, the method comprising: (a) administering to a subject in need of such imaging, a labeled polypeptide; and (b) detecting the labeled polypeptide to determine where the labeled polypeptide is concentrated in the subject. When used in imaging applications, the labeled polypeptides according to at least some embodiments of the present invention typically have an imaging agent covalently or noncovalently attached thereto. Suitable imaging agents include, but are not limited to, radionuclides, detectable tags, fluorophores, fluorescent proteins, enzymatic proteins, and the like. One of skill in the art will be familiar with other methods for attaching imaging agents to polypeptides. For example, the imaging agent can be attached via site-specific conjugation, e.g., covalent attachment of the imaging agent to a peptide linker such as a polyarginine moiety having five to seven arginines present at the carboxyl-terminus of and Fc fusion molecule. The imaging agent can also be directly attached via non-site specific conjugation, e.g., covalent attachment of the imaging agent to primary amine groups present in the polypeptide. One of skill in the art will appreciate that an imaging agent can also be bound to a protein via noncovalent interactions (e.g., ionic bonds, hydrophobic interactions, hydrogen bonds, Van der Waals forces, dipole-dipole bonds, etc.).

In certain instances, the polypeptide is radiolabeled with a radionuclide by directly attaching the radionuclide to the polypeptide. In certain other instances, the radionuclide is bound to a chelating agent or chelating agent-linker attached to the polypeptide. Suitable radionuclides for direct conjugation include, without limitation, 18 F, 124 I, 125 I, 131 I, and mixtures thereof. Suitable radionuclides for use with a chelating agent include, without limitation, 47 Sc, 64 Cu, 67 Cu, 89 Sr, 86 Y, 87 Y, 90 Y, 105 Rh, 111 Ag, 111 In, 117m Sn, 149 Pm, 153 Sm, 166 Ho, 177 Lu, 186 Re, 188 Re, 211 At, 212 Bi, and mixtures thereof. Preferably, the radionuclide bound to a chelating agent is 64 Cu, 90 Y, 111 In, or mixtures thereof. Suitable chelating agents include, but are not limited to, DOTA, BAD, TETA, DTPA, EDTA, NTA, HDTA, their phosphonate analogs, and mixtures thereof. One of skill in the art will be familiar with methods for attaching radionuclides, chelating agents, and chelating agent-linkers to polypeptides of the present invention. In particular, attachment can be conveniently accomplished using, for example, commercially available bifunctional linking groups (generally heterobifunctional linking groups) that can be attached to a functional group present in a non-interfering position on the polypeptide and then further linked to a radionuclide, chelating agent, or chelating agent-linker.

Non-limiting examples of fluorophores or fluorescent dyes suitable for use as imaging agents include Alexa Fluor® dyes (Invitrogen Corp.; Carlsbad, Calif.), fluorescein, fluorescein isothiocyanate (FITC), Oregon Green™; rhodamine, Texas red, tetrarhodamine isothiocynate (TRITC), CyDye™ fluors (e.g., Cy2, Cy3, Cy5), and the like.

Examples of fluorescent proteins suitable for use as imaging agents include, but are not limited to, green fluorescent protein, red fluorescent protein (e.g., DsRed), yellow fluorescent protein, cyan fluorescent protein, blue fluorescent protein, and variants thereof (see, e.g., U.S. Pat. Nos. 6,403,374, 6,800,733, and 7,157,566). Specific examples of GFP variants include, but are not limited to, enhanced GFP (EGFP), destabilized EGFP, the GFP variants described in Doan et al., Mol. Microbiol., 55:1767-1781 (2005), the GFP variant described in Crameri et al., Nat. Biotechnol., 14:315-319 (1996), the cerulean fluorescent proteins described in Rizzo et al., Nat. Biotechnol, 22:445 (2004) and Tsien, Annu. Rev. Biochem., 67:509 (1998), and the yellow fluorescent protein described in Nagai et al., Nat. Biotechnol., 20:87-90 (2002). DsRed variants are described in, e.g., Shaner et al., Nat. Biotechnol., 22:1567-1572 (2004), and include mStrawberry, mCherry, morange, mBanana, mHoneydew, and mTangerine. Additional DsRed variants are described in, e.g., Wang et al., Proc. Natl. Acad. Sci. U.S.A., 101:16745-16749 (2004) and include mRaspberry and mPlum. Further examples of DsRed variants include mRFPmars described in Fischer et al., FEBS Lett., 577:227-232 (2004) and mRFPruby described in Fischer et al., FEBS Lett., 580:2495-2502 (2006).

In other embodiments, the imaging agent that is bound to a polypeptide according to at least some embodiments of the present invention comprises a detectable tag such as, for example, biotin, avidin, streptavidin, or neutravidin. In further embodiments, the imaging agent comprises an enzymatic protein including, but not limited to, luciferase, chloramphenicol acetyltransferase, β-galactosidase, 3-glucuronidase, horseradish peroxidase, xylanase, alkaline phosphatase, and the like.

Any device or method known in the art for detecting the radioactive emissions of radionuclides in a subject is suitable for use in the present invention. For example, methods such as Single Photon Emission Computerized Tomography (SPECT), which detects the radiation from a single photon gamma-emitting radionuclide using a rotating gamma camera, and radionuclide scintigraphy, which obtains an image or series of sequential images of the distribution of a radionuclide in tissues, organs, or body systems using a scintillation gamma camera, may be used for detecting the radiation emitted from a radiolabeled polypeptide of the present invention. Positron emission tomography (PET) is another suitable technique for detecting radiation in a subject. Miniature and flexible radiation detectors intended for medical use are produced by Intra-Medical LLC (Santa Monica, Calif.). Magnetic Resonance Imaging (MRI) or any other imaging technique known to one of skill in the art is also suitable for detecting the radioactive emissions of radionuclides. Regardless of the method or device used, such detection is aimed at determining where the labeled polypeptide is concentrated in a subject, with such concentration being an indicator of disease activity.

Non-invasive fluorescence imaging of animals and humans can also provide in vivo diagnostic information and be used in a wide variety of clinical specialties. For instance, techniques have been developed over the years for simple ocular observations following UV excitation to sophisticated spectroscopic imaging using advanced equipment (see, e.g., Andersson-Engels et al., Phys. Med. Biol., 42:815-824 (1997)). Specific devices or methods known in the art for the in vivo detection of fluorescence, e.g., from fluorophores or fluorescent proteins, include, but are not limited to, in vivo near-infrared fluorescence (see, e.g., Frangioni, Curr Opin. Chem. Biol., 7:626-634 (2003)), the Maestro™ in vivo fluorescence imaging system (Cambridge Research & Instrumentation, Inc.; Woburn, Mass.), in vivo fluorescence imaging using a flying-spot scanner (see, e.g., Ramanujam et al., IEEE Transactions on Biomedical Engineering, 48:1034-1041 (2001), and the like.

Other methods or devices for detecting an optical response include, without limitation, visual inspection, CCD cameras, video cameras, photographic film, laser-scanning devices, fluorometers, photodiodes, quantum counters, epifluorescence microscopes, scanning microscopes, flow cytometers, fluorescence microplate readers, or signal amplification using photomultiplier tubes.

According to some embodiments, the sample taken from a subject (patient) to perform the diagnostic assay according to at least some embodiments of the present invention is selected from the group consisting of a body fluid or secretion including but not limited to blood, serum, urine, plasma, prostatic fluid, seminal fluid, semen, the external secretions of the skin, respiratory, intestinal, and genitourinary tracts, tears, cerebrospinal fluid, synovial fluid, sputum, saliva, milk, peritoneal fluid, pleural fluid, cyst fluid, secretions of the breast ductal system (and/or lavage thereof), broncho alveolar lavage, lavage of the reproductive system and lavage of any other part of the body or system in the body; samples of any organ including isolated cells or tissues, wherein the cell or tissue can be obtained from an organ selected from, but not limited to lung, prostate, colon, ovarian and/or breast tissue, and/or any other solid tissue; stool or a tissue sample, or any combination thereof. In some embodiments, the term encompasses samples of in vivo cell culture constituents. Prior to be subjected to the diagnostic assay, the sample can optionally be diluted with a suitable eluant.

In some embodiments, the phrase "marker" in the context of the present invention refers to a nucleic acid fragment, a peptide, or a polypeptide, which is differentially present in a sample taken from patients (subjects) having one of the herein-described diseases or conditions, as compared to a comparable sample taken from subjects who do not have one the above-described diseases or conditions.

In some embodiments, the phrase "differentially present" refers to differences in the quantity or quality of a marker present in a sample taken from patients having one of the herein-described diseases or conditions as compared to a comparable sample taken from patients who do not have one of the herein-described diseases or conditions. For example, a nucleic acid fragment may optionally be differentially present between the two samples if the amount of the nucleic acid fragment in one sample is significantly different from the amount of the nucleic acid fragment in the other sample, for example as measured by hybridization and/or NAT-based assays. A polypeptide is differentially present between the two samples if the amount of the polypeptide in one sample is significantly different from the amount of the polypeptide in the other sample. It should be noted that if the marker is detectable in one sample and not detectable in the other, then such a marker can be considered to be differentially present.

Optionally, a relatively low amount of up-regulation may serve as the marker, as described herein. One of ordinary skill in the art could easily determine such relative levels of the markers; further guidance is provided in the description of each individual marker below.

In some embodiments, the phrase "diagnostic" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As used herein the term "diagnosis" refers to the process of identifying a medical condition or disease by its signs, symptoms, and in particular from the results of various diagnostic procedures, including e.g. detecting the expression of the nucleic acids or polypeptides according to at least some embodiments of the present invention in a biological sample (e.g. in cells, tissue or serum, as defined below) obtained from an individual. Furthermore, as used herein the term "diagnosis" encompasses screening for a disease, detecting a presence or a severity of a disease, providing prognosis of a disease, monitoring disease progression or relapse, as well as assessment of treatment efficacy and/or relapse of a disease, disorder or condition, as well as selecting a therapy and/or a treatment for a disease, optimization of a given therapy for a disease, monitoring the treatment of a disease, and/or predicting the suitability of a therapy for specific patients or subpopulations or determining the appropriate dosing of a therapeutic product in patients or subpopulations. The diagnostic procedure can be performed in vivo or in vitro.

In some embodiments, the phrase "qualitative" when in reference to differences in expression levels of a polynucleotide or polypeptide as described herein, refers to the presence versus absence of expression, or in some embodiments, the temporal regulation of expression, or in some embodiments, the timing of expression, or in some embodiments, any post-translational modifications to the expressed molecule, and others, as will be appreciated by one skilled in the art. In some embodiments, the phrase "quantitative" when in reference to differences in expression levels of a polynucleotide or polypeptide as described herein, refers to absolute differences in quantity of expression, as determined by any means, known in the art, or in other embodiments, relative differences, which may be statistically significant, or in some embodiments, when viewed as a whole or over a prolonged period of time, etc., indicate a trend in terms of differences in expression.

In some embodiments, the term "diagnosing" refers to classifying a disease or a symptom, determining a severity of the disease, monitoring disease progression, forecasting an outcome of a disease and/or prospects of recovery. The term "detecting" may also optionally encompass any of the above.

Diagnosis of a disease according to the present invention can, in some embodiments, be affected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject, as described in greater detail below.

In some embodiments, the term "level" refers to expression levels of RNA and/or protein or to DNA copy number of a marker of the present invention.

Typically the level of the marker in a biological sample obtained from the subject is different (i.e., increased or decreased) from the level of the same marker in a similar sample obtained from a healthy individual (examples of biological samples are described herein).

Numerous well known tissue or fluid collection methods can be utilized to collect the biological sample from the subject in order to determine the level of DNA, RNA and/or polypeptide of the marker of interest in the subject.

Examples include, but are not limited to, fine needle biopsy, needle biopsy, core needle biopsy and surgical biopsy (e.g., brain biopsy), and lavage. Regardless of the procedure employed, once a biopsy/sample is obtained the level of the marker can be determined and a diagnosis can thus be made.

Determining the level of the same marker in normal tissues of the same origin is preferably effected along-side to detect an elevated expression and/or amplification and/or a decreased expression, of the marker as opposed to the normal tissues.

In some embodiments, the term "test amount" of a marker refers to an amount of a marker in a subject's sample that is consistent with a diagnosis of a particular disease or condition. A test amount can be either in absolute amount (e.g., microgram/ml) or a relative amount (e.g., relative intensity of signals).

In some embodiments, the term "control amount" of a marker can be any amount or a range of amounts to be compared against a test amount of a marker. For example, a control amount of a marker can be the amount of a marker in a patient with a particular disease or condition or a person without such a disease or condition. A control amount can be either in absolute amount (e.g., microgram/ml) or a relative amount (e.g., relative intensity of signals).

In some embodiments, the term "detect" refers to identifying the presence, absence or amount of the object to be detected.

In some embodiments, the term "label" includes any moiety or item detectable by spectroscopic, photo chemical, biochemical, immunochemical, or chemical means. For example, useful labels include 32P, 35S, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to a target. The label often generates a measurable signal, such as a radioactive, chromogenic, or fluorescent signal, that can be used to quantify the amount of bound label in a sample. The label can be incorporated in or attached to a primer or probe either covalently, or through ionic, van der Waals or hydrogen bonds, e.g., incorporation of radioactive nucleotides, or biotinylated nucleotides that are recognized by streptavadin. The label may be directly or indirectly detectable. Indirect detection can involve the binding of a second label to the first label, directly or indirectly. For example, the label can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules (see, e.g., P. D. Fahrlander and A. Klausner, Bio/Technology 6:1165 (1988)). Quantitation of the signal is achieved by, e.g., scintillation counting, densitometry, or flow cytometry.

Exemplary detectable labels, optionally and preferably for use with immunoassays, include but are not limited to magnetic beads, fluorescent dyes, radiolabels, enzymes (e.g., horse radish peroxide, alkaline phosphatase and others commonly used in an ELISA), and calorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture.

"Immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," or "specifically interacts or binds" when referring to a protein or peptide (or other epitope), refers, in some embodiments, to a binding reaction that is determinative of the presence of the protein in a heterogeneous population of proteins and other biologics. Thus, under designated immunoassay conditions, the specified antibodies bind to a particular protein at least two times greater than the background (non-specific signal) and do not substantially bind in a significant amount to other proteins present in the sample. Specific binding to an antibody under such conditions may require an antibody that is selected for its specificity for a particular protein. For example, polyclonal antibodies raised to seminal basic protein from specific species such as rat, mouse, or human can be selected to obtain only those polyclonal antibodies that are specifically immunoreactive with seminal basic protein and not with other proteins, except for polymorphic variants and alleles of seminal basic protein. This selection may be achieved by subtracting out antibodies that cross-react with seminal basic protein molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

In another embodiment, this invention provides a method for detecting the polypeptides of this invention in a biological sample, comprising: contacting a biological sample with an antibody specifically recognizing a polypeptide according to the present invention and detecting said interaction; wherein the presence of an interaction correlates with the presence of a polypeptide in the biological sample.

In some embodiments of the present invention, the polypeptides described herein are non-limiting examples of markers for diagnosing a disease and/or an indicative condition. Each marker of the present invention can be used alone or in combination, for various uses, including but not limited to, prognosis, prediction, screening, early diagnosis, determination of progression, therapy selection and treatment monitoring of a disease and/or an indicative condition.

Each polypeptide/polynucleotide of the present invention can be used alone or in combination, for various uses, including but not limited to, prognosis, prediction, screening, early diagnosis, determination of progression, therapy selection and treatment monitoring of disease and/or an indicative condition, as detailed above.

Such a combination may optionally comprise any sub-combination of markers, and/or a combination featuring at least one other marker, for example a known marker. Furthermore, such a combination may optionally and preferably be used as described above with regard to determining a ratio between a quantitative or semi-quantitative measurement of any marker described herein to any other marker described herein, and/or any other known marker, and/or any other marker.

In some embodiments of the present invention, there are provided of methods, uses, devices and assays for the diagnosis of a disease or condition. Optionally a plurality of markers may be used with the present invention. The plurality of markers may optionally include a markers described herein, and/or one or more known markers. The plurality of markers is preferably then correlated with the disease or condition. For example, such correlating may optionally comprise determining the concentration of each of the plurality of markers, and individually comparing each marker concentration to a threshold level. Optionally, if the marker concentration is above or below the threshold level (depending upon the marker and/or the diagnostic test being performed), the marker concentration correlates with the disease or condition. Optionally and preferably, a plurality of marker concentrations correlates with the disease or condition.

Alternatively, such correlating may optionally comprise determining the concentration of each of the plurality of markers, calculating a single index value based on the concentration of each of the plurality of markers, and comparing the index value to a threshold level.

Also alternatively, such correlating may optionally comprise determining a temporal change in at least one of the markers, and wherein the temporal change is used in the correlating step.

Also alternatively, such correlating may optionally comprise determining whether at least "X" number of the plurality of markers has a concentration outside of a predetermined range and/or above or below a threshold (as described above). The value of "X" may optionally be one marker, a plurality of markers or all of the markers; alternatively or additionally, rather than including any marker in the count for "X", one or more specific markers of the plurality of markers may optionally be required to correlate with the disease or condition (according to a range and/or threshold).

Also alternatively, such correlating may optionally comprise determining whether a ratio of marker concentrations for two markers is outside of a range and/or above or below a threshold. Optionally, if the ratio is above or below the threshold level and/or outside a range, the ratio correlates with the disease or condition.

Optionally, a combination of two or more these correlations may be used with a single panel and/or for correlating between a plurality of panels.

Optionally, the method distinguishes a disease or condition with a sensitivity of at least 70% at a specificity of at least 85% when compared to normal subjects. As used herein, sensitivity relates to the number of positive (diseased) samples detected out of the total number of positive samples present; specificity relates to the number of true negative (non-diseased) samples detected out of the total number of negative samples present. Preferably, the method distinguishes a disease or condition with a sensitivity of at least 80% at a specificity of at least 90% when compared to normal subjects. More preferably, the method distinguishes a disease or condition with a sensitivity of at least 90% at a specificity of at least 90% when compared to normal subjects. Also more preferably, the method distinguishes a disease or condition with a sensitivity of at least 70% at a specificity of at least 85% when compared to subjects exhibiting symptoms that mimic disease or condition symptoms.

A marker panel may be analyzed in a number of fashions well known to those of skill in the art. For example, each member of a panel may be compared to a "normal" value, or a value indicating a particular outcome. A particular diagnosis/prognosis may depend upon the comparison of each marker to this value; alternatively, if only a subset of markers is outside of a normal range, this subset may be indicative of a particular diagnosis/prognosis. The skilled artisan will also understand that diagnostic markers, differential diagnostic markers, prognostic markers, time of onset markers, disease or condition differentiating markers, etc., may be combined in a single assay or device. Markers may also be commonly used for multiple purposes by, for example, applying a different threshold or a different weighting factor to the marker for the different purposes.

In one embodiment, the panels comprise markers for the following purposes: diagnosis of a disease; diagnosis of disease and indication if the disease is in an acute phase and/or if an acute attack of the disease has occurred; diagnosis of disease and indication if the disease is in a non-acute phase and/or if a non-acute attack of the disease has occurred; indication whether a combination of acute and non-acute phases or attacks has occurred; diagnosis of a disease and prognosis of a subsequent adverse outcome; diagnosis of a disease and prognosis of a subsequent acute or non-acute phase or attack; disease progression (for example for cancer, such progression may include for example occurrence or recurrence of metastasis).

The above diagnoses may also optionally include differential diagnosis of the disease to distinguish it from other diseases, including those diseases that may feature one or more similar or identical symptoms.

In certain embodiments, one or more diagnostic or prognostic indicators are correlated to a condition or disease by merely the presence or absence of the indicators. In other embodiments, threshold levels of a diagnostic or prognostic indicators can be established, and the level of the indicators in a patient sample can simply be compared to the threshold levels. The sensitivity and specificity of a diagnostic and/or prognostic test depends on more than just the analytical "quality" of the test—they also depend on the definition of what constitutes an abnormal result. In practice, Receiver Operating Characteristic curves, or "ROC" curves, are typically calculated by plotting the value of a variable versus its relative frequency in "normal" and "disease" populations, and/or by comparison of results from a subject before, during and/or after treatment.

Immunoassays

In another embodiment of the present invention, an immunoassay can be used to qualitatively or quantitatively detect and analyze markers in a sample. This method comprises: providing an antibody that specifically binds to a marker; contacting a sample with the antibody; and detecting the presence of a complex of the antibody bound to the marker in the sample.

To prepare an antibody that specifically binds to a marker, purified protein markers can be used. Antibodies that specifically bind to a protein marker can be prepared using any suitable methods known in the art.

After the antibody is provided, a marker can be detected and/or quantified using any of a number of well recognized immunological binding assays. Useful assays include, for example, an enzyme immune assay (EIA) such as enzyme-linked immunosorbent assay (ELISA), a radioimmune assay (RIA), a Western blot assay, or a slot blot assay see, e.g., U.S. Pat. Nos. 4,366,241; 4,376,110; 4,517,288; and 4,837,168). Generally, a sample obtained from a subject can be contacted with the antibody that specifically binds the marker.

Optionally, the antibody can be fixed to a solid support to facilitate washing and subsequent isolation of the complex, prior to contacting the antibody with a sample. Examples of solid supports include but are not limited to glass or plastic in the form of, e.g., a microtiter plate, a stick, a bead, or a microbead. Antibodies can also be attached to a solid support.

After incubating the sample with antibodies, the mixture is washed and the antibody-marker complex formed can be detected. This can be accomplished by incubating the washed mixture with a detection reagent. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations and the like. Usually the assays will be carried out at ambient temperature, although they can be conducted over a range of temperatures, such as 10° C. to 40° C.

The immunoassay can be used to determine a test amount of a marker in a sample from a subject. First, a test amount of a marker in a sample can be detected using the immunoassay methods described above. If a marker is present in the sample, it will form an antibody-marker complex with an antibody that specifically binds the marker under suitable incubation conditions described above. The amount of an antibody-marker complex can optionally be determined by comparing to a standard. As noted above, the test amount of marker need not be measured in absolute units, as long as the unit of measurement can be compared to a control amount and/or signal.

Radio-immunoassay (RIA): In one version, this method involves precipitation of the desired substrate and in the methods detailed herein below, with a specific antibody and radiolabeled antibody binding protein (e.g., protein A labeled with I125) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Enzyme linked immunosorbent assay (ELISA): This method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot: This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Immunohistochemical analysis: This method involves detection of a substrate in situ in fixed cells by substrate specific antibodies. The substrate specific antibodies may be enzyme linked or linked to fluorophores. Detection is by microscopy and subjective evaluation. If enzyme linked antibodies are employed, a colorimetric reaction may be required.

Fluorescence activated cell sorting (FACS): This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Radio-Imaging Methods

These methods include but are not limited to, positron emission tomography (PET) single photon emission computed tomography (SPECT). Both of these techniques are non-invasive, and can be used to detect and/or measure a wide variety of tissue events and/or functions, such as detecting cancerous cells for example. Unlike PET, SPECT can optionally be used with two labels simultaneously. SPECT has some other advantages as well, for example with regard to cost and the types of labels that can be used. For example, U.S. Pat. No. 6,696,686 describes the use of SPECT for detection of breast cancer, and is hereby incorporated by reference as if fully set forth herein.

Theranostics:

The term theranostics describes the use of diagnostic testing to diagnose the disease, choose the correct treatment regime according to the results of diagnostic testing and/or monitor the patient response to therapy according to the results of diagnostic testing. Theranostic tests can be used to select patients for treatments that are particularly likely to benefit them and unlikely to produce side-effects. They can also provide an early and objective indication of treatment efficacy in individual patients, so that (if necessary) the treatment can be altered with a minimum of delay. For example: DAKO and Genentech together created HercepTest and Herceptin (trastuzumab) for the treatment of breast cancer, the first theranostic test approved simultaneously with a new therapeutic drug. In addition to HercepTest (which is an immunohistochemical test), other theranostic tests are in development which use traditional clinical chemistry, immunoassay, cell-based technologies and nucleic acid tests. PPGx's recently launched TPMT (thiopurine S-methyltransferase) test, which is enabling doctors to identify patients at risk for potentially fatal adverse reactions to 6-mercaptopurine, an agent used in the treatment of leukemia. Also, Nova Molecular pioneered SNP genotyping of the apolipoprotein E gene to predict Alzheimer's disease patients' responses to cholinomimetic therapies and it is now widely used in clinical trials of new drugs for this indication. Thus, the field of theranostics represents the intersection of diagnostic testing information that predicts the response of a patient to a treatment with the selection of the appropriate treatment for that particular patient.

Surrogate Markers:

A surrogate marker is a marker, that is detectable in a laboratory and/or according to a physical sign or symptom on the patient, and that is used in therapeutic trials as a substitute for a clinically meaningful endpoint. The surrogate marker is a direct measure of how a patient feels, functions, or survives which is expected to predict the effect of the therapy. The need for surrogate markers mainly arises when such markers can be measured earlier, more conveniently, or more frequently than the endpoints of interest in terms of the effect of a treatment on a patient, which are referred to as the clinical endpoints. Ideally, a surrogate marker should be biologically plausible, predictive of disease progression and measurable by standardized assays (including but not limited to traditional clinical chemistry, immunoassay, cell-based technologies, nucleic acid tests and imaging modalities).

The present invention is further illustrated by the following examples. This information and examples is illustrative and should not be construed as further limiting. The contents of all figures and all references, patents and published patent applications cited throughout this application are expressly incorporated herein by reference.

EXAMPLES

Example 1

Cloning of C1ORF32 Proteins

A. Human C1ORF32 Protein (SEQ ID NO:1)

Full length cloning of the short isoform of human C1ORF32 (encoding to SEQ ID NO:1) was performed by RT-PCR using cDNA derived from a sample of small cell lung cancer cDNA as a template, and gene specific primers delimiting the full ORF (SEQ ID NO:20).

PCR reaction of 50 µl contained 10 ng of small cell lung cancer as template, 2.5 µl (10 µM)—of each primer 100-746_For (SEQ ID NO:27) and 100-787_Rev (SEQ ID NO: 29) and Platinum PFX™ (Invitrogen., Carlsbad, Calif., USA, catalog number: 1178-021). The PCR program was: 5 minutes in 95° C.; 35 cycles of: 30 seconds at 94° C., 30 seconds at 55° C., 50 seconds at 68° C.; following 10 minutes at 68° C.

The PCR products were purified, digested with the Nhe and EcoRI restriction enzymes (New England Biolabs, Beverly, Mass., U.S.A.). The digested DNA was then ligated into pIRESpuro3 (pRp) vector (Clontech, cat No: 631619) previously digested with the above restriction enzymes, using T4 DNA ligase (Promega, catalog number: M1801).

The resulting DNA was transformed into competent E. Coli bacteria DH5α (RBC Bioscience, Taipei, Taiwan, catalog number: RH816) according to manufacturer's instructions, then plated on LB-ampicillin agar plates for selection of recombinant plasmids, and incubated overnight at 37° C. The following day, positive colonies were grown in 5 ml Terrific Broth supplemented with 100 µg/ml ampicillin, with shaking overnight at 37° C. Plasmid DNA was isolated from bacterial cultures using Qiaprep™ Spin Miniprep Kit (Qiagen, catalog number: 27106). The insert was verified by sequencing (Hylabs, Rehovot, Israel). The corresponding nucleic acid sequence is shown in SEQ ID NO:20.

B. Human C1ORF32-Ha Tagged Protein (SEQ ID NO: 22)

Full length cloning of human C1ORF32-HA tagged (encoding to SEQ ID NO: 22) was performed by PCR using as a template the full ORF of the untagged construct described above, and specific primers (SEQ ID NOs: 27 and 28) inserting the HA tag in frame within the extracellular domain region of C1ORF32 (SEQ ID NOs: 22), at amino acid position 51.

Cloning was done by PCR using Platinum PFX™, 10 ng of human C1ORF32_pIRESpuro3 (pRp) vector as template and 10 uM of primers 100-746_For (SEQ ID NO: 27) and 100-927_Rev (SEQ ID NO: 28). The resulting DNA was transformed into competent E. Coli bacteria DH5α. The cloning and the transformation procedures were carried out as described above. The corresponding nucleic acid sequence is shown in SEQ ID NO:22.

C. Chimeric Mouse-Human C1ORF32 (SEQ ID NO: 8)

The human C1ORF32 encoding to SEQ ID NO: 1, was used to generate a protein having a mouse extracellular domain by adding 2 amino acids mismatches present in the mouse ECD as follows: T75→P and 579→A, resulting in a chimeric protein with mouse ECD sequence and a short tail derived from the human short isoform. This was carried out by site directed mutagenesis as follows:

PCR reaction of 50 µl contained 10 ng of human C1ORF32_pRp construct (SEQ ID NO: 21) as template, 2.5 µl (10 µM)—of each primer 200-386_For (SEQ ID NO: 25) and 200-387_Rev (SEQ ID NO: 26) and PfuUltra II Fusion HS DNA Polymerase (Stratagene, Catalog no. 600670). The PCR program was: 3 minutes in 95° C.; 12 cycles of: 1 min at 95° C.' 1 min at 55° C., 3 min at 72° C.; followed by 1 min at 47° C. and 10 minutes at 72° C. The PCR product was treated with 2 µl of DpnI (New England Biolab, Catalog No. R0176S) at 37° C. for 2 hours. 5 µl of the PCR product were transformed into NEB 5-alpha Competent E. coli cells (catalog number: NEB-C2987H) according to manufacturer's instructions and processed as described above. DNA was verified by sequencing and is shown in SEQ ID NO:30.

D. Mouse C1ORF32_Flag Tagged Protein (SEQ ID NO: 21)

Full length cloning of mouse-C1ORF32-Flag encoding to SEQ ID NO: 21) was performed by gene synthesis (GENEWIZ, USA).

The synthesised DNA (SEQ ID NO:21) was digested with NheI and NotI restriction enzymes (New England Biolabs, Beverly, Mass., U.S.A.). After digestion, DNA was loaded onto a 1% agarose gel were loaded onto a 1% agarose gel stained with ethidium bromide, electrophoresed in 1×TAE solution at 100V, and visualized with UV light. After verification of expected band size, PCR product was excised and extracted from the gel using QIAquick™ Gel Extraction kit (Qiagen, catalog number: 28707). The digested DNA was then ligated into pIRESpuro3 (pRp) vector (Clontech, cat No: 631619) previously digested with the above restriction enzymes, using T4 DNA ligase (Promega, catalog number: M1801). The resulting DNA was transformed into NEB 5-alpha Competent E. coli cells as described above. Positive colonies were screened by PCR using pIRESpuro3 vector specific primer (data not shown) and the insert was verified by sequensing. The corresponding nucleic acid sequence is shown in SEQ ID NO:21.

Example 2

Production of Polyclonal Antibodies Specific to C1ORF32 Protein

The procedures of raising specific polyclonal antibodies (pAbs) against C1ORF32 including peptide synthesis, peptide conjugation, animal immunizations, bleeding and antibody purification were performed at Sigma-Aldrich (Israel). Two pairs of rabbits (one pair per epitope) were injected in order to generate C1ORF32 (SEQ ID NO: 1)—specific antibodies. All animal care, handling and injections were performed by Sigma (Israel).

Peptides used for rabbit immunization were as follows: C1ORF32-ep1 peptide (SEQ ID NO: 2), having an amino acid sequence corresponding to amino acid residues 75-93 from the C1ORF32 protein (SEQ ID NO: 1), set forth in SEQ ID NO:2: TRAQSLSKRNLEWDPYLDC. The second peptide used was C1ORF32-ep2 peptide (SEQ ID NO: 3), having an amino acid sequence corresponding to amino acid residues 148-163 from the C1ORF32 protein (SEQ ID NO: 1), set forth in SEQ ID NO:3: TTPDDLEGKNEDSVEL. A C-terminal Cystein was added to the C1ORF32-ep2 peptide (SEQ ID NO: 3), in order to conjugate the peptide to KLH carrier, as set forth in SEQ ID NO: 6: TTPDDLEGKNEDSVEL-C.

25 mg of each peptide were synthesized with 95% purity of which 10 mg were conjugated to KLH carrier. Each pair of rabbits was immunized with the corresponding conjugated peptide as follows: rabbits R1(R7531) and R2 (R7532) were immunized with C1ORF32-ep1 peptide (SEQ ID NO: 2), and rabbits R3 (R7533) and R4 (R7534) were immunized with C1ORF32-ep2 peptide (SEQ ID NO: 6) Animals were immunized every two weeks. 60 ml production bleeds from each rabbit were collected and affinity purification was performed with the peptide against which the respective antibodies were raised.

The binding of the polyclonal antibodies (pAbs) raised against C1ORF32 and the corresponding C1ORF32 protein as set forth in SEQ ID NO:4, corresponding to portion of C1ORF32-ECD fused to mouse IgG2a protein (SEQ ID NO:4) was determined by western blot analysis using testbleeds from rabbits #1, 2, 3 and 4, as described below.

25 µl of 4× NuPAGE® LDS sample buffer (Invitrogen, catalog number: NP0007) was added to 0.1 ug protein. In addition, 1,4-Dithiothreitol (DTT; a reducing agent) was added to a final concentration of 100 mM. The samples were then incubated at 70° C. for 10 minutes, followed by a 1 minute spin at 20,000×g.

Protein samples loaded into a 4-12% NuPAGE® Bis-Tris gels (Invitrogen, catalog number: NP0321), and gels were run in 1×MOPS SDS running buffer (Invitrogen, catalog number: NP0001), using the XCell SureLock™ Mini-Cell (Invitrogen, catalog number: E10001), according to manufacturer's instructions. The separated proteins were transferred to a nitrocellulose membrane (Schleicher & Schuell, catalog number: 401385) using the XCell™ II blotting apparatus (Invitrogen, catalog number E19051), according to manufacturer's instructions.

The membrane containing blotted proteins was processed for antibody detection as follows:

Non-specific regions of the membrane were blocked by incubation in 5% skim-milk diluted in Phosphate buffered saline (PBS) supplemented with 0.05% Tween-20 (PBST) for ½ hour at room temperature (all subsequent incubations occur for 1 hour at room temperature). Blocking solution was then replaced with primary antibodies solutions: Rabbit polyclonal to C1ORF32 described above diluted 1:250 in blocking solution. After 3 5-minute washes, secondary antibody was applied: goat anti-rabbit conjugated to Peroxidase conjugated Affipure Goat anti Rabbit IgG (Jackson, catalog number: 111-035-003) diluted 1:10,000 in blocking solution. After three 5-minute washes, ECL substrate (PIERCE, catalog number: PIR-34080) was applied for 1 minute, followed by exposure to X-ray film (Fuji, catalog number: 100NIF). The results are presented in FIG. 1.

FIG. 1 demonstrates that serum from immunized rabbits R1 (R7531), R2 (R7532) and R4 (R7534) binds to the recombinant C1ORF32-ECD-mouse IgG2a fusion protein (SEQ ID NO:4) as compared to the pre-immunized bleed, at the expected band size of ~50 kDa. Serum from rabbit R3 was not detectable under this experimental conditions.

Example 3

Generation of Stable Pools Expressing C1ORF32 Protein

Establishment of stable pool cells over expressing human C1ORF32 (SEQ ID NO:1), chimeric human-mouse C1ORF32(SEQ ID NO:8) and mouse C1ORF32(SEQ ID NO:21) proteins in HEK-293T cells.

Human C1ORF32 pIRESpuro3 construct (SEQ ID NO: 22) or pIRESpuro3 empty vector were stably transfected into HEK-293T cells as follows:

HEK-293T (ATCC, CRL-11268) cells were plated in a sterile 6 well plate suitable for tissue culture, using 2 ml pre-warmed of complete media, DMEM [Dulbecco's modified Eagle's Media, Biological Industries (Beit Ha'Emek, Israel), catalog number: 01-055-1A]+10% FBS [Fetal Bovine Serum, Biological Industries (Beit Ha'Emek, Israel), catalog number: 04-001-1A]+4 mM L-Glutamine [Biological Industries (Beit Ha'Emek, Israel), catalog number: 03-020-1A]. 500,000 cells per well were transfected with 2 µg of DNA construct using 6 µFuGENE 6 reagent (Roche, catalog number: 11-814-443-001) diluted into 94 ul OptiMEM (GIBCO 31985-047). The mixture was incubated at room temperature for 15 minutes. The complex mixture was added dropwise to the cells and swirled. Cells were placed in incubator maintained at 37° C. with 5% CO2 content. 48 hours following transfection, transfected cells were transferred to a 75 cm2 tissue culture flask containing 15 ml of selection media: complete media supplemented with 5 µg\ml puromycin (Sigma, catalog number P8833). Cells were placed in incubator, and media was changed every 3-4 days, until clone formation observed.

Upon sufficient quantities of cells passing through selection, cells were harvested. Cells were lysed in 300 µl RIPA buffer (50 mM Tris HCl pH 8, 150 mM NaCl, 1% NP-40, 0.5% sodium Deoxycholate, 0.1% SDS) supplemented with protease inhibitors (Roche, catalog number: 11873580001), for 20 min on ice. Following centrifugation at 4° C. for 15 minutes at 20,000×g, the clear supernatants were transferred to clean tubes and 100 µl of 4× NuPAGE® LDS sample buffer (Invitrogen, catalog number: NP0007) was added. In addition, 1,4-Dithiothreitol (DTT; a reducing agent) was added to a final concentration of 100 mM. The samples were then incubated at 70° C. for 10 minutes, followed by a 1 minute spin at 20,000×g. SDS-PAGE (Laemmli, U.K., Nature 1970; 227; 680-685) was performed upon loading of 30 µl of sample per lane into a 4-12% NuPAGE® Bis-Tris gels (Invitrogen, catalog number: NP0321), and gels were run in 1×MOPS SDS running buffer (Invitrogen, catalog number: NP0001), using the XCell SureLock™ Mini-Cell (Invitrogen, catalog number: E10001), according to manufacturer's instructions. The separated proteins were transferred to a nitrocellulose membrane (Schleicher & Schuell, catalog number: 401385) using the XCell™ II blotting apparatus (Invitrogen, catalog number E19051), according to manufacturer's instructions.

The samples were further processed and analyzed by SDS-PAGE as described above.

Establishment of Stable Pools Cells Over Expressing C1ORF32 Protein in CHO-K1 Cells CHO-K1 cells were stably transfected with Human C1ORF32 (SEQ ID NO: 1) and pIRESpuro3 empty vector plasmids as follows:

CHO-K1 (ATCC, CCL-61) cells were plated in a sterile 6 well plate suitable for tissue culture, containing 2 ml pre-warmed of complete media, F12 Nutrient Mixture (Ham) (Gibco, catalog number: 01-055-1A)+10% FBS [Fetal Bovine Serum, Biological Industries (Beit Ha'Emek, Israel), catalog number: 04-001-1A)+4 mM L-Glutamine (Biological Industries (Beit Ha'Emek, Israel), catalog number: 03-020-1A). 500,000 cells per well were transfected with 2 µg of DNA construct using 4.5 µl Lipofectamine2000 transfection reagent (Invitrogen, cat No: 11668019) diluted into 100 ul Opti-MEM® I Serum Free Medium (Invitrogen, cat No: 31985-047). The mixture was incubated at room temperature for 15 minutes. The complex mixture was added dropwise to the cells. The cells were placed in an incubator maintained at 37° C. with 5% CO2 content. 48 hours after the transfection, the cells were transferred to a 75 cm2 tissue culture flask containing 15 ml of selection medium: complete medium supplemented with 12 µg\ml puromycin (Sigma, catalog number P8833). Cells were placed in an incubator, and the medium was replaced every 3-4 days, until clone formation was observed.

Example 4

Characterization of Polyclonal Anti C1ORF32 Antibodies Using Stable Pools Expressing C1ORF32

A. Western Blot Analysis of Stable Pools Expressing C1ORF32 Using Polyclonal Anti C1ORF32 Antibodies To verify the antibodies specificity, whole cell extracts of stable pools expressing C1ORF32 in HEK293T recombinant cells were analyzed by western blot using anti C1ORF32 purified pAbs R7531.

Upon sufficient quantities of cells passing through selection, cells were harvested. Cells were lysed in 300 µl RIPA buffer (50 mM Tris HCl pH 8, 150 mM NaCl, 1% NP-40, 0.5% sodium Deoxycholate, 0.1% SDS) supplemented with protease inhibitors (Roche, catalog number: 11873580001), for 20 min on ice. Following centrifugation at 4° C. for 15 minutes at 20,000×g, the clear supernatants were transferred to clean tubes and 100 µl of 4× NuPAGE® LDS sample buffer (Invitrogen, catalog number: NP0007) was added. In addition, 1,4-Dithiothreitol (DTT; a reducing agent) was added to a final concentration of 100 mM. The samples were then incubated at 70° C. for 10 minutes, followed by a 1 minute spin at 20,000×g. SDS-PAGE (Laemmli, U.K., Nature 1970; 227; 680-685) was performed upon loading of 30 µl of sample per lane into a 4-12% NuPAGE® Bis-Tris gels (Invitrogen, catalog number: NP0321), and gels were run in 1×MOPS SDS running buffer (Invitrogen, catalog number: NP0001), using the XCell SureLock™ Mini-Cell (Invitrogen, catalog number: E10001), according to manufacturer's instructions. The separated proteins were transferred to a nitrocellulose membrane (Schleicher & Schuell, catalog number: 401385) using the XCell™ II blotting apparatus (Invitrogen, catalog number E19051), according to manufacturer's instructions.

The samples were further processed and analyzed by SDS-PAGE as described above.

Figure 2:
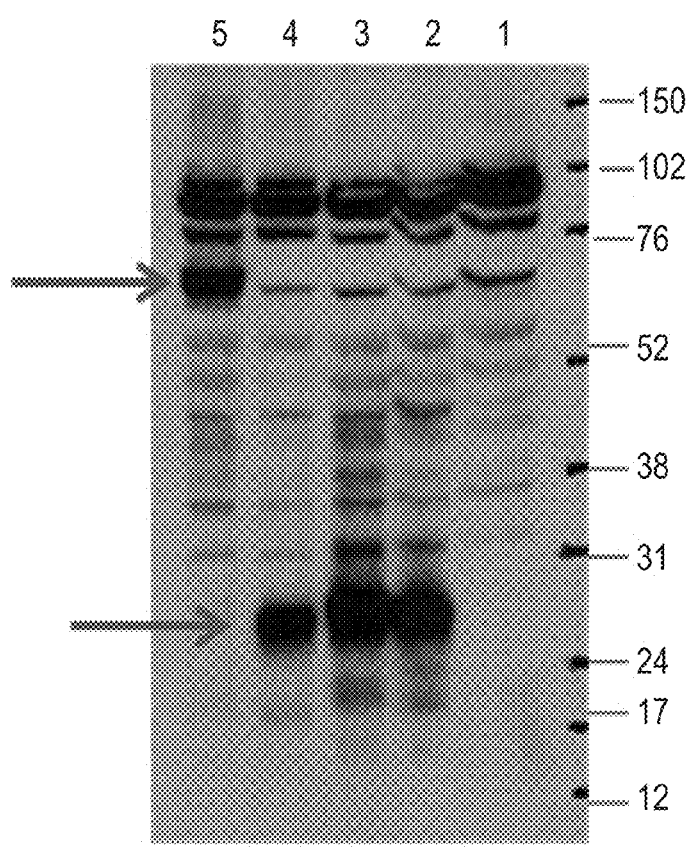
FIG. 2 demonstrates Western blot analysis on recombinant pools of C1ORF32 transfected HEK293T cells using affinity purified pAb R7531 antibody. The figure presents Western blot analysis of 30 ug lysates of HEK293T pool transfected with empty vector (lane1), human-C1ORF32 (SEQ ID NO: 1) (lane2), human-C1ORF32-HA tagged (SEQ ID NO: 22) (lane 3), mouse-human chimeric C1ORF32 (SEQ ID NO:8) (lane 4), mouse-C1ORF32-Flag tagged (SEQ ID NO:21) (lane5); using anti C1ORF32 pAbs R7531 (2 ug/ml). A band corresponding to the expected size of ~30 kDa human C1OFR32(SEQ ID NO:1) or ~70 kDa for the mouse-C1ORF32-Flag tagged (SEQ ID NO:21) was detected in the various HEK293T-C1ORF32-transfected cells as oppose to whole cell extract of stable HEK293T pool as negative control. Non specific bands were observed at higher molecular weights in all cell lines.

The results are presented in FIG. 2.

FIG. 2 demonstrates Western blot analysis of 30 ug lysates of HEK293T pool transfected with empty vector (lane 1), human-C1ORF32 (SEQ ID NO: 1) (lane 2), human-C1ORF32-HA tagged (SEQ ID NO: 22) (lane 3), chimeric mouse-human C1ORF32 (SEQ ID NO: 8) (lane 4), mouse-C1ORF32-Flag tagged (SEQ ID NO: 21) (lane 5); using anti C1ORF32 pAbs R7531 (2 ug/ml). A band corresponding to the expected size of ~30 kDa for the human-C1ORF32 or ~70 kDa for the mouse CORF32 (SEQ ID NO: 21) was detected in the various HEK293T-C1ORF32-transfected cells as oppose to whole cell extract of stable HEK293T pool transfected with pIRESpuro3 empty vector. However, non specific bands were observed at higher MW (molecular weight) in all cell lines.

B. FACS Analysis of Stable Pools Expressing C1ORF32 Using Polyclonal Anti C1ORF32 Antibodies To verify the pAbs binding to native cell-surfaced C1ORF32 protein (SEQ ID NO: 1) in stable transfections described above, Flow Cytometry analysis was performed, using anti C1ORF32 polyclonal antibodies R7531, R7532 and R7534 as described in section "Production of polyclonal antibodies specific to C1ORF32 protein", herein. Non relevant Rabbit IgG served as negative control (Sigma, cat 15006). Recombinant HEK293T cells expressing C1ORF32 were stained with anti C1ORF32 antibodies (A) or HEK293T transfected with empty vectot pIRESpuro3 followed by Donkey Anti Mouse-FITCconjugated secondary Ab (Jackson, cat 711-096-152), and were observed for the presence of fluorescent signal.

Recombinant HEK293T-C1ORF32 cells were dissociated from the plate using Cell dissociation buffer Enzyme-Free PBS-Based (Gibco; 13151-014), washed in FACS buffer [Dulbecco's Phosphate Buffered Saline (PBS) (Biological Industries, 02*023-1A)/1% Bovine Albumin (Sigma, A7030)] and counted. $0.5 \times 10^6$ cells were re-suspended in 100 µl of antibody solution, at 20 ug/ml, and incubated for 1 hour on ice. The cells were washed with ice-cold FACS buffer and incubated with secondary antibody as indicated for 1 hour on ice. The cells were washed with ice-cold FACS buffer and re-suspended in 300 µl FACS buffer, then analyzed on the FACS machine (FACSCalibur, BD). The data was acquired and analyzed using Cellquest Pro VER. 5.2. The results presented in FIG. 3.

Figure 3A:
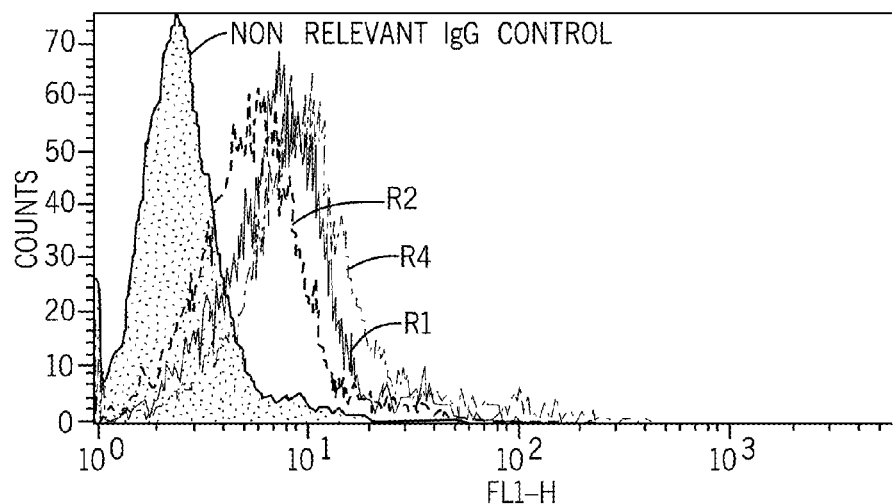
FIG. 3 demonstrate Flow Cytometry Analysis of polyclonal antibodies specific to C1ORF32 (R7531, R7532, R7534) in (FIG. 3A) recombinant HEK293T cells expressing human C1ORF32 protein (SEQ ID NO: 1) as compared to (FIG. 3B) HEK293T cells. Non relevant Rabbit IgG (Sigma, cat 15006) was used as a negative control. The results demonstrate cell surface expression of C1ORF32 using anti C1ORF32 antibodies.
Figure 3B:
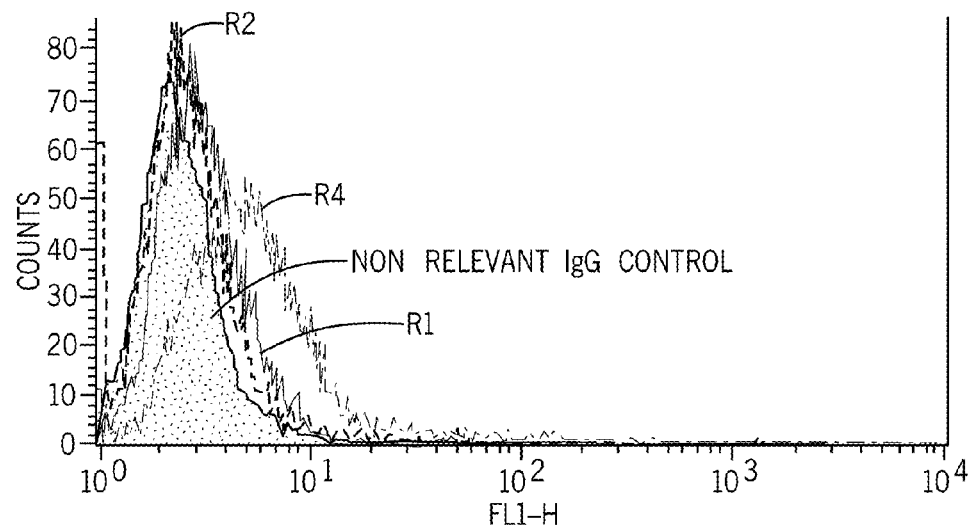

FIG. 3 demonstrates Flow Cytometry Analysis of recombinant HEK293T cells expressing C1ORF32 untagged protein (A) as compared to HEK293T transfected with empty vector pIRESpuro3(B) using polyclonal antibodies specific for C1ORF32 (R7531, R7532, R7534. Non relevant Rabbit IgG (Sigma, cat 15006) used as a negative control. The results represents specific binding of polyclonal antibodies to native cell-surfaced C1ORF32 protein.

Example 5A

Development of Mouse Monoclonal Antibodies Specific to C1ORF32 Protein

Development of monoclonal antibody to C1ORF32 protein (SEQ ID NO: 1) was performed at SLRC (Silver Lake Research Corporation, California, USA).

All procedures, including peptides synthesis, animal care and handling, animal immunizations, bleeding, fusions, hybridoma screening, and subcloning were performed at SLRC, according to procedures that are well known to someone of ordinary skill in the art.

The development of monoclonal antibody to C1ORF32 protein (SEQ ID NO: 1) was performed in two projects as follows: project 5159 (A) and project 5166 (B) as described bellow.

Project 5159

SLRC used proprietary EAP™ Affinity Platform), system to produce EAP-modified antigen for immunization using a peptide sequence, having an amino acid sequence corresponding to amino acid residues 63-85 from the extracellular domain of human C1ORF32 protein (SEQ ID NO: 1), with the additional Cys at the C' terminus of the peptide, as set forth in SEQ ID NO: 6, TTPDDLEGKNEDSVELC.

Binding screening was performed by ELISA using purified recombinant ECD-mIgG2a fusion protein (SEQ ID NO: 4) or stable pool of HEK-293T cells over expressing C1ORF32 protein previously described. Three positive clones were further processed for subcloning in order to establish stable hybridoma clones. Hybridomas were stabilized, subcloned and processed for antibody production and purification. Production and purification of mAbs 5159-1, 5159-2 and 5159-3 were carried out to generate large scale purified batches from each mAb for further analysis.

Isotyping for each antibody was determined as follows: 5159-1 murine IgG1 ƙ; 5159-2 murine IgG1 ƙ; 5159-3 murine IgM ƙ.

Project 5166

SLRC used proprietary EAP™ to produce EAP-modified antigen for immunization using fusion proteins C1ORF32-ECD-hIgG1, (SEQ ID NO:23) and C1ORF32-ECD-mIgG2a, (SEQ ID NO: 24) as an immunogen.

Binding screening was performed by ELISA using fusion proteins C1ORF32-ECD-hIgG1 (SEQ ID NO: 23) and C1ORF32-ECD-mIgG2a (SEQ ID NO: 24) or stable pool of HEK293T cells over expressing C1ORF32 described in section "Generation of stable pools expressing C1ORF32 protein" herein. Two positive clones 5166-2 and 5166-9 were further processed for subcloning in order to establish stable hybridoma clones and isotyped as follows: murine IgG1ƙ for 5166-2 and murine IgM ƙ for 5166-9. Hybridomas were stabilized, subcloned and processed for antibody production and purification. Production and purification of mAbs 5166-2 and 5166-9 were carried out to generate large scale purified batches from each mAb for further analysis.

Example 5B

Monoclonal Antibody Sequencing

Total RNA was extracted from frozen hybridoma cells following the technical manual of TRIzol® Plus RNA Purification System (Invitrogen, Cat. No.: 15596-026). The total RNA was analyzed by agarose gel electrophoresis. Total RNA was reverse transcribed into cDNA using isotype-specific anti-sense primers or universal primers following the technical manual of SuperScript™ III First-Strand Synthesis System (Invitrogen, Cat. No.: 18080-051). RT-PCR was then performed to amplify the heavy and light chains of the antibody. The antibody fragments of VH and VL were amplified according to the standard operating procedure of RACE of GenScript.

Amplified antibody fragments were separately cloned into a standard cloning vector using standard molecular cloning procedures.

Colony PCR Screening was Performed to Identify Clones with Inserts of Correct Sizes.

Ten single colonies with correct VH and VL insert sizes were sent for sequencing. The VH and VL genes of ten different clones were found nearly identical.

The consensus sequence, shown below is the sequence of the antibody produced by the hybridoma 5166-2 antibody 5166-2, deposited as described herein. The DNA and amino acid sequence of the heavy chain of the 5166-2 antibody is shown in SEQ ID NOs: 39 and 40, respectively. The DNA and amino acid sequence of the light chain of the 5166-2 antibody is shown in SEQ ID NOs: 41 and 42, respectively. The leader sequence is shown in Italic font; the sequences of CDR1, CDR2, CDR3 are shown in bold. The constant regions FR1, FR2, FR3 and FR4 are shown in a regular font. The nucleic acid sequences of 5166-2 antibody Heavy chain CDR1, CDR2, CDR3 are set forth in SEQ ID NOs: 43, 44, 45, respectively. The corresponding amino acid sequences of 5166-2 antibody Heavy chain CDR1, CDR2, CDR3 are set forth in SEQ ID NOs: 46, 47, 48, respectively. The nucleic acid sequences of 5166-2 antibody Light chain CDR1, CDR2, CDR3 are set forth in SEQ ID NOs: 49, 50, 51, respectively. The corresponding amino acid sequences of 5166-2 antibody Light chain CDR1, CDR2, CDR3 are set forth in SEQ ID NOs: 52, 53, 54, respectively.

```
5166-2 Heavy chain: DNA sequence (411 bp)
Leader sequence-FR1-CDR1-FR2-CDR2-FR3-CDR3-FR4
                                                         SEQ ID NO: 39
ATGGCTTGGGTGTGGACCTTGCTATTCCTGATGGCAGCTGCCCAAAGTATCCAAGCACAGATCCAGT

TGGTGCAGTCTGGACCTGAGCTGAAGAAGCCTGGAGAGACAGTCAAGATCTCCTGCAAGGCTTC

TGCTTATACCTTCACAGACTATTCAATGCACTGGGTGAAGCAGGCTCCAGGAAAGGGTTTAAA

GTGGATGGGCTGGATAAACACTGAGACTGGTGAGCCAACATATGCAGGTGACTTCAAGGGA
```

```
CGGTTTGCCTTCTCTTTGGAAACCTCTGCCAGCACTGCCTATTTGCAGATCAACAACCTCAAAAA

TGAGGACACGGCTACATATTTCTGTGTTAGAGCTGGTTACTACGACTACTTTGACTACTGGGG

CCAAGGCACCACTCTCACAGTCTCCTCA, 5166-2 Heavy chain: Amino acids sequence (137 AA)
Leader sequence-FR1-CDR1-FR2-CDR2-FR3-CDR3-FR4
                                                  SEQ ID NO: 40
MAWVWTLLFLMAAAQSIQAQIQLVQSGPELKKPGETVKISCKASAYTFTDYSMHWVKQAPGKGLKW

MGWINTETGEPTYAGDFKGRFAFSLETSASTAYLQINNLKNEDTATYFCVRAGYYDYFDYWGQGT

TLTVSS, 5166-2 Light chain: DNA sequence (381 bp)
Leader sequence-FR1-CDR1-FR2-CDR2-FR3-CDR3-FR4
                                                  SEQ ID NO: 41
ATGGAGACACATTCTCAGGTCTTTGTATACATGTTGCTGTGGTTGTCTGGTGTTGAAGGAGACATTG

TGATGACCCAGTCTCACAAATTCATGTCCACATCAGTAGGAGACAGGGTCAGCATCACCTGCAA

GGCCAGTCAGGATGTGGTTACTGCTGTAGCCTGGTATCAACAGAAACCAGGTCAATCTCCTA

AACTACTGATTTACTGGGCATCTAACCGGCACACTGGAGTCCCTGATCGCTTCACAGGCAGTG

GATCTGGGACAGATTTCACTCTCACCATTACCAATGTGCAGTCTGAAGACTTGGCAGATTATTTC

TGTCAGCAATATAGCAGCTATCCTCTCACGTTCGGAGGGGGGACCAAGCTGGAAATAAAA, 5166-2 Light chain: Amino acids sequence (127 AA)
Leader sequence-FR1-CDR1-FR2-CDR2-FR3-CDR3-FR4
                                                  SEQ ID NO: 42
METHSQVFVYMLLWLSGVEGDIVMTQSHKFMSTSVGDRVSITCKASQDVVTAVAWYQQKPGQSPKL

LIYWASNRHTGVPDRFTGSGSGTDFILTITNVQSEDLADYFCQQYSSYPLTFGGGTKLEIK,
```

The consensus sequence, shown below is the sequence of the antibody produced by the hybridoma 5166-9, antibody 5166-9, deposited as described herein. The DNA and amino acid sequence of the heavy chain of the 5166-9 antibody is shown in SEQ ID NOs: 55 and 56, respectively. The DNA and amino acid sequence of the light chain of the 5166-9 antibody is shown in SEQ ID NOs: 57 and 58, respectively. The leader sequence is shown italic; the sequences of CDR1, CDR2, CDR3 are shown in bold. The constant regions FR1, FR2, FR3 and FR4 are shown in a regular font. The nucleic acid sequences of the 5166-9 antibody Heavy chain CDR1, CDR2, CDR3 of are set forth in SEQ ID NOs: 59, 60, 61, respectively. The corresponding amino acid sequences of the 5166-9 antibody Heavy chain CDR1, CDR2, CDR3 are set forth in SEQ ID NOs: 62, 63, 64, respectively. The nucleic acid sequences of the 5166-9 antibody Light chain CDR1, CDR2, CDR3 of are set forth in SEQ ID NOs: 65, 66, 67, respectively. The corresponding amino acid sequences of the 5166-9 antibody Light chain CDR1, CDR2, CDR3 are set forth in SEQ ID NOs: 68, 69, 70, respectively.

```
5166-9 Heavy chain: DNA sequence (420 bp)
Leader sequence-FR1-CDR1-FR2-CDR2-FR3-CDR3-FR4
                                                  SEQ ID NO: 55
ATGAACTTGGGGCTCAGCTTGATTTTCCTTGTCCTTGTTTTAAAAGGTGTCCAGTGTGAAGTGAAGA

TGGTGGAGTCTGGGGGAGGCTTAGTGCAGCCTGGAGGGTCCCTGAAACTCTCCTGTGCAACCTCT

GGATTCACTTTCAGTGACTATTACATGTATTGGGTTCGCCAGACTCCAGAGAAGAGGCTGGAG

TGGGTCGCATACATTAGTAATGGTGGTGGTAGCACCTATTATCCAGACACTGTAAAGGGCCG

ATTCACCATCTCCAGAGACAATGCCAAGAACACCCTGTACCTGCAAATGAGCCGTCTGAAGTCTG

AGGACACAGCCATGTATTACTGTGCAAGACAAGGGTATTACTACGGTAGTAGCCCCTTTGCTT

ACTGGGGCCAAGGGACTCTGGTCACTGTATCTGCA, 5166-9 Heavy chain: Amino acids sequence (140 AA)
Leader sequence-FR1-CDR1-FR2-CDR2-FR3-CDR3-FR4
                                                  SEQ ID NO: 56
MNLGLSLIFLVLVLKGVQCEVKMVESGGGLVQPGGSLKLSCATSGFTFSDYYMYWVRQTPEKRLEW

VAYISNGGGSTYYPDTVKGRFTISRDNAKNTLYLQMSRLKSEDTAMYYCARQGYYYGSSPFAYWG

QGTLVTVSA, 5166-9 Light chain: DNA sequence (381 bp)
```

```
Leader sequence-FR1-CDR1-FR2-CDR2-FR3-CDR3-FR4
                                                SEQ ID NO: 57
ATGGAGTCACAGATTCAGGTCTTTGTATTCGTGTTTCTCTGGTTGTCTGGTGTGACGGAGACATTG

TGATGACCCAGTCTCACAAATTCATGTCCACATCAGTAGGAGACAGGGTCAGCATCACCTGCAA

GGCCAGTCAGGATGTGAGTACTGCTGTAGCCTGGTATCAACAGAAACCAGGACAATCTCCTA

AACTATTGATTTACTCGGCATCCTACCGGTACACTGGAGTCCCTGATCGCTTCACTGGCAGTGG

ATCTGGGACGGATTTCACTTTCACCATCAGCAGTGTGCAGGCTGAAGACCTGGCAGTTTATTACT

GTCAGCAACATTATAGTACTCCGTACACGTTCGGAGGGGGGACCAAGCTGGAAATAAAA, 5166-9 Light chain: Amino acids sequence (127 AA)
Leader sequence-FR1-CDR1-FR2-CDR2-FR3-CDR3-FR4
                                                SEQ ID NO: 58
MESQIQVFVFVFLWLSGVDGDIVMTQSHKFMSTSVGDRVSITCKASQDVSTAVAWYQQKPGQSPKL

LIYSASYRYTGVPDRFTGSGSGTDFTFTISSVQAEDLAVYYCQQHYSTPYTFGGGTKLEIK,
```

The consensus sequence, shown below is the sequence of the antibody 5159-1. The DNA and amino acid sequence of the heavy chain of the 5159-1 antibody is shown in SEQ ID NOs: 71 and 72, respectively. The DNA and amino acid sequence of the light chain of the 5159-1 antibody is shown in SEQ ID NOs: 73 and 74, respectively. The leader sequence is shown in italic font; the sequences of CDR1, CDR2, CDR3 are shown in bold font. The constant regions FR1, FR2, FR3 and FR4 are shown in a regular font.

The nucleic acid sequences of the 5159-1 antibody Heavy chain CDR1, CDR2, CDR3 of are set forth in SEQ ID NOs: 75, 76, and 77, respectively. The corresponding amino acid sequences of the 5159-1 antibody Heavy chain CDR1, CDR2, CDR3 are set forth in SEQ ID NOs: 78, 79, and 80, respectively. The nucleic acid sequences of the 5159-1 antibody Light chain CDR1, CDR2, CDR3 of are set forth in SEQ ID NOs: 81, 82, and 83, respectively. The corresponding amino acid sequences of the 5159-1 antibody Light chain CDR1, CDR2, CDR3 are set forth in SEQ ID NOs 84, 85, and 86, respectively.

```
5159-1 Heavy chain: DNA sequence (411 bp)
Leader sequence-FR1-CDR1-FR2-CDR2-FR3-CDR3-FR4
                                                SEQ ID NO 71
ATGGGCAGGCTTACTTCTTCATTCTTGCTACTGATTGTCCCTGCCTATGTCCTGGCCCAGG

TTACTCTGAAAGAGTCTGGCCCTGGGATATTGCAGCCCTCCCAGACCCTCAATCTGACTTG

TTCTTTCTCTGGGTTTTCACTGAGTTCTTCTTATATGGGTGTAGGCTGGATTCGTCAGCCT

TCAGGGAAGGGTCTGGAGTGGCTGGCACACATTTGGTGGGATGATGTCAAGCGCTATAATC

CAGCCCTGAAGAGCCGACTGACAATCTCCAAGGATATCTCCAACAACCAGGTTTTCCTAAA

GATCGCCAGTGTGGACACTGCAGATTCTGCCACATATTATTGTGGTCGAATAGACAGACAC

TACTTTGACTACTGGGGCCAAGGCACCATTCTCACGGTCTCCTCC, 5159-1 Heavy chain: Amino acids sequence (137 AA)
Leader sequence-FR1-CDR1-FR2-CDR2-FR3-CDR3-FR4
                                                SEQ ID NO: 72
MGRLTSSFLLLIVPAYVLAQVTLKESGPGILQPSQTLNLICSFSGFSLSSSYMGVGWIRQP

SGKGLEWLAHIWWDDVKRYNPALKSRLTISKDISNNQVFLKIASVDTADSATYYCGRIDRH

YFDYWGQGTILTVSS,

Light chain5159-1: DNA sequence (381 bp)
Leader sequence-FR1-CDR1-FR2-CDR2-FR3-CDR3-FR4
                                                SEQ ID NO 73
ATGAGGACCCCTGCTCAGTTTCTTGGAATCTTGTTGCTCTGGTTTCCAGGTATCAAATGTG

ACATCAAGATGACCCAGTCTCCATCTTCCATATATGCATCTCTAGGAGAGAGTCACTAT

CACTTGCAAGGCGAGTCAGGACATTAATGGATATTTAACCTGGTTCCAGCAGAAACCAGGA

AAATCTCCTAAGACCCTGATCTATCGCGCAAACAGATTGTTAGATGGTGTCCCATCAAGGT

TCAGTGGCAGTGGATCTGGGCAAGATTATTCTCTCACCATCAGCAGCCTGGATTATGAAGA

TATGGGAATTTACTATTGTCTGCAGTATGATGAGTTTCCGTGGACGTTCGGTGGAGGCACC

AAACTGGAAATCAAA,
```

```
Light chain5159-1: Amino acids sequence (127 AA)
Leader sequence-FR1-CDR1-FR2-CDR2-FR3-CDR3-FR4
                                                      SEQ ID NO 74
MRTPAQFLGILLLWFPGIKCDIKMTQSPSSIYASLGERVTITCKASQDINGYLTWFQQKPG

KSPKTLIYRANRLLDGVPSRFSGSGSGQDYSLTISSLDYEDMGIYYCLQYDEFPWTFGGGT

KLEIK,
```

The consensus sequence shown below is the sequence of the antibody 5159-2. The DNA and amino acid sequence of the heavy chain of the 5159-2 antibody is shown in SEQ ID NOs: 87 and 88, respectively. The DNA and amino acid sequence of the light chain of the 5159-2 antibody is shown in SEQ ID NOs: 89 and 90, respectively. The leader sequence is shown in italic font; the sequences of CDR1, CDR2, CDR3 are shown in bold font. The constant regions FR1, FR2, FR3 and FR4 are shown in a regular font.

The nucleic acid sequences of the 5159-2 antibody Heavy chain CDR1, CDR2, CDR3 of are set forth in SEQ ID NOs: 91, 92, and 93, respectively. The corresponding amino acid sequences of the 5159-1 antibody Heavy chain CDR1, CDR2, CDR3 are set forth in SEQ ID NOs: 94, 95, and 96, respectively. The nucleic acid sequences of the 5159-2 antibody Light chain CDR1, CDR2, CDR3 of are set forth in SEQ ID NOs: 97, 98, and 99, respectively. The corresponding amino acid sequences of the 5159-2 antibody Light chain CDR1, CDR2, CDR3 are set forth in SEQ ID NOs 100, 101, and 102, respectively.

```
Heavy chain 5159-2: DNA sequence (411 bp)
Leader sequence-FR1-CDR1-FR2-CDR2-FR3-CDR3-FR4
                                                      SEQ ID NO 87
ATGGGCAGGCTTACTTCTTCATTCCTGCTACTGATTGTCCCTGCATATGTCCTGTCCCAGG

TTACTCTGAAAGAGTCTGACCCTGGGATATTGCAGCCCTCCCAGACCCTCAGTCTGACTTG

TTCTTTCTCTGGGTTTTCACTGAGCACTTCTGGTATGGGTGTAGGCTGGATTCGTCAGCCA

TCAGGGAAGGGTCTGGAATGGCTGGCACACATTTGGTGGGATGATGTCAAGCGCTATAACT

CAGCCCTGAAGAACCGACTGACTATCTCCAAGGATACCTCCAGCAGCCAGGTATTCCTCAA

GATCGCCAATGTGGACACTGCAGATACTGCCACATACTACTGTGCTCGAATAGCCCGGCAC

TTCTTTGACTACTGGGGCCAAGGCACCACTCTCACAGTCTCCTCA,

Heavy chain5159-2: Amino acids sequence (137 AA)
Leader sequence-FR1-CDR1-FR2-CDR2-FR3-CDR3-FR4
                                                      SEQ ID NO 88
MGRLTSSFLLLIVPAYVLSQVTLKESDPGILQPSQTLSLTCSFSGFSLSTSGMGVGWIRQP

SGKGLEWLAHIWWDDVKRYNSALKNRLTISKDTSSSQVFLKIANVDTADTATYYCARIARH

FFDYWGQGTTLTVSS,

Light chain 5159-2: DNA sequence (381 bp)
Leader sequence-FR1-CDR1-FR2-CDR2-FR3-CDR3-FR4
                                                      SEQ ID NO 89
ATGAGGACCCCTGCTCAGTTTCTTGGAATCTTGTTGCTCTGGTTTCCAGGTATCAAATGTG

ACATCAAGATGACCCAGTCTCCATCTTCCATGTATGCATCTCTGGGAGAGAGAGTCACTAT

CACTTGCAAGGCGAGTCAGGACATTCATGGCTATTTAAGCTGGTTCCACCAGAAACCCGTG

AAATCTCCTAAGACCCTGATCTATCGTGCAAACAGATTGATAGATGGGGTCCCATCAAGGT

TCAGTGGCAGTGGATCTGGGCAAGATTATTTTCTCACCATCAGCAGCCTGGAGTATGAAGA

TATGGGAATTTATTATTGTCTACAGTATGATGAGTTTCCGTGGACGTTCGGTGGAGGCACC

AAGCTGGAAATCAAA,

Light chain5159-2: Amino acids sequence (127 AA)
Leader sequence-FR1-CDR1-FR2-CDR2-FR3-CDR3-FR4
                                                      SEQ ID NO 90
MRTPAQFLGILLLWFPGIKCDIKMTQSPSSMYASLGERVTITCKASQDIHGYLSWFHQKPV

KSPKTLIYRANRLIDGVPSRFSGSGSGQDYFLTISSLEYEDMGIYYCLQYDEFPWTFGGGT

KLEIK,
```

Example 6

Characterization of Monoclonal Anti C1ORF32 Antibody Using Stable Pool Recombinant Cells Expressing C1ORF32

A. Western Blot Analysis of Recombinant Cells Expressing C1ORF32 Using Anti C1ORF32 MABs 5159

Antibody-Protein interaction was observed upon western blot analysis on whole cell lysates from HEK-293T (ATCC, CRL-11268) cells transfected with C1ORF32 pIRESpuro constructs or with empty vector (pIRES-puro3 negative control). 25 µl of 4× NuPAGE® LDS sample buffer (Invitrogen, catalog number: NP0007) was added to 30 ug whole cell lysates and proceeded as described Example 4, herein.

Figure 4:
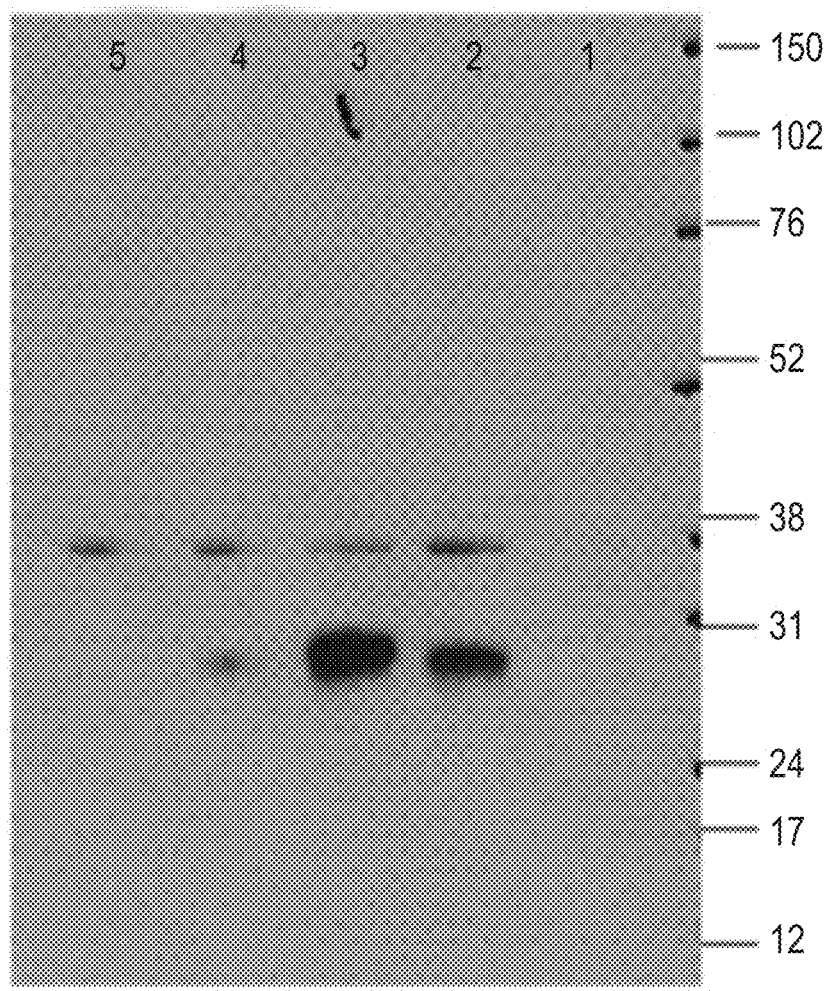
FIG. 4 presents Western blot analysis of HEK293T cells expressing C1ORF32 protein, using anti C1ORF32 monoclonal antibody 5159-1(2 ug/ml). The figure demonstrates Western blot analysis of whole cell lysates of HEK293T pool transfected with: empty vector (negative control cells) (lane1), human-C1ORF32 (SEQ ID NO: 1), expressing cells (lane 2) human-C1ORF32-HA tagged (SEQ ID NO:22) expressing cells (lane 3), mouse-human chimeric C1ORF32 (SEQ ID NO: 8) expressing cells, (lane 4), mouse-C1ORF32-Flag tagged (SEQ ID NO: 21) expressing cells (lane 5). Specific band corresponding to ~30 kDa for human-C1ORF32 (lane 2) and human-C1ORF32-HA tagged (lane 3) was detected as opposed to whole cell extract of stable HEK293T pool transfected with pIRES-puro3 empty vector (lane 1). Low signal was observed in the mouse-human chimeric C1ORF32 (SEQ ID NO:8) (lane 4), and no signal was detected in the mouse-C1ORF32—Flag (SEQ ID NO: 21) expressing cells.
Figure 5A:
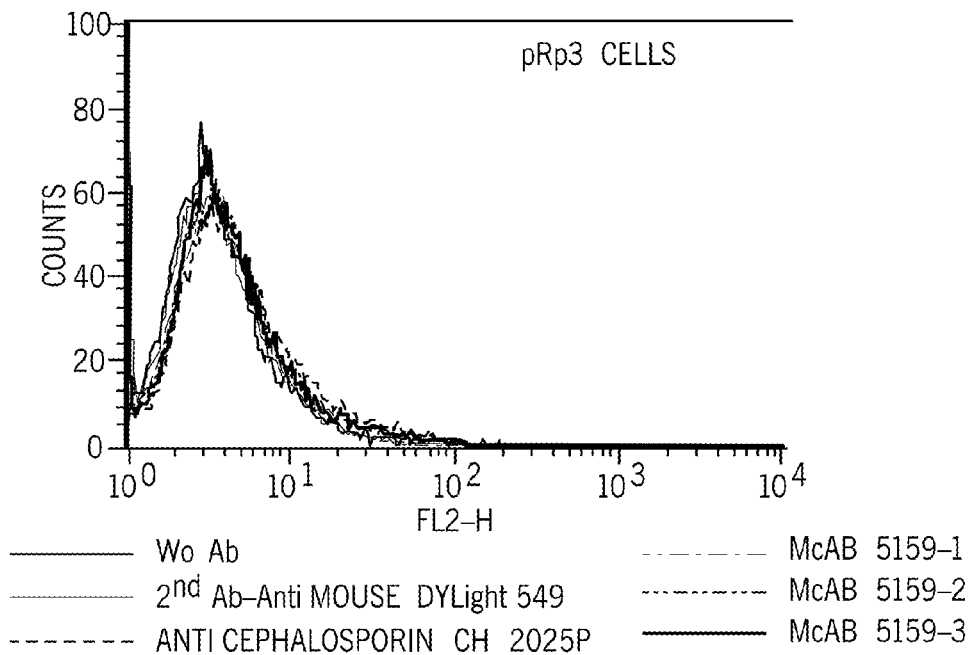
FIG. 5A presents empty vector transfected cells.
Figure 5B:
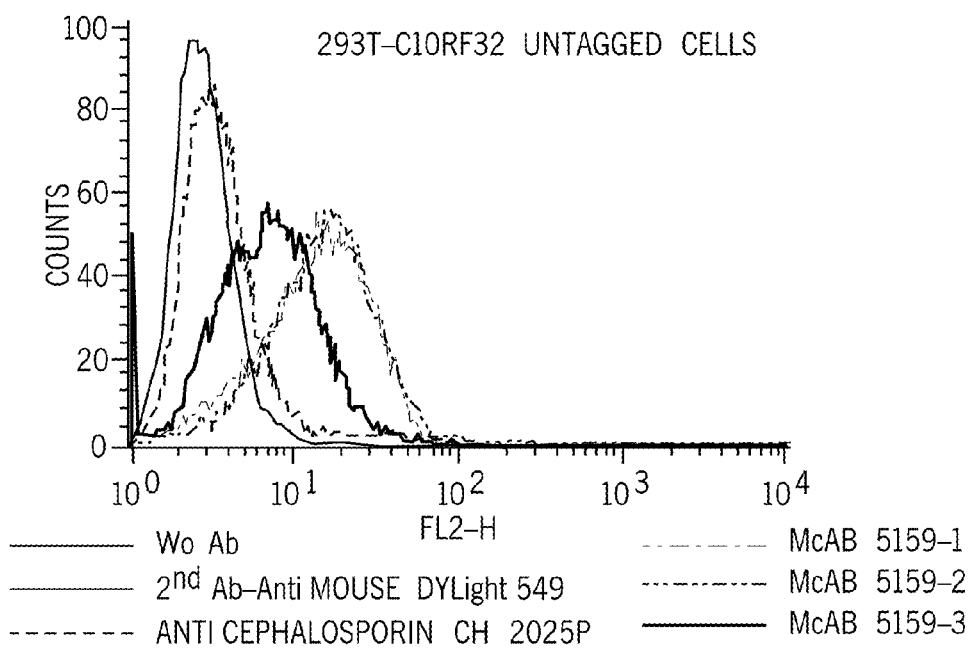
FIG. 5B presents human-C1ORF32 transfected cells (SEQ ID NO:1)
Figure 5C:
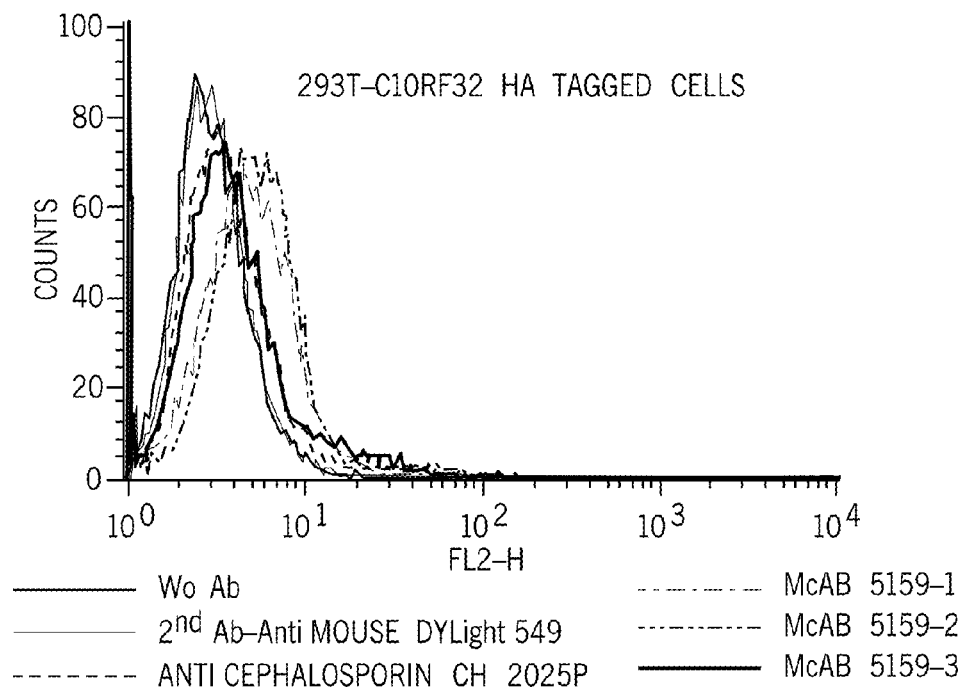
FIG. 5C presents human-C1ORF32-HA tagged transfected cells (SEQ ID NO: 22)
Figure 5D:
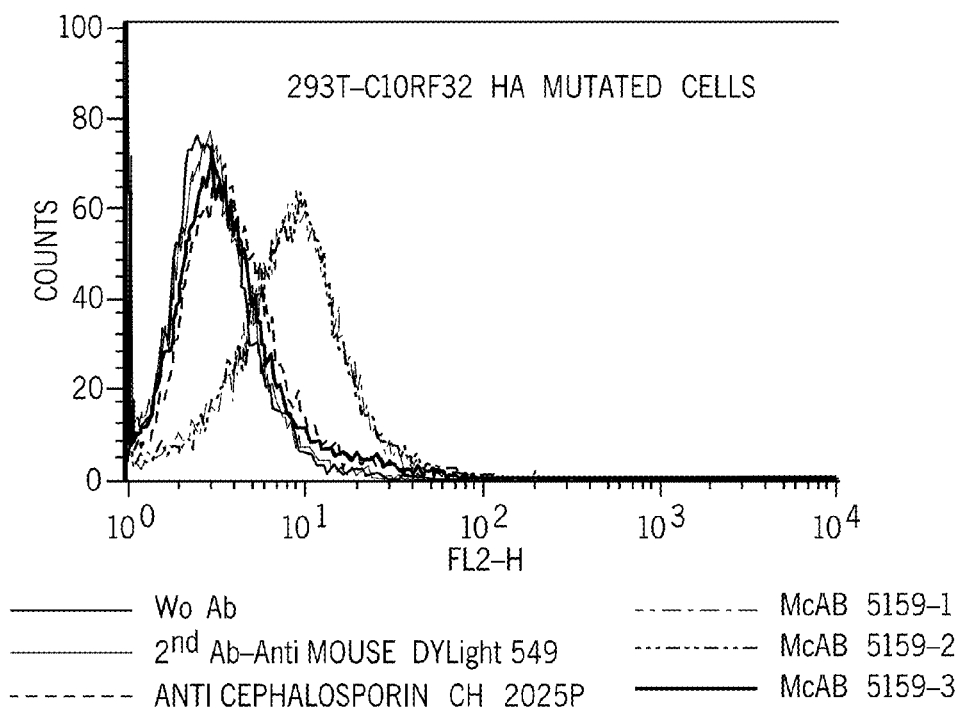
FIG. 5D presents chimeric mouse-human C1ORF32 transfected cells (SEQ ID NO: 8)
Figure 5E:
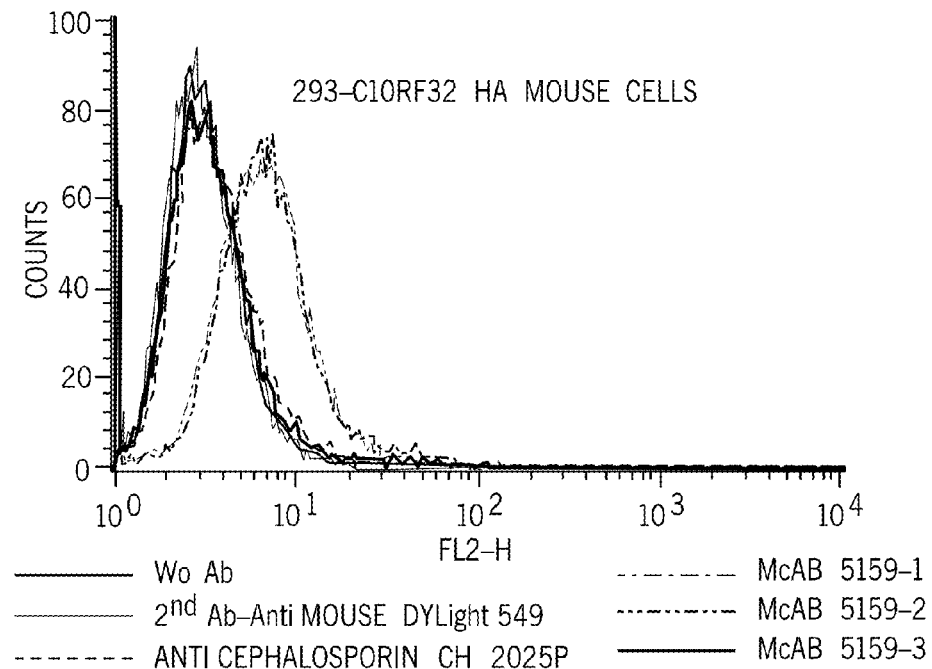
FIG. 5E presents mouse C1ORF32 transfected cells (SEQ ID NO: 21).

FIG. 4 demonstrates Western blot analysis of whole cell lysates of HEK293T pool transfected with empty vector (lane 1), human-C1ORF32 (lane 2) (SEQ ID NO: 1), human-C1ORF32-HA tagged (SEQ ID NO:22)(lane 3), chimeric mouse-human-C1ORF32 (SEQ ID NO: 8)(lane 4), mouse-C1ORF32-Flag tagged (SEQ ID NO: 21)(lane 5), using purified anti C1ORF32 monoclonal Antibody 5159-1 (2 ug/ml). Specific band corresponding to ~30 kDa for human-C1ORF32 (lane 2) and human-C1ORF32-HA tagged (lane 3) was detected as opposed to whole cell extract of stable HEK293T pool transfected with pIRES-puro3 empty vector (lane 1). Low signal was observed in the mutated C1ORF32 (lane 4), and no signal was detected in the mouse-C1ORF32 transfected cells.

B. FACS Analysis of Recombinant Cells Expressing C1ORF32 Using Anti C1ORF32 MABs 5159

Flow Cytometry analysis was performed to verify the mAbs binding to native cell surfaced C1ORF32 protein (SEQ ID NO: 1) in stable transfected cells described above. Detection was performed using monoclonal antibodies specific to C1ORF32: 5159-1, 5159-2, 5159-3. Anti-Cephalosporin served as negative control (SLRC, CH2025P). Recombinant HEK293T cells expressing C1ORF32 proteins, i.e. human C1ORF32 (SEQ ID NO:1), chimeric human-mouse C1ORF32 (SEQ ID NO:8) and mouse C1ORF32—Flag tagged (SEQ ID NO:21) were stained with anti C1ORF32 antibodies or anti-Cephalosporin followed by Donkey Anti Mouse-DyLight 549 conjugated secondary Ab (Jackson 715-506-150) as described in Example 6, herein. Fluorescent signal was observed. The results are presented in FIG. 5.

FIG. 5 demonstrates membrane expression of the various C1ORF32 proteins using mouse monoclonal anti C1ORF32 antibodies (20 ug/ml) as compared to non-relevant IgG control anti Cephalosporin, followed by Donkey Anti mouse IgG DyLight 549 conjugated secondary Ab diluted 1:250. FIG. 5A refers to empty vector transfected cells; FIG. 5B refers to human-C1ORF32 transfected cells (SEQ ID NO:1), FIG. 5C refers to human-C1ORF32-HA tagged transfected cells (SEQ ID NO: 22); FIG. 5D refers to chimeric human-mouse C1ORF32 transfected cells (SEQ ID NO:8), FIG. 5E refers to mouse C1ORF32—Flag tagged transfected cells (SEQ ID NO: 21).

In addition, Flow Cytometry analysis was performed on recombinant CHO-K1 cells expressing human C1ORF32 protein (SEQ ID NO: 1), as compared to CHO-K1 cells transfected with empty pIRESpuro3 vector. Monoclonal anti C1ORF32 antibody 5159-1 diluted to 2 ug/ml incubated with cells for 1 hr on ice, followed by Goat Anti Mouse-Alexa Fluor 488 conjugated secondary Ab (Invitrogen A11001), diluted 1:100. Mouse anti-Cephalosporin served as negative control. Fluorescent signal was observed. The results are presented in FIG. 6.

Figure 6:
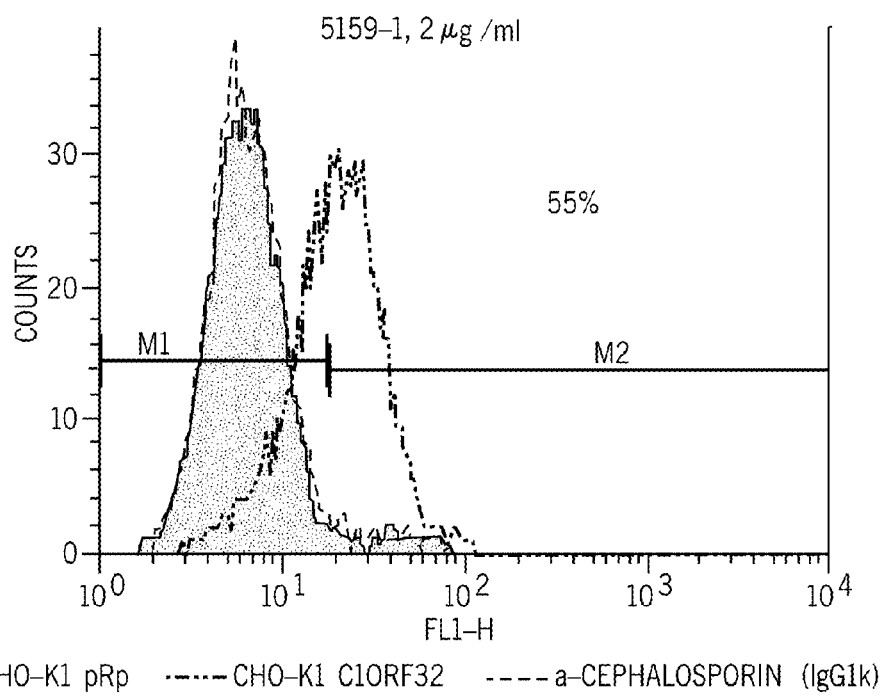
FIG. 6 presents FACS analysis of recombinant CHO-K1 cells expressing human C1ORF32 protein (SEQ ID NO:1), or stable pool transfected cells with empty vector pIRESpuro3 using anti C1ORF32 monoclonal antibodies 5159-1 and mouse anti-Cephalosporin as irrelevant Ab negative control.

FIG. 6 demonstrates Flow Cytometry Analysis of monoclonal 5159-1 anti C1ORF32 antibody binding to C1ORF32 protein, in CHO-K1 (ATCC, CCL-61) cells expressing human C1ORF32 protein (SEQ ID NO: 1), as compared to CHO-K1 cells.

Example 7

FACS Analysis of MABs 5166 Binding to Cell Surface C1ORF32 Protein

To verify the MABs binding to native cell-surfaced C1ORF32 protein (SEQ ID NO:1) in stable transfection described above, Flow Cytometry analysis performed, using anti C1ORF32 monoclonal antibodies 5166-2, and 5166-9. Anti-Cephalosporin (Silver Lake, CH2025P) and Normal Mouse Serum (Jackson, cat 015-000-120) were used as negative controls.

Recombinant CHO-K1 cells expressing C1ORF32 (SEQ ID NO: 1) were stained by MABs to C1ORF32 5166 or by anti-Cephalosporin followed by Goat Anti Mouse-Alexa Fluor 488 (Invitrogen A11001) secondary Ab diluted 1:100 and were observed for the presence of fluorescent signal.

Recombinant CHO-K1_ human C1ORF32 (SEQ ID NO: 1) cells were treated as described in section "Stable pool characterization C1ORF32 by FACS analysis using anti C1ORF32 MABs 5159"). The results are presented in FIG. 7.

Figure 7:
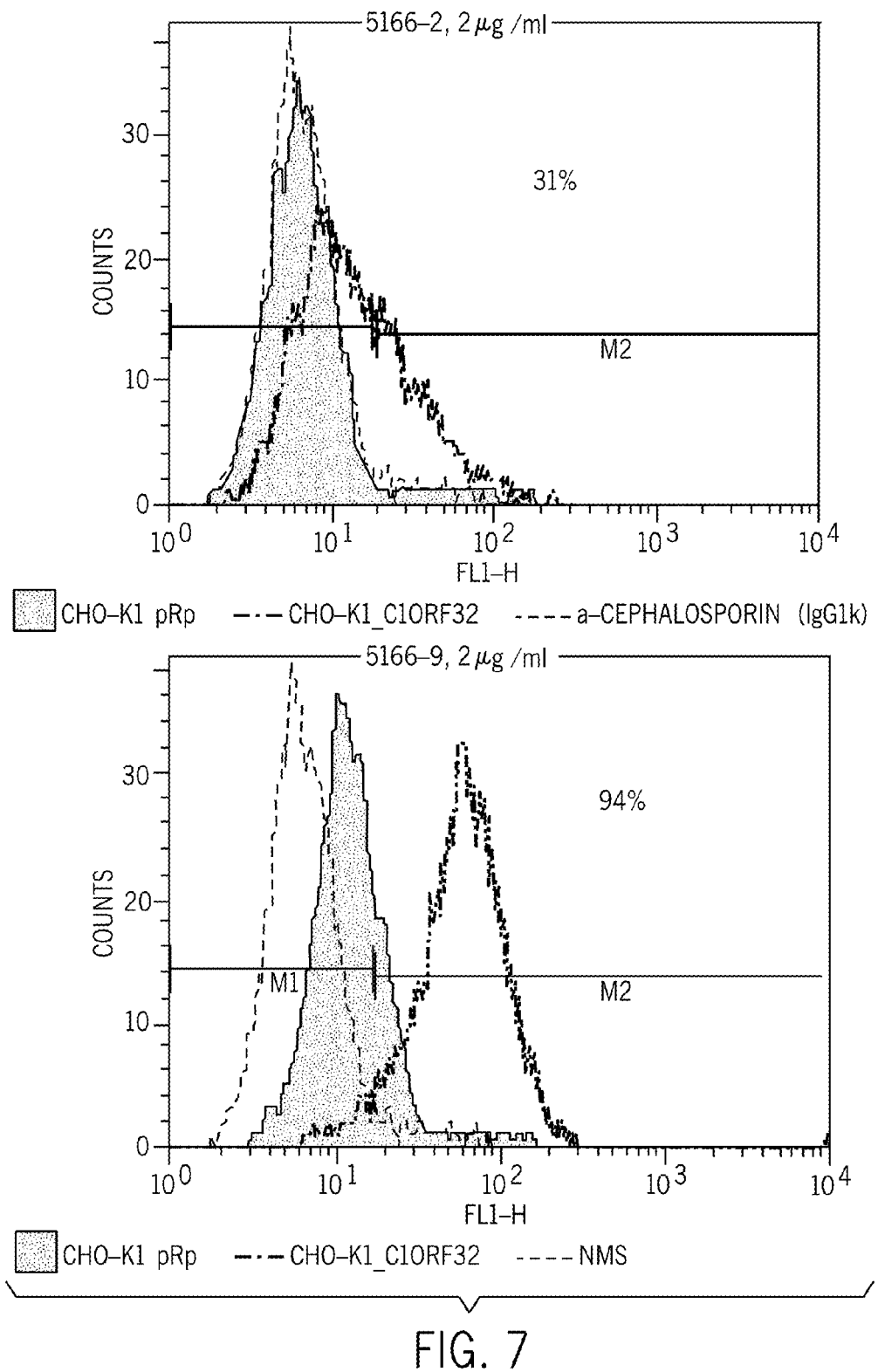
FIG. 7 demonstrates binding of monoclonal anti C1ORF32 antibodies 5166-2 (left) and 5166-9 (right) to human C1ORF32 protein, in CHO-K1 recombinant cells expressing C1ORF32 (SEQ ID NO:1) as compared to CHO-K1 stable pool transfected cells with empty vector pIRESpuro3. Mouse Anti-Cephalosporin and Normal Mouse Serum were used as negative controls.

FIG. 7 demonstrates binding of monoclonal anti C1ORF32 antibodies 5166-2 (left) and 5166-9 (right) to human C1ORF32 protein, in CHO-K1 recombinant cells expressing C1ORF32 human protein as compared to CHO-K1 stable pools. Mouse Anti-Cephalosporin was used as a negative control.

Example 8

Immunohistochemistry (IHC) Studies Using Anti-C1ORF32 Poly Clonal Antibody R1 (R7531)

To assess the tissue binding profiles of R1 (R7531) anti-C1ORF32, the antibody was examined in a panel of normal (non-neoplastic) human tissues, and on a panel of tumor tissues. HEK-293 cells transfected with C1ORF32 were used as a positive control and for calibration of the pAb for staining. Rabbit serum IgG was used as isotype control antibodies.

Affinity purified anti C1ORF32 antibody R1 (R7531) described above was used as the primary antibody and the principal detection system consisted of a Vector anti-rabbit secondary (BA-1000) and a Vector ABC-AP kit (AK-5000) with a Vector Red substrate kit (SK-5100), which was used to produce a fuchsia-coloured deposit. The negative control consisted of performing the entire immunohistochemistry procedure on adjacent sections in the absence of primary antibody. Human formaline fixed paraffin embedded tissue were purcheced from either (Biomax Inc., or Asterand plc). The slides were interpreted by a pathologist and each antibody was evaluated for the presence of specific signal and level of background. Staining intensity was recorded on a 0-4 scale (0=negative, 1=blush, 2=faint, 3=moderate, 4=strong). Slides were imaged with a DVC 1310C digital camera coupled to a Nikon E400 microscope. At a concentration of 1.25 µg/ml, Antibody R7531 showed moderate staining in the positive transfected control cell line and the empty vector negative control cells were negative.

Table 1 presents a summary of the results, describing the neoplastic tissues that showed moderate to strong staining in the majority of cells from the antibody. As can be seen from Table 1, the following tumors demonstrate moderate to strong expression of C1ORF32: Hepatocellular carcinomas (stage II and III), kidney chromophobe adenomas, pancreatic islet cell carcinomas, malignant melanomas (stage IV), osteogenic sarcomas, chondrosarcomas, leiomyosarcomas, transitional cell carcinomas of the baldder (stage II to IV) and Hodgkin's lymphomas. Weak to moderate to moderate staining was also observed in B- and T-cell lymphomas, breast carcinomas (Invasive ductal carcinoma stage IIa, IIb to IIIb) papillary thyroid carcinomas (stage II), ovarian serous and mucinous carcinomas (stages Ic to IIIb), ovarian granular cell tumours, renal clear cell carcinomas (stage I to II) and carcinoma sarcomatoides, prostate adenocarcinomas (stage I to III), hepatic cholangiocarcinomas, pancreatic ductal and mucinous adenocarcinomas, skin squamous carcinomas, seminomas of the testis, rhabdomyosarcomas, angiosarcomas and uterine endometrioid adenocarcinomas. Two of two spinal cord tumours also showed moderate staining. Cells that showed staining may therefore be assumed to be potential targets of the antibodies described herein.

TABLE 1

Summary of the Cancer Tissue Microarray IHC:

| Cancer Array | Number of samples with IHC Score negative | Number of samples with IHC Score weak to moderate | Number of samples with IHC Score moderate to strong |
| --- | --- | --- | --- |
| Kidney, Chromophobe adenoma | 0 | 0 | 3 |
| Liver, Hepatocellular carcinoma (stage II and III) | 0 | 0 | 3 |
| Pancreas, Islet cell carcinoma | 0 | 0 | 3 |
| Skin, Malignant melanoma (stage IV) | 0 | 0 | 3 |
| Bone, Chondrosarcoma | 0 | 0 | 3 |
| Soft Tissue, Leiomyosarcoma | 0 | 0 | 3 |
| Lymph node, Hodgkin's lymphoma | 0 | 0 | 3 |
| Bladder, Transitional Cell carcinoma (stage II and IV) | 0 | 0 | 3 |
| Ovary, Papillary Serous and Mucinous (stages Ic, IIIb, IIIb) | 0 | 3 | 2 |
| Pancreas, Ductal and Mucinous Adenocarcinoma | 1 | 3 | 2 |
| Skin, Squamous carcinoma | 0 | 1 | 2 |
| Bone, Osteogenic sarcoma | 0 | 0 | 2 |
| Soft Tissue, Angiosarcoma | 0 | 1 | 2 |
| Lymph node, T-cell Lymphoma | 0 | 1 | 2 |
| Spinal cord tumour | 0 | 0 | 2 |
| Uterus, Endometroid Adenocarcinoma (stages I, IIa, IIIc) | 0 | 1 | 2 |
| Kidney, Clear cell carcinoma (stage I and II) | 0 | 2 | 1 |
| Kidney, Carcinoma sarcomatoides | 0 | 2 | 1 |
| Testis, Seminoma | 0 | 2 | 1 |
| Soft tissue, Rhabdomyosarcoma | 0 | 2 | 1 |
| Lymph node, B-cell Lymphoma | 0 | 2 | 1 |
| Follicular and papillary thyroid carcinomas (stage II and III) | 1 | 5 | 0 |
| Breast carcinoma (Invasive ductal carcinoma stage IIa, IIb, IIIb) | 0 | 3 | 0 |

Within peripheral tissues (1 specimen per tissue), moderate to strong staining was observed in endometrial glands, subsets of macrophages and subsets of cells within the islets of Langerhans. Moderate staining was observed in breast epithelium, plasma cells, Kupffer cells, Leydig cells of the testis, mast cells, placental trophoblasts, chondrocytes, occasional endothelia lining vessels and endometrial stromal cells.

An IHC study specific for normal lymph nodes was also carried out on a lymphatic tissue array, which consisted of 48 cores of formalin-fixed human lymph nodes from a variety of locations within the body. C1ORF32 pAb was used at a concentration of 1.25 µg/ml. C1ORF32 showed faint staining in 9 of 48 and faint or faint to moderate staining of lymphocytes within 39 of 48 normal lymph node samples. Three normal lymph node samples were also contained in the tumour array and these samples showed blush to faint staining within lymphocytes. In addition to lymphocytes, plasma cells and occasional macrophages and endothelial cells also showed staining.

Immunohistochemistry (IHC) Analysis on TOP4 Cancer TMA

The anti-C1ORF32 rabbit polyclonal antibody was calibrated by immunohistochemistry in FFPE sections of the positive control cell line. Sections were incubated at 0.3 µg/ml following de-waxing, rehydration and antigen retrieval in Flex+3-in-1 pH9.0 antigen retrieval solution in a PT link apparatus. Bound antibodies were detected using DAKO Envision Flex+ detection reagents. The antibody detected specific signal in the positive control cell line sample tested.

Following calibration of optimal conditions, the anti C1ORF32 pAb was tested on a human cancer tissue microarray (Asterand's 'Top4' TMA™). Overall, C1ORF32 protein was expressed in several of the tumors studied. The tumor type most consistent exhibiting C1ORF32-immune reactivity was prostate adenocarcinoma where all samples appeared positive (see Table 2).

Within the breast tumour set, the intensity of staining was low (1+) with only three tumors scoring 2+(poorly differentiated infiltrating ductal carcinoma (IDC), grade 3 IDC and comedocarcinoma). 3 breast cancer samples in which epithelial cells were largely negative showed positive staining in immune infiltrating cells (Infiltrating Ductal Carcinoma Grade 2 and 3, Medullary Carcinoma Grade 2). Within the large bowel set, all tumors were adenocarcinomas and low immunoreactivity was seen in all tumors analyzed. Five samples had immunoreactivity of 2+ (indicating that they were Moderate to Poorly Differentiated). In the lung tumors set, two of the tumors were strongly immunoreactive with a score of 2+ and both were poorly to moderately differentiated either of Squamous cell carcinoma or Large cell carcinoma histology. One lung tumor core appeared to be >50% immunoreactive at an intensity of 1+. The normal lung samples were positive in at least one core from each of all donors sampled. One sample of lung squamous cell carcinoma moderately differentiated in which the tumor was negative for C1ORF32 reactivity had moderate staining infiltrating immune cells. In the prostate tumors, a higher level of immunoreactivity was recorded. From a cohort of 26 prostate adenocarcinomas, all tumors appeared to be C1ORF32 immunoreactive in this study, with the majority scoring +1. Two tumors recorded a 3+ score (Gleason scores 6 and 7) and six tumors (Gleason scores 5, 6 and 7) scored 2+. Within the normal prostate samples staining was seen in the glandular epithelium.

TABLE 2 expression of prostate samples in the TOP4 tissue array.

| CoreTissue | IR score and % tumour stained IR score | Max IHC score |
|---|---|---|
| Normal | | 0 |
| Normal | | 1 |
| Normal | | 1 |
| Normal | | 2 |
| Adenocarcinoma | Adenocarcinoma Gleason Score 3 + 4 = 7 | 1 |
| Adenocarcinoma | Adenocarcinoma: Gleason Score 3 + 3 = 6 | 1 |
| Adenocarcinoma | Benign prostatic hyperplasia (BPH): Gleason Score 3 + 4 = 7 | 1 |
| Adenocarcinoma | Adenocarcinoma: Gleason Score 2 + 3 = 5 | 2 |
| Adenocarcinoma | Adenocarcinoma: Gleason Score 3 + 3 = 6 | 1 |
| Adenocarcinoma | Adenocarcinoma: Gleason Score 4 + 3 = 7 | 1 |
| Adenocarcinoma | Adenocarcinoma: Gleason Score 4 + 5 = 9 | 1 |
| Adenocarcinoma | Adenocarcinoma | 1 |
| Adenocarcinoma | Adenocarcinoma: Gleason Score 2 + 3 = 5 | 1 |
| Adenocarcinoma | Adenocarcinoma: Gleason Score 3 + 3 = 6 | 1 |
| Adenocarcinoma | Adenocarcinoma: Gleason Score 4 + 4 = 8 | 1 |
| Adenocarcinoma | Adenocarcinoma: Gleason Score 3 + 4 = 7 | 2 |
| Adenocarcinoma | Adenocarcinoma: Gleason Score 3 + 4 = 7 | 1 |
| Adenocarcinoma | Adenocarcinoma: Gleason Score 3 + 4 = 7 | 1 |
| Adenocarcinoma | Adenocarcinoma: Gleason Score 3 + 4 = 7 | 1 |
| Adenocarcinoma | Adenocarcinoma: Gleason Score 3 + 4 = 7 | 3 |
| Adenocarcinoma | High grade prostatic intraepithelial neoplasia: Gleason Score 3 + 4 = 7 | 2 |
| Adenocarcinoma | Adenocarcinoma: Gleason Score 3 + 4 = 7 | 1 |
| Adenocarcinoma | Adenocarcinoma: Gleason Score 3 + 4 = 7 | 2 |
| Adenocarcinoma | Adenocarcinoma: Gleason Score 3 + 4 = 7 | 1 |
| Adenocarcinoma | Adenocarcinoma: Gleason Score 3 + 4 = 7 | 2 |
| Adenocarcinoma | Adenocarcinoma | 1 |
| Adenocarcinoma | Adenocarcinoma: Gleason Score 3 + 4 = 7 | 2 |
| Adenocarcinoma | Adenocarcinoma: Gleason Score 3 + 3 = 6 | 3 |
| Adenocarcinoma | Adenocarcinoma: Gleason Score 3 + 3 = 6 | 2 |
| Adenocarcinoma | Adenocarcinoma: Gleason Score 3 + 3 = 6 | 1 |

Figure 8:
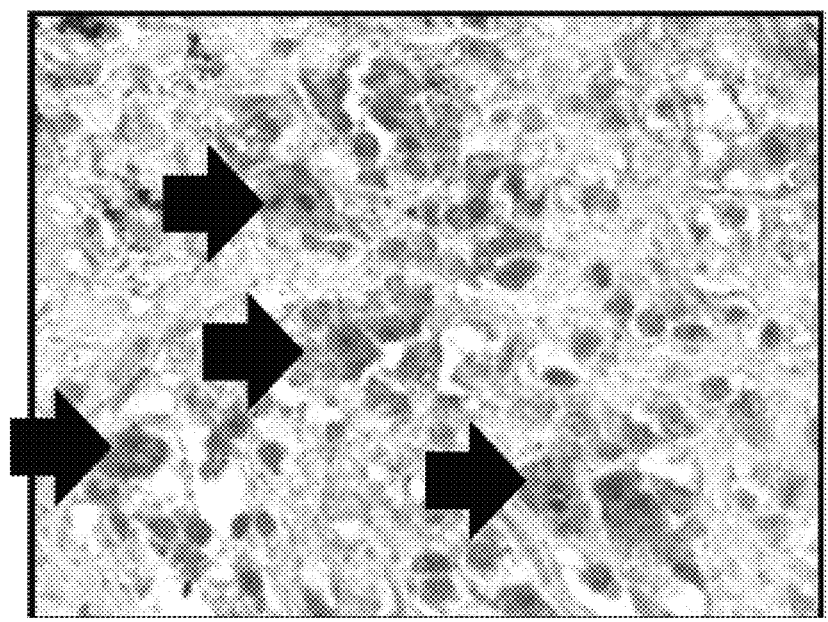
FIG. 8 presents positive immune infiltrating cells staining for C1ORF32 in small cell lung cancer. The immunoreactivity of cancer cells is low, but macrophages infiltrating the tumor show high positivity of C1ORF32 (arrows).

Expression of C1ORF32 in Prostate Tumors Full Sections and Immune Infiltrating Cells 10 prostate cancer paraffin-embedded sections were deparaffinized and stained following antigen retrieval. For antigen retrieval and staining Ventana Ultra IHC/ISH system was used according to manufacture protocols. Protease retrieval was used for anti C1ORF32 pAb (Part Number 760-2018), anti CD68 KP-1 Mouse Monoclonal was purchased for Ventana and standard retrieval protocol was used (CC1 module, Ventana), Giemsa Stain was purchased from Ventana (cat. 860-006). At least a faint staining was observed in all samples stained with the anti C1ORF32 pAb. Six tumors had a score of +1, and 4 tumors had a score of +2. A subset of immune infiltrating cells, which were identified morphologically as macrophages and mast cells, were also positive for C1ORF32 immunoreactivity. The nature of these cells was further confirmed using an anti-CD68 antibody for macrophages and Giemsa Stain for mast cells. More over evaluating morphologically the various TMA data obtained positive immune infiltrating cells were observed also in breast cancer, small cell lung cancer (stage I, II, IIIa and IIIb) (FIG. 8) and non small cell lung cancer, colo-rectal cancer (stage III). All these cancers had low to negative staining in cancer cells, but the positive immunoreactivity of C1ORF32 in the immune infiltrating cells indicates potential anti cancer therapy by stimulation of the immune system and hence also indicates that these cell types may optionally be targets for antibody therapy as described herein.

Example 9

Effect of C1ORF32 Expressed on HEK 293T Cells on Activation of Jurkat T Cells

Figure 9:
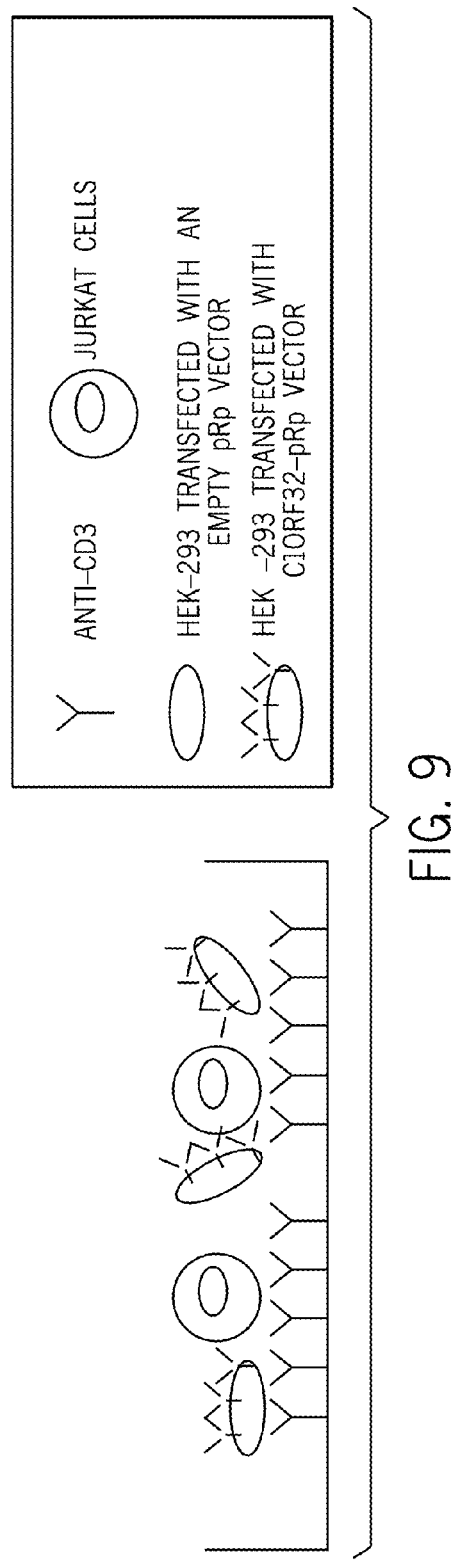
FIG. 9: presents a schematic illustration of the experimental setting of evaluation of the effect of C1ORF32 expressed on HEK 293T cells on activation of Jurkat cells.

In order to further evaluate the inhibitory effect of C1ORF32 protein (SEQ ID NO: 1) in its membrane form on T cell activation, co-culture assays of HEK 293T cells over expressing C1ORF32 was used (expression was verified by flow cytometry using both polyclonal and monoclonal antibodies against the ectodomain of C1ORF32) or transfected with the vector only (pRp3) as negative control, and primary CD4+ murine T cells or Jurkat T cells, activated in the presence of plate-bound anti-CD3 antibodies. The experimental setting is depicted in FIG. 9.

HEK 293T cells overexpressing C1ORF32 protein were produced as described in Example 3 herein.

a) Anti-CD3 mediated activation of Jurkat T cells as measured by CD69 expression.

Day 1:
1. Anti-CD3 (Clone OKT3, eBioscience; cat#16-0037-85 or clone UCHT1, BD Bioscience; cat#555329) diluted in 1×PBS was immobilized on 96-well plate in 75 μL/well at the indicated concentrations
2. Plates were wrapped with parafilm and incubated at 4° C. O.N. (overnight)
3. HEK 293T_pRp and HEK 293T cell pools ectopically expressing C1ORF32 protein (SEQ ID NO: 1) were seeded at a concentration of 12×10$^6$ cells per T75 plate and cultured in DMEM medium supplemented with 10% FBS, L-glutamine, penicillin, and streptomycin in a humidified incubator O.N.

Day 2:
1. Wells coated with anti-CD3 were washed ×3 with 200 μl of ×1 PBS. Fluid was decanted in a sterile environment. After the last wash, plate was blotted on a sterile absorbent paper to remove any residual fluid.
2. HEK 293T cells, seeded the day before, were treated with mitomycin C (Sigma, M4287): 900 μl of a 0.5 mg/ml solution freshly prepared in H2O were added directly to 8.1 ml of growth medium, to obtain a final concentration of 50 μg/ml. Cells were incubated with mitomycin C for 1 hour at 37° C.
3. Mitomycin C treated HEK 293T cells were washed ×3 with 10 ml of 1×PBS and removed by addition of 2 ml of cell dissociation buffer (Gibco; Cat. 13151-014).
4. Detached HEK 293T cells were re-suspended in 8 ml of RPMI supplemented with 10% FBS, L-glutamine, penicillin, and streptomycin (Jurkat cells' growth medium).
5. Cells were counted using a Beckman coulter counter and diluted to 0.5×10$^6$ cells per ml.

6. Cells were serially diluted and seeded at the indicated concentrations in 100 µl of RPMI Jurkat cells' growth medium (described above) per well.
7. HEK 293T cells were incubated for 2 hours to allow attachment.
8. 50,000 Jurkat cells (ATCC, clone E6-1, TIB-152, derived from human T cell leukemia) were added to each well at a volume of 100 µl per well in RPMI Jurkat cells' growth medium, in the absence or presence of 2 µg/ml soluble anti CD28 (Clone CD28.2, eBioscience, cat#16-0289-85).
9. Cells were co-cultured in a humidified incubator O.N.

Day 3:
1. Cells were transferred to U-shape plates, centrifuged 5 minutes at 1500 rpm, 4° C., and supernatant was decanted.
2. Anti-CD69 Ab (Biolegend, PE-anti human CD69, clone FN50, cat#310906, 10 µg/ml, 2 µl/well) and Fc-blocker (Miltenyi Biotec, human FcR blocking reagent, cat#120000-442, 1 µl/well) were diluted in ice-cold FACS buffer (1×PBS+0.5% BSA+2 mM EDTA+0.05% azide) and added in a final volume of 50 µl per well.
3. The wells contents were mixed gently by pipetting (without making air bubbles).
4. Plates were incubated on ice for 30 minutes.
5. Cells were washed once with 200 µl of FACS buffer and the plates were centrifuged 5 mM at 1500 rpm, 4° C. Sup was discarded by decanting.
6. Cells were resuspended in 200 µl of FACS buffer and transferred to FACS tubes filled with additional 100 µl FACS buffer.
7. Jurkat cells were analyzed by flow cytometry for cell surface expression of CD69 (Mean Fluorescence Intensity (MFI)). Jurkat cells were gated according to Forward Scatter (FSC) vs. Side Scatter (SSC). Gating procedure was validated by staining the cells with anti-CD2 antibody (Biolegend; clone RPA-2.10, Cat. 300206) in order to identify the T cells.

Inhibition of Anti CD3 Mediated Activation of Jurkat T Cells as Measured by CD69 Expression.

The effect of the C1ORF32 (SEQ ID NO: 1 expressed on the cell membrane on T cell activation was evaluated using HEK 293T cells transfected with the C1ORF32 (SEQ ID NO: 1) that were co-cultured with Jurkat T cells activated by plate-bound anti-CD3 antibodies. HEK 293T cells transfected with the vector only (pRp3) were used as a negative control.

Representative results, shown in FIGS. 10 and 11, indicate that Jurkat T cells stimulated with two different anti-CD3 clones (OKT2 and UCHT1, respectively) in the presence of HEK 293T/C1ORF32 cells exhibited reduced activation, as manifested by the decreased level of CD69, an early marker of T cell activation. As shown in FIG. 12, similar results were obtained when Jurkat cells were activated by a combination of anti-CD3 antibodies together with anti-CD28 antibodies. A significant inhibition of Jurkat cells activation can be seen even after 7.5 hours of co-culturing (FIG. 13).

Figure 10A:
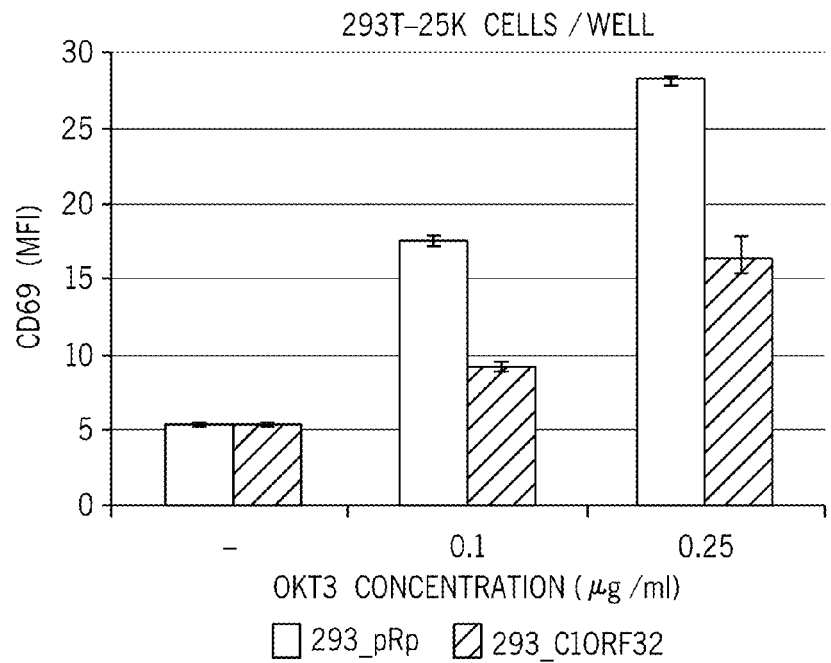
FIG. 10: demonstrates that C1ORF32 (SEQ ID NO: 1) expressed on HEK 293T cells inhibits Jurkat cells activation. 25K (FIG. 10A) or 50K (FIG. 10B) HEK 293T cells expressing C1ORF32 or the pRp vector were co-cultured with Jurkat cells (50K per well) and analyzed for the expression of CD69 by flow cytometry. ΔMFI values of CD69 are shown in FIG. 10C.
Figure 10B:
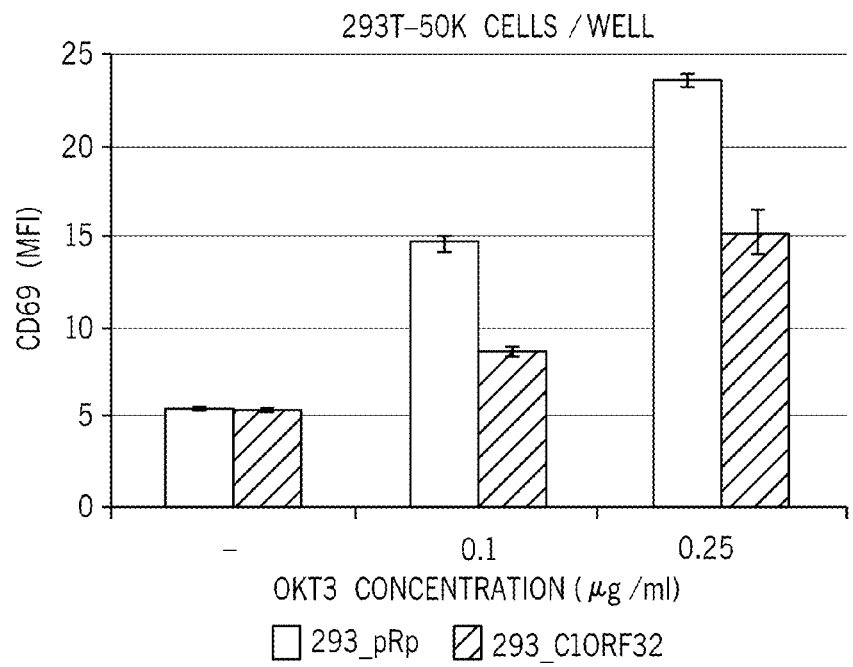
Figure 10C:
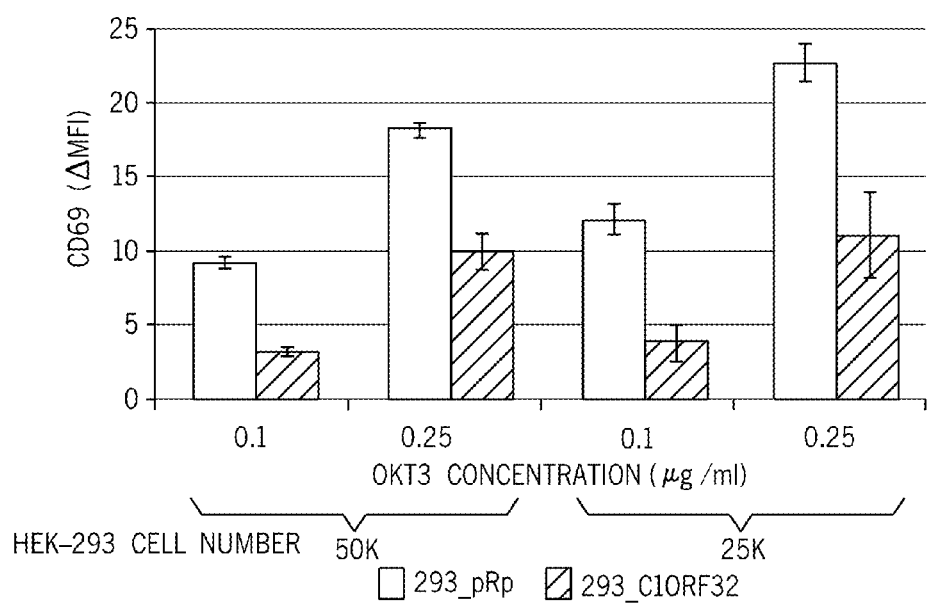

FIG. 10 shows that C1ORF32 (SEQ ID NO: 1) expressed on HEK 293T cells inhibits Jurkat cells activation. 25K (FIG. 10A) or 50K (FIG. 10B) cells of HEK 293T cells expressing C1ORF32 or the pRp vector were seeded in wells pre-coated with 0.1 or 0.25 µg/ml of anti-CD3 (OKT3 clone). Jurkat cells (50K per well) were added 2 hours later and the cells were incubated O.N. Cells were analyzed for the expression of CD69 by flow cytometry. ΔMFI values of CD69 are shown in (FIG. 10C).

Figure 11A:
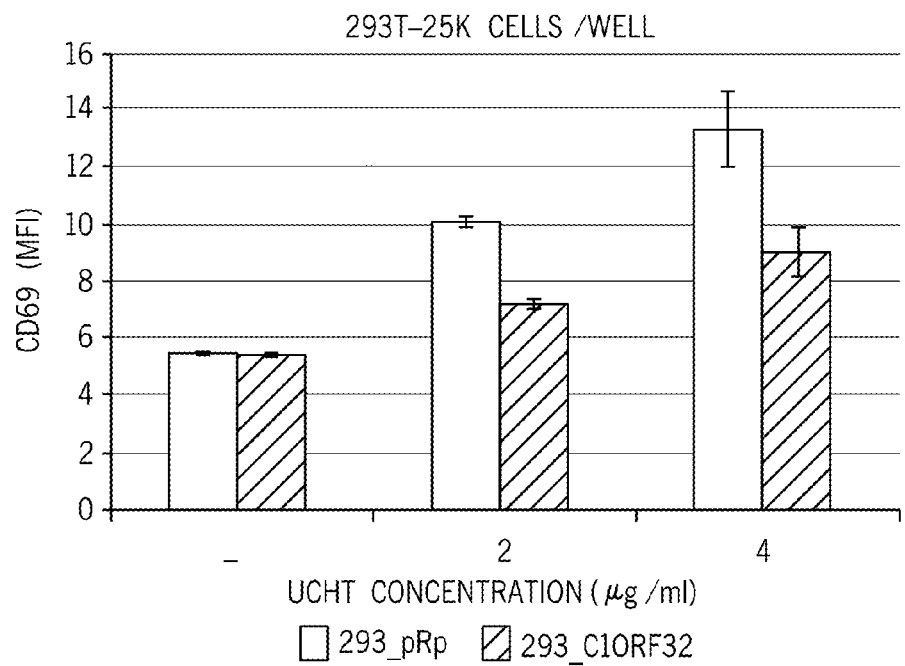
FIG. 11 demonstrates that C1ORF32 (SEQ ID NO: 1) expressed on HEK 293T cells inhibits Jurkat cells activated with anti CD3-UCHT clone. 25K (FIG. 11A) or 50K (FIG. 11B) HEK 293T cells expressing C1ORF32 or the pRp vector were incubated O.N. with Jurkat cells (50K per well), and analyzed for the expression of CD69 by flow cytometry. ΔMFI values of CD69 are shown in (FIG. 11C).
Figure 11B:
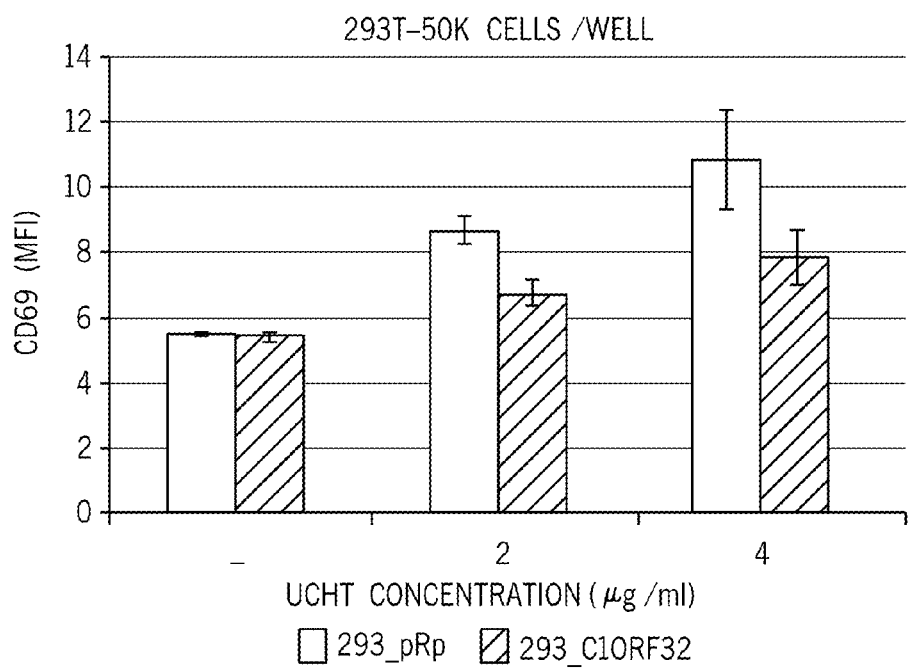
Figure 11C:
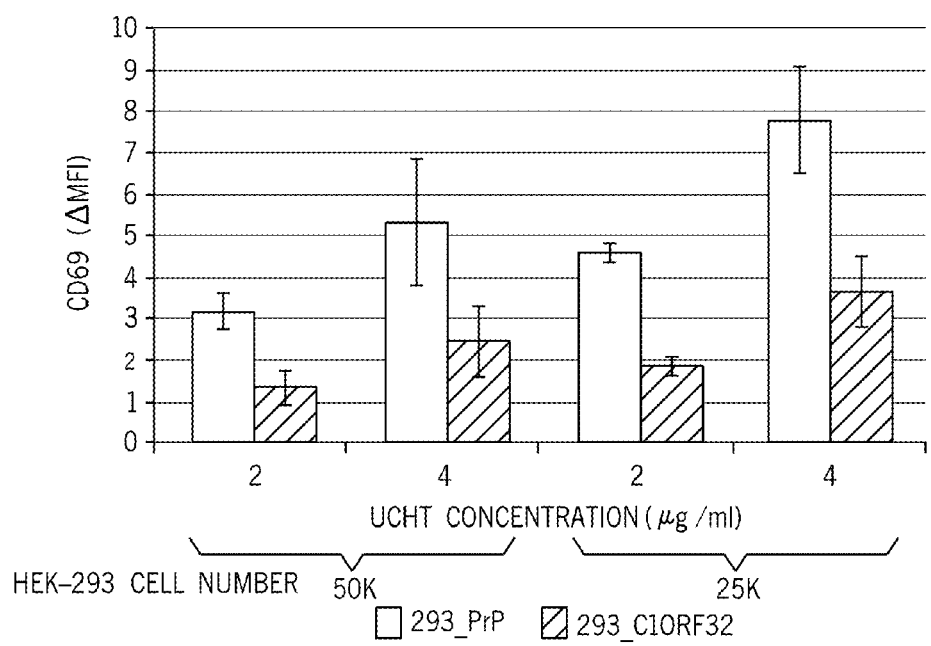
Figure 12A:
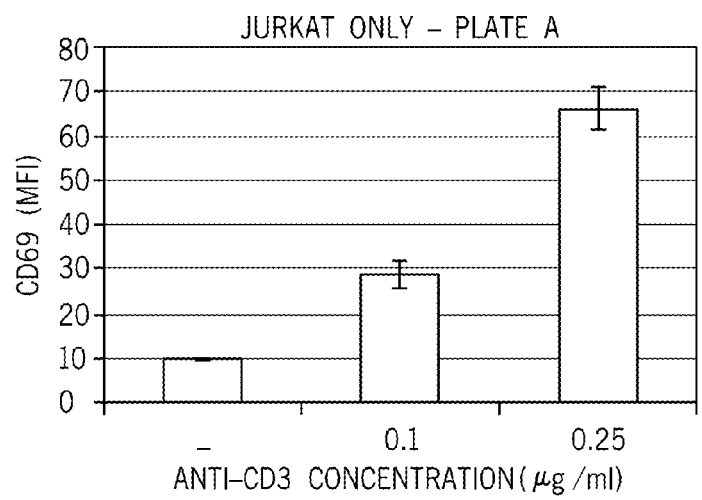
FIG. 12 demonstrates that C1ORF32 (SEQ ID NO: 1) expressed on HEK 293T cells inhibits Jurkat cells activated with anti CD3 and anti CD28. Jurkat cells activated by plate bound anti CD3 (0.1 or 0.25 µg/ml) (FIG. 12A) or plate bound anti CD3 (0.1 or 0.25 µg/ml) plus soluble anti CD28 (FIG. 12 B) were incubated O.N and analyzed for the expression of CD69 by flow cytometry.
Figure 12B:
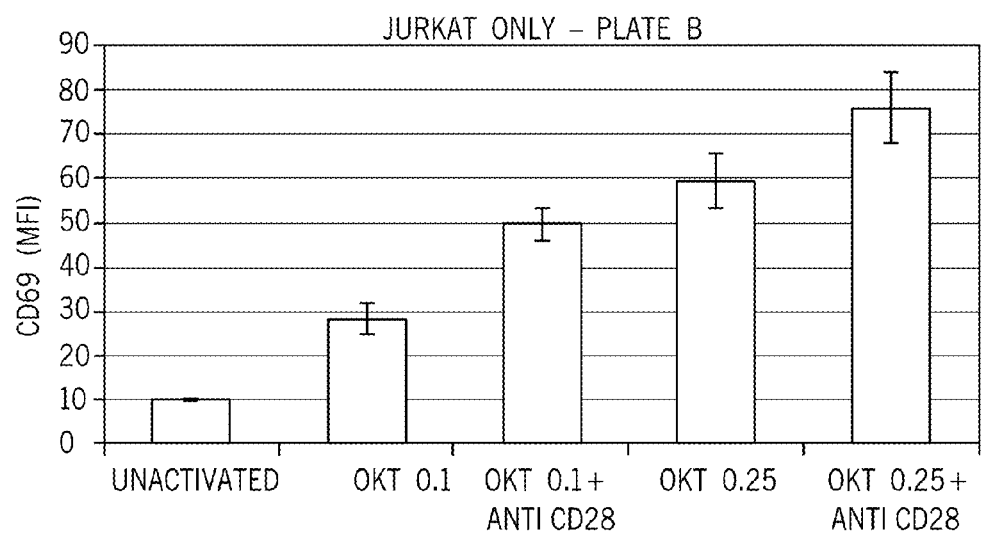
Figure 12C:
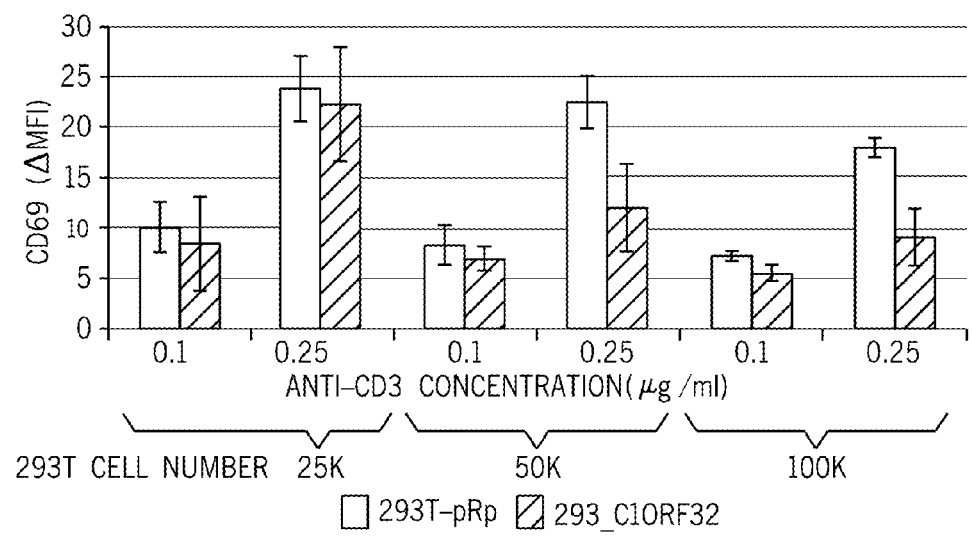
Figure 12D:
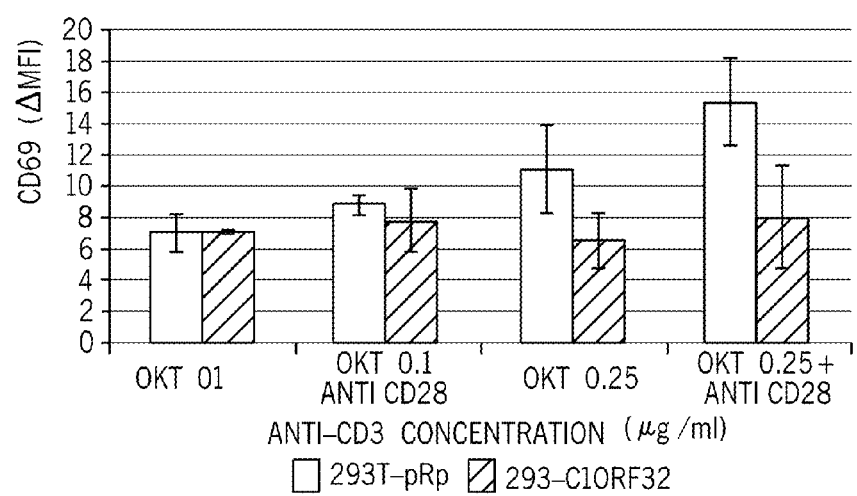
Figure 13A:
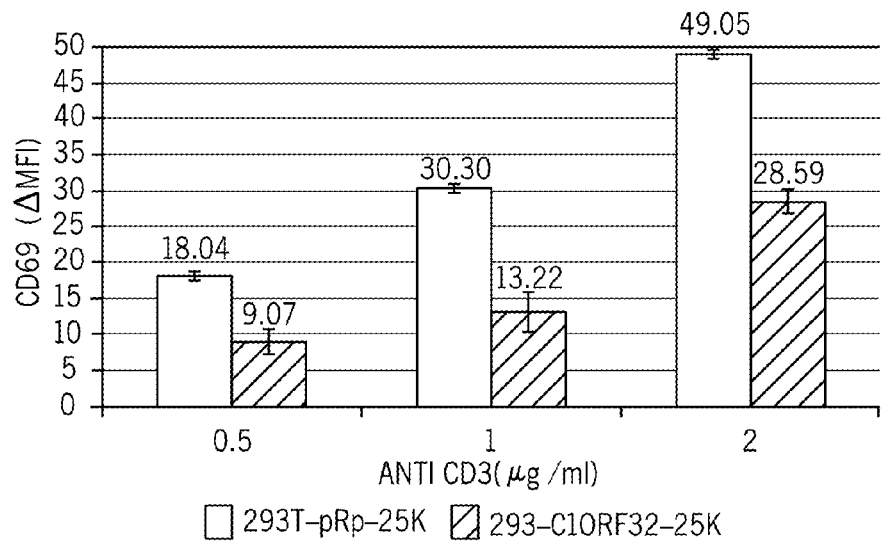
FIG. 13A or C present results of 25K HEK 293T cells expressing C1ORF32 (SEQ ID NO: 1) or the pRp vector incubated with 50K Jurkat cells for 7.5 hours or O.N., respectively.
Figure 13B:
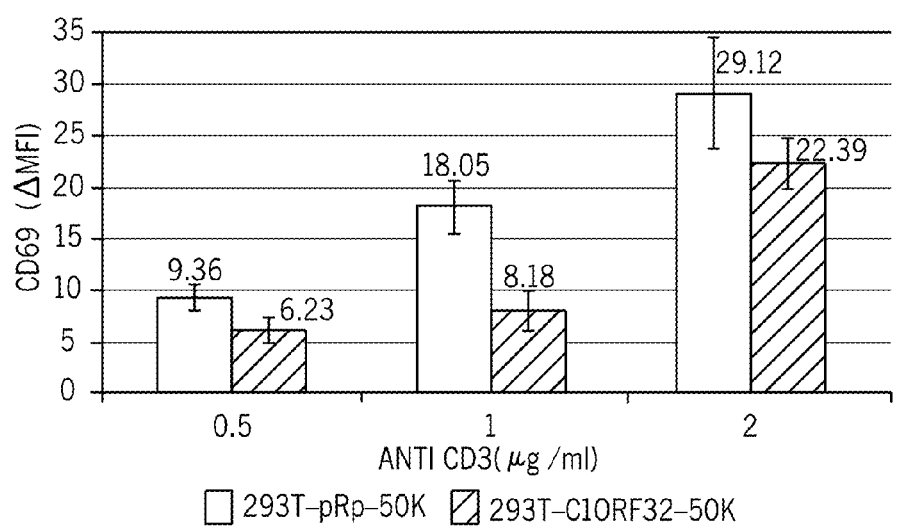
FIG. 13B or D present results of 50K HEK 293T cells expressing C1ORF32 (SEQ ID NO: 1) or the pRp vector incubated with 50K Jurkat cells for 7.5 hours or O.N., respectively. Cells were analyzed for the expression of CD69 by flow cytometry. ΔMFI values of CD69 are shown.
Figure 13C:
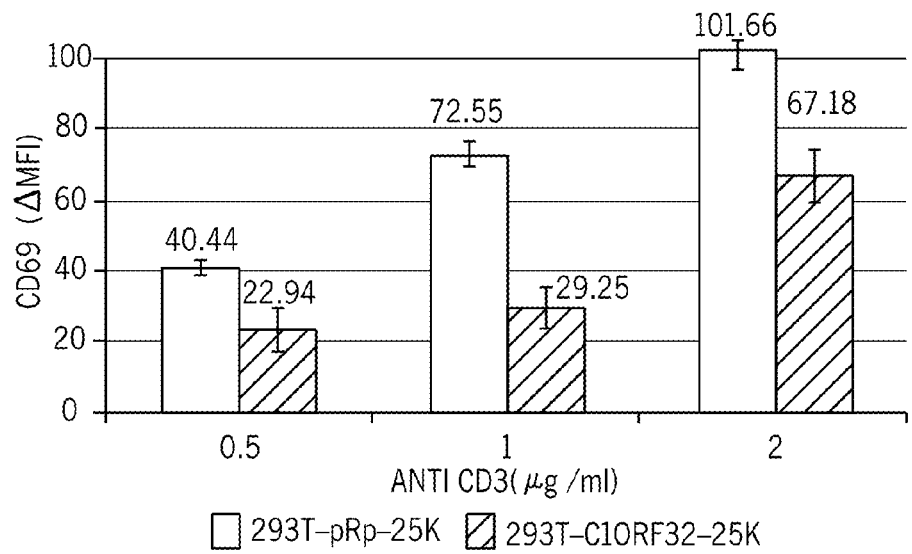
FIG. 13 demonstrates that C1ORF32 (SEQ ID NO: 1) expressed on HEK 293T cells inhibits Jurkat cells activation.
Figure 13D:
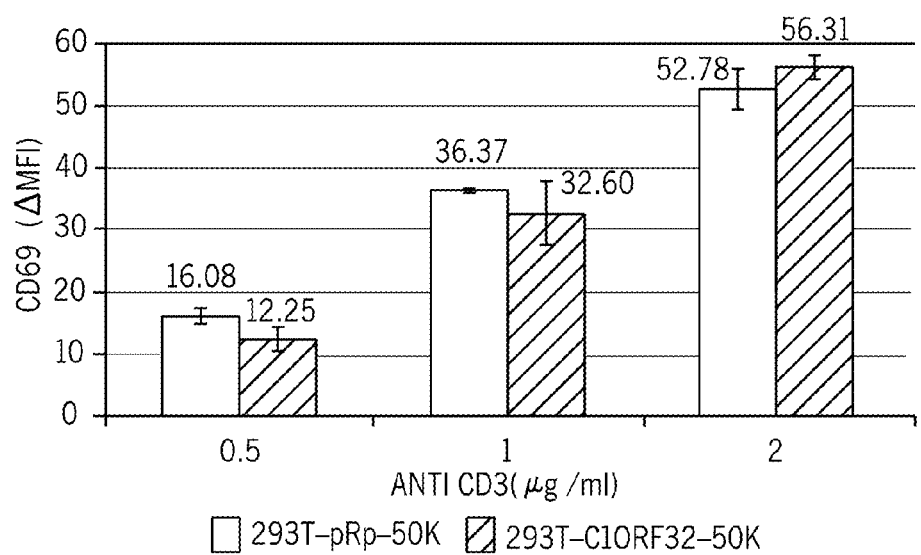

FIG. 11 shows that C1ORF32 (SEQ ID NO: 1) expressed on HEK 293T cells inhibits Jurkat cells activated with anti CD3-UCHT clone. 25K (FIG. 11A) or 50K (FIG. 11B) cells of HEK 293T cells expressing C1ORF32 (SEQ ID NO: 1) or the pRp vector were seeded in wells pre-coated with 2 or 4 µg/ml of anti-CD3 (UCHT1 clone). Jurkat cells (50K per well) were added 2 hours later and the cells were incubated O.N. Cells were analyzed for the expression of CD69 by flow cytometry. ΔMFI values of CD69 are shown in (FIG. 11C).

FIG. 12 shows that C1ORF32 (SEQ ID NO: 1) expressed on HEK 293T cells inhibits Jurkat cells activated with anti CD3 and anti CD28. Jurkat cells activated by plate bound anti CD3 (0.1 or 0.25 µg/ml) (FIG. 12A) or plate bound anti CD3 (0.1 or 0.25 µg/ml) plus soluble anti CD28 (FIG. 12B) were incubated O.N and analyzed for the expression of CD69 by flow cytometry. (FIG. 12C) HEK 293T cells expressing C1ORF32 (SEQ ID NO: 1) or the pRp vector were seeded at concentrations of 25, 50 or 100K per well, in wells coated with 0.1 or 0.25 of anti-CD3 (OKT clone). 50K Jurkat cells were added 2 hours later and the cells were incubated O.N. Jurkat cells were analyzed for the expression of CD69 by flow cytometry. ΔMFI values are shown. (FIG. 12D) HEK 293T cells expressing C1ORF32 (SEQ ID NO: 1) or the pRp vector were seeded at concentrations of 50K per well, in wells coated with 0.1 or 0.25 of anti-CD3 (OKT clone). 50K Jurkat cells were added 2 hours later with or without 2 µg/ml of soluble anti CD28, and the cells were incubated O.N. Jurkat cells were analyzed for the expression of CD69 by flow cytometry. ΔMFI values are shown.

FIG. 13 shows that C1ORF32 (SEQ ID NO: 1) expressed on HEK 293T cells inhibits Jurkat cells activation. 25K (FIGS. 13A, C) or 50K (FIGS. 13 B, D) of HEK 293T cells expressing C1ORF32 (SEQ ID NO: 1) or the pRp vector were seeded in wells coated with 0.5, 1 or 2 µg/ml of anti-CD3 (OKT clone). 50K Jurkat cells were added 2 hours later and the cells were co-incubated for 7.5 hours (FIGS. 13 A, B) or overnight (FIGS. 13 C, D). Cells were analyzed for the expression of CD69 by flow cytometry. ΔMFI values of CD69 are shown.

C1ORF32 (SEQ ID NO: 1) expressed on the membrane of HEK 293T cells inhibit T cell activation. The highest inhibitory effect was observed using a matrix of two concentrations of anti-CD3 (OKT clone, 0.25-1 µg/ml or UCHT1 clone, 2-4 µg/ml) and two concentrations of HEK 293T cells (25,000 or 50,000 cells per well) Inhibition of T cell activation was observed after over night incubation, and even after 7.5 hours of incubation. These results indicate that, similarly to the Fc fused form of the extracellular domain of the C1ORF32 protein, the native membrane protein expressed on the cell surface also has functional inhibitory activity and thus may serve as a target for therapeutic antagonistic monoclonal Abs suitable for anti-cancer therapy. These results are in agreement with other findings, indicating that ectopic expression of membrane C1ORF32 protein in "T cell stimulator" BW-5147 cells inhibits human T cell proliferation, as described below herein.

Example 10

C1ORF32 Expressed on HEK-293 Cells Membrane Suppresses Mouse CD4 T Cells

In order to confirm the inhibitory activity of the C1ORF32 protein on mouse I cells, the C1ORF32 protein (SEQ ID NO: 1) was ectopically expressed on HEK-293 cells, as described in in Example 3 herein. Expression vector coding for human C1ORF32 (SEQ ID NO: 1) or empty vector were used. Cell membrane expression of C1ORF32 in the transfectants was validated by FACS analysis using specific anti-C1ORF32 polyclonal Ab (data not shown). An inhibitory effect of C1ORF32 expressed on HEK-293 was evident using CFSE labeled mouse CD4+ T cells activated with plate bound anti-CD3 (FIG. 15). As shown in FIG. 15, the inhibitory effect was higher when there were more HEK-293 cells per given number of T cells (i.e. 1:2 vs. 1:4 HEK-293: CD4).

Figure 15A:
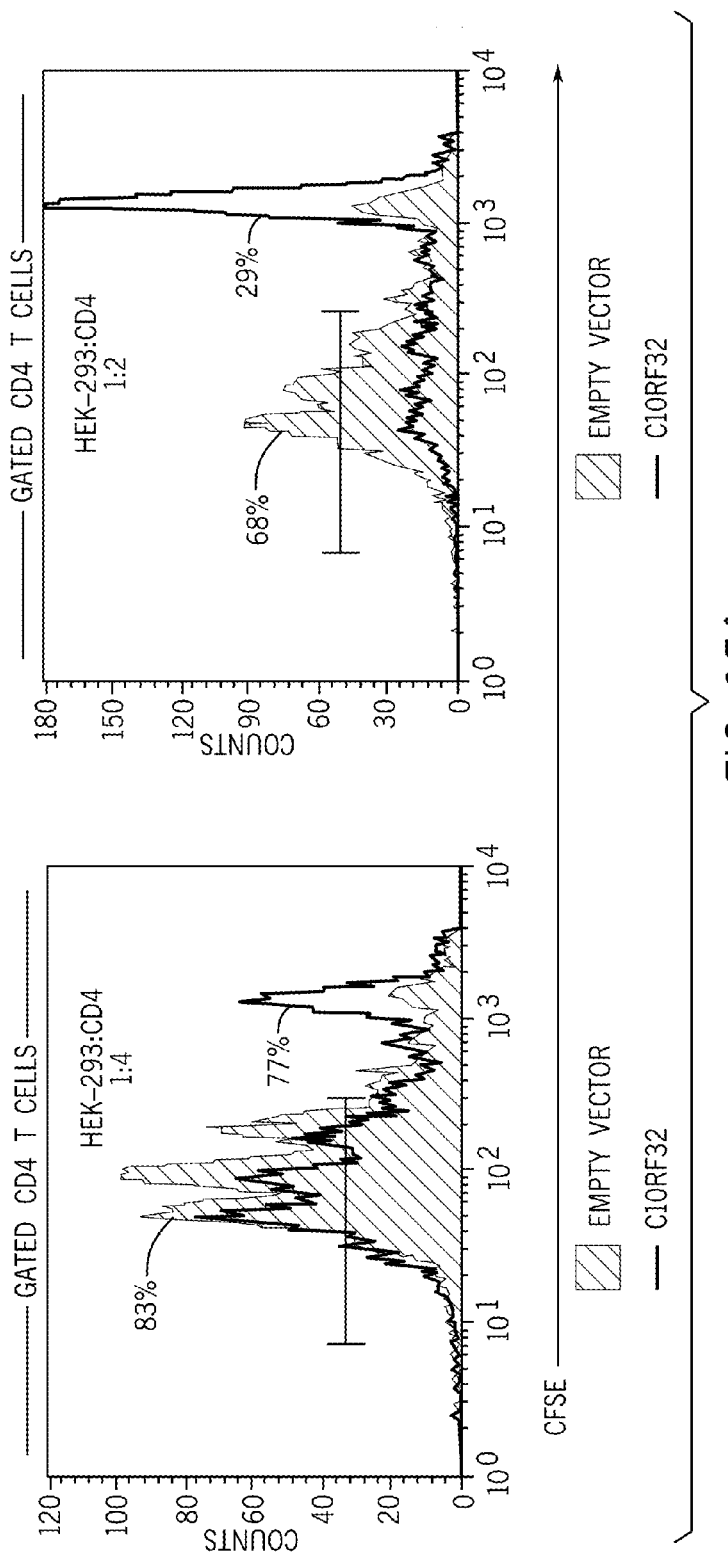
FIG. 15A presents flow cytometry results of mouse CD4+CD25− T cells (1×10$^5$), labeled with CFSE and stimulated with plate-bound anti-CD3 (0.5 µg/ml) in the presence of HEK-293 transfectants expressing C1ORF32T (blue) or empty vector (gray) at 1:4 or 1:2 HEK-293:CD4 ratio. Percentages refer to fraction of cells that have divided more than twice.
Figure 15B:
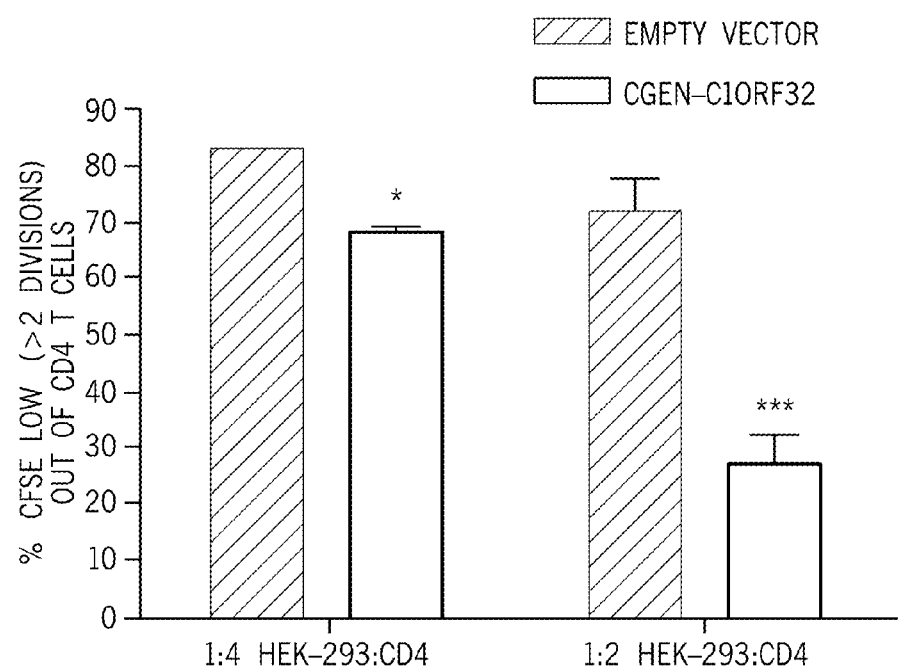
FIG. 15B presents histograms indicating the percentage (mean±SD) of cells that have divided more than twice (*P value<0.05, P value<0.001, student's T test).

FIG. 15 shows that ectopic expression of C1ORF32 (SEQ ID NO: 1) suppresses mouse CD4 T cell divisions upon TCR stimulation. FIG. 15A presents results of Mouse CD4+ CD25− T cells ($1\times10^5$) that were labeled with CFSE and stimulated with plate-bound anti-CD3 (0.5 µg/ml) in the presence of HEK-293 transfectants expressing C1ORF32 or empty vector at 1:4 or 1:2 HEK-293:CD4 ratio. On day 4, cells were harvested, and analyzed by flow cytometry. Percentages refer to fraction of cells that have divided more than twice. FIG. 15B presents histograms indicating the percentage (mean±SD) of cells that have divided more than twice (*P value<0.05, P value<0.001, student's T test).

Example 11

The Functional Role of C1ORF32 in Human T Cell Responses

The aim of this study was to evaluate the functional role of C1ORF32 during the activation of human T cells using T cell stimulator cells expressing C1ORF32. Generation and characterization of expression constructs encoding C1ORF32 cDNAs (Codon-optimized for expression in murine cells, SEQ ID NO: 31 and SEQ ID NO: 32) of the C1ORF32 proteins (SEQ ID NO: 17 and SEQ ID NO: 1, respectively) were gene-synthesized and directionally cloned into retroviral vectors via Sfi-I sites.

Figure 16:
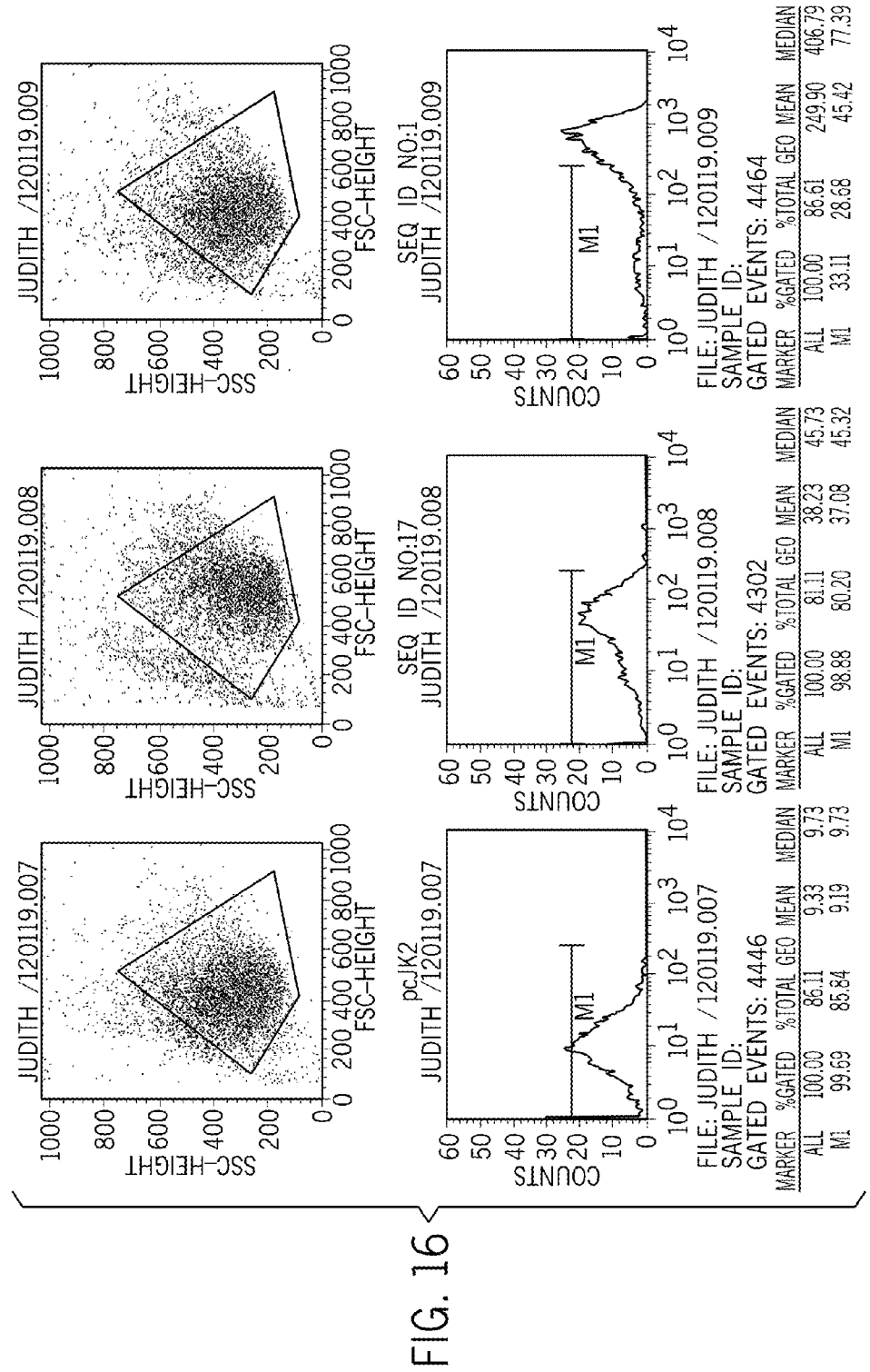
FIG. 16 presents FACS analysis performed on stimulator cells expressing empty vector, SEQ ID NO: 17 and SEQ ID NO: 1 using a specific polyclonal antibody (rb-anti-7531) that recognizes the extracellular domain of C1ORF32 proteins (SEQ ID NOs: 1 and 17), in order to assess the levels of membrane expression of these proteins.

Bicistronic and monocistronic expression constructs encoding full length C1ORF32 proteins SEQ ID NO: 17 and SEQ ID NO: 1 were generated in pMIGII and pCJK2 vectors, respectively. The constructs were validated by agarose gel electrophoresis and were expressed in Bw5147 cells displaying high levels of membrane bound anti-CD3 antibody (Bw-3/2) ("mb-anti-CD3 high stimulator cells" (Leitner, J., W. Et al., 2010. *J. Immunol. Methods.* 362: 131-141.)). For control purposes, Bw5147 cells were transduced with an "empty" vector, pCJK2, for monocistronic expression, or pMIGII, for bistronic expression. In addition, Bw-3/2 cells expressing activating costimulatory molecules (ICOSL and CD70), Bw-3/2-cells expressing B7-H3 driven from a monocistronic pBMN-B7-H3="B7-H3" and a bi-cistronic vector pMIGII-B7-H3, and B7-H1 (PD-L1) were generated as negative costimulatory/coinhibitory molecules. Experiments with ICOSL, CD70 or B7-H3 expressing stimulator cells have been described previously (Pfistershammer, K., C. Et al., 2006. *Eur. J. Immunol.* 36: 1104-1113; Kober, J., et al., 2008. *Eur. J. Immunol.* 38: 2678-2688; Leitner, J., W. Et al. 2010. *J. Immunol. Methods.* 362: 131-141.) The presence and expression of the bi-cistronic constructs was confirmed by FACS-analysis for GFP. Homogenously high expression of the stimulating membrane-bound anti-CD3 antibody was confirmed by FACS using a DyLight-649 anti-mouse IgG (H+L) antibody that reacts with the murine single chain antibody expressed on the stimulator cells. From previous experiments with other molecules (e.g. B7-H3) a much higher surface expression can be expected with monocistronic retroviral expression. High transcription level of expression of the monocistronic constructs in the respective stimulator cells was confirmed by qRT-PCR using primer-pairs SEQ ID NOs: 35-36 and 35-37, generated with the primer3 program. The expression of SEQ ID NO: 17 and SEQ ID NO: 1, which have an identical extracellular domain, was examined using a specific polyclonal Ab. FACS analysis using this pAb showed very weak membrane expression in cells bearing SEQ ID NO: 17, while SEQ ID NO: 1 showed a robust expression (FIG. 16).

T Cells

The use of human blood from volunteer donors for the experiments carried out within this project was approved by the ethics committee of the Medical University of Vienna (EK Nr.: 865/2011). T cells were purified from buffy coats or heparinised blood derived from healthy volunteer donors and the mononuclear fraction was obtained by standard density centrifugation using Ficoll-Paque (GE-Healthcare). Bulk human T cells were obtained through MACS-depletion of CD11b, CD14, CD16, CD19, CD33 and MHC-class II-bearing cells with the respective biotinylated mAb in conjunction with paramagnetic streptavidin beads (Leitner, J., et al., 2009. *Eur. J. Immunol.* 39: 1754-1764.) Purified CD8 T cells and CD4 T cells were obtained by addition of biotinylated CD4 and CD8 mAb to the pools. Naïve CD4 T cells were isolated using the Naïve CD4+ T cell Isolation Kit II from Miltenyi Biotec. Following isolation, cells were analyzed for purify by FACS analysis, and samples with sufficient purity (>90%) were used for the experiments.

T Cell Stimulation Experiments with Stimulator Cells Expressing C1ORF32 Molecules and Control Stimulator Cells A series of T cell activation experiments with the stimulator cells expressing C1ORF32 molecules and control stimulator cells were performed under standard conditions as described (Leitner, J., et al., 2010. *J. Immunol. Methods.* 362: 131-141.) RPMI 1640 medium (Invitrogen) supplemented with 10% FBS (Sigma), antibiotics and anti-mycotics (PenStrep and Amphotericin, respectively) was used for culturing Bw cells and also for the functional experiments. Briefly, the stimulator cells were harvested, counted, irradiated (2×3000 rad) and seeded in flat-bottom 96-well plates (20.000 cells/well). Liquid nitrogen stored MACS-purified T cells were thawed, counted and added to the wells (100.000 cells/well); total volume was 200 Triplicate wells were set up for each condition. Following 48 hours of co-culture, supernatant (SN) was harvested (50 µl/well) pooled from triplicate wells and frozen for cytokine-analysis. Luminex-based multiplex cytokine-analysis was performed using antibody pairs to IFN-γ, IL-2, IL-10, IL-13 in conjunction with purified recombinant cytokines to establish a standard curve. In some experiments IL-17 or IL-4 were also measured, but since the concentration of these cytokines was generally very low these measurements were omitted for most samples. Triplicate measurements were done and the results are depicted as mean+/−SEM. After removal of 50 µl of SN at 48 hrs, as described, Methyl-$^3$H-thymidine (50 µl/well of a 1:80 dilution in culture medium; final concentration: 0.025 mCi; PerkinElmer/New England Nuclear Corporation, Wellesley, Mass.) was added to the wells as described. Following additional 18 hours of culture, the plates were harvested on filter-plates and incorporation of $^3$H-Thymidine was determined in a B-counter. In addition a series of similar experiments using MACS-purified T cell subsets (CD4 T cells, CD45RA-positive CD4 T cells as well as CD8 T cells) were performed.

Additional controls in all experiments included wells with stimulator cells alone (data not shown). This was done to assess the cells microscopically and also to determine $^3$H-Thymidine incorporation of the stimulator cell w/o T cells. Data from experiments in which quick disintegration of stimulator cells was observed following irradiation were excluded from the analysis. This phenomenon occurred occasionally after irradiation; and its cause is currently unknown. In addition, unstimulated and PMA/Ionomycin stimulated T cells were also analyzed for $^3$H Thymidine incorporation.

Furthermore, standard CFSE-dilution experiments were performed: T-cells were CFSE-labelled and 100.000 T cells were co-cultured with irradiated stimulator cells (20.000 cells per well). Following 7 days of co-culture, FACS analysis was performed—cells were stained with anti-CD8-APC and CFSE-dilution was assessed by electronically gating on CD8 and CD4 (CD8-negative) T cells.

Stimulator cell-based experiments to assess potential regulation of activation markers (CD25 and CD69) by C1ORF32 proteins were also performed. However, in these experiments, a very weak induction of these molecules was observed, which was not regulated by C1ORF32– proteins (data not shown).

Statistical comparison was done in a way that only experiments where results from the C1ORF32-proteins and the control group were available were included in the analysis. T-test was used for statistical analysis (adjustment for multiple comparisons was not performed) to evaluate the proliferation of T cells in co-cultures with stimulator cells expressing C1ORF32-proteins or CD70, ICOSL and B7-H3 vs. control stimulator cells (pCJK2). All experiments were performed in triplicates.

Results:

T Cell Stimulator Experiments with Bulk T Cells

Figure 17:
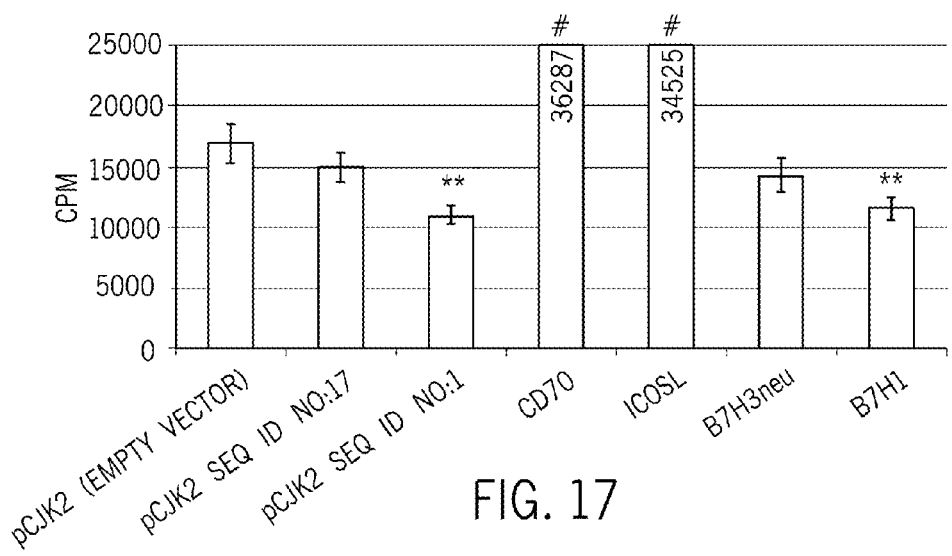
FIG. 17 presents the results of Bulk T cell proliferation in response to stimulator cells expressing SEQ ID NO:1 or SEQ ID NO:17 C1ORF32 molecules, empty vector, known costimulatory, or known coinhibitory molecules as controls. Shown is the mean+/−SEM of 6 experiments. **p<0.01, and #p<0.0001 (Student's T-test) represent significantly different results compared to empty vector.

Statistical analysis of 6 independent experiments measuring proliferation of bulk T cells stimulated with control or C1ORF32 (SEQ ID NO:17 or SEQ ID NO:1) expressing stimulator cells showed significantly lower proliferation (35% inhibition) in the SEQ ID NO:1 expressing cells compared to the pCJK2 control stimulator cells. This effect was comparable to that of B7-H1 (32%) (FIG. 17). The proliferation induced by stimulator cells expressing SEQ ID NO: 17 was reduced to a lesser extent (12% inhibition), but did not reach statistical significance, although it should be noted that SEQ ID NO:17 has an identical extracellular domain as SEQ ID NO:1. This finding may be a result of its much lower expression, as assessed by FACS analysis, using a specific antibody that recognizes the common extracellular domain (FIG. 16). As expected, stimulator cells expressing the costimulatory molecules CD70 and ICOSL induced significant higher T cell proliferation than control stimulator cells. The proliferation induced by B7-H3 expressing stimulator cells was somewhat lower than the one obtained with control stimulator cells 15%, but this did not reach statistical significance.

T Cell Stimulator Experiments with CD4 T Cells

Three independent experiments with CD4 T cells were performed. The proliferation induced by stimulator cells expressing CD70 or ICOSL was significantly higher compared to the control stimulator cells. The stimulator cells expressing B7-H3 significantly inhibited the proliferation (53%, p<0.05), however, only a mild reduction (~20%) was observed for cells expressing B7-H1, which did not reach statistical significance. The proliferation induced by stimulator cells expressing SEQ ID NO:17 or SEQ ID NO:1 was not affected. The results are shown in FIG. 18.

Figure 18:
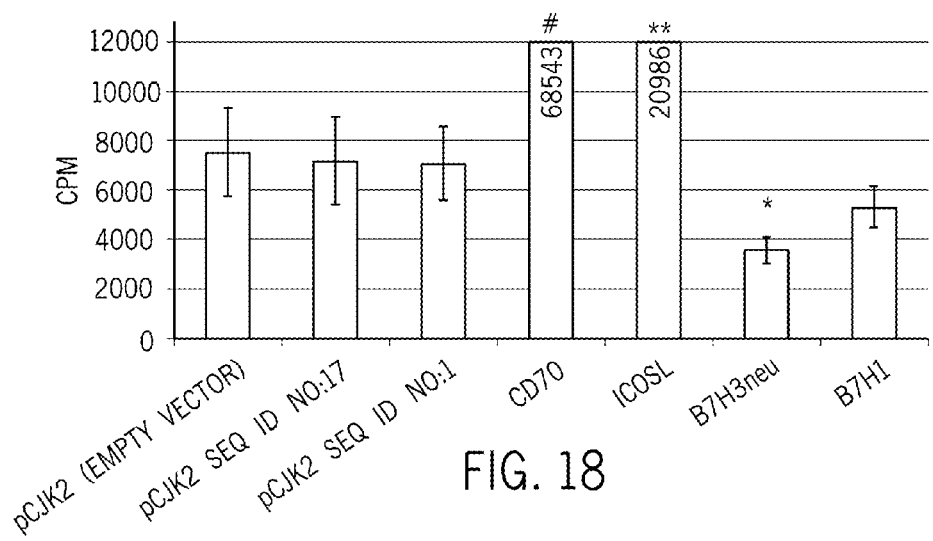
FIG. 18 presents the results of T cell (CD4+) proliferation in response to stimulator cells expressing empty vector or vector expressing the different C1ORF32 molecules, costimulatory, or coinhibitory molecules. Shown is the mean+/−SEM of 3 experiments.*P<0.05, **p<0.01, and #p<0.0001 (Students T-test) represent significantly different results compared to empty vector.

FIG. 18 presents the results of T cell (CD4+) proliferation in response to stimulator cells expressing empty vector or vector expressing the different C1ORF32 molecules, costimulatory, or coinhibitory molecules. Shown is the mean+/−SEM of 3 experiments.*P<0.05, **p<0.01, and #p<0.0001 (Students T-test) represent significantly different results compared to empty vector.

T Cell Stimulator Experiments with CD8 T Cells

Figure 19:
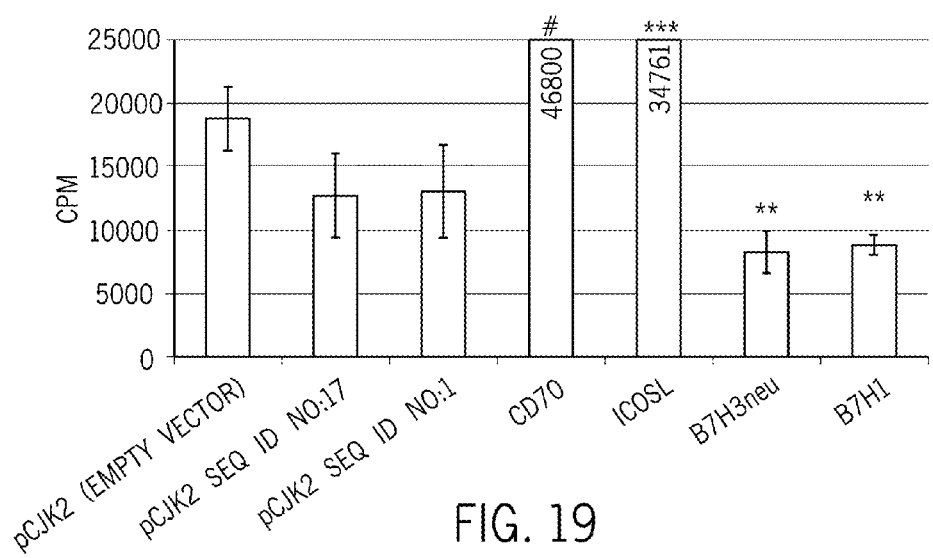
FIG. 19 presents results of T cell (CD8+) proliferation in response to stimulator cells expressing empty vector or vector expressing the different C1ORF32 molecules, costimulatory, or coinhibitory molecules. Shown is the mean+/−SEM of 3 experiments. p<0.01, *p<0.001, and #p<0.0001 (Students T-test) represent significantly different results compared to empty vector.

Three independent experiments with CD8 T cells were performed. Stimulator cells expressing C1ORF32 proteins induced lower proliferation of CD8 T cells as compared to control stimulator cells (31-32% inhibition; FIG. 19), however, this effect did not reach statistical significance. The proliferation induced by stimulator cells expressing CD70 or ICOSL was significantly higher, whereas the proliferation obtained with B7-H3 and B7-H1 expressing stimulator cells was significantly lower compared to the control stimulator cells (53-56%).

FIG. 19 presents results of T cell (CD8+) proliferation in response to stimulator cells expressing empty vector or vector expressing the different C1ORF32 proteins, costimulatory, or coinhibitory molecules. Shown is the mean+/−SEM of 3 experiments. p<0.01, *p<0.001, and #p<0.0001 (Students T-test) represent significantly different results compared to empty vector.

T Cell Stimulator Experiments with Naïve CD4 T Cells

Figure 20:
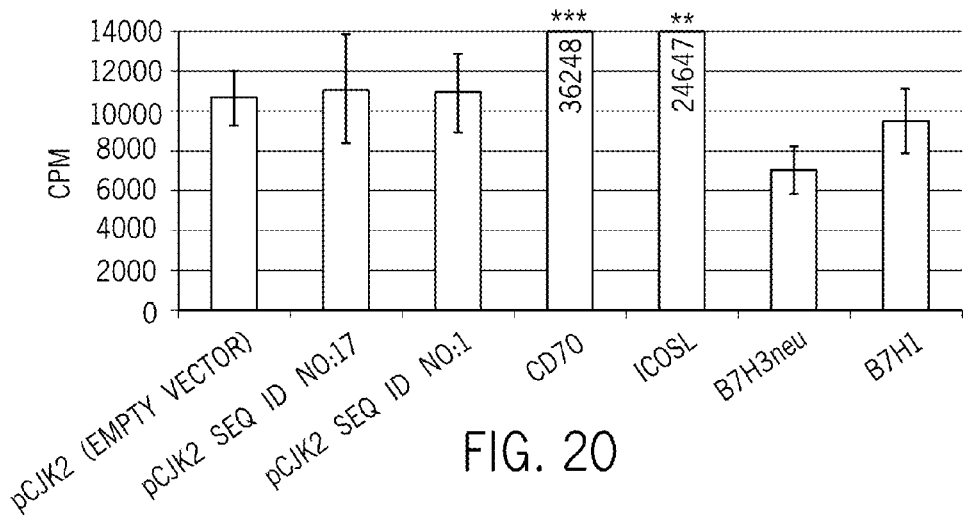
FIG. 20 presents results of T cell (Naïve CD4+ CD45RA+) proliferation in response to stimulator cells expressing empty vector or vector expressing the different C1ORF32 molecules, costimulatory, or coinhibitory molecules. p<0.01, and *p<0.001 (Students T-test) represent significantly different results compared to empty vector.
Figure 21A:
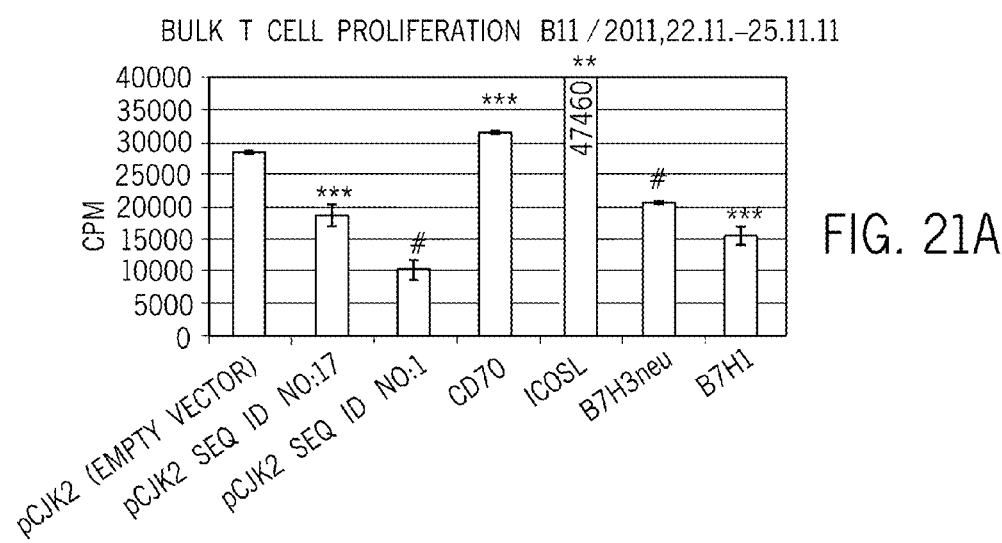
FIG. 21 presents the results of T cell (Bulk) proliferation (A) and cytokine secretion (B-G) in response to stimulator cells expressing the different C1ORF32 molecules, or costimulatory, coinhibitory molecules, or empty vector as controls. Cytokine data represent triplicate measurements from SN pooled from the triplicate wells. *p<0.05, p<0.01, *p<0.001, and #p<0.0001 (Student's T-test) represent significantly different results compared to empty vector.
Figure 21B:
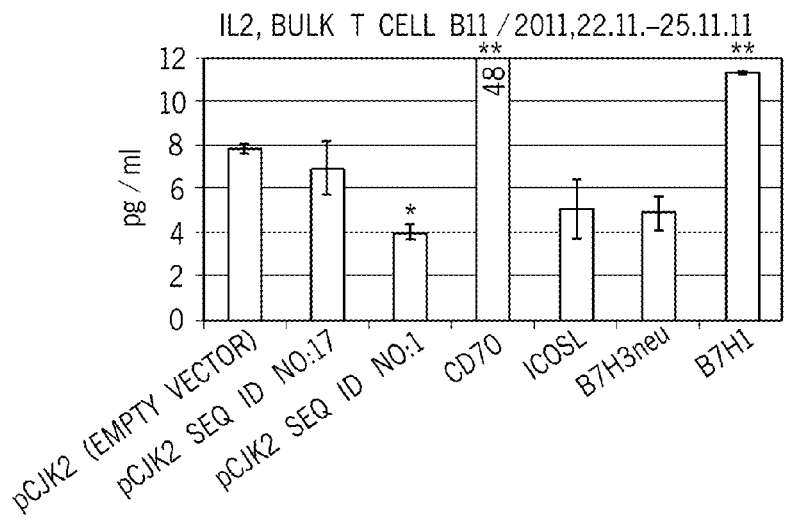
Figure 21C:
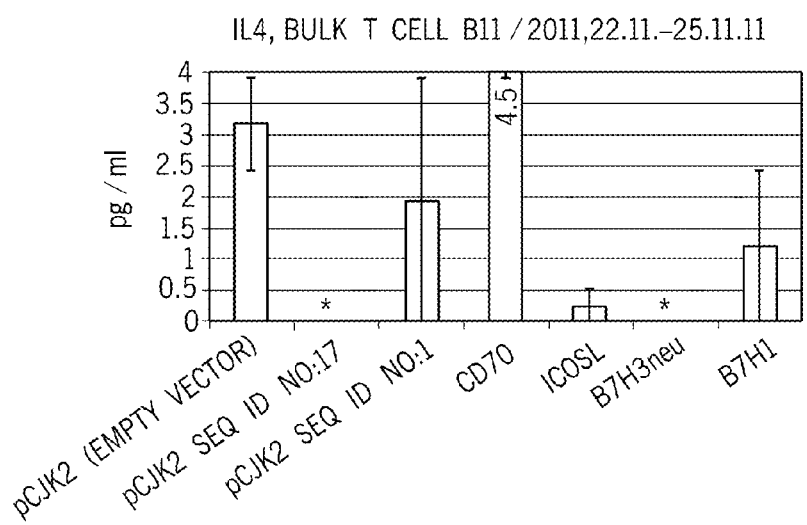
Figure 21D:
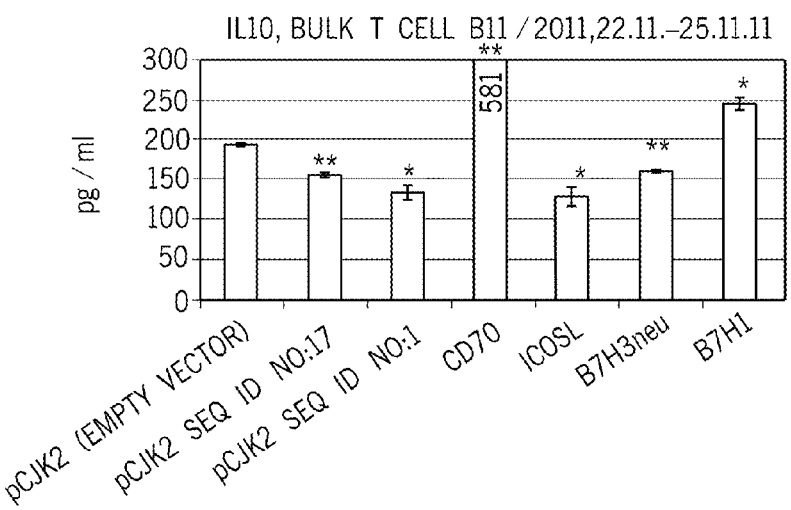

Three independent experiments with naïve CD4 T cells were performed. The proliferation induced by stimulator cells expressing SEQ ID NO:17 or SEQ ID NO:1 was not different from the proliferative response induced by control stimulator cells (pCJK2; FIG. 20). The proliferation induced by B7-H3 and B7-H1 expressing stimulator cells was lower compared to the control stimulator cells, but the difference did not reach statistical significance. The proliferation induced by stimulator cells expressing CD70 or ICOSL was significantly higher.

FIG. 20 presents results of T cell (Naïve CD4+ CD45RA+) proliferation in response to stimulator cells expressing empty vector or vector expressing the different C1ORF32 molecules, costimulatory, or coinhibitory molecules. p<0.01, and *p<0.001 (Students T-test) represent significantly different results compared to empty vector.

CFSE-Labeling Experiments

Two CFSE-labeling experiments were performed, one with bulk T cells and one with naïve CD4 T cells. In both experiments, the CFSE-dilution induced by C1ORF32-expressing stimulator cells or cells expressing B7-H3 and B7-H1 was comparable to the one obtained with the control stimulator cells. With the notable exception of CD70 expressing stimulator T cells all stimulator cells induced little proliferative response (data not shown).

Cytokines

The concentration of cytokines (IL-2, IL-4, IL-10, IL-13, IL-17 and IFN-γ) was determined in the co-culture SNs of bulk, CD4+, CD8+, and naïve T cells from most experiments. Results in FIGS. 21A-G show effect of SEQ ID NO:17 and SEQ ID NO:1 on proliferation and cytokine secretion from a representative experiment with bulk T cells. Generally it was observed that with co-inhibitory molecules the inhibition of cytokine production is a function of inhibition of T cell proliferation. The concentration of some of the cytokines (IL-2, IL-13 and especially IL-4) was in the lower pg range, which is regarded as extremely low.

FIG. 21 presents the results of T cell (Bulk) proliferation (A) and cytokine secretion (B-G) in response to stimulator cells expressing the different C1ORF32 proteins, or costimulatory, coinhibitory molecules, or empty vector as controls. Cytokine data represent triplicate measurements from SN pooled from the triplicate wells. *p<0.05, p<0.01, *p<0.001, and #p<0.0001 (Student's T-test) represent significantly different results compared to empty vector.

The results obtained in experiments with the stimulator cells expressing C1ORF32 molecules indicate that they are able to inhibit human T cell responses when present during their activation. Results obtained with stimulator cells expressing SEQ ID NO:1 demonstrate lower proliferation of human T cells compared to T cells stimulated with control stimulator cells (summarized in Table 3). The extent of this effect was similar to that exerted by one or both of the positive controls, B7-H3 and B7-H1. As mentioned above, SEQ ID NO:17 was only weakly expressed, which may explain its poor inhibitory activity.

The proliferation induced by stimulator cells expressing C1ORF32 molecules was examined using bulk T cells, purified CD8 T cells, CD4 T cells or naïve CD4 T cells. The effects were most prominent in CD8 T cells, while the effect on the other cell types was weaker in most cases (Table 3) Inhibition of cytokine secretion was usually in line with the inhibition of T cell proliferation. Taken together, these results suggest an inhibitory effect of the C1ORF32 proteins during activation of human T cells.

Table 3 presents Summary of the inhibitory effects of C1ORF32-proteins and coinhibitory controls expressed on stimulator cells on the activation (as assessed by proliferation) of different subtypes of T cells. Shown is % inhibition compared to stimulator cells expressing empty vector. * represent statistically significant results.

TABLE 3

| Protein name | Bulk T cells | CD4 | CD8 | CD45RA (naïve) |
|---|---|---|---|---|
| C1ORF32 SEQ ID NO: 17 | 12% | — | 32% | — |
| C1ORF32 SEQ ID NO: 1 | 35%* | — | 31% | — |
| B7-H3 | 15% | 53%* | 56%* | 34% |
| B7-H1 | 32%* | 30% | 53%* | 11% |

In addition to the above examples, demonstrating that the the membrane bound form of C1ORF32 generates a negative signal for T cell activation, Examples 5 and 8 in WO/2012/001647, owned in common with the present application, which is hereby incorporated by reference, as if fully set forth herein, demonstrate in various experimental systems that a fusion protein of the C1ORF32 ECD fused to mouse IgG2A Fc domain, has an inhibitory effect on the activation of T cells. In all experimental systems, the presence of C1ORF32-ECD-Fc caused a reduction in T cell activation in comparison to isotype matched antibody serving as a negative control. This was observed by reduction in T cell proliferation as well as inhibition of cytokine secretion. Thus, without wishing to be limited by a single hypothesis, a neutralizing antibody specific for C1ORF32 would be expected to abrogate the inhibitory activity of such receptor and by that, would be expected to enhance tumor immune surveillance.

Example 12

Effect of C1ORF32 on Cytotoxic T Lymphocyte (CTL) Functional Activity

The effect of ectopically expressed C1ORF32 (SEQ ID NO: 1) on the functional activity of human Cytotoxic T Lymphocytes (CTLs) was tested in an experimental system in which C1ORF32 (SEQ ID NO: 1) was over expressed on human cancer cells as target cells (SK-MEL-23, mel624.38 and mel526 described previously (Topalian, S. L., et al. 1989, J. Immunol. 142: 3714-3725; Houghton, A. N., et al., 1987. J. Exp. Med. 165: 812-829)), which were then co-cultured with primed human CD8+ T cells (CTLs) over expressing a Tumor Associated Antigen (TAA) specific and HLA-A2 restricted T cell receptor (TCR). Readouts to be tested include activation dependent cytokine secretion, expression of activation markers and killing activity.

Expression of C1ORF32 (SEQ ID NO: 1) in melanoma cell lines: In order to express the C1ORF32 (SEQ ID NO: 1) in target cells, the cDNA encoding this protein was amplified using specific primers (SEQ ID NOs: 33 and 34), digested with the enzymes PciI and NotI and cloned into an MSCV-based retroviral vector (pMSGV1) (Cary Hsu., et al., J Immunol. 2005 Dec. 1; 175(11): 7226-7234).

Verification of the cloning was done first using restriction enzyme and subsequently by sequencing. Upon sequence confirmation, large amounts of the retroviral vector (Maxi-prep) were produced for subsequent use.

Three human melanoma cell lines (SK-MEL-23, mel624.38 and mel526) were transduced with retroviral constructs encoding C1ORF32 (SEQ ID NO: 1) using a retronectin-based protocol; briefly, retroviral supernatant was produced in 293GP cells (a retroviral packaging cell line) following transfection with the retroviral vector and an amphotropic envelop gene (VSV-G). The retroviral supernatant was plated on retronectin-coated plates prior to the transduction to enable the binding of virions to the plate. Then, the melanoma cells were added to the plate for 6 hours. After that, the cells were replenished in a new culture vessel. Transduction efficiency and expression of the protein was determined by staining the transduced tumor cells with a C1ORF32-specific antibody (5159-1, described herein) and analyzed by flow cytometry.

Transduction of Effector Cells:

To perform functional assays with human CTLs, primary human lymphocytes which were engineered to express the F4 TCR which is a MART-1-specific HLA-A2+ restricted TCR, that recognizes HLA-A2+/MART1+ melanoma cells was used. This TCR was recently used in clinical trials in terminally-ill melanoma patients to specifically confer tumor recognition by autologous lymphocytes from peripheral blood by using a retrovirus encoding the TCR (Morgan et al, 2006 Science, 314:126-129). Freshly isolated PBLs (peripheral blood leukocytes) that were stimulated with PHA 5-10 days were transfected with in vitro-transcribed mRNA for both α and β chains from the MART-126-35-specific TCR termed F4 by electroporation. Briefly, electroporation was performed at 400V/500 us using an ElectroSquare Porator. The amount of in vitro-transcribed mRNA for each chain was 1 ug per 106 cells. The transfected lymphocytes were subsequently transferred to a new culture vessel and cultured in lymphocyte medium containing 300 IU of IL-2, replenished every 2-3 days.

Cytokine Secretion Mediated by Candidate-Transduced Cells:

A co-culture of melanoma cells expressing C1ORF32 (SEQ ID NO: 1) with F4-TCR transduced T-cells was set up. Cytokine secretion (IFN-γ and IL-2) was measured by ELISA to assess the specific recognition and response of the effector CD8 T cells to the different transduced tumor cell lines. For these assays, $10^5$ effectors were co-cultured with $10^5$ melanoma target cells for 16 hours. Cytokine secretion was measured in culture supernatants diluted to be in the linear range of the ELISA assay.

Figure 22:
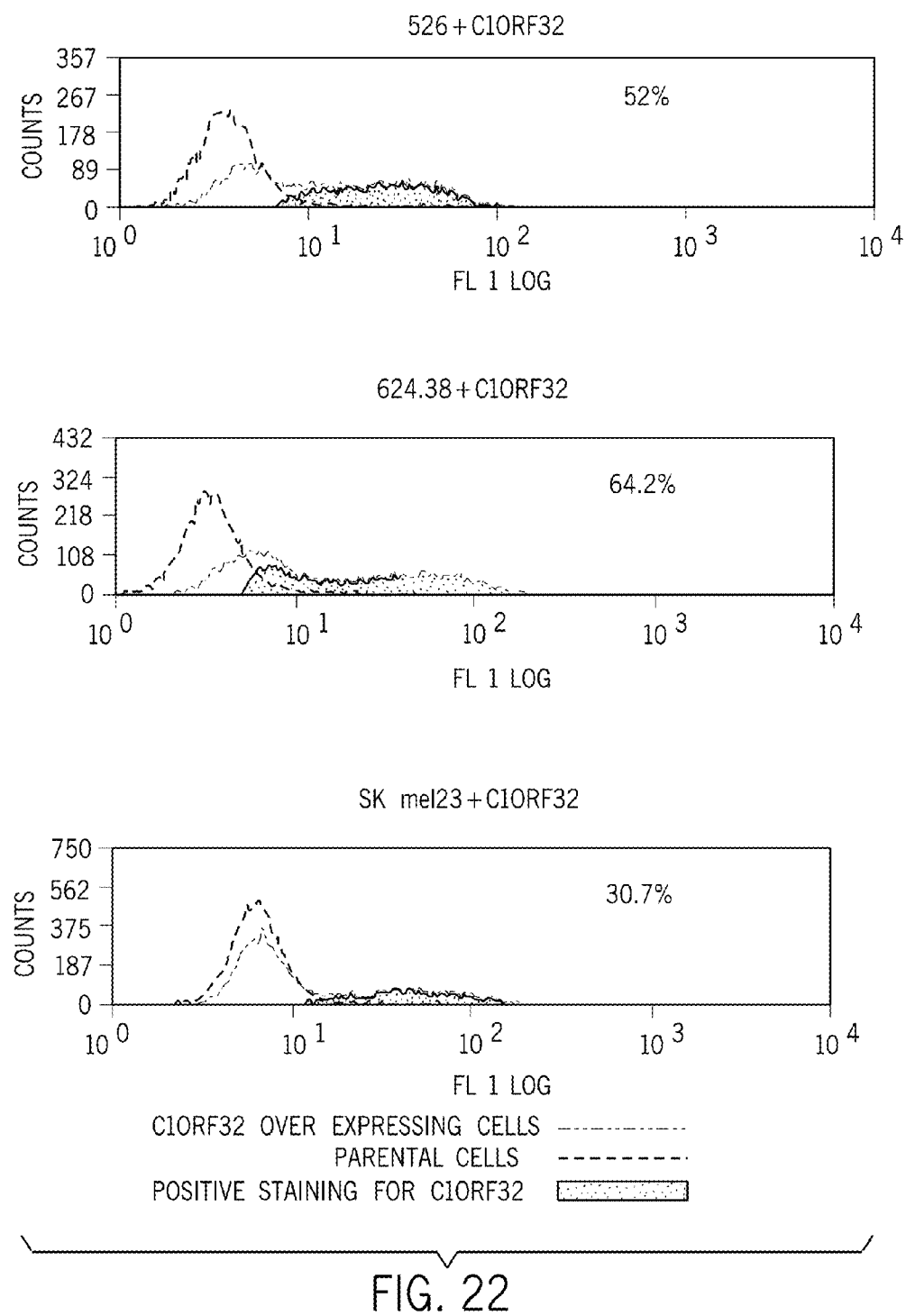
FIG. 22 presents FACS analysis performed on C1ORF32 transduced melanoma cells (mel526, mel624.38 and SK-mel23) using a specific monoclonal antibody (5159-1) that recognizes the extracellular domain of C1ORF32, in order to assess the levels of membrane expression of these proteins.

Human melanoma cell lines (SK-MEL-23, mel624.38 and mel526) were first stained for the expression of the C1ORF32 protein using C1ORF32-specific monoclonal antibody 5159-1. C1ORF32 was not detected on the surface of parental (non-transduced cells) as assayed by flow cytometry (data not shown). These cell lines were then transduced with a retroviral vector encoding the C1ORF32 protein SEQ ID NO:1, as described herein. 48 hrs following transduction, the levels of C1ORF32 expression were assessed by flow cytometry and compared to those of the parental cell line. The levels of protein expression ranged between 30-60% above the background for the different cell lines tested (FIG. 22).

Figure 23:
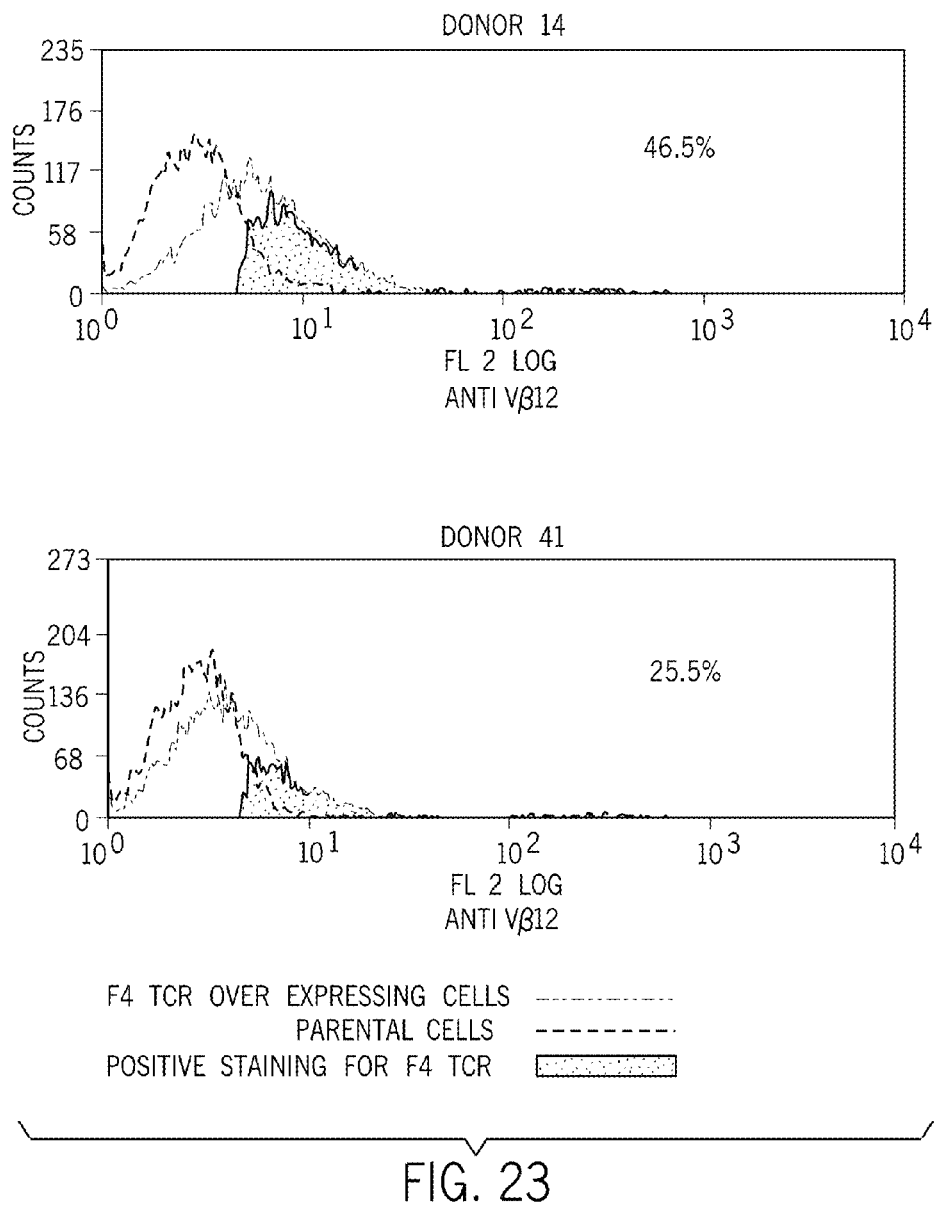
FIG. 23 presents FACS analysis performed on TCR F4 transduced stimulated CD8+ cells (CTLs) using a specific monoclonal antibody (5159-1) that recognizes the extracellular domain of the transduced specific TCR, in order to assess the levels of membrane expression of this specific TCR.

As described in herein, PBLs were stimulated with PHA for 5-10 days and subsequently electroporated with the MART-1 specific TCR F4. The effector CD8+ PBLs were cultured in lymphocyte medium containing IL-2. FIG. 23 shows the level of TCR expression obtained for two different donors.

Figure 24:
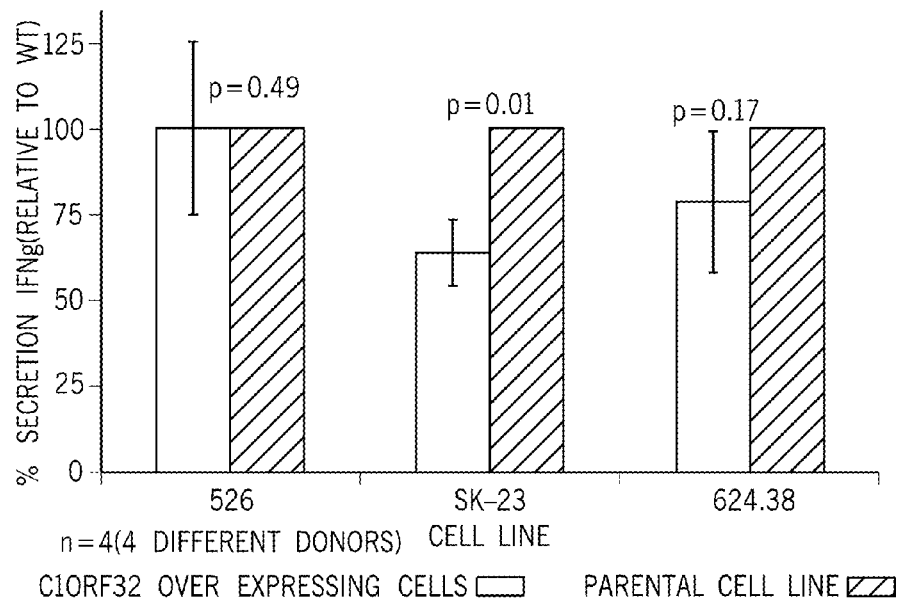
FIG. 24 demonstrates that C1ORF32 (SEQ ID NO: 1) expressed on SK-mel 23 melanoma cells inhibits activation of F4 TCR expressing CTLs in a co-culture assay as observed by reduced IFNγ secretion. The graph represents four independent experiments with CTLs from four different donors transduced with F4 TCR. C1ORF32 expressed on mel624.38 melanoma cells also inhibits CTL activation but this effect did not reach statistical significance. C1ORF32 expressed on mel526 melanoma cells does not inhibit CTL activation *p<0.01.

The effector CD8+ PBLs were added to either the parental melanoma line (mel526, mel624.38 or SK-MEL 23) or to the respective C1ORF32-transfectant. 16-hours after the beginning of the co-culture, the levels of IFNγ and IL-2 secretion were assessed. In 4 independent experiments using 4 different T-cell donors, a significant reduction (~40%) of IFNγ secretion from the CTLs was observed following co-culture with the C1ORF32 expressing SK-MEL-23 cell line, as compared to the parental cell line (p=0.01). With the other C1ORF32 expressing cell lines, the differences in IFNγ secretion observed were not found statistically significant (FIG. 24).

However, in a second set of experiments (total of 3) the reduction observed in co-cultures with C1ORF32 expressing SK-MEL23 cells was less pronounced (around 10%) (data not shown). Additionally, it appears also that the levels of C1ORF32 expression in the transduced melanoma lines were slightly reduced with time (6 weeks).

In regard to IL-2 secretion, inconsistent results were obtained, that showed in some cases a slight increase in a few co-culture experiments was observed (data not shown), which did not reach statistical significance.

This study analyses the effect of ectopically expressed C1ORF32 on CTL effector function. These results indicate that C1ORF32 expression on melanoma cells results in reduced IFNγ secretion by CTLs. These results point out to a trend in activity. Additional optimization of several features in the experimental system is being done:
1) Level and homogeneity of C1ORF32 ectopic expression on melanoma cell lines.
2) Expression levels of F4 T cell receptor on primary activated CD8 cells.
3) Extension of the study to test direct effect on CTLs killing activity.
Without wishing to be limited by a single hypothesis, the difference in the effect on CTLs of C1ORF32 expressed on different melanoma cell lines can be explained by a different repertoire of endogenously expressed co-stimulatory/co-inhibitory proteins on different melanoma lines.

Example 13

C1ORF32-ECD-MOUSE IgG2a Fusion Protein (SEQ ID NO:18) Upregulates Differentiation of Inducible Regulatory T Cells (iTregs) In Vitro Tregs play an essential role in the immunosuppressive networks that contribute to tumor-immune evasion. To test the ability of an anti C1ORF32 antibody to block Treg differentiation, it was first tested whether the interaction of C1ORF32 fusion protein with naïve T cells affects their differentiation to iTregs. To this aim, C1ORF32-ECD-mouse IgG2a fusion protein (SEQ ID NO:18) was used, and its effect on differentiation of regulatory T cells was evaluated by testing the expression of the regulatory T cell marker, FoxP3, by CD4+CD25+ purified T cells when incubated in the presence of iTreg driving conditions.

Naïve CD4+ T cells were isolated from DO11.10 mice via automax sort (CD4-negative sort plus and CD25 positive isolation, followed by CD62L-positive sort).

The cells were activated in the presence of IL-2 (100 U/ml), TGF-beta (10 ng/ml) and either Control Ig (10 ug/ml) or C1ORF32-ECD-mouse IgG2a fusion protein (SEQ ID NO:18) (1 or 3 ug/ml) in the presence of irradiated Balb/c splenocytes (at 1:1 ratio; $5 \times 10^5$ T cells per well) and OVA323-339 (20 ug/ml). On day 4 of culture, cells were harvested and stained for viability, CD4, CD25, and FoxP3 expression.

Figure 25:
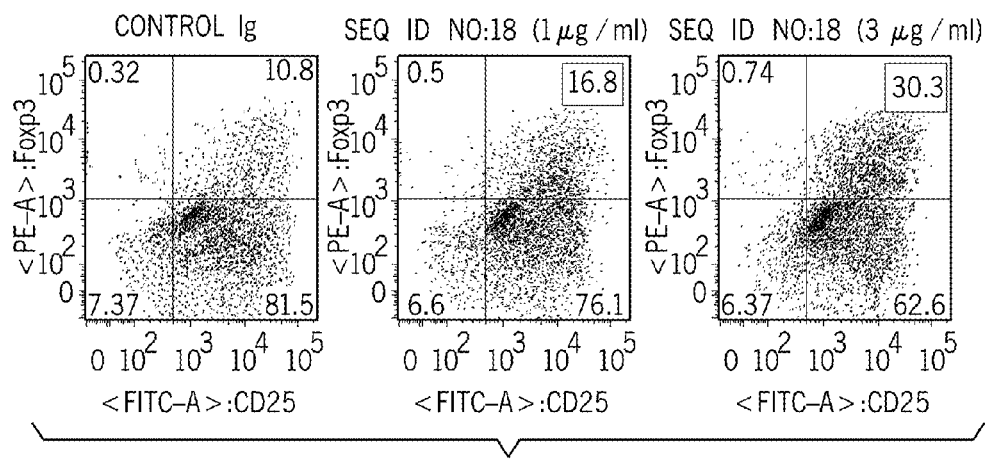
FIG. 25 shows induction of Tregs differentiation by C1ORF32-ECD-mouse IgG2a fusion protein (SEQ ID NO:18). Naïve CD4+ T cells were activated in the presence of iTreg cell-promoting conditions and either Control Ig (10 ug/ml) or C1ORF32-ECD-mouse IgG2a fusion protein (SEQ ID NO:18) (1 or 3 ug/ml) in the presence of irradiated Balb/c splenocytes (at 1:1 ratio; 5×105 T cells per well) and OVA323-339 peptide (20 ug/ml). Cells were analyzed after 4 days of culture for the expression the Treg marker, FoxP3, by flow cytometry.

As demonstrated in FIG. 25, incubation of naïve CD4+ CD25+ T cells in the presence of C1ORF32-ECD-mouse IgG2a fusion protein (SEQ ID NO:18) resulted in a potent and dose dependent increase in the percentage of CD4+ CD25+FoxP3+ T cells. These results indicate that the interaction of C1ORF32 protein with it counterpart receptor on T cells leads to induction of iTregs differentiation. Thus, without wishing to be bound by a single theory, using a C1ORF32 specific antibody that blocks this interaction is useful in downregulating iTreg differentiation, and by that increasing immune system activity against cancer.

As shown herein, the ex vivo results demonstrate that the C1ORF32-Ig fusion protein enhanced the differentiation of CD4 T cells to iTregs. These results suggest that the C1ORF32 pathway is involved in iTregs induction and differentiation, and imply that targeting C1ORF32 with blocking monoclonal antibodies inhibits iTregs accumulation and immunosuppressive function. Furthermore, by inhibiting C1ORF32 immune checkpoint activity, such blocking antibodies would also enhance effector T cell activity. Thus the enhancement of effector T cell activity and inhibition of iTreg immunosuppressive activity activity by C1ORF32 blocking antibodies lead to enhanced beneficial effects in cancer therapy using such antibodies, alone, or in combination with a potentiating agent.

In addition to the above results demonstrating a role for C1ORF32 in promoting differentiation of iTregs, Examples 5, 6 and 11, in WO/2012/001647, incorporated by reference, as if fully set forth herein, demonstrate the effect of C1ORF32 on Th differentiation using mouse and human CD4+ T cells upon activation under specific Th driving conditions. Murine T cell activation was either antigen-specific or polyclonal. The results in the majority of these experimental settings, using mouse or human cells, point to an immunomodulatory effect of C1ORF32 on T cells, whereby Th1 and Th17 driven responses (secretion of proinflammatory cytokines and cell proliferation under Th1 and Th17 driving conditions) are inhibited, while secretion of anti-inflammatory cytokines (Th2 derived, and IL-10) are promoted.

It is known that one of the mechanisms by which tumors evade immune surveillance is promotion of a Th2/M2 oriented immune response (Biswas S K, et al., 2010 October; 11(10):889-96). Thus, without wishing to be limited by a single hypothesis, a neutralizing antibody which suppresses the above demonstrated immunomodulatory effect of C1ORF32 (i.e. promotion of Th2 response and inhibition of Th1 response) is beneficial for treatment of cancer.

Example 14

Binding of C1ORF32 to NK Cells and of the Effect of C1ORF32 Ectopic Expression on NK Killing Activity The aim of this analysis was to evaluate the binding potential of C1ORF32 (Fc fused protein containing the extracellular domain of C1ORF32 to the Fc of mIgG2a, (SEQ ID NO: 24)); to NK cells and to evaluate whether ectopic expression of C1ORF32 on HEK293T cells affects their susceptibility to killing by NK cells. The HEK293T cells overexpressing C1ORF32 (SEQ ID NO:1) used are described herein.

Isolation of NK Cells from Peripheral Blood Mononuclear Cells:

Human NK cells were isolated from PBLs (peripheral blood cells) using the human NK cell isolation kit and the autoMACS instrument (Miltenyi Biotec, Auburn, Calif.).

Generation of Primary NK Cell Lines:

Human primary NK cell lines were obtained by seeding purified human primary NK cells at one cell/well in 96-well U-bottomed plates in complete medium supplemented with 10% FCS, 10% leukocyte-conditioned medium and 1 µg/ml PHA. Irradiated feeder cells ($2.5 \times 10^4$ allogeneic PBMCs from two donors and $5 \times 10^3$ RPMI 8866 B cell line in each well) were added. Proliferating clones, as defined by growth at cell densities where growth of cells occurred in less than one third of the wells plated, were expanded in complete medium in 96-well plates. These human activated primary NK cell lines were cultured in RPMI, 10% human serum supplemented with 1 mM glutamine, 1 mM nonessential amino acids, 1 mM sodium pyruvate, $2 \times 10^{-5}$M β-ME and 50 U/ml rhuIL-2. The binding and killing assays presented here were performed using a polyclonal population of NK cells (i.e. after unification of all viable NK clones from each donor).

Cytotoxic Assay:

The cytotoxic activity of NK cells against HEK-293 ectopically expressing C1ORF32 was evaluated using $S^{35}$ release assay, in which effector cells were admixed with $5 \times 10^3$ [$S^{35}$] methionine-labeled target cells at different E/T ratios in U-bottomed microtiter plates. Following an overnight incubation at 37° C., assays were terminated by centrifugation at 1,000 rpm for 10 min at 4° C. and 100 µl of the supernatant was collected for liquid scintillation counting. Percent specific lysis was calculated as follows: % lysis=[(cpm experimental well–cpm spontaneous release)/(cpm maximal release–cpm spontaneous release)]×100. Spontaneous release was determined by incubation of the $S^{35}$-labeled target cells with medium only. Maximal release was determined by solubilizing target cell in 0.1M NaOH. In all presented experiments, the spontaneous release was <25% of maximal release.

Binding Assay:

NK cells were incubated with 5 µg of C1ORF32 (SEQ ID NO: 24) or isotype control (mIgG2a) for 2 hours on ice. Following cell washing, secondary anti mouse antibody was added and binding was evaluated by flow cytometry.

C1ORF32 Binding to NK Cells

In these experiments, the binding of C1ORF32 (SEQ ID NO: 24) to NK cells (i.e. Activated primary NK cell lines) as well as to freshly isolated NK cells from several different donors was evaluated.

Figure 26A:
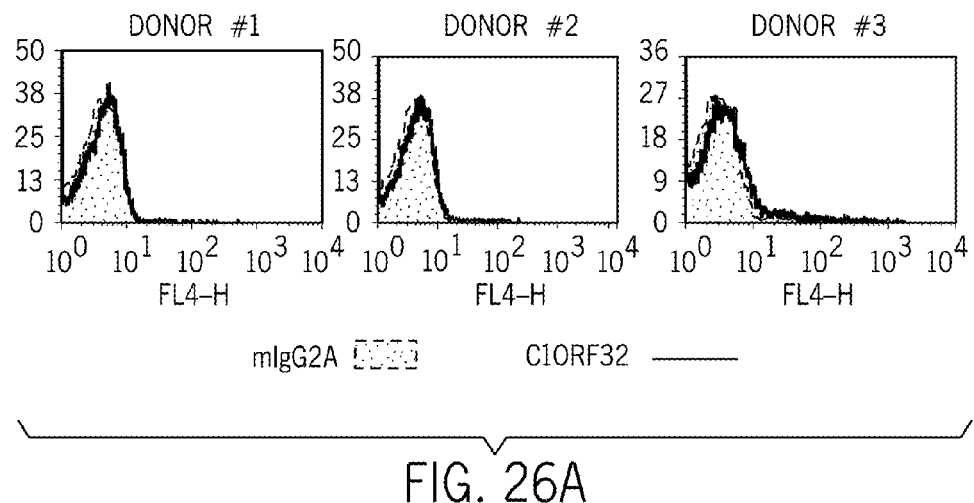
FIG. 26 shows C1ORF32 (SEQ ID NO: 24) binding to primary activated and freshly isolated NK cells. Human NK primary cell lines from three different donors (FIG. 26A) or freshly isolated NK cells from three other donors (FIG. 26B) were incubated with 5 μg unlabeled C1ORF32 (SEQ ID NO: 24) or control isotype mIgG2a. Grey histograms are of mIgG2a, the red or black histograms are of C1ORF32.
Figure 26B:
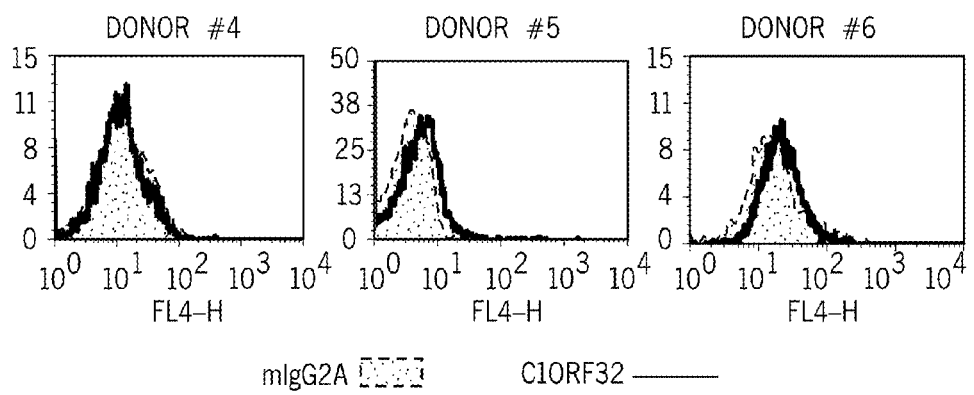

The results are presented in FIG. 26, demonstrating C1ORF32 (SEQ ID NO: 24) binding to primary activated and freshly isolated NK cells. Human NK primary cell lines from three different donors (FIG. 26A) or freshly isolated NK cells from three other donors (FIG. 26B) were incubated with 5 µg unlabeled C1ORF32 ((SEQ ID NO: 24)) or control isotype mIgG2a. Grey histograms are of mIgG2a, the red or black histograms belong to C1ORF32.

As shown in FIG. 26, C1ORF32 (SEQ ID NO: 24) displayed largely no binding to NK cells, although in some cases a very weak binding was apparent (as in Donors #3, 5 and 6).

Figure 27:
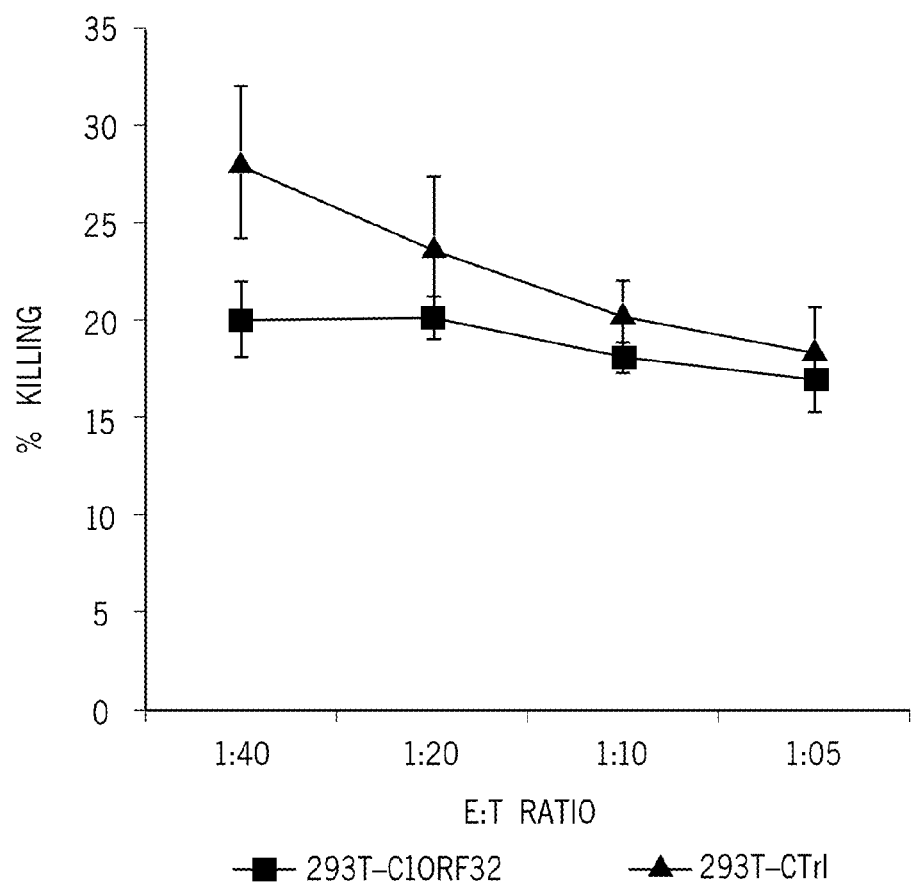
FIG. 27 demonstrates that C1ORF32 (SEQ ID NO: 1) expression on HEK293T cells results in a minor reduction of HEK293T susceptibility to killing by NK cells. Y axis presents percentage of killing. X axis presents Effector to target (E:T) ratios. * designates p value<0.05.

Over Expression of C1ORF32 in HEK293T Cells Results in Reduction of NK Cells Cytotoxicity The effect of ectopic expression of C1ORF32 (SEQ ID NO: 1) on HEK293T cells on their susceptibility to killing by NK cells was assessed. FIG. 27 presents the results of C1ORF32 (SEQ ID NO: 1) expression on HEK293T cells resulting in a minor reduction of their susceptibility to killing by NK cells. Human NK primary cells were co-incubated with HEK293T cells over expressing C1ORF32 (293T-001) or un-transfected HEK293T cells (293T-CTr1) and percentage of killing was assessed as described in Materials and Methods herein. Effector to target (E:T) ratios (X axis) range from 1:40 to 1:5 (two fold dilution of effector cells). * designates p value<0.05.

Results shown in FIG. 27 show that expression of C1ORF32 (SEQ ID NO: 1) results in a minor reduction of NK killing activity which reaches statistical significance (p<0.05) only at the highest E:T ratio.

Without wishing to be limited by a single hypothesis, the data showing the effect for C1ORF32 (SEQ ID NO: 1) over expression on the susceptibility of HEK293T cells to killing by NK cells raises the possibility that NK cells are involved in C1ORF32 mechanism of action. Expression of a counter receptor for C1ORF32 on NK cells by binding assays was detected in low levels. Without wishing to be limited by a single hypothesis, it is possible that the binding affinity of C1ORF32 to the counter receptor on NK cells is variable among different NK clones, and thus could not be detected robustly in this assay.

NK cells use a variety of receptors to detect abnormal cells, including tumors and their metastases. The activity of NK cells is dictated by the balance between activatory and inhibitory receptors. The results depicting that C1ORF32 is an inhibitory ligand which binds to a counterpart receptor on NK cells and inhibits their cytolytic activity support the use of a neutralizing C1ORF32 specific antibody that inhibits this negative regulation and thus enhances the clearance of the tumor by the immune system.

Example 15

Expression of C1ORF32 Putative Receptor on Activated T Cells

The expression of the putative counterpart receptor of C1ORF32 was investigated by testing the binding of C1ORF32 to resting or activated mouse CD4 T cells with plate bound anti-CD3 and soluble anti-CD28. In order to prevent binding to Fcγ receptors, an aglycosylated version of C1ORF32 (Fc containing the N278A mutation, SEQ ID NO:38) was used. In addition, anti-CD16/CD32 antibodies were used for blocking of Fcγ-receptors. Results, shown in FIG. 14, indicate no detectable binding of C1ORF32 to unactivated T cells, and a small but clear increase of binding to activated CD4+ T cells. These results suggest that activated T cells express the putative counterpart receptor for C1ORF32. As can be seen in FIGS. 10-13, 15-21, the membrane bound form of C1ORF32 generates a negative signal for T cell activation. Thus, without wishing to be limited by a single hypothesis, a neutralizing antibody specific for C1ORF32 abrogates the inhibitory activity of such receptor and by that, enhance tumor immune surveillance.

Figure 14:
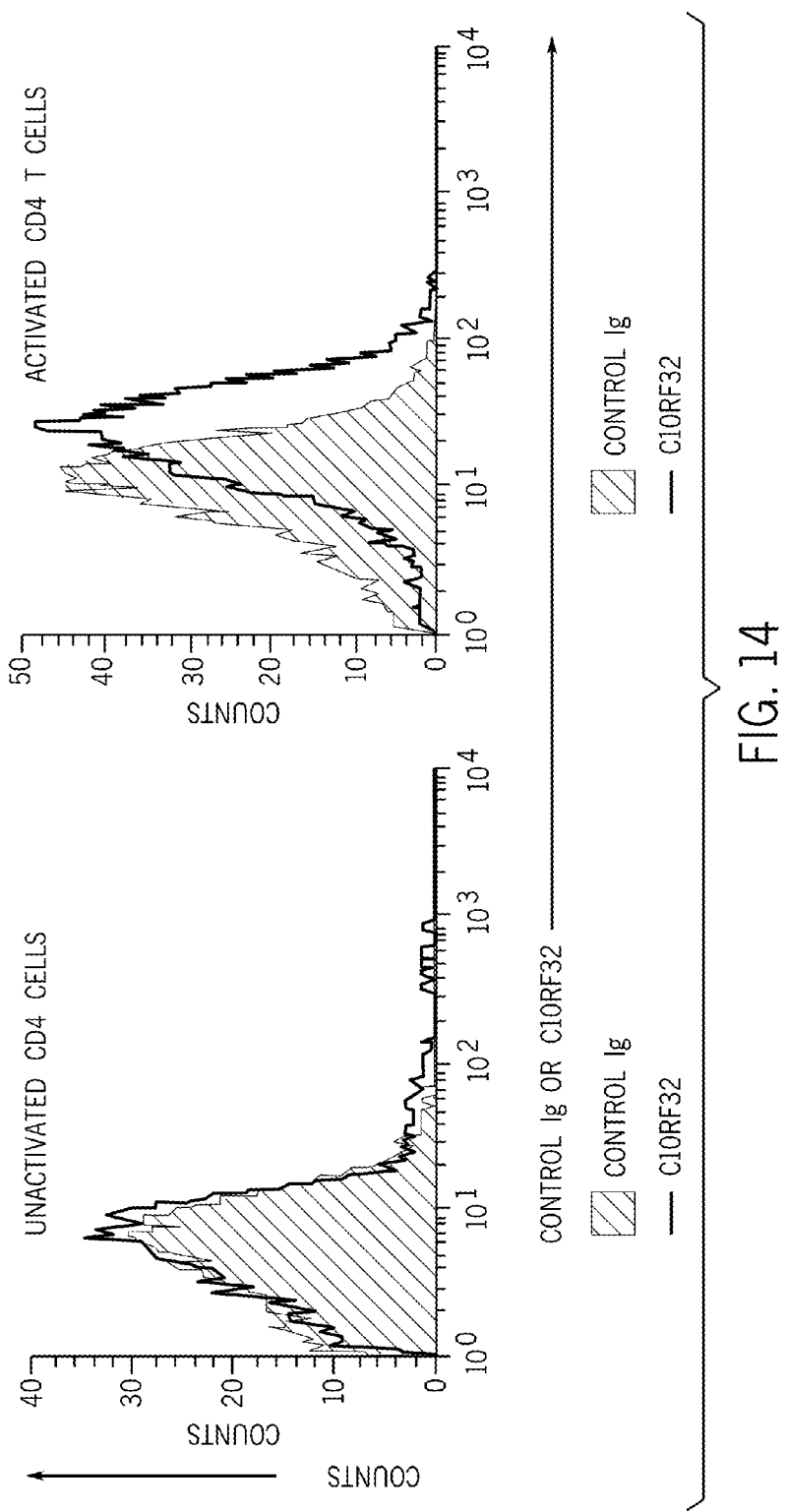
FIG. 14 shows C1ORF32 (SEQ ID NO:24) binding profile to resting and activated mouse T cells. Mouse CD4+ CD25-CD4 T cells were left 'unactivated' or stimulated with immobilized anti-CD3 (2 µg/ml) in the presence of soluble anti-CD28 (2 µg/ml). After 48 hr, anti-CD3/28 stimulated CD4 cells were stained with biotinylated C1ORF32 H:M (N278A; aglycosylated, SEQ ID NO:38) or isotype control (biotinylated mouse IgG2a; Biolegend), followed by streptavidin-PE, in the presence of mouse anti-CD16/32 for blocking of Fcγ-receptors.

FIG. 14 shows C1ORF32 binding profile to resting and activated mouse T cells. Untouched mouse CD4+CD25−CD4 T cells were left in medium ('unactivated') or stimulated with immobilized anti-CD3 (2 μg/ml) in the presence of soluble anti-CD28 (2 μg/ml). After 48 hr, anti-CD3/28 stimulated CD4 cells were stained with biotinylated C1ORF32 H:M (N278A; aglycosylated) (SEQ ID NO:38) or isotype control (biotinylated mouse IgG2a; Biolegend), followed by streptavidin-PE, in the presence of mouse anti-CD 16/32 for blocking of Fcγ-receptors.

Example 16

Effector Function Activity Through Complement Dependent Cytotoxicity (CDC) of Anti C1ORF32 Antibody, 5166-9, on C1ORF32 Ectopic Expressing Cell Lines The aim of this experiment was to establish a functional assay addressing the complement fixing ability of C1ORF32 monoclonal antibodies on cell lines that express C1ORF32 and to use this assay to screen for potential therapeutic antibodies for CDC effector function.

C1ORF32 Expressing Cell Lines:

HEK293T and CHOK1 cells expressing human C1ORF32 or empty vector were generated as described above. HEK293T transfected cells were cultured under selection of 5 ug/ml puromycin in DMEM supplemented with 10% FBS, Glutamine-Penstrep. Similarly, CHOK1 transfected cells were cultured under selection of 12 ug/ml puromycin in F12 supplemented with 10% FBS, Glutamine-Penstrep. Complete media (CM) refers to the culture media for the respective cell lines.

Antibodies: 5166-9 (IgM), 5159-3 (IgG2a) and 5159-1 (IgG1) purified mouse monoclonal antibodies against C1ORF32 were generated at Silverlake, USA according as described herein. Purified mouse IgM Isotype control, clone MM-30 (cat#401602) and Purified mouse IgG2a Isotype control, clone MOPC-173 (cat#400224) was purchased from Biolegend, USA.

Reagents: Purified rabbit complement (cat# CL-3441) was purchased from Cedarlane laboratories, Canada. Cell Titer Glo reagent was purchased from Promega, USA (cat# G7570).

Cytotoxic assay: The CDC activity of C1ORF32 antibodies against HEK293 and CHOK1 ectopically expressing C1ORF32 was evaluated using cell titer CellTiter-Glo reagent. Cells were plated at a density of $5 \times 10^3$ cells per well in a 96 well tissue culture plate in 50 ul of CM. After culturing overnight, serial dilutions of 2× antibody, isotype, media alone were added in equal volume to respective wells. Freshly reconstituted complement was added and the plates incubated at 37 degrees. After 1 hr plates were equilibrated to room temperature, 100 ul of cell titer CellTiter-Glo reagent added per well and incubated at RT for 5 to 10 mins 170 ul was transferred to a white plate and luminescence measured on Victor2 plate reader (Perkin Elmer). Data was exported and analyzed in Excel and plotted in GraphPad Prism.

Percent CDC was calculated as follows: 100−[(RLU experimental well/RLU complement alone)×100]. Conditions were run in triplicate and data is representative of 2 experiments.

FACS Staining: HEK293T and CHOK1 parental and CGEN15001T expressing cells were washed and stained in 25 ul of different concentrations of 5159-1 in FACS buffer (PBS (Life Technologies), 1% BSA (Sigma Aldrich) and 0.01% sodium azide (Sigma Aldrich)) at 4 degrees C. for 60 minutes. The cells were washed once in FACS buffer, re-suspended in 25 ul of Alexa Fluor 647 conjugated F(ab')2 fragment of goat anti mouse IgG (Jackson Immunoresearch cat#115-606-146) for 30 minutes at 4 degrees C. The cells were washed again in FACS buffer, re-suspended in 35 ul of FACS buffer and 35 ul of 4% paraformaldehyde and analysed on either a FACS Calibur or an Intellicyt HTFC. Data was analyzed by FlowJo, Excel and GraphPad Prism.

Anti C1ORF32 Antibody, Such as 5166-9, has Potent CDC Activity on C1ORF32 Expressing Cells, for Example, on HEK293 Ectopically Expressing C1ORF32

Figure 28:
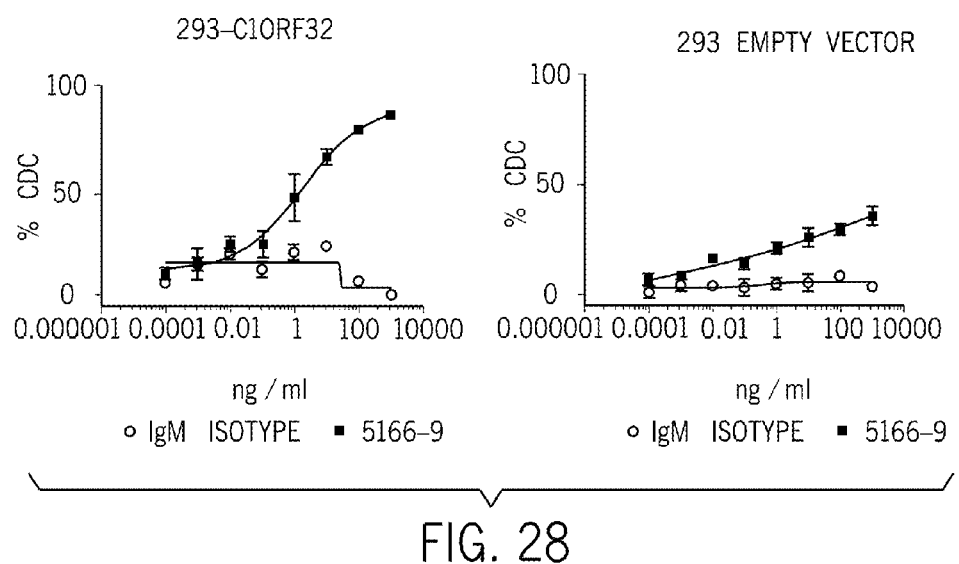
FIG. 28 demonstrates that 5166-9 anti C1ORF32 antibody shows potent CDC activity against HEK293 expressing C1ORF32. HEK293 cell lines were incubated with 5166-9 or control isotype mIgM in the presence of complement and viability measured after 1 hr.
Figure 29:
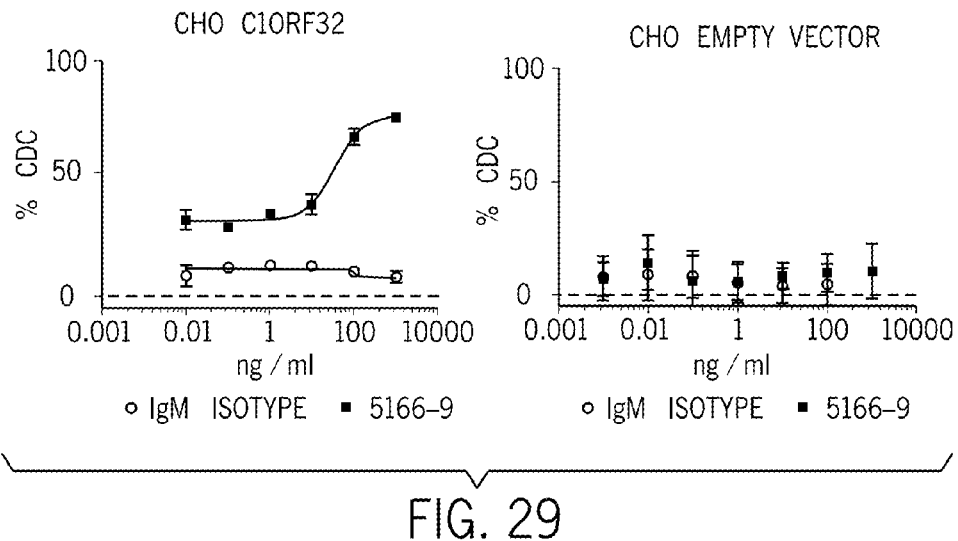
FIG. 29 demonstrates that 5166-9 anti C1ORF32 antibody shows CDC activity against CHOK1 cells expressing C1ORF32. CHOK1 cell lines were incubated with 5166-9 or control isotype mIgM in the presence of complement and viability measured after 1 hr.
Figure 30:
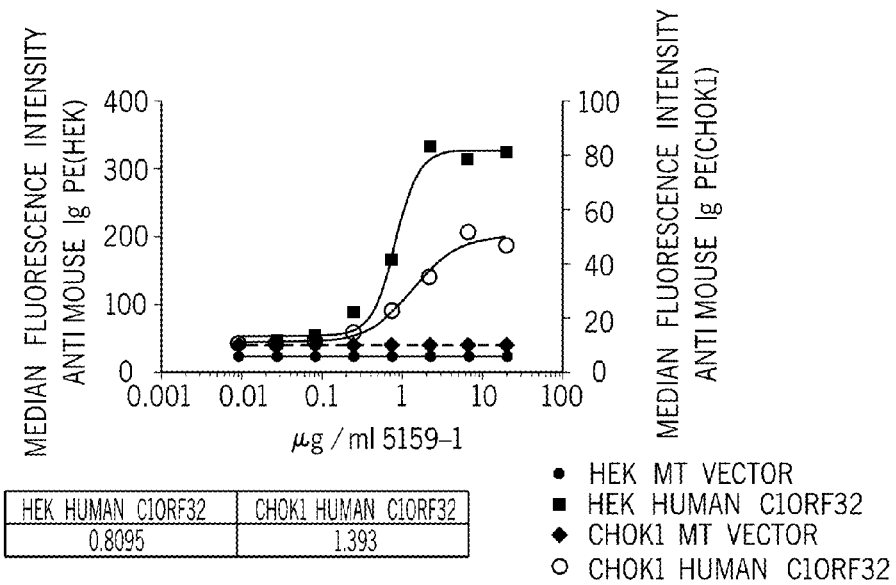
FIG. 30 presents C1ORF32 expression on HEK293T cells compared to CHOK1. HEK293 C1ORF32 cells express more target antigen compared to CHOK1 C1ORF32 based on detection of C1ORF32 using a C1ORF32 antibody 5159-1.

In these experiments the activity of antibody 5166-9, a mouse IgM monoclonal, on HEK293T and CHOK1 cells expressing C1ORF32 was evaluated. As shown in FIG. 28, 5166-9 displayed potent CDC activity on HEK293T expressing C1ORF32 cells with an EC50 of 1.8 ng/ml or 0.01 nM. Significantly lower level of activity was observed on the empty vector control cell line (right panel). The low level of activity on the empty vector line is likely due to low level of endogenous expression of the antigen (data not shown). Similar to HEK293T cells, antibody 5166-9 displayed dose dependent CDC activity in CHOK1 cells, with an EC50 of 33 ng/ml or 0.2 nM (FIG. 29). The maximum killing effect was less compared to HEK293T expressing C1ORF32. These differences in potency can be explained by the incomplete expression on the CHOK1 transfectant expressing C1ORF32 (40% of the cells showed no expression by FACS—data not shown) as well as lower level of C1ORF32 expression as seen by FACS (FIG. 30). The activity of 5159-3, an IgG2a mouse monoclonal showed minimal activity in these assays (data not shown).

FIG. 28 demonstrates that 5166-9 anti C1ORF32 antibody shows potent CDC activity against HEK293 expressing C1ORF32. HEK293 cell lines were incubated with 5166-9 or control isotype mIgM in the presence of complement and viability measured after 1 hr.

FIG. 29 demonstrates that 5166-9 anti C1ORF32 antibody shows CDC activity against CHOK1 cells expressing C1ORF32. CHOK1 cell lines were incubated with 5166-9 or control isotype mIgM in the presence of complement and viability measured after 1 hr.

FIG. 30 presents C1ORF32 expression on HEK293T cells compared to CHOK1. HEK293 C1ORF32 cells express more target antigen compared to CHOK1 C1ORF32 based on detection of C1ORF32 using a C1ORF32 antibody 5159-1.

These data showed CDC activity of anti C1ORF32 Ab, 5166-9, on HEK293T and CHOK1 cells expressing C1ORF32. These assays could be used to characterize functional Abs of C1ORF32. The results raise the possibility that C1ORF32 therapeutic antibodies of the human IgG1 sub-class, known for complement fixing activity, could potentially act through multiple mechanisms of action, including CDC mediated effector function on C1ORF32 expressing cancer cell.

Example 17

Role of C1ORF32 Proteins as Modulators of Cancer Immune Surveillance

1) In Vivo Proof of Concept a) Mouse Cancer Syngeneic Model:

(i) Tumor cells, over expressing C1ORF32 proteins or a non-relevant control protein are transplanted to genetically matched mice. Tumor volume (and tumor weight after sacrificing the animals) are then examined to demonstrate delay in the tumor growth (i.e. tumor over expressing C1ORF32 grow faster than tumors over expressing the non-relevant control protein). Ex vivo analysis of immune cells from tumor draining lymph nodes is carried out to evaluate the ratio of regulatory T cells and effector T cells.

(ii) Treatment of syngeneic tumor with neutralizing antibodies directed against C1ORF32 protein as mono-therapy. Tumor cells are transplanted to genetically identical mice. Tumor bearing mice are injected with different doses of neutralizing antibodies aimed against C1ORF32 protein. As a result of treatment with neutralizing antibodies specific for C1ORF32 protein the rejection of the tumor is increased (i.e. in mice treated with neutralizing antibodies against C1ORF32 protein tumors grow slower than tumors in mice treated with non-relevant antibody). Ex vivo analysis of immune cells from tumor draining lymph nodes is carried out to determine of the ratio of regulatory T cells and effector T cells.

The tumor cells lines tested are from various origins including colon, breast, and ovary carcinomas, melanoma, sarcomas and hematological cancers. Syngeneic models are performed in several mouse strains including BALB/c, C57bl/6 and C3H/Hej. In the first set of experiments the syngeneic transplantable models used are primarily those proved as predictive for cancer immunotherapy. These include: B16-F10 melanoma (according to the method described in Tihui Fu et al Cancer Res 2011; 71: 5445-5454), MC38 colon cancer (according to the method described in Ngiow S F et al. Cancer Res. 2011 May 15; 71(10):3540-51), ID8 ovarian cancer (according to the method described in Krempski et al. *J Immunol* 2011; 186:6905-6913), MCA105 sarcoma (according to the method described in Wang et al. J. Exp. Med. Vol. 208 No. 3 577-592), CT26 colon carcinoma (according to the method described in Ngiow S F et al. Cancer Res. 2011 May 15; 71(10):3540-51) and 4T1 mammary carcinoma (according to the method described in Takeda K et al. J Immunol. 2010 May 15; 184(10):5493-501) of BALB/c background.

(iii) Establishment of a syngeneic tumor and treatment with neutralizing antibodies directed against C1ORF32 protein in combination with additional lines of treatment. Tumor cells are transplanted to genetically identical mice. After the establishment of tumors, mice are injected IP with different doses of neutralizing antibodies aimed against C1ORF32 protein in combination with conventional chemotherapy (e.g. cyclophosphamide, according to the method described in Mkrtichyan et al. Eur. J immunol. 2011; 41, 2977-2986), in combination with other immune checkpoint blockers (e.g. PD1 and CTLA4, according to the method described in Curran et al.; Proc Natl Acad Sci USA. 2010 Mar. 2; 107(9):4275-80), in combination with other immune-modulators (e.g. anti-IL18, according to the method described in Terme et al.; cancer res. 2011; 71: 5393-5399), in combination with cancer vaccine (according to the method described in Hurwitz et al. Cancer Research 60, 2444-2448, May 1, 2000) or in combination with radio-therapy (according to the method described in Verbrugge et al. Cancer Res 2012; 72:3163-3174).

(iv) Human cancer Xenograft model: Human cancer cell lines, endogenously expressing C1ORF32 are transplanted into immune-deficient mice. Tumor volume in mice treated with anti-C1ORF32 antibody vs. mice treated with non-relevant isotype matched antibody will be assessed. In one arm of the study anti-C1ORF32 antibodies are conjugated to a toxin (according to the method described in Luther N et al. Mol Cancer Ther. 2010 April; 9(4):1039-46) to assess antibody drug conjugate (ADC) activity. In another arm of the experiment, mice are treated with human IgG1 or mouse IgG2a isotype antibodies against C1ORF32 (according to the method described in Holbrook E. Kohrt et al. J Clin Invest. 2012 Mar. 1; 122(3): 1066-1075). These antibody isotypes are used to assess antibody-dependent cellular cytotoxicity (ADCC) mediated tumor elimination.

2) Expression Analysis a) Expression of C1ORF32 Proteins on Tumor and Immune Cells Isolated from Human Tumor Biopsies (i) Expression validation of C1ORF32 proteins using specific antibodies directed against the C1ORF32 proteins is carried out on separated cell populations from the tumor. Various cell populations are freshly isolated from tumor biopsies (e.g. Tumor cells, endothelia, tumor associated macrophages (TAMs) and DCs, B cells and different T cell sub-sets (CD4, CD8 and Tregs) as described in Kryczek I. et al., J. Exp. Med.; 2006; Vol. 203; p.871-881 and Cancer res. 2007; 67; 8900-8905, to demonstrate expression of C1ORF32 in tumor cells and on tumor stroma and immune infiltrate.

(ii) Binding assay is performed with the human C1ORF32 ECD-FC proteins on separated cell populations from the tumor. Various cell populations from tumor biopsies (e.g. Tumor cells, endothelia, tumor associated macrophages (TAMs) and DCs, B cells and different T cells (CD4, CD8 and Tregs) are freshly isolated from tumors as described in J. Exp. Med.; 2006; Vol. 203; p.871-881 and Cancer res. 2007; 67; 8900-8905, to show expression of the counter receptor for C1ORF32 in tumor cells and on tumor stroma and immune cells.

b) Expression of C1ORF32 Proteins on Cells Isolated from Draining Lymph Nodes and Spleens of Tumor Bearing Mice (i) Expression validation of C1ORF32 proteins using specific antibodies directed against C1ORF32 proteins is done on epithelial cancer cells as well as on immune cells from tumor draining lymph nodes vs. spleen of tumor bearing C57 mice, as described in M Rocha et al., Clinical Cancer Research 1996 Vol. 2, 811-820. Three different cancer types are tested: B16 (melanoma), ID8 (ovarian) and MC38 (colon)), in order to evaluate expression of C1ORF32 in tumor cells and in immune cells within the tumor draining lymph node.

(ii) Binding assay with mouse C1ORF32 ECD-FC proteins on cells isolated from epithelial cancer as well as on immune cells from tumor draining lymph nodes versus spleen of tumor bearing C57 mice is carried out as described above, to show expression of the counter receptor for C1ORF32 in tumor cells and in immune cells in the tumor draining lymph node.

c) Expression of C1ORF32 Proteins on M2 Polarized Macrophages (i) Expression validation of C1ORF32 proteins using specific antibodies directed against C1ORF32 proteins, is done on primary monocytes isolated from peripheral blood, differentiated into macrophages and exposed to "M2 driving stimuli" (e.g. IL4, IL10, Glucocorticoids, TGF beta), as described in Biswas SK, Nat. Immunol. 2010; Vol. 11; p. 889-896, to show expression of C1ORF32 in M2 differentiated Macrophages.

ii) Binding assay with C1ORF32 human ECD-FC proteins on primary monocytes isolated from peripheral blood, differentiated into macrophages and exposed to "M2 driving stimuli" (e.g. IL4, IL10, glucocorticoids, TGF beta) is carried out as described above, to evaluate expression of the counter receptor for C1ORF32 in M2 differentiated Macrophages.

Example 18

Anti-Tumor Effect of Blocking Antibody Against the C1ORF32 Protein in Combination with Blockade of Known Immune Checkpoints Inhibitory receptors on immune cells are pivotal regulators of immune escape in cancer. Among these are known immune checkpoints such as CTLA4, PD-1 and LAG-3. Blockade of a single immune checkpoint often leads to enhanced effector T cell infiltration of tumors, but may also lead to compensatory upregulation in these T cells of the other unblocked negative receptors. However, blockade of more than one inhibitory pathway allows T cells to carry out a more efficient tumor response, and increases the ratio of effector T cells (Teffs) to regulatory T cells (Tregs). Specifically, dual blockade of such inhibitory receptors has been shown to exert synergistic therapeutic effect in animal tumor models (Curran et al 2010 PNAS 107: 4275-4280; Woo et al 2011 Cancer Res. 72: 917-927). Based on these findings, the combination of anti-CTLA-4 and anti-PD-1 blocking antibodies is being tested in clinical trials in patients with metastatic melanoma.

The combination of blocking antibodies against C1ORF32 and against PD-1 is tested in the syngeneic cancer MC38 model in the C57B1/6 background (as described in Woo et al 2011 Cancer Res. 72: 917-927). Briefly, MC38 cells ($2\times10^6$) are implanted s.c. C57B1/6 mice. Mice with palpable tumors are injected i.p. at a dosage of 10 mg/kg anti-C1ORF32 mAb and/or anti-PD-1 mAb (4H2). Isotype Control Ab is dosed at 20 mg/kg or added to individual anti-PD-1 or anti-C1ORF32 antibody treatments at 10 mg/kg. Tumor volumes are measured with an electronic caliper, and effect on tumor growth is calculated. The therapeutic effect, manifested as inhibition of tumor growth, is enhanced upon combination of the blocking antibodies against the two targets, PD-1 or C1ORF32. The frequency of effector T cells=Teffs (CD8+IFNg+) cells and the ratio of Teffs and Tregs are determined in tumor draining lymph nodes and non-draining lymph nodes.

Example 19

Anti-Tumor Effect of Blocking Antibody Against the C1ORF32 Protein in Combination with Metronomic Therapy with Cyclophosphamide Cyclophosphamide has been used as a standard alkylating chemotherapeutic agent against certain solid tumors and lymphomas because of its direct cytotoxic effect and its inhibitory activity against actively dividing cells. While high doses of cyclophosphamide may lead to depletion of immune cells, low doses have been shown to enhance immune responses and induce anti-tumor immune-mediated effects, primarily by reducing the number and function of immunosuppressive Treg cells (Brode and Cooke 2008 Crit. Rev. Immunol. 28: 109-126). Metronomic therapy using classical chemotherapies other than cyclophosphamide has also been shown to have immunostimulatory effects, including gemcitabine; platinum based compounds such as oxaliplatin, cisplatin and carboplatin; anthracyclines such as doxorubicin; taxanes such as paclitaxel and docetaxel; microtubule inhibitors such as vincristine.

Combination therapy of cyclophosphamide with other immunotherapies, such as anti-4-1BB activating Ab or anti-PD1 blocking Ab, resulted in synergistic anticancer effects (Kim et al. 2009 Mol Cancer Ther 8:469-478; Mkrtichyan et al. 2011 Eur. J. Immunol. 41:2977-2986).

Anti-C1ORF32 blocking mAb is tested in combination with cyclophosphamide in the syngeneic B16 melanoma model in the C57BL/6 background (as described in Kim et al. 2009 Mol Cancer Ther 8:469-478). Briefly, C57BL/6 mice are injected s.c. with $4\times10^5$ B16-F10 melanoma cells. A single i.p. injection of cyclophosphamide (150 mg/kg) is administered on the day of tumor implantation, and five injections of 100 μg of the neutralizing antibody against C1ORF32, 5 d apart beginning on the day of tumor implantation. To examine the antitumor effects of combination therapy on established tumors, the combination therapy is given beginning either at day 5 or day 10 after tumor cells injection. Tumor volumes are measured with an electronic caliper, and effect on tumor growth is calculated. The therapeutic effect, manifested as inhibition of tumor growth, is enhanced upon combination of cyclophosphamide with the blocking antibodies against C1ORF32. The frequency of effector T cells=Teffs (CD8+IFNg+) cells and the ratio of Teffs and Tregs are determined in tumor draining lymph nodes and non-draining lymph nodes.

Example 20

Anti-Tumor Effect of Blocking Antibody Against the C1ORF32 Protein in Combination with Cellular Tumor Vaccines Therapeutic cancer vaccines enable improved priming of T cells and improved antigen presentation as agents potentiating anti-tumor responses. Among these, are cellular tumor vaccines that use whole cells or cell lysates either as the source of antigens or as the platform in which to deliver the antigens. Dendritic cell (DC)-based vaccines focus on ex vivo antigen delivery to DCs. Other therapeutic cancer vaccines consist of tumor cells genetically modified to secrete immune stimulatory cytokines or growth factors, such as GM-CSF (granulocyte-macrophage colony-stimulating factor) or Flt3-ligand, aim to deliver tumor antigens in vivo in an immune stimulatory context to endogenous DCs.

Several in vivo studies have shown a potent therapeutic effect of immunecheckpoint blockade, such as anti-CTLA-4 antibodies, in poorly immunogenic tumors only when combined with GM-CSF or Flt3-ligand-transduced tumor vaccines, termed Gvax and Fvax, respectively (van Elsas et al 1999 J. Exp. Med. 190: 355-366; Curran and Allison 2009 Cancer Res. 69: 7747-7755), and that the antibody alone was effective only in the most immunogenic tumor models in mice. Furthermore, combination of two immunotherapeutic agents, such as anti-CTLA4 and anti-PD-1 blocking antibodies, is more effective in conjunction with therapeutic cancer vaccine, such as Gvax or Fvax (Curran et al 2010 PNAS 107: 4275-4280)

The effect of C1ORF32 neutralizing antibody in combination with tumor cell vaccine, is tested using irradiated melanoma cells engineered to secrete GMCSF or Flt3-ligand (GVAX or FVAX respectively) in the presence or absence of anti-PD-1 blocking antibody (as described in Curran et al 2010 PNAS 107: 4275-4280). Briefly, mice are injected in the flank i.d. at day 0 with $5 \times 10^4$ B16-BL6 cells and treated on days 3, 6, and 9 with $10^6$ irradiated (150 Gy) gene-modified B16 cells (expressing GMCSF or Flt3-ligand) on the contralateral flank in combination with intraperitoneal administration of 100 ug of anti-C1ORF32 blocking antibody, with or without 100 ug of anti-PD-1 blocking antibody (clone RMP1-14) or anti-PDL-1 blocking antibody (9G2). Isotype Ig is used as negative control. Tumor volumes are measured with an electronic caliper, and effect on tumor growth is calculated. The therapeutic effect, manifested as inhibition of tumor growth, is enhanced upon combination of the blocking antibodies against C1ORF32 with the gene modified tumor cell vaccine. Anti-PD-1 or anti-PDL-1 blocking antibodies further enhance this effect. The frequency of effector T cells=Teffs (CD8+IFNg+) cells and the ratio of Teffs and Tregs are determined in tumor draining lymph nodes and non-draining lymph nodes.

Example 21

Anti-Tumor Effect of Blocking Antibody Against the C1ORF32 Protein in Combination with Radiotherapy Radiotherapy has long been used as anti-cancer therapy because of its powerful anti-proliferative and death-inducing capacities. However, recent preclinical and clinical data indicate that immunogenic cell death may also be an important consequence of ionizing radiation, and that localized radiotherapy can evoke and/or modulate anti-tumor immune responses (Reits et al 2006 J. Exp. Med. 203:1259-1271). Preclinical studies have shown enhanced therapeutic effects in combined treatment of radiotherapy and immunotherapy, including blocking antibodies to immune checkpoints such as CTLA4 and PD-1, in the absence or presence of an additional immunotherapy such as activating anti-4-1BB Abs (Demaria et al 2005 Clin. Can. Res. 11:728-734; Verbruge et al 2012 Can. Res. 72:3163-3174).

The combination of blocking anti-C1ORF32 antibodies and radiotherapy will be assessed using a syngeneic 4T1 mammary carcinoma cell line in the BALB/c background (as described in Demaria et al 2005 Clin. Can. Res. 11:728-734). Briefly, $5 \times 10^4$ 4 T1 cells are injected s.c. in the flank of BALB/c mice. Treatment begins when tumors reach an average diameter of 5 mm (65 $mm^3$ in volume) Animal groups include treatment with each modality alone (anti-C1ORF32 or radiotherapy) and with the isotype Ig Control, and combination of anti-C1ORF32 with radiotherapy, or of Ig Control with radiotherapy. Radiotherapy is delivered to the primary tumor by one or two fractions (48 hrs interval) of 12Gy. Anti-C1ORF32 Ab or Ig control are given i.p. at 200 ug, on days 1, 4 and 7 after radiotherapy. In an additional set of experiments, blocking anti-PD-1 mAb (RMP1-14) and activating anti-4-1BB mAb (3E1). Tumor volumes are measured with an electronic caliper, and effect on tumor growth is calculated. The therapeutic effect, manifested as inhibition of tumor growth, is enhanced upon combination of the blocking antibodies against C1ORF32 with radiotherapy. Anti-PD-1 blocking antibodies or anti-4-1BB activating Abs, further enhance this effect. The frequency of effector T cells=Teffs (CD8+IFNg+) cells and the ratio of Teffs and Tregs are determined in tumor draining lymph nodes and non-draining lymph nodes.

The present invention has been described and embodiments provided relating to manufacture and selection of desired anti-C1ORF32 antibodies for use in treatment and diagnosis of cancer. The present invention is now further described by the claims which follow. Optionally, any of the above embodiments or sub-embodiments described herein may be combined to form any suitable combination or sub-combination.

What is claimed is:

1. A method of a treating a subject for cancer, comprising determining if the cancer expresses one or more C1ORF32 polypeptides on the cancer cells or in immune cells infiltrating the cancer cells congregated as a tumor, wherein the C1ORF32 polypeptides have a sequence selected from the group consisting of SEQ ID Nos: 1, 7, 9, 13, and 17; administering to the subject, having an increase in C1ORF32 polypeptide level on the cancer cell or in immune cells infiltrating the cancer cells congregated as a tumor, a monoclonal or polyclonal antibody or an antigen binding fragment thereof comprising an antigen binding site that binds specifically to any one of the C1ORF32 polypeptides having the sequence of any one of SEQ ID Nos: 1, 7, 9, 13, and 17, wherein the cancer is selected from the group consisting of Thyroid Carcinoma, carcinoma of the esophagus, Invasive Ductal breast Carcinoma, breast comedocarcinoma, breast Medullary Carcinoma Grade 2, ovarian cancer selected from the group consisting of Serous and Mucinous, Granular cell tumor, Surface epithelial-stromal tumor (Adenocarcinoma), cystadenocarcinoma and Endometrioid tumor; kidney cancer selected from the group consisting of Clear cell carcinoma, Chromophobe adenoma, and sarcomatoides carcinoma; prostate adenocarcinoma having a Gleason score of 5 or higher, stage I to III prostate adenocarcinoma, Benign prostatic hyperplasia, stage II and III hepatocellular carcinoma, malignant hepatoma, fibrolamellar hepatocellular carcinoma, pseudoglandular (adenoid) hepatocellular carcinoma, pleomorphic (giant cell) hepatocellular carcinoma, clear cell HCC, Cholangiocarcinoma, pancreas cancer selected from Ductal and Mucinous Adenocarcinoma, Islet cell carcinoma, familial atypical multiple mole melanoma-pancreatic cancer syndrome (FAMMM-PC), Exocrine pancreas cancers, ductal adenocarcinoma, denosquamous carcinomas, signet ring cell carcinomas, hepatoid carcinomas, colloid carcinomas, undifferentiated carcinomas, and undifferentiated carcinomas with osteoclast-like giant cells, Low- to intermediate-grade neuroendocrine carcinomas and pancreatic carcinoid tumors, stage IV malignant melanoma, Lentigo maligna melanoma, Superficial spreading melanoma, Acral lentiginous melanoma, Mucosal melanoma, Nodular melanoma, Polypoid melanoma, Desmoplastic melanoma, Amelanotic melanoma, Soft-tissue melanoma, Osteogenic sarcoma, Chondrosarcoma, Leiomyosarcoma, Angiosarcoma, Askin's Tumor, Ewing's sarcoma, Kaposi's sarcoma, Liposarcoma, Malignant fibrous histiocytoma, Rhabdomyosarcoma, Neurofibrosarcoma, Hodgkin's lymphoma, B-cell Lymphoma, Mantle cell lymphoma (MCL), T-cell Lymphoma, Endometroid Adenocarcinoma, Bladder Transitional Cell carcinoma, Small Cell Lung Cancer, Non Small Cell Lung Cancer, Large-cell lung carcinoma, testicular seminoma, moderate to poorly differentiated Colo-rectal adenocarcinoma, and spinal cord tumor; and measuring an increase in interferon-gamma production of T-cells in the subject after administration of the monoclonal or polyclonal antibody or fragment.

2. The method of claim 1, wherein said administering said monoclonal or polyclonal antibody or an antigen binding fragment thereof comprises administering said monoclonal or polyclonal antibody or an antigen binding fragment thereof in a pharmaceutical composition.

3. The method of claim 1, further comprising administering an additional therapy to the subject, wherein the additional therapy is radiation therapy, additional antibody therapy, chemotherapy, photodynamic therapy, surgery or combination therapy with conventional drugs.

4. The method of claim 3, wherein said additional therapy is selected from the group consisting of immunosuppressants, cytotoxic drugs, peptides, pepti-bodies, small molecules, chemotherapeutic agents, cytotoxic and cytostatic agents, immunological modifiers, interferons, interleukins, immunostimulatory growth hormones, cytokines, vitamins, minerals, aromatase inhibitors, RNAi, Histone Deacetylase Inhibitors, and proteasome inhibitors.

5. The method of claim 4, wherein said additional therapy is selected from the group consisting of bevacizumab, erbitux, paclitaxel, cisplatin, vinorelbine, docetaxel, gemcitabine, temozolomide, irinotecan, 5FU, carboplatin, folic acid, Gemcitabine, Oxaliplatin, cisplatin, carboplatin, cyclophosphamide, anthracyclines, doxorubicin, daunorubicin, taxanes, paclitaxel, docetaxel, microtubule inhibitors, vincristine, Folate antagonists, methotrexate, mTOR pathway inhibitors, temsirolimus, rapamycin, oxaliplatin, cyclophosphamide, doxorubicin, and mitoxantrone.

6. The method of claim 4, wherein said additional therapy is selected from the group consisting of histone deacetylase (HDAC) inhibitors, vorinostat, sodium butyrate and MS-275, Bortezomib, Vemurafenib, JAK2 inhibitors, tyrosine kinase inhibitors (TKIs), erlotinib, imatinib, sunitinib, sorafenib, anti-EGFR mAbs cetuximab, anatimumab and trastuzumab.

7. The method of claim 4, wherein said administering said additional therapy comprises administering said additional therapy together with said monoclonal or polyclonal antibody or an antigen binding fragment thereof in a pharmaceutical composition.

8. The method of claim 1, wherein the antibody is coupled to a moiety selected from a drug, a radionuclide, a fluorophore, an enzyme, a toxin, a therapeutic agent, or a chemotherapeutic agent; and wherein the detectable marker is a radioisotope, a metal chelator, an enzyme, a fluorescent compound, a bioluminescent compound or a chemiluminescent compound.

9. The method of claim 1, wherein said antibody or fragment modulates B7 related costimulation, increases T cell activation, alleviates T-cell suppression, increases cytokine secretion, increases IL-2 secretion; increases Th1 response, decreases Th2 response, promotes cancer epitope spreading, reduces inhibition of T cell activation, increases T cell response in a mammal, stimulates antigen-specific memory responses, elicits apoptosis or lysis of cancer cells, stimulates cytotoxic or cytostatic effect on cancer cells, induces direct killing of cancer cells, induces complement dependent cytotoxicity and/or antibody dependent cell-mediated cytotoxicity, and/or has CDC activity.

10. The method of claim 9, wherein said antibody or fragment increases immune response against the cancer.

11. The method of claim 10, wherein said antibody or fragment reduces activity of regulatory T lymphocytes (T-regs).

12. The method of claim 10, wherein said antibody or fragment inhibits iTreg differentiation.

13. The method of claim 10, further comprising administering one or more of therapeutic agents targeting Treg, MDSCs or both, an immunostimulatory antibody, a therapeutic cancer vaccine or adoptive cell transfer.

14. The method of claim 13, wherein the therapeutic agent targeting immunosuppressive cells Tregs, MDSCs or both is selected from antimitotic drugs, cyclophosphamide, gemcitabine, mitoxantrone, fludarabine, thalidomide, thalidomide derivatives, COX-2 inhibitors, depleting or killing antibodies that directly target Tregs through recognition of Treg cell surface receptors, anti-CD25 daclizumab, basiliximab, ligand-directed toxins, denileukin diftitox (Ontak)—a fusion protein of human IL-2 and diphtheria toxin, or LMB-2—a fusion between an scFv against CD25 and the *pseudomonas* exotoxin, antibodies targeting Treg cell surface receptors, TLR modulators, agents that interfere with the adenosinergic pathway, ectonucleotidase inhibitors, or inhibitors of the A2A adenosine receptor, TGF-.beta. inhibitors, chemokine receptor inhibitors, retinoic acid, all-trans retinoic acid (ATRA), Vitamin D3, phosphodiesterase 5 inhibitors, sildenafil, ROS inhibitors and nitroaspirin.

15. The method of claim 13, wherein the immunostimulatory antibody is selected from antagonistic antibodies targeting one or more of CTLA4, ipilimumab, PD-1, BMS-936558, MDX-1106, PDL-1, BMS-936559/MDX-1105, LAG-3, IMP-321, TIM-3 or BTLA, or agonistic antibodies targeting one or more of CD40, CP-870,893, CD137, BMS-663513, OX40, Anti-OX40, GITR or TRX518, or both.

16. The method of claim 13, wherein the therapeutic cancer vaccine is selected from exogenous cancer vaccines including proteins or peptides used to mount an immunogenic response to a tumor antigen, recombinant virus and bacteria vectors encoding tumor antigens, DNA-based vaccines encoding tumor antigens, proteins targeted to dendritic cells, dendritic cells and gene modified tumor cells expressing at least one of GM-CSF or Flt3-ligand.

17. The method of claim 16, wherein the therapeutic cancer vaccine comprises a dendritic-cell-based vaccine.

18. The method of claim 1, wherein said Thyroid Carcinoma is selected from one or more of Thyroid Papillary Carcinoma, Thyroid Follicular Carcinoma (preferably stage II and III), incidental papillary carcinoma (IPC), Medullary thyroid cancer, Anaplastic thyroid cancer; or wherein said carcinoma of the esophagus is a squamous cell carcinoma of the esophagus; or wherein said Invasive Ductal Carcinoma is selected from stage II to IV and/or poorly differentiated Invasive Ductal Carcinoma, and/or wherein said Medullary Carcinoma is Grade 2 Medullary Carcinoma; or wherein said Serous and Mucinous ovarian carcinoma is selected from stages Ic to IIIb Serous and Mucinous ovarian carcinoma; or wherein said kidney Clear cell carcinoma is selected from stage I to II renal Clear cell carcinoma; or wherein said hepatocellular carcinoma is selected from stage II and III hepatocellular carcinoma; or wherein said Hodgkin's lymphoma is selected from Nodular sclerosing, Mixed-cellularity subtype, Lymphocyte-rich or Lymphocytic predominance, Lymphocyte depleted and Unspecified; or wherein said B-cell Lymphoma is selected from the group consisting of Diffuse large B cell lymphoma, Follicular lymphoma, Mucosa-Associated Lymphatic Tissue lymphoma (MALT), Small cell lymphocytic lymphoma, Burkitt lymphoma, Mediastinal large B cell lymphoma, Waldenstrom macroglobulinemia, Nodal marginal zone B cell lymphoma (NMZL), Splenic marginal zone lymphoma (SMZL), Intravascular large B-cell lymphoma, Primary effusion lymphoma, Lymphomatoid granulomatosis; or wherein said T-cell Lymphoma is selected from the group consisting of Extranodal T cell lymphoma, Cutaneous T cell lymphomas: Sezary syndrome and Mycosis fungoides, Anaplastic large cell lymphoma, and Angioimmunoblastic T cell lymphoma; or wherein said Endometroid Adenocarcinoma is selected from stage I to Inc Endometroid Adenocarcinoma; or wherein said bladder Transitional Cell carcinoma is selected from stage II to IV Transitional Cell carcinoma; or wherein said Small Cell Lung Cancer is selected from stage I to IIIb Small Cell Lung Cancer, and/or wherein said Non Small Cell Lung Cancer is selected from poorly to moderately differentiated squamous and adeno carcinoma.

19. The method of claim 1, wherein said monoclonal or polyclonal antibody or antigen binding fragment thereof comprises an antigen binding site that binds specifically to any of SEQ ID NOS: 2, 3, 5, 6.

20. The method of claim 1, wherein the antibody is a chimeric antibody, humanized or primatized antibody.

21. The method of claim 1, wherein the antibody is selected from the group consisting of Fab, Fab', F(ab')2, F(ab'), F(ab), Fv or scFv fragment and minimal recognition unit.

22. The method of claim 1, wherein the C1ORF32 polypeptide has the sequence of SEQ ID No: 1.

23. The method of claim 1, wherein the cancer is selected from the group consisting of: wherein the cancer is selected from the group consisting of Thyroid Carcinoma, carcinoma of the esophagus, Invasive Ductal breast Carcinoma, breast comedocarcinoma, breast Medullary Carcinoma Grade 2, ovarian cancer selected from the group consisting of Serous and Mucinous, Granular cell tumor, Surface epithelial-stromal tumor (Adenocarcinoma), cystadenocarcinoma and Endometrioid tumor; kidney cancer selected from the group consisting of Clear cell carcinoma, Chromophobe adenoma, and sarcomatoides carcinoma; prostate adenocarcinoma having a Gleason score of 5 or higher, stage I to III prostate adenocarcinoma, stage II and III hepatocellular carcinoma, malignant hepatoma, fibrolamellar hepatocellular carcinoma, pseudoglandular (adenoid) hepatocellular carcinoma, pleomorphic (giant cell) hepatocellular carcinoma, clear cell HCC, Cholangiocarcinoma, pancreas cancer selected from Ductal and Mucinous Adenocarcinoma, Islet cell carcinoma, familial atypical multiple mole melanoma-pancreatic cancer syndrome (FAMMM-PC), Exocrine pancreas cancers, ductal adenocarcinoma, denosquamous carcinomas, signet ring cell carcinomas, hepatoid carcinomas, colloid carcinomas, undifferentiated carcinomas, and undifferentiated carcinomas with osteoclast-like giant cells, Low- to intermediate-grade neuroendocrine carcinomas and pancreatic carcinoid tumors, Lentigo maligna melanoma, Superficial spreading melanoma, Acral lentiginous melanoma, Mucosal melanoma, Nodular melanoma, Polypoid melanoma, Desmoplastic melanoma, Amelanotic melanoma, Soft-tissue melanoma, Chondrosarcoma, Leiomyosarcoma, Angiosarcoma, Askin's Tumor, Ewing's sarcoma, Kaposi's sarcoma, Liposarcoma, Malignant fibrous histiocytoma, Rhabdomyosarcoma, Neurofibrosarcoma, Mantle cell lymphoma (MCL), T-cell Lymphoma, Endometroid Adenocarcinoma, Bladder Transitional Cell carcinoma, testicular seminoma, moderate to poorly differentiated Colo-rectal adenocarcinoma, and spinal cord tumor.

\* \* \* \* \*